(12) United States Patent
Mankin et al.

(10) Patent No.: US 11,096,345 B2
(45) Date of Patent: *Aug. 24, 2021

(54) METHOD FOR TREATING POST-EMERGENT RICE

(71) Applicant: BASF SE, Ludwigshafen (DE)

(72) Inventors: S. Luke Mankin, Raleigh, NC (US); Leon Neuteboom, Morrisville, NC (US); Sherry R. Whitt, Raleigh, NC (US); Ulrich Schoefl, Apex, NC (US); Haiping Hong, Cary, NC (US); Allan Wenck, Durham, NC (US); Dale R. Carlson, Apex, NC (US); John A. McElver, Durham, NC (US); Jill M. Stevenson-Paulik, Cary, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/395,832

(22) Filed: Dec. 30, 2016

(65) Prior Publication Data

US 2017/0231225 A1 Aug. 17, 2017

Related U.S. Application Data

(63) Continuation-in-part of application No. 15/156,671, filed on May 17, 2016, and a continuation-in-part of application No. 14/357,691, filed as application No. PCT/US2012/064831 on Nov. 13, 2012, now Pat. No. 9,540,627, said application No. 15/156,671 is a continuation of application No. 13/393,780, filed as application No. PCT/US2010/047571 on Sep. 1, 2010, now abandoned.

(60) Provisional application No. 61/559,618, filed on Nov. 14, 2011, provisional application No. 61/365,298, filed on Jul. 16, 2010, provisional application No. 61/238,906, filed on Sep. 1, 2009.

(51) Int. Cl.
| | |
|---|---|
| *A01H 5/10* | (2018.01) |
| *A01H 1/04* | (2006.01) |
| *A01H 1/02* | (2006.01) |
| *A01N 43/40* | (2006.01) |
| *A01N 39/02* | (2006.01) |
| *C12N 15/82* | (2006.01) |
| *A01N 43/60* | (2006.01) |

(52) U.S. Cl.
CPC .............. *A01H 5/10* (2013.01); *A01N 39/02* (2013.01); *A01N 43/40* (2013.01); *C12N 15/8274* (2013.01); *A01H 1/02* (2013.01); *A01H 1/04* (2013.01); *A01N 43/60* (2013.01)

(58) Field of Classification Search
CPC ........ A01H 5/10; A01H 1/04; C12N 15/8274; A01N 43/40; A01N 43/60; C12Y 604/01002
See application file for complete search history.

(56) References Cited

U.S. PATENT DOCUMENTS

| | | | |
|---|---|---|---|
| 5,162,602 A | 11/1992 | Somers et al. | |
| 5,290,696 A | 3/1994 | Somers et al. | |
| 5,801,233 A | 9/1998 | Haselkorn | |
| 5,910,626 A | 6/1999 | Haselkorn | |
| 5,925,805 A | 7/1999 | Ohlrogge et al. | |
| 6,027,945 A | 2/2000 | Smith | |
| 6,069,298 A | 5/2000 | Gengenbach | |
| 6,281,168 B1 | 8/2001 | Shaner et al. | |
| 6,306,636 B1 | 10/2001 | Haselkorn et al. | |
| 6,368,800 B1 | 4/2002 | Smith et al. | |
| 2003/0236208 A1 | 12/2003 | Kmiec et al. | |
| 2004/0123343 A1 | 6/2004 | La Rosa et al. | |
| 2006/0039943 A1 | 2/2006 | Applebaum et al. | |
| 2007/0074303 A1 | 3/2007 | McCutchen et al. | |
| 2008/0234130 A1 | 9/2008 | McCutchen et al. | |
| 2008/0256668 A1* | 10/2008 | Beetham ............ | C12N 15/8213 800/300.1 |
| 2009/0093366 A1* | 4/2009 | Wright ................ | C12N 9/0071 504/142 |
| 2010/0048405 A1 | 2/2010 | Raymer et al. | |
| 2011/0214196 A1 | 9/2011 | Raymer et al. | |

(Continued)

FOREIGN PATENT DOCUMENTS

| | | |
|---|---|---|
| CN | 102083303 A | 6/2011 |
| CN | 102905516 A | 1/2013 |

(Continued)

OTHER PUBLICATIONS

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).*

(Continued)

*Primary Examiner* — Weihua Fan
(74) *Attorney, Agent, or Firm* — Lowenstein Sandler LLP

(57) ABSTRACT

The present disclosure provides a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, postemergence; thereby creating a treated rice plant; and growing the resulting treated rice plant.

15 Claims, 48 Drawing Sheets

Specification includes a Sequence Listing.

(56) References Cited

U.S. PATENT DOCUMENTS

| | | |
|---|---|---|
| 2013/0023416 A1 | 1/2013 | Hinga et al. |
| 2013/0111618 A1 | 5/2013 | Mankin et al. |
| 2014/0045686 A1 | 2/2014 | Mankin et al. |
| 2016/0108423 A1 | 4/2016 | Mankin et al. |
| 2016/0244780 A1 | 8/2016 | Mankin et al. |
| 2016/0251677 A1 | 9/2016 | Mankin et al. |
| 2017/0275645 A1 | 9/2017 | Mankin et al. |

FOREIGN PATENT DOCUMENTS

| | | | | |
|---|---|---|---|---|
| EP | 0374753 A2 | 6/1990 | | |
| EP | 0427529 A1 | 5/1991 | | |
| EP | 0451878 A1 | 10/1991 | | |
| EP | 2473024 A2 | 7/2012 | | |
| JP | 2013-526833 | 7/2012 | | |
| WO | 1993/007278 | 4/1993 | | |
| WO | 9534656 A1 | 12/1995 | | |
| WO | 9854330 A1 | 12/1998 | | |
| WO | 0192512 A2 | 12/2001 | | |
| WO | 02015701 A2 | 2/2002 | | |
| WO | 03018810 A2 | 3/2003 | | |
| WO | 03052073 A2 | 6/2003 | | |
| WO | 2005123946 A1 | 12/2005 | | |
| WO | 2008089061 A2 | 7/2008 | | |
| WO | WO-2009056333 A2 * | 5/2009 | ............ | A01N 25/00 |
| WO | 2011028832 A2 | 3/2011 | | |
| WO | 2011028836 A2 | 3/2011 | | |

OTHER PUBLICATIONS

Okuzaki, A., and K. Toriyama. "Chimeric RNA/DNA oligonucleotide-directed gene targeting in rice." Plant cell reports 22.7 (2004): 509-512. (Year: 2004).*

Délye, Christophe, Annick Matéjicek, and Séverine Michel. "Cross-resistance patterns to ACCase-inhibiting herbicides conferred by mutant ACCase isoforms in *Alopecurus myosuroides* Huds.(black-grass), re-examined at the recommended herbicide field rate." Pest management science 64.11 (2008): 1179-1186. (Year: 2008).*

O'Sullivan, P. A., WH Vanden Born, and H. A. Friesen. "Influence of herbicides for broad-leaved weeds and adjuvants with dichlorfop methyl on wild oat control." Canadian Journal of Plant Science 57.1 (1977): 117-125. (Year: 1977).*

Maneechote, Chanya, et al. "Resistance to ACCase-inhibiting herbicides in sprangletop (*Leptochloa chinensis*)." Weed science 53.3 (2005): 290-295. (Year: 2005).*

Griffin, James L., and John B. Baker. "Tolerance of rice (*Oryza sativa*) cultivars to fenoxaprop, sethoxydim, and haloxyfop." Weed Science 38.6 (1990): 528-531. (Year: 1990).*

Maneechote, Chanya, S. Jamjod, and B. Rerkasem. "Controlling invasive wild rice with ACCase-inhibiting herbicides." Proceedings of the 4th International Crop Science Congress, Brisbane, Australia. 2004. (Year: 2004).*

Anyszka, Zbigniew, and A. Dobrzanski. "The response of snap bean and barnyard grass [*Echinochloa crus-galli*] on quizalofop-P-tefuryl." Vegetable Crops Research Bulletin 51 (1999): 95-102. (Year: 1999).*

Till, Bradley J., et al. "Discovery of chemically induced mutations in rice by TILLING." BMC plant biology 7.1 (2007): 19. (Year: 2007 ).*

Baldwin, John L., et al. "Effect of growth stage and application site on tolerance of rice (*Oryza sativa*) to haloxyfop." Weed technology 10.2 (1996): 268-272. (Year: 1996).*

NoIdin, José A., et al. "Red rice (*Oryza sativa*) biology. II. Ecotype sensitivity to herbicides." Weed Technology (1999): 19-24. (Year: 1999).*

Yu, et al., "The Genomes of Oryza sativa: A History of Duplications", PLoS Biology, vol. 3, Issue 2, e38, Feb. 2005, pp. 0266-0281.

Zagnitko, et al., "An isoleucine/leucine residue in the carboxyltransferase domain of acetyl-CoA carboxylase is critical for interaction with aryloxyphenoxypropionate and cyclohexanedione inhibitors", PNAS, vol. 98, No. 12, Jun. 5, 2001, pp. 6617-6622.

Zhang, et al., "The molecular bases for resistance to acetyl co-enzyme A carboxylase (ACCase) inhibiting herbicides in two target-based resistant biotypes of annual ryegrass (*Lolium rigidum*)", Planta., vol. 223, Issue 3, Feb. 2006, pp. 550-557.

Zhu, et al., "Computational Simulations of the Interactions between Acetyl-Coenzyme-A Carboxylase and Clodinafop: Resistance Mechanism Due to Active and Non active Site Mutations", Journal of Chemical Information and Modeling, vol. 49, No. 8, Jul. 13, 2009, pp. 1936-1943.

Georges, F. and Ray H., Gm Crops and Food 2017, 8:1-12, pp. 2-6.

Custers, R., Emerging Topics in Life Sciences (2017), Portland Press, "The regulatory status of gene-edited agricultural products in the EU and beyond" pp. 1-9.

Sprink, T. et al., "Regulatory hurdles for genome editing: process—vs. product-based approaches in different regulatory aontexts." Plant Cell Rep 2016, 35: 1493-1506.

EU Directive 2001/18/EC, Official Journal of the European Communities (Apr. 17, 2001 ):L106/1-38.

M. Lusser & E. Rodriguez-Cerezo "Comparative Regulatory Approaches for New Plant Breeding Techniques," presented Jun. 26, 2012 at the 16th ICABR Conference, Ravello, Italy.

M. Lusser et al., "Deployment of new biotechnologies in plant breeding," Nature Biotechnology 30(3):231-239 (2012); Abstract.

BIO Product Launch Stewardship Policy of May 21, 2007.

OropLife International (CLI) Product Launch Stewardship Guidance of 2008.

Excellence Through Stewardship (ETS) Guide for Product Launch of Biotechnology-Derived Plant Products of 2009; 13 pages.

Diclofop Methyl herbicide directions for use, Cheminova Australia PTY LTD, pp. 1-4.

Aramo, Tepraloxydim herbicide directions for use, BASF (2015), pp. 1-8.

BASF, "Segment Herbicide" pp. 1-2, 2008. APN 08-14-002-0051.

Gressel, et al., "A strategy to provide long-term control of weedy rice while mitigating herbicide resistance transgene flow, and its potential use for other crops with related weeds," Wiley Interscience, Apr. 14, 2009. DOI 10.1002/ps. 1754 pp. 723-731.

Johnson, et al., "Managing the potential for developing herbicide-resistant weeds in herbicide-tolerant rice" Weed Science, pp. 551-557.

Valverde, et al., "Status and Management of Grass-Weed Herbicide Resistance in Latin America," Weed Technology 2007 21:310-323.

Zhu et al., "Engineering herbicide-resistant maize using chimeric RNA/DNA oligonucleotides." Nature Biotechnology vol. 18 May 2000, pp. 555-558.

U.S. Department of Agriculture, Agricultural Resource Management Survey: U.S. Rice Industry. Jan. 2015, No. 2015-02, pp. 1-4.

K. Johnson et al., "Managing the potential for developing herbicide-resistant weeds in herbicide-tolerant rice," at p. 556 in J.E. Hill & B. Hardy (eds ), Proceedings of the Second Temperate Rice Conference (Int. Rice Res. Inst.) (2002).

Page 37 in "Implementing Integrated Weed Management for Herbicide Tolerant Crops" (CropLife International, Feb. 2012; https://croplife.org/wp-content/uploads/2014/04/Implementing-Integrated-Weed-Management-for-Herbicide-Tolerant-Crops.pdf.

J.W.Heiser (U. Missour—Weed Science), Rice News (Sep. 5, 2014), in AgFax (http://agfax.com/2014/09/05/rice-herbiade-tolerant-provisia-highlighted-missouri-delta-center-field-day/).

Khush, G.S., Plant Mol. Biol., 1997, 35:25-34.

EMBL Accession No. EAY97401, Submitted on Sep. 12, 2003.

Delye et al, Pest Management Science, 2008 64:1179-1186.

Delye et al, Plant Physiol (2003) 132:1716-1723.

Collavo, A., PhD Dissertation, University of Padova, Jan. 2008.

Okuzaki et al, "Chimeric RNA/DNA oligonucleotide-directed gene targeting in rice," Plant Cell Reports, 22:7, 2004, 509-512.

Rutger et al, Crop Science, 2005, 45:1170-1171.

UniProt Accession No. A2Y2U1, integrated into database Mar. 20, 200T.

Suzuki et al, Mol. Genet Genomics, 2008, 279:213-223.

Heong, Kong Luen, and M.M. Escalada, eds. Pest Management of rice farmers in Asia, Int. Rice Res. Inst, 1997.

(56) References Cited

OTHER PUBLICATIONS

Till, et al, "Discovery of chemically induced mutations in rice by TILLLING." BMC Plant Biology 7.1, 2007, 19.
Hongle, et al, "Mutations of codon position 1991 of acetyl-CoA carboxylase confer resistance to ACCase-inhibiting herbicides in Japanese foxtail (*Alopecurus japonicas*)." Pest Management Science 70.12, 2014, 1894-1901.
Delye et al, WEed Res. (2005) 45:323-330.
Delye, Weed Science (2005) 56:728-746.
Okuzaki et al. Plant Cell Rep. (2004) 22:509-512.
UniProt Accession No. A2Y2U1, integrated into the database on Mar. 20, 2007.
Liu et al, Proc. Natl. Acad. Sci. (2007) 104:3627-3632.
Powles, et al., Resistance and World Grains, CRC Press (2001), Boca Raton Florida, pp. 31-33.
Beetham et al., "A Toold for Functional Plant Genomics: Chimeric Rna/Dna Oligonucleotides Cause In Vivo Gene-Specific Mutations," Proc Natl Acad Sci USA, vol. 96, pp. 8774-8778, 1999.
Hugh, A. and Eudes, F., "Study of Uptake of Cell Penetrating Peptides and Their Cargoes in Permeabilized Wheat Immature Embryos," FEBS J. vol. 275, pp. 2403-2414, 2008.
Getz et al., "Improved Method for High Efficiency Transformation of Intact Yeast Cells," Nuci Acids Res, vol. 20, p. 1425, 1992.
Hasslacher et al., "Acetyl-CoA Carboxylase from Yeast is an Essential Enzyme and is Regulated by Factors that Control Phospholipid Metabolism," J Biol Chem, vol. 268, No. 15, pp. 10946-10952, 1993.
Mumberg et al., "Yeast Vectors for the Controlled Expression of Heterologous Proteins in Different Genetic Backgrounds," Gene, vol. 156, pp. 119-122, 1995.
Schneiter et al., A Yeast Acetyl Coenzyme A Caboxylase Mutant Links Very-Long-Chain Fatty Acid Synthesis to the Structure and Function of the Nuclear Membrane-Pore Complex, Mol Cell Biol, vol. 16, pp. 7161-7172, 1996.
Tong et al., Systematic Genetic Analysis with Ordered Arrays of Yeast Deletion Mutants, Science, vol. 294, No. 5550, pp. 2364-2368, 2001.
Tong, A.H.Y. And Boone, C., "Synthetic Genetic Array Analysis in *Saccharomyces cerevisiae*," Methods Mol Biol, vol. 313, pp. 171-192, 2006.
"Extended European Search Report issued in European Application No. 10814-446.0", dated Jun. 6, 2013, 14 pages.
"Extended European Search Report issued in European Application No. 16202167.9", dated Mar. 16, 2017, 9 pages.
"Genotyping Sethoxydim Resistant Maize: A method for the detection of the ACC1-11781 (Am)L allele in *Zea mays*", BASF internal manual.
"International Search Report issued in International Application No. PCT/US2010/047571", dated May 18, 2011,4 pages.
Ashley, Jr., James Elton, "Evaluation of Weed Control and Crop Tolerance With Postemergence Herbicides in Sethoxydim-Tolerant Corn", Thesis submitted to Virginia Polytechnic Institute, Apr. 27, 1998, 4 pages.
Balgheim, et al., "Resistance to ACCase inhibiting herbicides is due to target-site modification in a biotype of Aopecurus myosuroides Huds", The BCPC International Congress—Crop Science & Technology, 2005, pp. 155-162.
Buell, C. Robin, "Poaceae Genomes: Going from Unattainable to Becoming a Model Glade for Comparative Plant Senomics", Plant Physiology, vol. 149, Issue 1, Jan. 2009, pp. HI-116.
Callan, "In Vitro Selection for and Biochemical Analysis of Sethoxydim-Tolerant winter Wheat (*Triticum aestivum* L.)", In partial fulfillment of the requirements for the Degree of Doctor of Philosophy, Colorado State University, Fort Collins, Colorado, Fall, 1996, 30 pages.
Carlson, et al., "Tissue Culture Selection System in Poa Pratensis", NCWSS Proceedings, vol. 45, 1990, Abstract, 1 page.
Christoffers, et al., "An Isoleucine to Leucine Mutation in Acetyl-CoA Carboxylas Confers Herbicide Resistance in Wild Oat", Genome, National Research Council Canada, vol. 45, Issue 6, Jan. 1, 2002, pp. 1049-1056.
Delye, et al., "An isoleucine-leucine substitution in chloroplastic acetyl-CoA carboxylase from green foxtail (*Setaria viridis* L. Beauv.) is responsible for resistance to the cyclohexanedione herbicide sethoxydim", Planta. vol. 214, Issue 3, Jan. 2002, pp. 421-427.
Delye, et al., "Molecular Bases for Sensitivity to Acetyl-Coenzyme A Carboxylase Inhibitors in Black-Grass", Plant Physiology, vol. 137, Mar. 2005, pp. 794-806.
Delye, et al., "PCR-based detection of resistance to acetyl-CoA Carboxylase-inhibitor herbicides in black-grass (*Alopecurus myosuroides* Huds) and ryegrass (*Lolium rigidum* Gaud)", Pest Management Science, vol. 58, Issue 5, May 2002, pp. 474-478.
Delye, et al., "SNP markers for black-grass (*Alopecurus myosuroides* Huds) genotypes resistant to acetyl CoA-carboxylase inhibiting herbicides", Theoretical and Applied Genetics, vol. 104, Issue 6-7, May 2002, pp. 1114-1120.
Delye, et al., "Universal primers for PCR-sequencing of grass chloroplastic acetyl-CoA carboxylase domains involved in resistance to herbicides", Weed Research, vol. 45, 2005, pp. 323-330.
Delye, "Weed resistance to acetyl coenzyme A carboxylase inhibitors: an update", Weed Science, vol. 53, No. 5, Sep. 2005, pp. 728-746.
Heckart, et al., "Obtaining Sethoxydim Resistance in Seashore Paspalum", Crop Science, vol. 50, Nov.-Dec. 2010, pp. 2632-2640.
Heckart, Douglas Lee, "Obtaining Sethoxydim Resistance in Seashore Paspalum (*Paspalum vaginatum*)", A Thesis Submitted to the Graduate Faculty of the University of Georgia in Partial Fulfillment of the Requirements for the Degree, Athens, GA, 2009, 51 pages.
Herbert, et al., "Susceptibilities of Different Test Systems from Maize (*Zea mays*), Pea annua, and Festuca rubrato Herbicides that Inhibit the Enzyme Acetyl-Coenzyme A Carboxylase", Pesticide Biochemistry and Physiology, vol. 55, Issue 2, Jun. 1996, pp. 129-139.
Hiei, et al., "Agrobacterium-mediated Transformation of Rice Using Immature Embryos or Call Induced from Mature Seed", Nature Protocols, vol. 3, No. 5, Apr. 17, 2008, pp. 824-834.
Jain, S.M., "Tissue culture-derived variation in crop improvement", Euphytica, vol. 118, Issue 2, Mar. 2001, pp. 153-166.
Joachimiak, et al., "Wheat cytosolic acetyl-CoA carboxylase complements an ACC1 null mutation in yeast", Proceeding of the National Academy Science, Plant Biology, vol. 94, Sep. 1997, pp. 9990-9995.
Maneechote et al., "Controlling invasive wild rice with ACCase-inhibiting herbicides." Proceedings of the 4th International Crop Science Congress, Brisbane, Australia. 2004. (Year: 2004).
JP Ruiz-Santaella, et al., "Basis of selectivity of cyhalofop-butyl in *Oryza sativa* L.", Planta, vol. 223, Issue 2, Jan. 2006, pp. 191-199.
JP Ruiz-Santaella, et al., "Detection of a new mutation of glycine to serine in the ACCase of a Resistant Biotype of Phalaris Paradoxa", Weed Science Sec. Am. Abstr. 46:93, 2006 (New York: WSSA 2006 Annual Meeting, Abstract, 1 page.
JP Ruiz-Santaella, et al., "Is it possible to detect Echinochloa spp. tolerance to ACCaseinhibiting herbicides using a simple quick tolerance test?", Commun. Agric. Appl. Biol. ScL, vol. 68, (4 Pt A), 2003, pp. 331-334.
Kellogg, Elizabeth A., "The Evolutionary History of Ehrhartoideae, Oryzeae, and *Oryza*", Rice, vol. 2, Issue 1, Mar. 2009, pp. 1-14.
Liu, et al., "Single-site mutations in the carboxyltransferase domain of plastid acetyl-CoA carboxylase confer resistance to grass-specific herbicides", PNAS, vol. 104, Issue 9, Feb. 2007, pp. 3627-3632.
Madoka, et al., "Chloroplast Transformation with Modified accD Operon Increases Acetyl-CoA Carboxylase and Causes Extension of Leaf Longevity and Increase in Seed Yield in Tobacco", Plant and Cell Physiology, vol. 43, Issue 12, Dec. 15, 2002, pp. 1518-1525.
Marshall, et al., "Allelic mutations in acetyl-coenzyme A carboxylase confer herbicide tolerance in maize", Theoretical and Applied Genetics, vol. 83, Issue 4, Feb. 1992, pp. 435-442.
Mathews, et al., "Phylogenetic Structure in the Grass Family (Poaceae): Evidence From the Nuclear Gene Phytochrome B", American Journal of Botany 87(1), 2000, pp. 96-107.

(56) References Cited

OTHER PUBLICATIONS

Menchari, et al., "Fitness costs associated with three mutant acetyl-coenzyme A carboxylase alleles endowing herbicide resistance in black-grass *Alopecurus myosuroides*", Journal of Applied Ecology, vol. 45, Issue 3, Jun. 2008, pp. 939-947.

Neve, et al., "High survival frequencies at low herbicide use rates in populations of Lolium rigidum result in rapid evolution of herbicide resistance", Heredity, vol. 95, Jul. 2005, pp. 485-492.

Nikolau, et al., "Plant biotin-containing carboxylases", Archives of Biochemistry and Biophysics, vol. 414, Issue 2, Jun. 15, 2003, pp. 211-222.

Nikolskaya, et al., "Herbicide sensitivity determinant of wheat plastid acetyl-CoA carboxylase is located in a 400-amino acid fragment of the carboxyltransferase domain", Pnas, vol. 96 No. 25, Dec. 7, 1999, pp. 14647-14651.

Parker, et al., "Dominant mutations causing alterations in acetyl-coenzyme A carboxylase confer tolerance to cyclohexanedione and aryloxyphenoxypropionate herbicides in maize", Proceedings of the National Academy of Science, vol. 87, Sep. 1990, pp. 7175-7179.

Parker, et al., "Selection and Characterization of Sethoxydim-Tolerant Maize Tissue Cultures", Plant Physiology, vol. 92, 1990, pp. 1220-1225.

Podkowinski, et al., "Expression of Cytosolic and Plastid Acetyl-Coenzyme A Carboxylase Genes in Young Wheat Plants", Plant Physiology, vol. 131, Feb. 2003, pp. 763-772.

Rafael De Prado, et al., "Resistance to ACCase inhibitor herbicides in a green foxtail (*Setaria viridis*) biotype in Europe", Weed Science, vol. 52, No. 4, Jul.-Aug. 2004, pp. 506-512.

Roesler, et al., "Targeting of the Arabidopsis Homomeric Acetyl-Coenzyme A Carboxylase to Plastids of Rapeseeds", Plant Physiology, vol. 113, Issue 1, Jan. 1997, pp. 75-81.

Ruiter, et al., "Spontaneous Mutation Frequency in Plant Obscures the Effect of Chimeraplasty", Plant Molecular Biology, vol. 53, Nov. 2003, pp. 715-729.

Maneechote, Chanya, et al. "Resistance to ACCase-inhibiting herbicides in sprangletop (*Leptochloa chinensis*)." Weed science 53 (2005): 290-295. (Year: 2005).

Shivrain, et al., "Gene flow between Clearfield™ rice and red rice", Crop Protection, vol. 26, Issue 3, Mar. 2007, pp. 349-356.

Somers, David A., "Chapter 11: Aryloxyphenoxypropionate- and Cyclohexanedione-Resistant Crops", Herbicide-Resistant Crops: Agricultural, Environmental, Economic, Regulatory and Technical Aspects, CRC Press, Inc., 1996, pp. 175-188.

Xiang, et al., "A different mechanism for the inhibition of the carboxyltransferase domain of acetyl-coenzyme A arboxylase by tepraloxydim", PNAS, vol. 106, No. 49, Dec. 8. 2009, pp. 20723-20727.

Tal, et al., "Molecular characterization and inheritance of resistance to ACCase-inhibiting herbicides in Lolium rigidum", Pest Management Science, vol. 60, Issue 10, Oct. 2004, pp. 1013-1018.

Tate, Trent Matthew, "Characterization of acetyl coenzyme A inhibitor resistance in turfgrass and grassy weeds", A Thesis Submitted to the Graduate Faculty of the University of Georgia in Partial Fulfillment of the Requirements for the Degree, Dec. 2012, 64 pages.

White, et al., "Differences in the molecular basis of resistance to the cyclohexanedione herbicide sethoxydim in Lolium multiflorum", Weed Research, vol. 45, Issue 6, Dec. 2005, pp. 440-448.

Yu, et al., "Diversity of Acetyl-Coenzyme A Carboxylase Mutations in Resistant Lolium Populations: Evaluation Using Clethodim", Plant Physiology, vol. 145, Issue 2, Oct. 2007, pp. 547-558.

\* cited by examiner

FIGURE 5

```
   1 MGSTHLPIVG FNASTTPSLS TLRQINSAAA AFQSSSPSRS SKKKSRRVKS IRDOGDGSVP
  61 DPAGHGQSIR QGLAGIIDLP KEGASAPDVD ISHGSEDHKA SYQMNGILNE SHNGRHASLS
 121 KVYEFCTELG GKTPIHSVLV ANNGMAAAKF MRSVRTWAND TFGSEKAIQL IAMATPEDMR
 181 IKAEKIRIAD QFVEVPGGTN NNNYANVQLI VEIAERTGVS AVWPGWGHAS SNPELPDALT
 241 AKGIVFLCPP ASSMNALGDK VGSALIAQAA GVPTLAWSGS SVEIPLELCL DSIPEEMYRK
 301 ACVTTADEAV ASCQMIGYPA MIKASWGGGG KGIRKVNNDD EVKALFKQVQ GSVPGSPIFI
 361 MRLASQSRHL EVQLLCDSYG NVAALHSRDC SVQRRHQKII EEGPVTVAFR ETVKELEQAA
 421 RRLAKAVGYV GAATVEYLYS METGEYYPLE LNPRLQVEHP VIESIAEVNL PAAQVAVGMG
 481 IPLKQIPEIR RFYGMDNGGG YDIWRKTAAL ATPFNFDEVD SQWPKGHCVA VRITSENPDD
 541 GFKFTGGKVK KISFKSKPNV WGYFSVKSGG GIREFADSQF GHVFAYGEIR SAAITSMSLA
 601 LKEIQIRGEI HINVDYTVDL LNAPDFRENT IHTGWLDTRI AMRVQAERPP WYISVVGGAL
 661 YKTITTNAET VSEYVSYLIK GQIPPKHISL VHSTISLNIS ESKYTISIVR SGQGSYRLRI
 721 NGSLIEANVQ TLCDSGLLMQ LDGNSHVIYA EEEAGGTRLL IDGKTCLLQN DHDPSRLLAE
 781 TPCKLLRFLI ADGAHVDADV FYAEVEVMKM CMPLLSPAAG VINVLLSEGQ AMQAGDLIAR
 841 LDLDDPSAVK RAEPFEGSPP EMSLPIAASG QVHKRCAASL NAARMVLAGY DHARNKVVQD
 901 LVWCLDTPAL PFLQWEELMS VLATRLPRRL KSELRGKYNS YKLNVDHVKI KDFPTEMLRE
 961 TIEENLACVS EKEMVTIERL VDPLMSLLKS YEGGRESHAH FIVKSLFEEY LSVEELFSDG
1021 IQSDVIERLR LQYSKDLQKV VDIVLSRQGV RNKTKLILAL MEKLVYPNPA AYRDQLIRFS
1081 SLNHKRYYKL ALKASELLSQ TKLSELRTSI ARNLSALDMF TEEKADFSLQ DRKLAINESM
1141 GDLVTAFLPV EDALVSLFDC TDQTLQQRVI QFYISRLYQP QLVKDSIQLK YQDSGVIALW
1201 EFTEGNHEKR LGAMVILKSL ESVSTAIGAA LKDASHYASS AGNTVHIALL DADTQLNTYS
1261 DSGDNDQAQD KMDKLSFVLK QDVVMADLRA ADVKVVSCIV QRDGAIMFMR RTFLLSEEKI
1321 CYEESPILRH VEPPLSALLE LDKLKVKGYN EMKYTPSRDR QWHIYTLSNT SNPKMLNRVF
1381 FRTLVRQPSA GKRFTSDHIT DVEVGHAEEP LSFTSGSILK SLKIAKEELE LHAIRTGHEN
1441 MYLCILKEQK LLDLVFVSGN TVVDVGQDRA TACSLLKEMA LKIHELVGAR MHHLSVCQWE
1501 VKLKLVSDGP ASGSWRVVTT NVTGNTCTVD IYREVEDTES QKLVYHSTAL SSGPLHGVAL
1561 NTSYQFLSVI DLKRCSARNN KTTYCYDFPL TFEAAVCKSW SNISSENNQC YVKATELVFA
1621 EKNGSWGTPI IPMQRAAGLN DIGMVAKILD MSTPEFPSGR QIIVIANDIT FRAGSFGPRS
1681 DAFFEAVTNL ACEKKLPLIY LAANSGARIG IADEVKSCFR VGWTODSSPE RGFRYIYMTD
1741 EDHDRIGSSV IAHKMQLDSG EIRWVIDSVV GKEDGLGVEN IRGSAAIASA YSRAYEETPT
1801 LTFVYGRTVG IGAYLARLGI RCIQRIDQPI ILTGFSALNK LLGREVYSSH MQLGGPKIMA
1861 TNGVVHLTVP DDLEGVSNIL RWLSYVPANI GGPLPITKSL DPIDSPVAYI PENTCDPRAA
1921 ISGIDDSQGK WIGGMPDKDS FVETFEGWAK TVVRGRAKLG GIPVGVIAVE TQTMKQLVFA
1981 DPGQFDSHER SVFRAGGVWF PDSATKTAQA MLDFNREGLP LFILANWBGF SGGQRDLFEG
2041 ILQAGSTIVE NLRTYNQPAF VYIPKAAELR GGARVVIDSK INPDRIECYA ERIAKGNVLS
2101 PQGLIEIKFR SEELKECMGR LDPELIDLKA RLQGANGSLS DGESLQKSIR ARKKQLLPLY
2161 TQIAVRFAEL HDTSLRMAAK GVIRKVVDWE DSRSFFYKRL RARLSEDVLA KEIRGVIGEK
2221 FPHKSAIELI KKWYLASEAA AAGSTDWDDD DAFVAWRENP ENYKEYIKEL RAQRVSRLLS
2281 DVASSSSDLQ ALPQGLSMLL DKMDFSKRAQ FIEEVMKVLK
```

FIGURE 6

```
   1 ATGGATCCA CACATCTGCC CATTGTCGGG TTTAATGCAT CCACAACACC ATCGCTATCC
  61 ACTCTTCGCC AGATAAACTC AGCTGCTGCT GCATTCCAAT CTTCTCCCC TTCAAGGTCA
 121 TCCAAGAAGA AAAGCTGACG TGTTAAGTCA ATAAGGGATG ATGGTGATGG AAGCGTGCCA
 181 GACCCTGCAG GCCATGGCCA GTCTATTCGC CAAGGTCTCG CTGGCATCAT CGACCTCCCA
 241 AAGGAGGGCG CATCAGCTCC AGATGTGGAC ATTTCACATG GGTCTGAAGA CCACAAGGCC
 301 TCCTACCAAA TGAATGGGAT ACTGAATGAA TCACATAACG GGAGGCACGG CTCTCTGTCT
 361 AAAGTCTATG AATTTGCAC GGAATTGGCT GGAAAAACAC CAATTCACAG TGTATTAGTC
 421 GCCAACAATG GAATGGCAGC AGCTAAGTTC ATGCGGAGTG TCCGGACATG GGCTAATGAT
 481 ACATTTGGGT CAGAGAAGGC GATTCAGTTG ATAGCTATGG CAACTCCGGA AGACATGAGA
 541 ATAAATGCAG AGCACATTAG AATTGCTGAT CAGTTTGTTG AAGTACCTGG TGGAACAAAC
 601 AATAACAACT ATGCAAATGT CCAACTCATA GTGGAGATAG CAGAGAGAAC TGGTGTCTCC
 661 GCCGTTTGGC CTGGTGGGG CCATGCATCT GAGAATCCTG AACTTCCAGA TCCACTAACT
 721 GCAAAAGGAA TTGTTTTTCT TGGGCCACCA GCATCATCAA TGAACGCACT AGGCGACAAG
 781 GTTCGTTCAG CTCTCATTGC TCAAGCAGCA GGGGTTCCCA CTCTTGCTTG GAGTGGATCA
 841 CATGTGGAAA TTCCATTAGA ACTTTGTTTG GACTCGATAC CTGAGGAGAT GTATAGGAAA
 901 GCCTGTGTTA CAACCGCTGA TGAAGCAGTT GCAAGTTGTC AGATGATGG TTACCCTGCC
 961 ATGATCAAGG CATCCTGGGG TGGTGGTGGT AAAGGGATTA GAAAGGTTAA TAATGATGAC
1021 GAGGTGAAAG CACTGTTTAA GCAAGTACAG GGTGAAGTTC CTGGCTCCCC GATATTTATC
1081 ATGAGACTTG CATCTCAGAG TGGTCATCTT GAAGTCCAGC TGCTTTGTGA TGAATATGGC
1141 AATGTAGCAG CACTTCACAG TCGTGATTGC AGTGTGCAAC GACGACACCA AAAGATTATC
1201 GAGGAAGGAC CAGTTACTGT TGCTCCTCGT GAAACAGTGA AAGAGCTAGA GCAAGCAGCA
1261 AGGAGGCTTG CTAAGCCCGT GGGTTACGTC GGTGCTGCTA CTGTTGAATA TCTCTACAGC
1321 ATGGAGACTG GTGAATACTA TTTTCTGGAG CTTAATCCAC GGTTGCAGGT TGAGCACCCA
1381 GTCACCGAGT CGATAGCTGA AGTAAATTTG CCTGCAGCCC AAGTTGCAGT TGGGATGGGT
1441 ATACCCTTT GGCAGATTCC AGAGATCAGA CGTTTCTACG GAATGGACAA TGGAGGAGGC
1501 TATGATATTT GGAGGAAAAC AGCAGCTCTC CCTACTCCAT TCAACTTTGA TGAAGTAGAT
1561 TCTCAATGGC CGAAGCGTCA TTGTGTGGCA GTTAGGATAA CCAGTGAGAA TCCAGATGAT
1621 GGATTCAAGC CTACTGGTGG AAAAGTAAAG GAGATAAGTT TTAAAAGTAA GCCAAATGTC
1681 TGCCGATATT TCTCAGTTAA GTCTGGTGGA GGCATTCATG AATTGCGGA TTCTCAGTTT
1741 GGACACGTTT TTGCCTATGG AGAGACTAGA TCAGCAGCAA TAACCAGCAT GTCTCTTGCA
1801 CTAAAAGAGA TTCAAATTCG TGGAGAAATT CATACAAACG TTGATTACAC GGTTGATCTC
1861 TTGAATGCCC CAGACTTCAG AGAAAACACG ATCCATACCG GTTGGCTGGA TACCAGAATA
1921 GCTATGCGTG TTCAAGCTGA GAGGCCTCCC TGGTATATTT CAGTGGTTGG AGGAGCTCTA
1981 TATAAAACAA TAACCACCAA TGCGGAGACC GTTTCTGAAT ATGTTAGCTA TCTCATCAAG
2041 GGTCAGATTC CACCAAAGCA CATATCCCTT GTCCATTCAA CTATTTCTTT GAATATAGAG
2101 GAAAGCAAAT ATACAATTCA CATTGTGAGG AGTCGACACG CTAGCTACAG ATTGAGACTG
2161 AATGGATCAC TTATTGAAGC CAATGTACAA ACATTATGTG ATGGAGGCCT TTTAATGCAG
2221 CTGGATGGAA ATAGCCATGT TATTTATGCT GAAGAAGAAG CGGGTGGTAC ACGGCTTCTT
2281 ATTGATGGAA AAACATGCTT GCTACAGAAT GACCATGATC CGTCAAGGTT ATTAGCTGAG
2341 ACAGCCTGCA AACTTCTTCG TTTCTTCATT GCCGATGGTG CTCATGTTGA TGCTGATGTA
2401 CCATACGCGG AAGTTGAGGT TATGAAGATG TGCATGCCCC TCTTGTCGCC TGCTGCTGGT
2461 GTCATTAATG TTTTGTTCTC TGAGGGCCAG GCGATGCAGG CTGGTGATCT TATAGCGAGA
2521 CTTGATCTCG ATGACCCTTC TGCTGTGAAG AGAGCCGAGC CATTGAAGG ATCTTTCCA
2581 GAAATGAGCC TTCCTATTGC TGCTTCTGGC CAAGTTCACA AAAGATGTGC TGCAAGTTTG
2641 AACGCTGCTC GAATGGTCCT TGCAGGATAT GACCATGCGG CCAACAAAGT TGTGCAAGAT
2701 TTGGTATGGT GCCTTGATAC ACCTGCTCTT CCTTCCTAC AATGGGAAGA GCTTATGTCT
2761 GTTTTAGCAA CTAGACTTCC AAGACGTCTT AAGAGCGAGT GGAGGGCAA ATACAATGAA
2821 TACAAGTTAA ATGTTGACCA TGTGAAGATC AAGGATTTCC CTACCGAGAT GTTAGAGAG
2881 ACAATCGAGG AAAATCTTGC ATGTGTTTCC GAGAAGGAAA TGGTGACAAT TGAGAGGTT
2941 GTTGACCCTC TGATGAGCCT GCTGAAGTCA TACGAGGGTG GGAGAGAAAG CCATGCCCAC
```

FIGURE 6 (continued)

```
3001 TTTATTGTCA AGTCCTTTTT TGAGGAGTAT CTCTCGGTTG AGGAACTATT CAGTGATGGC
3061 ATTCAGTCTG ACGTGATTGA ACGCCTGCGC CTACAATATA GTAAAGACCT CCAGAAGGTT
3121 GTAGACATTG TTTGTCTCA CCAGGGTGTG AGAAACAAAA CAAAGCTGAT ACTCGCGCTC
3181 ATGGAGAAAC TGGTCTATCC AAACCCTGCT GCCTACAGAG ATCAGTTGAT TCGCTTTTCT
3241 TCCCTCAACC ATAAAAGATA TTATAAGTTG GCTCTTAAAG CTACTGAACT TCTTGAACAA
3301 ACCAAGCTCA GCGAACTCCG CACAAGCATT GCAAGGAACC TTTCAGCGCT GGATATGTTC
3361 ACCGAGGAAA AGGCAGATTT CTCCTTGCAA GACAGAAAAT TGGCCATTAA TGAGAGCATG
3421 GGAGATTTAG TCATGCCCC ACTGCCAGTT GAAGATGCAC TTGTTCTTT GTTTGATTGT
3481 ACTGATCAAA CTCTTCAGCA GAGAGTGATT CAGACATACA TATCTCGATT ATACCAGCCT
3541 CAACTTGTGA AGGATAGCAT CCAGCTGAAA TATCAGRTT CTGGTGTTAT TGCTTTATGG
3601 GAATTCACTG AAGGAAATCA TGAGAAGAGA TTGGGTGCTA TGGTTATCCT GAAGTCACTA
3661 GAATCTGTGT CAACAGCCAT TGGAGCTGCT CTAAAGGATG CATCACATTA TGCAAGCTCT
3721 GCGGGCAACA CGGTGCATAT TGCTTTGTTG GATGCTGATA CCCAACTGAA TACAACTGAA
3781 GATAGTGGTG ATAATGACCA AGCTCAAGAC AAGATGGATA AACTTTCTTT TCTACTGAAA
3841 CAAGATGTTG TCATGGCTGA TCTACGTGCT GCTGATGTCA AGGTTGTTAG TTGCATTGTT
3901 CAAACAGATG GAGCAATCAT GCCTATGCGC CGTACCTTCC TCTTGTCAGA GGAAAAACTT
3961 TGTTACGAGG AAGAGCCGAT TCTTCGGCAT GTGGAGCCTC CACTTTCTGC ACTTCTTCAG
4021 TTGGATAAAT TGAAAGTGAA AGGATACAAT GAGATGAAGT ATACACCGTC ACGTGATCGT
4081 CAGTGGCATA TATACACACT TAGAAATACT GAAAATCCAA AAATGCTGCA CAGGGTATTT
4141 TTCCGAACAC TTGTCAGACA ACCCAGTGCA GGCAACAGGT TTACATCAGA CCATATCACT
4201 GATGTTGAAG TACGACACGC AGAGGAACCT CTTTCATTTA CTTCAAGCAG CATATTAAAA
4261 TGGTTGAAGA TTGCTAAAGA AGAATTGGAG CTTCACGCGA TCAGGACTGG CCATTCTCAT
4321 ATGTACTTGT GCATATTGAA AGAGCAAAAG CTTCTTGACC TTGTTCCTGT TTCAGGGAAC
4381 ACTGTTGCG ATGTTCGTCA AGATGAAGCT ACTGCATGCT CTCTTTTGAA AGAAATGGCT
4441 TTAAAGATAC ATGAACTTGT TGGTGCAAGA ATGCATCATC TTTCTGTATC CCAGTGGAA
4501 GTGAAACTTA AGTTGGTGAG CGATGGGCCT GCCAGTGGTA GCTGGAGAGT TGTAACAACC
4561 AATGTTACTG GTCACACCTG CACTGTGGAT ATCTACCGGG AGGTCGAAGA TACAGAATCA
4621 CAGAAACTAG TATACCACTC CACCCCATTG TCATCTGCTC CTTTGCATGG TGTTGCACTG
4681 AATACTTCGT ATCAGCCTTT GAGTGTTATT GATTTAAAAC GTTGCTCTGC CAGGAACAAC
4741 AAAACTACAT ACTGCTATGA TTTTCCATTG ACATTTGAAG CTGCAGTGCA GAAGTCGTGG
4801 TCTAACATTT CCAGTGAAAA CAACCAATGT TATGTAAAG CGACAGAGCT TGTGTTTGCT
4861 GAAAAGAATG GGTCGTGGGG CACTCCTATA ATTCCTATGC AGCGTGCTGC TGGGCTGAAT
4921 GACATTGGTA TGGTAGCCTG GATCTTGGAC ATGTCGACTC CTGAATTTCC CAGCGGCAGA
4981 CAGATCATTG TTATCGCAAA TGATATTACA TTTAGAGCTG GATCATTTGG CCCAAGGGAA
5041 GATGCATTTT TCGAAGCTGT AACCAACCTG GCTTGTGAGA AGAAGCTTCC ACTTATCTAC
5101 TTGGCTGCAA ACTCTGGTGC TCGGATTGGC ATTGCTGATG AAGTAAAATC TTGCTTCCGT
5161 GTTGGATGGA CTGATGATAG CAGCCCTGAA CGTGGATTTA GGTACATTTA TATGACTGAC
5221 GAAGACCATG ATCGTATTGG CTCTTCAGTT ATAGCACACA AGATGCAGCT AGATAGTGGC
5281 GAGATCAGGT GGTTATTGA TTCTGTTGTG GAAAAGAGG ATGGACTAGG TGTGGAGAAC
5341 ATACATGGAA GTGCTGCTAT TGCCAGTGCC TATTCTAGGG CGTACGAGGA GACATTTACA
5401 CTTACATTCG TTACTGGACG AACTGTTGGA ATCGGAGCCT ATCTTGCTCG ACTTGGCATA
5461 CGGTGCATAC AGCGTATTGA CCAGCCCATT ATTTTGACCG GTTTTCTGC CCTGAACAAG
5521 CTTCTTGGGC GGAGGTGTA CAGCTCCCAC ATGCAGTTGG GTGGTCCCAA AATCATGGCG
5581 ACGAATGGTG TTGTCCATCT GACTGTTCCA GATGACCTTG AAGGTGTTTC TAATATATTG
5641 AGGTGGCTCA GCTATGTTCC TGCAAACATT GGTGGACCTC TTCCTATTAC AAAATCTTTG
5701 GACCCAATAG ACAGACCCGT TGCATACATC CCTGAGAATA CATGTGATCC TCGTGCAGCC
5761 ATCAGTGGCA TTGATGACAG CCAAGGGAAA TGGTTGGGTG GCATGTTTGA CAAAGACAGT
5821 TTTGTGGAGA CATTTGAAGG ATGGGCGAAG ACAGTAGTTA CTGGCAGAGC AAAACTTGGA
5881 GGGATTCCTG TTGGTGTTAT AGCTGTGGAG ACACAGACCA TGATGCAGCT CGTCCCGCT
5941 GATCCAGGCC AGCCTCATTC CCACCAGCGG TCTGTTCCTC GTGCTGGGCA AGTTTGGTTT
6001 CCAGATTCTG CTACCAAGAC AGCGCAGGCG ATGTTGGACT TCAACCGTGA AGGATTACCT
6061 CTGTTCATAC TTGCTAACTG GAGAGGCTTC TCTGGAGGGC AAAGAGATCT TTTTGAAGGA
6121 ATTCTGCAGG CTGGGTCAAC AATTGTTGAG AACCTTAGGA CATACAATCA GCCTGCCTTT
6181 GTATATATCC CCAAGGCTGC AGAGCTACGT GGAGGAGCCT GGGTCGTGAT TGATAGCAAG
```

FIGURE 6 (continued)

```
6241 ATAAACCCAG ATCGCATCGA GTGCTATGCT GAGAGGACTG CAAAGGTAA TGTTCTCGAA
6301 CCTCAAGCGT TCATTCACAT CAAGTTCACC TCAGACGAAC TCAAAGAATC CATGGGTACG
6361 CTTGATCCAG AATTGATAGA TCTGAAAGCA AGACTCCAGG GAGCAAATGG AAGCCTATCT
6421 GATGGAGAAT CCCTTCAGAA GAGCATAGAA GCTCGGAAGA AACAGTTGCT GCCTCTGTAC
6481 ACCCAAATCG CGGTACGTTT TGCGGAATTG CACGACACTT CCCTTAGAAT GGCTGCTAAA
6541 GGTGTGATCA GGAAAGTTGT AGACTGGGAA GACTCTCGGT CTTTCTTCTA CAAGAGATTA
6601 CGGAGGAGGC TATCCGAGGA CGTTCTGGCA AAGGAGATTA GAGGGTAAT TGGTGAGAAG
6661 TTTCCTCACA AATCAGCGAT CGAGCTGATC AAGAAATGGT ACTGGCTTC TGAGGCAGCT
6721 GCAGCAGGAA GCACCGACTG GGATGACGAC GATGCTTTTG TCGCCTGGAG GGAGAACCCT
6781 CAAAACTATA ACGAGTATAT CAAAGAGCTT AGGGCTCAAA GCGTATCTCG GTTGCTCTCA
6841 GATGTTGCAG GCTCCAGTTC GGATTTACAA GCCTTGCCGC AGGGTCTTTC CATGCTACTA
6901 GATAAGATGG ATCCTCTAA GAGAGCACAG TTTATCGAGG AGGTCATGAA GGTCCTGAAA
6961 TGA
```

FIGURE 7A

>Oryza sativa Plastidic ACCase genomic sequence

ATGACATCCACACATGTGGCCACATTGGGAGTTGGTGCCCAGGCACCTCCTCGTCACCAGAAAAGTCAGCTGG
CACTGCATTTGTATCATCTGGGTCATCAAGACCCTCATACCGAAAGAATGGTCAGCGTACTCGGTCACTTAGGG
AAGAAAGCAATGGAGGAGTGTCTGATTCCAAAAAGCTTAACCACTCTATTCGCCAAGGTGACCACTAGCTACTT
TACATATGCTATAATTTGTGCCAAACATAAACATGCAATGGCTGCTATTATTTAAACGTTAATGTTGAAATAGC
TGCTATAGGATACAGCAAAAATATATAATTGACTGGGCAAGATGCAACAATTGTTTTTCACTAAAGTTAGTTAT
CTTTTGCTGTAAAACACAACTGTTTTTTACATAAAATGGTATTAATAACCTTGTAATATTCAATGCAACATGTT
CTCAAGTAAAAAAAAACATTGCCTGGTTGTATAAGCAAATGTGTCGTTGTAGACATCTTATTAAACCTTTTTGT
GATATCTATTACCGTAGGGAACAGGGGACCTGTTTAAATCTGTTATCATAGAGTAATATGAGAAAAGTGGATTG
TGCGACTTTGCCATCTATACCTCCTCAATTTCAAATATATGTCTATGTGCAGGTCTTGCTGGCATCATTGACCT
CCCAAATGACGCAGCTTCAGAAGTTGATATTTCACAGTAAGGACTTTATATTTTATAATAATTATTATATAATT
TTCTGACATGTTTTGAGAACCTCAAAACATGTGATTGCACCTTCCTTTTTTATGTCTGGTTCAGAAACTGATAA
GTTTTGACAGTGTTTAGGATGGATCTTTGATGCGCACAGTGCTTTCTAATGTTTTCATTTTTGAAAGTAATGTT
TTAGGAAGAAATATCTGATTAAATTTATACTTTATCTTTACAAAAGTCAAATGCGTTCTGTATCAATTGCGGTT
TGTAATATGGCAAGAACATGCTTTCAGAATTTGTTCATACAATGCTTTCTTTCTATTATTATGTAGAACAAATA
CCTAATACTTTGTTCACCTTTTATAGTGGACACCTCTCACAGCTTTTTCAGTAAGTGATGCAATTTTGTACATT
TGTAAGATGTGTTCCAGAAACCTTTTCTCCTGCAATTCTAATGTACCCACTCAAACTGGTATCACCAAAGATCT
CCATCTGATTGAAAAAAAGCTGCGTGAAGTATGCTTATTTATGCTAACCATACATGATTTATACTGTTTTATAG
TACAATGCTTATTTATGCTAACCATACATAATTTTATTCTGTTTTCTAGTACATTATTTGTGCCCCTGACCATA
AATGATCCTTTCTTTTACAGTGGTTCCGAAGATCCCAGGGGGCCTACGGTCCCAGGTTCCTACCAAATGAATGG
GATTATCAATGAAACACATAATGGGAGGCATGCTTCAGTCTCCAAGGTTGTTGAGTTTTGTACGGCACTTGGTG
GCAAAACACCAATTCACAGTGTATTAGTGGCCAACAATGGAATGGCAGCAGCTAAGTTCATGCGGAGTGTCCGA
ACATGGGCTAATGATACTTTTGGATCAGAGAAGGCAATTCAGCTGATAGCTATGGCAACTCCGGAGGATCTGAG
GATAAATGCAGAGCACATCAGAATTGCCGATCAATTTGTAGAGGTACCTGGTGGAACAAACAACAACAACTATG
CAAATGTCCAACTCATAGTGGAGGTTAGTTCAGCTCATCCCTCAACACAACATTTTCGTTTCTATTTAAGTTAG
GGAAAAATCTCTACGACCCTCCAATTTCTGAACATCCAATTTTCACCATCAACTGCAATCACAGATAGCAGAGA
GAACAGGTGTTTCTGCTGTTTGGCCTGGTTGGGGTCATGCATCTGAGAATCCTGAACTTCCAGATGCGCTGACT
GCAAAAGGAATTTGTTTTTCTTGGGCCACCAGCATCATCAATGCATGCATTAGGAGACAAGGTTGGCTCAGCTCT
CATTGCTCAAGCAGCTGGAGTTCCAACACTTGCTTGGAGTGGATCACATGTGAGCCTTGTCTTCTCTTTTTTAG
CTTATCATCTTATCTTTTCGGTGATGCATTATCCCAATGACACTAAACCATAGGTGGAAGTTCCTCTGGAGTGT
TGCTTGGACTCAATACCTGATGAGATGTATAGAAAAGCTTGTGTTACTACCACAGAGGAAGCAGTTGCAAGTTG
TCAGGTGCTTGGTTATCCTGCCATGATTAAGGCATCTTGGGGTGGTGGTGGTAAAGGAATAAGGAAGGTTTGTT
CTTCTTGTAGTTATCAAGAGATTGTTTGGATTGCAAGTGTTTAGTGCCCATAGTTAACTCTGGTCTTTCTAACA
TGAGTAACTCAACTTTCTTGCAGGTTCATAATGATGATGAGGTTAGGACATTATTTAAGCAAGTTCAAGGCGAA
GTACCTGGTTCCCCAATATTTATCATGAGGCTAGCTGCTCAGGTGGGGCCTTTTATGGAAGTTACACCTTTTCC
CTTAATGTTGAGTTATTCCGGAGTTATTATGGTTATGTTCTGTATGTTTGATCTGTAAATTATTGAAATTCACC
TCCATTGGTTCTCCAGATTAGCAGACCTACAATTCTACATATGCTTTATACTTTATAAATACTAGGATTTAGGG
ATCTTCATATAGTTTATACATGGTATTTAGATTTCATTTGTAACCCTATTGAAGACATCCTGATTGTTGTCTTA
TGTAGAGTCGACATCTTGAAGTTCAGTTGCTTTGTGATCAATATGGCAACGTAGCAGCACTTCACAGTCGAGAT
TGCAGTGTACAACGGCGACACCAAAAGGTCTGCTGTCTCAGTTAAATCACCCCTCTGAATGATCTACTTCTTGC
CTGCTGCGTTGGTCAGAGGAATAATGGTTGTATTCTACTGAACAGATAATCGAGGAAGGACCAGTTACTGTTGC
TCCTCGTGAGACTGTGAAAGAGCTTGAGCAGGCAGCACGGAGGCTTGCTAAAGCTGTGGGTTATGTTGGTGCTG
CTACTGTTGAATACCTTTACAGCATGGAAACTGGTGAATATTATTTTCTGGAACTTAATCCACGGCTACAGGTC
GGCTCCTTTGACATTCTTCAGGAATTAATTTCTGTTGACCACATGATTTACATTGTCAAATGGTCTCACAGGTT
GAGCATCCTGTCACTGAGTGGATAGCTGAAGTAAATTTGCCTGCGGCTCAAGTTGCTGTTGGAATGGGTATACC
CCTTTGGCAGATTCCAGGTAATGCTTCTTCATTTAGTTCCTGCTCTTTGTTAATTGAATGAGCTCTTATACAGA
CCATGAGACACATTCTACTGTTAATTCATAGTATCCCCTGACTTGTTAGTGTTAGAGATACAGAGATGTATCAC

FIGURE 7A (continued)

```
AAATTCATTGTATCTCCTCAAGGACTGTAAAAATCCTATAATTAAATTTCTGAAAATTTGTTCTTTTAAGCAGA
AAAAAAATCTCTAAATTATCTCCTCTATACACACATCAGGGCCTTCTACGGAATGAACCATGGAGGAGGCTAT
GACCTTTGGAGGAAAACAGTAGCTCTAGCGACTCCATTTAACTTTGATGAAGTAGATTCTAAATGGCCAAAAGG
CCACTGCGTAGCTGTTAGAATAACTAGCGAGGATCCAGATGATGGGTTAAGCCTACTGGTGGAAAAGTAAAGG
TGCGGTTCCCTGATGTTAGGTGTATGAATTGAACACATTGCTATATTGCAGCTAGTGAAATCACTGGATCATGG
TTCTCTTATTTCAGGAGATAAGTTTCAAGAGTAAACCAAATGTTTGGGCCTATTTCTCAGTAAAGGTAGTCCT
CAATATTGTTGCACTGCCACATTATTTGAGTTGTCCTAACAATTGTGCTGCAATTGTTAGTTTTCAACTATTTG
TTGTTCTGTTTGGTTGACTGGTACCCTCTCTTTGCAGTCTGGTGGAGGCATCCATGAATTCGCTCATTCTCAGT
TCGGTATGTAAAGTTAAAAGAGTAATAPTGTCTTTGCTATTTATGTTTGTCCTCACTTTTAAAAGATATTGCCT
TCCATTACAGGACATGTTTTTGCGTATGGAACTACTAGATCGGCAGCAATAACTACCATGGCTCTTGCACTAAA
AGAGGTTCAAATTCGTGGAGAAATTCATTCAAACGTAGACTACACAGTTGACCTATTAAATGTAAGGACTAAAT
ATCTGCTTATTGAACCTTGCTTTTTGGTTCCCTAATGCCATTTTAGTCTGGCTACTGAAGAACTTATCCATCAT
GCCATTTCTGTTATCTTAAATTCAGGCCTCAGATTTTAGAGAAAATAAGATTCATACTGGTTGGCTGGATACCA
GGATAGCCATGCGTGTTCAAGCTGAGAGGCCTCCATGGTATATTTCAGTCGTTGGAGGGGCTTTATATGTAAGA
CAAACTATGCCACTCATTAGCATTTATGTGAAGCAAATGCGGAAAACATGATCAATATGTCGTCTTATTTAAAT
TTATTTATTTTTGTGCTGCAGAAAACAGTAACTGCCAACACGGCCACTGTTTCTGATTATGTTGGTTATCTTAC
CAAGGGCCAGATTCCACCAAAGGTACTATTCTGTTTTTTCAGGGATATGAATGCTGTTTGAATGTGAAAACCATT
GACCATAAATCCTGTTGTGCAGCTATATATCCCTTGTCTATACGACTGTTGCTTTGAATATAGATGGGAAAAAAT
ATACAGTAAGTGTGACATTCTTAATGGGGAAACTTAATTTGTTGTAAATAATCAATATCATATTGACTCGTGTA
TGCTGCATCATAGATCCATACTGTGAGGAGTGGACATGGTAGCTACAGATTGCGAATGAATGGATCAACGGTTG
ACGCAAATCTACAAATATTATGTCATCGTTGGGCTTTTAATGCAGGTAATATCTTCTTCCTAGTTAAAGAAGATA
TATCTTGTTCAAAGAATTCTGATTATTGATCTTTTAATGTTTTCAGCTGGATGGAAACAGCCATGTAATTTATG
CTGAAGAAGAGGCCAGTGGTACACGACTTCTTATTGATGGAAAGACATGCATGTTACAGGTAATGATAGCCTTG
TTCTTTTTAGTTCTAGTCACGGTGTTTGCTTGCTATTTGTTTATCTATTTAATGCATTCACTAATTACTATAT
TAGTTTGCATCATCAAGTTAAAATGGAACTTCTTTCTTGCAGAATGACCATGACCCATCAAAGTTATTAGCTGA
GACACCATCCAAACTTCTTGCGTTCTTGGTTGCTGATGGTGCTCATGTTGATGCTGATGTACCTATATCGGAAG
TTGAGGTTATGAAGATGTGCATGCCCCTCTTATCACCCGCTTCTGGTGTCATACATGTTGTAATGTCTGAGGCC
CAAGCAATGCAGGTACATTCCTACATTCTATTCATTGTGCTGTGCTGACATGAACATTTCAAGTAAATACCTGT
AACTTGTTTATTATTCTAGGCTGGTGATCTTATAGCTAGGCTGGATCTTGATGACCCTTCTGCTGTTAAGAGAG
CTGAGCCGTTCGAAGACATCTTTTCCAAGAACATGGGTCTGCCTATTGCTGCTTCTGGCCAAGTTCACAAATTATGT
GCTGCAAGTCTGAATGCTTGTGTCGAATGATCCTTGCGGGGTATGAGCATGATATTGACAAGGTAAACATCATGTC
CTCTTGTTTTTCTTTGTTTATCATGCATTCTTATGTTCAGCATGTCCTCTGCCAAATCTAGATTCCGCTGTC
GTTTCACACAGATTTTCTCATTCTCATAATGGTGCCAAACATAAATATGCTGCTATATTCATCAATGTTTCA
CTCGATTTCTAATTTTGCTTTTGAGTTTTAAACTTTAGTACAATCCATATCTAATCTCCTTTGGCAACAGTGAA
TCCATTATATATATTTTAATAAACTGCTTTCTTTTTCAGGTTGTGCCAGAGTTGGTATACTGCCTAGACACTC
CGGAGCTTCCTTCCTGCAGTGGAGGAGCTTATGTCTGTTTAGCAACTAGACTTCCAAGAAATCTTAAAAAGT
GAGGTATATTATGCTTGACAAGATAGCTAGTCTCATGCTCTAAGGACTTGTACATTCGCCACATAGGTTAATT
TTCCATATCAAGTTCTAATGTACGATATAAAGTAGTACTGGCCTAAAACAGTATTGGTGGTTGACTATCTTTG
TTGTGTAAGATCAAGTATTTCTTTTTCATGCTTAGTTTGTCAATACTTCACATTTATCACTGACTTGTCGAGCT
AAATGAGATTTTATTTGATTTCTGTGCTCCATTATTTTTGTATATATATATATATATTTAACTATGACTATATG
TTATGCCTCAAACGTTTCAAACTCTTTCAGTTGGAGGGCAAATATGAGGAATACAAAGTAAAAATTTGACTCTGG
GATAATCAATGATTTGCCTGCCAATATGCTACGAGTGATAATTGAGGTCAGTTATTCAATTTGTTGTGATAATC
ACTGCCTTAACTGTTCGTTCTTTTAACAAGCGGTTTTATACGAAAATCTTGCATGTGGTTCTGAGAAGGAGAAG
GCTACAAATGAGAGGCTTGTTGAGCCTCTTATGAGCCTACTGAAGTCATATGAGGGTGGGAGAGAAAGTCATGC
TCACTTTGTTGTCAAGTCCCTTTTTGAGGAGTATCTCTATGTTGAAGAATTGTTCAGTGATGGAATTCAGGTTA
ACTTACCTATTCGCATTAAACAAATCATCAGTTGTTTTATGATAAAGTCAAAATGTTTATATTTCCCATTCTTC
TGTGATCAAATATATCACGGACATGATATAGTTTCTTAGGTTATATAATGGTTCTTCATCAAATAATATTGC
AGGAAACGGTATAGCCAAACTATTTCTATATACTCGACATGGAAATTGTAGAACATCATTGACTAAATCTGTC
CTTTGTTACGCTGTTTTTGTAGTCTGATGTGATTGAGCGTCTGCGCCTTCAACATAGTAAAGACCTACAGAAGG
TCGTAGACATTGTGTTGTCCCACCAGGTAAATTCTTCATGGTCTGATGACTTCACTGCGAATGGTTACTGAAC
TGTCTTCTTGTTCTGACAAATGTGACTTTTCTTTGTAGAGTGTTAGAAATAAAACTAAGCTGATACTAAAACTCA
TGGAGTCTGGTCTATCCAAATCCTGCTGCCTACAGGGATCAATTGATTCGCTTTTCTTCCCTTAATCACAAA
GGGTATTACAAGGTGACCAGGATAAACATAAATAAACGTGAATTTTTCAATGACCTTTCTTCTGACATCTGAA
TCTGATGAATTCTTGCATATTAATACAGTTGGCACTAAAGCTAGTGAACTTCTTCAACAAACAAAACTTAGT
```

ACTGGAAGAATCACCATCTTTCTTCTATAAGAGATTACGGAGGAGGATCTCTGAGGATGTTCTTGCAAAAGAA
ATTAGAGCTGTAGCAGGTGAGCAGTTTTCCCACCAACCAGCAATCGAGCTGATCAAGAAATGGTATTCAGCTTC
ACATGCAGCTGAATGGGATGATGACGATGCTTTTGTTGTCTTGGATGGATAACCCTGAAAACTACAAGCATTATA
TTCAATATCTTAAGGCTCAAAGAGTATCCCAATCCCTGTCAAGTCTTTCAGATTCCAGCTCAGATTGCAAGCC
CTCCCACAGGGTCTTTCCATGTTACTAGATAAGGTAATTAGCTTACTGATGCTTATATAAATTCTTTTTCATTA
CATATGGCTGGAGAACTATCTAATCAAATAATGATTATAATTCCAATCGTTCTTTTTATGCCATTATGATCTTC
TGAAATTTCCTTCTTTGGACACTTATTCAGATGGATCCCTCTAGAACAGCTCAACTTGTTCAAGAAATCAGGAA
GGTCCTTGGTTGA

FIGURE 7B

```
>Oryza sativa Plastidic ACCase protein coding sequence
ATGACATCCACACATGTGGCGACATTGGGAGTTGGTGCCCAGGCACCTCCTCGTCACCAGAAAAAGTCAGCTGG
CACTGCATTTGTATCATCTGGTCATCAAGACCCTCATACCGAAAGAATGGTCAGCGTACTCGGTCACTTAGGG
AAGAAAGCAATGGAGCAGTGTCTGATCCAAAAAGCTTAACCACTCTATTCGCCAAGGTCTTGCTGGCATCATT
GACCTCCCAAATGACGCAGCTTCAGAAGTTGATATTTCACATGGTTCCGAAGATCCCAGGGGGCCTACGGTCCC
AGGTTCCTACCAAATGAATGGGATTATCAATGAAACACATAATGGGAGGCATGCTTCAGTCTCCAAGGTTGTTG
AGTTTTGTACGGCACTTGGTGGCAAAACACCAATTCACAGTGTATTAGTGGCCAACAATGGAATGGCAGCAGCT
AAGTTCATGCGGAGTGTCCGAACATGGGCTAATGATACTTTGGATCAGAGAAGGCAATTCAGCTGATAGCTAT
GGCAACTCCGGAGGATCTGAGGATAAATGCAGAGCACATCAGAATTGCCGATCAATTTGTAGAGGTACCTGGTG
GAACAAACAACAACAACTATGCAAATGTCCAACTCATAGTGGAGATAGCAGAGAGAACAGGTCTTTCTGGTCTT
TGGCCTGGTTGGGGTCATGCATCTGAGAATCCTGAACTTCCAGATGCGCTGACTGCAAAAGGAATTGTTTTCT
TGGGCCACCAGCATCATAATCATTCATTAGGCTCAGCTCTCATTGCTCAAGCAGCTGGAG
TTCCAACACTTGCTTGGAGTGGATCACATGTGGAAGTTCCTCTGGAGTGTTGCTTGGACTCAATACCTGATGAG
ATGTATAGAAAAGCTTGTGTTACTACACACAGAGGAAGCAGTTGCAAGTTGTCAGCTGGTTGGTTATCCTGCCAT
GATTAAGCCATCTTGCCCTCCTCGTGCTAAAGGAATAAGGAAGGTTCATAATGATGATGAGGTTAGGACATTAT
TTAAGCAAGTTCAAGGCGAAGTACCTGGTTCCCCAATATTTATCATGAGGCTAGCTGCTCAGACTCGACATCTT
GAAGTTCAGTTGCTTTGTGATCAATATGGCAACGTAGCAGCACTTCACAGTCGAGATTGCAGTGTACAACGGCG
ACACCAAAAGATAATCGAGGAAGGACCAGTTACTGTTGCTCCTCGTGACACTGTGAAAGAGCTTCAGCAGGCAG
CACGGAGGCTTGCTAAAGCTGTGGTTATGTTGGTGCTTCTACTGTTGAATACTTTACAGCATGGAAACTGGT
GAATATTATTTCTCGAACTTAATCCACGGCTACAGGTTGAGCATCCTGTCACTGAGTGGATAGCTGAAGTAAA
TTTGCCTGCGGCTCAAGTTGCTGTTGGAATGGGTATACCCCTTTGGCAGATTCCAGAGATCAGGCGCTTCTACG
GAATGAACCATGGAGGAGGCTATGACCTTTGGAGGAAAACAGCAGCTCTAGCGACTCCATTTAACTTTGATGAA
GTAGATTCTAAATGGCCAAAAGCCCACTGCGTAGCTGTTAGAATAACTAGCGAGGATCCAGATGATGGGTTAA
GCCTACTGGTGGAAAAGTAAAGGAGATAAGTTTCAAGAGTAAACCAAATGTTTGGGCCTATTTCTCAGTAAAGT
CTGGTGGAGGCATCCATGAATCGCTGATTCTCAGTTCGGACATGTTTTGCGTATGGAACTACTAGATCGGCA
GCAATACTACCATGGCTCGTGCACTAAAGAGGTTCAAATGTGGACAAATCCATTCAAACGTAGACTACAC
AGTTGACCTATTAAATGCCTCAGATTTTAGAGAAAATAAGATTCATACTGGTTGGCTGGATACCAGCATAGCCA
TGCGTGTTCAAGCTGAGAGCCTCCATGGTATATTTCAGTCGTTGGAGGGGCTTTATATAAAACAGTAACTGCC
AACACGGCCACTGTTTCTGATTATGTTGGTTATCTTACCAAGGGCCAGATTCCACCAAAGCATATATCCCTTGT
CTATACGACTGTTGCTTTGAATATAGATGGGAAAAAATATACAATCGATACTGTGAGGAGTGGACATGGTAGCT
ACAGATTGCGAATGAATGGATCAACGGTTGACGCAAATGTACAAATATTATGTGATGGTGGGCTTTTAATGCAG
CTGGATGGAAACAGCCATGTAATTATGCTGAAGAAGAGGCCAGTGGTACACGACTTCTTATTGATGGAAAGAC
ATGCATGTTACAGAATGACCATGACCCATCAAAGTTATTAGCTGAGACACCATGCAAACTTCTTCGTTTCTTGG
TTGCTGATGGTGCTCATGTTGATGCTGATGTACCATATGCGGAAGTTGAGGTTATGAAGATGTGCATGCCCCTC
TTATCACCCGCTTCTGGTGTCATACATGTTGTAATGTCTGAGGGCCAAGCAATGCAGGCTGGTGATCTTATAGC
TAGGCTGGATCTTGATGACCCTTCTGCTGTTAAGAGAGCTGAGCCGTTCAAGATACTTTCCACAAATGGGTC
TCCCTATTGCTGCTTCTGGCCAAGTTCACAAATTATGTGCTGCAAGTCTGAATGCTTGTCGAATGATCCTTGCG
GGGTATGAGCATGATATTGACAGGTTGACGCAGAGTTGGTATACTGCCTAGACACTCCGGAGCTTCCTTTCCT
GCAGTGGAGGAGCTTATGTCTGTTTTAGCAACTAGGCCTCCAAGAAATCTTAAAAGTGAGTTGGAGGGCAAAT
ATGAGGAATACAAAGTAAAATTTGACTCTGGGATAATCAATGATTTCCCTGCCAATATGCTACGAGTGATAATT
GAGGAAAATCTTGCATGTGTTCTGAGAAGGAGAAGGCTACAAATGAGAGGCTTGTTGAGCCTCTTATGAGCCT
ACTGAAGTCATATGAGGGTGGGAGAGAAAGTCATGCTCACTTTGTTGTCAAGTCCCTTTTTGAGGAGTATCTCT
ATGTTGAAGAATTGTTCAGTGATGGAATTCAGTCTGATGTGATTGAGCGTCTGCGCCTTCAACATAGTAAAGAC
CTACAGAAGGTCGTAGACATTGTGTTGTCCACCAGAGTGTTAGAAATAAAACTAAGCTGATACTAAAACTCAT
GGAGAGTCTGGTCTATCCAAATCCTGCTGCCTACAGGGATCAATTGATTCCTTTCTTCCCTAATCACAAAG
CGTATTACAAGTTGGCACTTAAAGCTAGTCAAACTTCTTGAACAAACAAAACTTAGTGAGCTCCGTGCAAGAATA
GCAAGGAGCCCTTCAGAGCTGGAGATGTTTACTGAGGAAAGCAAGGGTCTCCTCCATGCATAAGCGAGAAATTGC
```

FIGURE 7B (continued)

```
CATTAAGGAGAGCATGGAAGATTTAGTCACTGCTCCACTGCCAGTTGAAGATCCGCTCATTTCTTTATTTGATT
GTAGTGATACAACTGTTCAACAGAGAGTGATTGAGACTTATATAGCTCGATTATACCAGCCTCATCTTGTAAAG
GACAGTATCAAAATGAAATGGATAGAATGGGTGTTATTGCTTTATGGGAATTTCCTGAAGGGCATTTTGATGC
AAGAAATGGAGGAGCGGTTCTTGGTGACAAAAGATGGGGTGCCATGGTCATTGTCAAGTCTCTTGAATCACTTT
CAATGGCCATTAGATTTGCACTAAAGGAGACATCACACTACACTAGCTCTGAGGGCAATATGATGCATATTGCT
TTCTTGGGTGCTGATAATAAGATGCATATAATTCAAGAAAGTGGTGATGATGCTGACAGAATAGCCAAACTTCC
CTTGATACTAAAGGATAATCTAACCGATCTGCATGCCTCCTGTCTCAAAACAATAAGTTTCATTGTTCAAAGAG
ATCAAGCACGGATGACAATGCCTCGTACCTTCCTTTGGTCTGATGAAAAGCTTTCTTATGAGGAAGAGCCAATT
CTCCGCATGTGGAACCTCCTCTTTCTGCACTTCTTGAGTTGGACAAGTTGAAAGTGAAAGGATACAATGAAAT
GAAGTATACCCCATCACGGGATCGTCAATGGCATATCTACACACTTAGAAATACTGAAAACCCCAAAATGTTGC
ACCGGGTATTTTTCGAACCCTTGTCAGGCAACCCAGTGTATCAACAAGTTTTCTTCGGGCCAGATTGGTGAC
ATGGAAGTTGGAGTGCTGAAGAACCTCTGTCATTTACACTCAACCAGCAATATTAAGATCTTTCATGACTGCTAT
AGAGGAATGGAGCTTCACGCAATTAGAACTGGCCATTCACACATGTATTTGCATGTATTGAAAGAACAAAAGC
TTCTTGATCTTGTTCCAGTTTCAGGGAATACAGTTTTGGATGTTGGTCAAGATGAAGCTACTGCATATTCACTT
TTAAAACAAATGGCTATCAAGATACATCAACTTCTTCCTGCAACAATCCACCATCTTTCTGTATGCCAAAGGGA
AGTGAAACTTAAGTTGGACTGCGATGGTCCTGCCAGTGGTACCTGGAGGATTGTAACAACCAATGTTACTAGTC
ACACTTGCTCTGTGATATGTACCGTCAGATGAAGATAAAGAATCACGAAGTTAGTATACTATCCGCCACT
CCGGCGGCTGGTCCTCTGCATGGTGTGGCACTGAATAATCCATATCAGCCTTTGAGGGTCATTGATCTCAAACG
CTGTTCTGCTAGGAATAATAGAACTACATACTGCTATGATTTTCCACTGGCATTTGAAACTGCAGTCAGGAAGT
CATGGTCCTCTAGTACCTCTGGTGCTTCAAAGGTGTTGAAAATGCCCAATGTTATGTTAAAGCTACAGAGTTG
GTATTTGCCGGACAAACATGGGTCATGGGGCACTCCTTTAGTTCAAATGGACCGGCCCTGCTGGGCTCAATGACAT
TGGTATGGTAGGTTTGGGCCTTGAAGATGTCCACTCGTGAATTTCTTAGTGGTAGGGAGATTATTGTTGTTGCAA
ATCATATTACCTTCAGAGCTGCATCATTTGGCCCAAGCGAACATCGATTTTTCAACCTCTTACCAACCTAGCC
TGTGAGAAGAAACTTCCTCTTATTTATTTGGCAGCAAATTCTGGTGCTCGAATTGGCATAGCAGATGAAGTGAA
ATCTTGCTTCCGTGTTGGGTGGTGTGATGATGGCAGCCCTGAACCGTGGGTTTCAGTACATTTATCTAAGCGAAG
AAGACTATGCTCGTATTGGCACTTCTGTCATAGCACATAAGATGCAGCTAGACAGTGGTGAAATTACGTGGTT
ATTGATTCTGTTGTGGGCAAGGAAGATGGACTTGGTGTGGAGAATATACATGGAAGTGCTGCTATTGCCAGTGC
TTATTCTAGGGCATATAAGGAGACATTTACACTTACATTTGTGACTGCAAGAACTGTTGGAATAGGAGCTTATC
TTGCTCGACTTGGCATCGGGTGCATACAGCGTCTTGACCAGCCTATTATCTTACAGGCTATTCTGCACTGAAC
AAGCTTCTTGGGCGGGAAGTGTACAGCTCCCACATGCAGTTGGGTGGTCCCCAAAATCATGGCAACTAATGGTGT
TGTCCATCTTACTGTTTCAGATCACCTTGAACGCCGTTCTAATATATGGGGTGGCTCAGTTATGTTCCTGCCT
ACATTGGTGGACCACTTCCAGTAACAACACCGTTGGACCCACCGGACAGACCTGTTGCATACATTCCTGAGAAC
TGGTGTGATCCTGGAGCGCTATCCGTGGTGTTGATAGACAGCCAAGCGAAATGTTAGGTGGTATGTTTGATAA
AGACAGCTTTGTGGAAACATTTGAAGTTGCGTCTAAGACACGTGGTTACTGCAGAGCAAAGCTTGGTGGAATTC
CAGTGGGTGTGATAGCTGTGGAGACTCAGACCCATGATGCAAACTATCCCTGCTGACCCTGGTCAGCTTGATTCC
CGTGAGCAATCGTTCCTCGTGCTGGACAAGTGTGGTTTCCAGATTCTGCAACCAAGACTGCGCAGGCATTGCT
GGACTTCAACCGTGAAGGATTACCTCTGTTCATCCTCGCTAACTGGAGAGGCTTCTCTGGTGGACAAAGAGATC
TTTTTGAAGGAATTCTTCAGGCTGGCTCGACTATTGTTGAGAACCTTAGGACATACAATCAGCCTGCCTTTGTC
TACATTCCCATGGCTGCAGAGCTACGAGGAGGGGCTTGGGTTGTGGTTGATAGCAAGATAAACCCAGACCGCAT
TGAGTGCTATGCTGAGAGGACTGCAAAAGGCAATGTTCTGGAACGGCAAGGGTTAATTGAGATCAAGTTCAGGT
CACAGGAACTCCAGGATTGCATGAGTCGGCTTGACCCAACATTAATTGATCTGAAAGCAAAACTGGAAGTAGCA
AATAAAAATGGAAGTGCTCACACAAAATCGCTTCAAGAAAATATAGAAGCTCGAACAAAACACTTCATGCCTCT
ATATACTCAGATTGCGATACGGTTTGCTGAATTGCATGATACATCCCTCAGAATGGCTGCGAAAGGTGTGATTA
AGAAAGTTGTGGACTGGAAGAATCACGATCTTTCTTCTATAAGAGATTACGGAGGAGGATCTCTGAGGATGTT
CTTGCAAAAGAAATTAGAGCTGTAGCAGGTGAGCAGTTTTCCCAGCAACCAGCAATCGAGCTGATCAAGAAATG
GTATTCAGCTTCACATGCAGCTGAATGGGATGATGACGATGCTTTTGTTGCTTGGATGGATAACCCTGAAAACT
ACAAGGATTATATTCAATATCTTAAGGCTCAAACAGTATCCCAATCCCTCTCAAGTCTTTCAGATTCCAGCTCA
GATTTGCAAGCCCTGCCACAGGGTCTTCCATGTTACTAGATAAGATGGATCCCTCTAGAAGAGCTCAACTTGT
TGAAGAAATCAGGAAGGTCCTTGGTTGA
```

FIGURE 7C

>Oryza sativa Plastidic ACCase protein
MTSTHVATLGVGAQAPPREQKKSAGTAFVSSGSSRPSYRKNGQRTRSLSEESNGGVSDSKKLNHSIRQGLAGII
DLPNDAASEVDISHGSEDPRGPTVPGSYQMNGIINETHNGRRASVSKVVEFCTALGGKTPISSVLVANNGMAAA
RPMRSVBTWANDTFGSEKAIQLIAMATPEDLRINAEHIRIADQFVEVPGGTNNMNYANVQLIVEIAERTGVSAV
WPGWGHASENPELPDALTAKGIVPLGPPASSMHALGDKVGSALIAQAAGVPTLANSGSHVEVPLECCLDSIFDE
MYRRACVTTTREAVASCQVVGYPAMIKASWGSGGKGIRKVENDDEVRTLFKQVQSEVPGSPIFIMRLAAQSRHL
EVQLICDQYGNVAALHSRDCSVQRRHQKIIEKGPVTVAPRETVKELSQAARRLAKAVGYVGAATVEYLYSMETG
SYYFLEINPRLQVEHFVTEWIAEVNLPAAQVAVGMGIPLWQIPEIRRFYGMNHGSGYDLWRKTAALATPPNEDE
VDSKWPKGRCVAVRITSEDPDDGPKPTGGKVKEISEKSKPNVWAYPSVKSGGGIREFADSQFGEVFAYGTTRSA
AITTNALALKEVQIEGEIHSNVDYTVDLLNASDFRENKIRTGWLDTRIAMPVQAERPPWYISVVGGALYKTVTA
NTATVSDYVGYLPKGQIPPKHISLVYTTVALNIDGKKYTIDTVRSGHGSYRLRMNGSTVDAMVQILCDGCLLMQ
LDGNSRVIYAREEASGTRLLIDGKTCMLQNDHDPSKLLAETPCKLLRFLVADGAHVDADVPYAEVEVMKMCMPL
LSPASGVIHVVKSEGQAMQAGDLIARLDLDDPSAVKRAEPEEDTPPQMGLPIAASGQVEKLCAASLNACRMILA
GYRDIDKVVPELVYCLOTPELPELQWEELMSVLATRLPRNLKSELEGKYEEYKVKFDSGIINDFPANMLRVII
EENLACGSEKEKATNERLVEPIMSLLRSYEGGRESHARFVVKSLFEEYLYVEELFSDSIQSDVIERLRLQHSKD
LGKVVDIVLSEQSVRNKTKLILKIMESLVYPNPAAYRDQLIRFSSLNHKAYYKLALKASELLEQTKLSELRARI
ARSLSELEMFTEESKGLSMHKREIAIKESMEDLVTAPLPVEDALISLFDCSDTTVQQRVISTYIARLYQPHLVK
DSIKMKWIESGVIALWEFPEGHFDARNGGAVLGDKRWGAMVIVKSLESLSMAIRFALKETSHYTSSEGNMNHIA
LLGADNEMRIIQESGDEADRIAKLPLILKENVTDLHASGVRTISPIVQRDEARMTMRETYLWSDEKLSYEEEPT
LREHVEPPLSALIELDKLKVKGYNEMKYTPSRDRQWHIYTLPNTENPKMLRRVFPRTLVRQFSVSNRFSSGQIGD
MEVGSAEPLSFTSTSILRSLMTAIEELELEAIRTGRSRMYLRVLKEQKLLDLVPVSGNTVLDVGQDEATRVSL
LKEMAMKIRELVGARMHELSVCQWEVKLKLDCDGPASGTWRIVTTNVTSRTCTVDIYREMEDKESRKLVYHPAT
PAAGPLHGVALMNPYQPLSVIDLKRCSARNNRTTYCYDFPIAPETAVRKSWSSSTSGASKGVENAQCYVKATEL
VPADKEGSWGTPLVQNDRPAGINDIGMVAWTLKMSTPEFPSGREIIVVANDITFRAGSFGPREDAFFEAVTNLA
CEKKLPLTYLAANSGARIGIADEVKSCFRVGWSDDGSPERGFQYIYLSEEDYARIGTSVIARKMQLDSGEIRRV
IDSVVGKEDGLGVENIHGSARIASAYSRAYKETFTLTFVTGRTVGIGAYLARLGIRCIQRLDQPIILTGYSALS
KLLGREVYSSRMQLGGFKIMATNGVVRLTVSDDLEGVSNILRWLSYVPAYIGGPLPVTTPLDPPDRPVAYIPRN
SCDPRAAIRGVDDSQGRWLGGMFDKDSFVETFEGWAKIVVTGPAKLGGIPVGVIAVETQTMRQTIEADPGQLDS
REQSVPRAGQVWFPDSATKTAQALLDFNREGLPLPTLANWRGFSGGQRDLFEGILQAGSTIVENLRTYNQPAFV
YIPMAARELRGGANVVVDSKINPDRIECYAERTAKGNVLEPQGLIEIKFRSEELQOCMSRLDPTLIDLKAKLEVA
NKNGSADTKSLQENIEARTKQIMPLYTQIAIRPARLRDTSLRMAAKGVIKKVVDWEESRSFFYKRLRRRISEDV
LRKEIRAVAGEQFSHQPAIELIKKWYSASHAAEWDDEDAFVAWKDNPENYKDYIQYLKAQRVSQSLSSLSDSSS
DLQALPQGLSMLLDKMDPSRRAQLVERIRKVLG*

FIGURE 8A

```
>AY312172_Zea mays
ATGTCACAGCTTGGATTAGCCGCAGCTGCCTCAAAGGCCTTGCCACTACTCCCTAATCGCCGAGAAGTTCAGCTGG
GACTACATTCTCATCATCTTCATTATCGAGGCCCTTAAACAGAAGGAAAAGCCGTACTCGTTCACTCCGTGATGGCG
GAGATGGGGTATCAGATGCCAAAAAGCACAGCCAGTCTGTTCGTCAAGGTCTTGCTGGCATTATCGACCTCCCAAGT
GAGGCCACCTTCCGAGGTGGATATTTCACATGGATCTGAGGATCCTAGGGGGCCAACAGATTCTTATCAAATGAATGG
GATTATCAATGAAACACATAATGGAAGACATGCCTCAGTGTCCAAGGTTGTTGAATTTGTGCCGCACTAGGTGGCA
AAACACCAATTCACAGTATATTAGTGGCCAACAATGGAATGGCAGCAGCAAAATTTATGAGGAGTGTCCGGACATGG
GCTAATGATACTTTTGGATCTGAGAAGCAATTCAACTCATAGCTATGCAACTCTTGGAGACATGAGGATAAATGC
AGAACACATTAGAATTGCTGACCAATTCGTAGAGGTGCCTGGTGGAACAAACAATAATAACTACGCCAATGTTCAAC
TCATAGTGGAGATGCACAAAAACTAGTTGTTTCTGCTGTTTGGCCTGGTTGCGGTCATGCTTCTGAGAATCCTCAA
CTGCCAGATGCATTGACCGCAAAAGGGATCGTTTTTCTTGGCCCACCTGCATCATCAATGAATGCTTTGGGAGATAA
GGTCGGCTCAGCTCTCATGGCTCAAGCAGCCGGGGTCCAACTCTTGCTGCGAGTCGATACATGTTGAAGTTCCAT
TAGACTGCTCCTTAGACGGCATACCTGACCACATGTATACAAAAGCTTGCCTTACTACCACAGAGGAAGCAGTTGCA
AGTTCTCAAGTGCTTCCTTATCCTGCCCATCATTAAGCCATCCTGGCGAGCTGCTCCTAAACGAATAACAAAGGTTCA
TAATGATGATGAGGTTAGACCGCTGTTAAGCAAGTACAAGGTGAAGTCCCTGGCTCCCCAATATTGTCATGACGC
TTGCATCCCAGATTCGGCATCTTGAAGTTCAGTTGCTTTGTGATCAATATGGTAATGTAGCAGCACTTCACAGTCGT
GATTGCAGTGTGCAACGGCGACACCAGAAGATTATTGAAGAAGCTCCAGTTACTGTTGCTCCTCGTGAGACAGTTAA
AGCACTTGAGCAGGCAGCAAGGAGGCTTGCTAAGGCTGTCGGTTATGTTGCTCCTGCTACTCTTCAGTATCTTTACA
GCATGGAAACTGGAGACTACTATTTTCGGAACTTAATCCCCGACTACAGGTTGAGCATCCAGTCACCGAGTGGATA
GCTGAAGTAAATCTGCCTGCAGCTCAAGTTGCTGTTTGAATGGGCATACCTCTTGGCAGATTCCAGAAATCAGACG
TTTCTATGGAATGCACTATGGAGGAGGGTATGACATTGGAGGAAAACAGCAGCTCTTGCTACACCATTTAATTTTG
ATGAAGTAGATTCTCAATGGCCAAAGGGCCATTGTGTAGCAGTTAGAATTACTAGTCAGGACCCAGATGATGGTTTC
AAACCTACTGGGGAAAGTGAAGGAGATAAGTTTAAAAGCAAGCCTAATGTTTGGGCCTACTTCTCAGTAAAGTC
TGGTGGAGGCATTCATGAATTGCTCATATCTCAGTTCGGACATGTTTTGCATATGGGCTCTCTAGATCAGCAGCAA
TAACAAACATGACTCTTGCATTAAAAGAGATTCAAATTCGTGGAGAAATTCATTCAAATGTTGATTACACAGTTGAC
CTCTTAAATGCTTCAGACTTTAGAGAAAACAAGATTCATACTGGTTGGCTCGACACCAGAATAGCTATGCGTGTTCA
AGCTGAGAGGCCCCATGGTATATTTCAGTGGTTGGAGGTGCTTTATATAAACAGTAACCACCAATGCAGCCACTG
TTTCTGAATATGTTAGTTATCTCACCAAGGGCCAGATTCCACCAAAGCATATATCCCTTGTCAATTCTACAGTTAAT
TTGAATATAGAAGCTAGCAAATACACAATTGAAACTGTAAGGACTGGACATGGTAGCTACAGGTTGAGAATGAATGA
TTCAACAGTTGAAGCCAATGTACAATCTTATCTGATGGTGGCCTCTTAATCCAGTTGGATGGAAACAGCCATGTAA
TTTATGCAGAAGAAGAAGCTGGTGGTACACGGCTTCAGATTGATGGAAAGACATGTTATTGCAGAATGACCATGAT
CCATCAAGTTATTAGCTGAGACACCCTGTTCTTCGTTCCTTGGTTGCTGATGGTGCTCAGTTTGATGCGGA
TGTACCATACGCGGAAGTTGAGGTTATGAAGATGTGCATGCCTCCTTGTCACCGCTTCTGGCTGCATTCATTGTA
TGATGTCTGAGGGCCAGGCATTGCAGGCTGGTGATCTTATAGCAAGGTTGGATCTTGATGACCCTTCTGCTGTGAAA
AGAGCTGAGCCATTTGATGGAAATTTCCACAAATGGAGCTCCCTGTTGCTGTCTCTAGTCAAGTACACAAAAGATA
TGCTGCAAGTTTGAATGCTGCTCGAATGGTCCTTGCAGGATATGAGCACAATATTAATAAGTCCTTCAAGATTTGG
TATGCTGCCTGGACTACCCTGAGCTTCCTTTCCTACAGTGGGATGAACTTATGTCTGTTCTGGCAACGAGGCTTCCA
AGAAATCTCAAGAGTGAGTTAGAGGATAAATACAAGGAATACAAGTTGAATTTTTACCATGGAAAAAACGAGGACTT
TTCCATCCAAGTTGCTAAGAGACATCATTGAGGAAATCTTTCTTATGGTTCAGAGAAGGAAAAGGCTACAAATGAGA
GGCTTGTTGAGCTTCTTATGAACCTACTGAAGTCATATGAGGGTGGGAGAGAGAGCCATGCACATTTGTTGTCAAG
TCTCTTTTCCGACGACTATCTTACAGTGCAAGACATTTTTAGTCATCGGCATCACTCTGACGTCATTGAAACATTGCG
GCATCAGCACAGTAAAGACCTGCAGAAGCTTGTAGACATTGTGTCTCACCAGGGTGTGAGCGAACAAAGCTAAGC
TTGTAACGGCACTTATGAAAACTGGTTATCCAAATCCTGGTGGTTACAGGGATCTGTTAGTTCGCTTTTCTTCC
CTCAATCATAAAAGATATTATAAGTTGGCCCTTAAACCAAGTGAACTTCTTGAAAAACCAAACTAAGTGAACTCCG
TGCAAGCGTTGCAAGAAGCCTTCGGATCGGGGATCCATAAGGGAGAAATCAGTATTAAGGATAACATGGAAGATT
TAGTCTCTGCCCCATTACCTGTTGAAGATGCTCTGATTCTTTGCTTGATTACAGTCATCGAACTGTTCAGCAGAAA
GTGATTGAGACATACATATCACGATTGTACCAGCCTCATCTTGTAAAGGATAGCATCCAAATGAAATTCAAGGAATC
TGGTGCTATTACTTTTTGGAATTTATGAAGGGCATGTTGATACTAGAAATGGACATGGGGCTATTATTGGTGGCA
AGCGATGGGGTGCCATGGTCGTTCTCAAATCACTTGAACTGCGTCAACAGCCATGTGGCTGCATTAAAGGATTCG
GCACAGTTCAACAGCTCTGAGGGCAACATGATGCACATTGCATTATTGAGTGCTGAAAATGAAAGTAATATAAGTGG
AATAAGCAGTGATGATCAAGCTCAACATAAGATGGAAAGCTTAGCAAGATACTGAAGGATACTAGCGTTGCAAGTG
ATCTCCAAGCTGCTGGTTTGAAGGTTATAAGTTGCATTGTTCAAAGAGATGAAGCTCGCATGCCAATGCGCCACACA
```

```
>AAP78897_Zea Mays
MSQLGLAAAASKALPLLPSRQSSAGTTFSSSSLSRPLNRRKSRTRSLRDGGDGVSDAKKHSQSVRQGLAGIID
LPSEAPSEVDISHGSEDPRGPTDSYQMNGIINRTHNGRHASVSKVVEFCAALGGKTPIHSILVANNGMAAAKFM
RSVRTWANDTFGSEKAIQLIAMATPEIMRINAEHIRIADQFVEVPGGTNNNNYANVQLIVEMAQKLGVSAVWPG
WGHASENPELPDALTAKGIVFLGPPASSMNALGDKVGSALIAQAAGVFTLAPSGSRVEVPLSCCLDAIPESMYR
KACVTTTSEAVASCQVVGYPAMIKASWSGGGKGIRKVHNDDEVRALFKQVQGEVPGSPIFVMRLASQSRRLEVQ
LLCDQYGNVAALHSRDCSVQRRHQKIIEEGPVTVAPRETVKALEQAARRLAKAVGYVGAATVEYLYSMETSDYY
FLELNPRLQVEHPVTENIAEVNLPAAQVAVGMGIPLWQIPEIRRFYGMDYGGYDIWRKTAALATPFNFDEVDS
QWEKGHCVAVRITSEDPDDGFKPTGGKVKEISFKSKPNVWAYFSVKSGGGIHEFADSQFGRVEAYGLSRSAAIT
NMTLALKEIQIRGEIHSNVDYTVDLLNASDFRENKIHTGWLDTRIANRVQAERPPWYISVVGGALYKTVTTNAA
TVSEYVSYLIKGQIPFKHISLVNSTVNLNIEGSKYTIETVRTGHSSYRLRMNDSTVEANVQSLCDGGLLMQLDG
NSHVIYASEEAGGTRLQIDGKTCLLQSDHDPSKLLARTPCKLLRFLVADGAHVDADVPYAEVEVMKMCNPLLSP
ASGVIHCMMSEGQALQRGDLIARLDLDDPSAVKRAEPFDGIFPQMELFVAVSSQVHKRYAASLNAARMVLAGYE
HNINEVVQDLVCCLDNPELPPLQWDELMSVLATRLPRNLKSELEDKYKEYKLNPYHGKNEDFPSKLLRDIIEEN
LSYGSEKEKATNERLVEPLMNLLKSYEGGRESHAKFVVKSLPEEYLTVEELFSDGIQSDVIETLRHQRSKDLQK
VVDIVLSHQGVRNKAKLVTALMEKLVYPNPGGYRDLLVRFSSLNHKRYYKLALKASELLEQTKLSELRASVARS
LSDLGMHKGRNSIKDNMEDLVSAFLPVEDALISLFDYSDRTVQQRVIETYISRLYQPHLVKDSIQMKFKESGAI
TFWEFYESHVDTRNGHGAIIGGKRWGAMVVLKSLESASTAIVAALKDSAQFNSSEGNMMHIALLSAENESNISG
ISSDDQAQHKNEKLSKILKDTSVASDLQAAGLKVISCIVQRDEARMPHRHTFLWLDDMSCYEEEQILRNVEPPL
STLLELDKLKVKGYNEMKYTPSRDRQWHIYTLRNTENPKMLHRVFFRTIVRQPNAGNAKFTSAQISDAEVGCPES
SLSFTSNSILRSLMTAIEELELHAIRTGHSHMYLCILKEQKLLDLIFFSGSTIVDVGQDEAPACSLLKSMALKI
HRLVGARMHRLSVCQWEVKLKLDCDGPASGTWRVVTTNVTGHTCTIDIYREVEEIESQKLVYHEATSSAGFLSG
VALNNPYQPLSVISLKRCSARMNRTTYCYDFPLAPETALQKSWQSNGSTVSEGNENSKSYVKATELVFAEKSGS
WGTPIIPMERPAGLHDIGMVAWIMEMSTPEFPNGRQIIVVANDITFRAGSFGPREDAPPETVTNLACERKLFLI
YLAANSGARIGIADEVKSCFRVGWSDEGSPERGFQYIYLTEEDYARISSSVIAHKLELDSGEIRNIIDSVVGKS
DGLGVENIHGSAAIASAYSRAYEETFTLTFVTGRTVGIGAYLARLGIRCIQRLDQPSILTGFSALNKLLGREVY
SSHMQLGGPFKIMATNGVVHITVPDDLEGVSNILRNLSYVFANIGGPLFITKFLDPPDRPVAYIFENTCDPRAAI
CGVDDSQGKWLGGMFDKDSFVETFPGWAKTVVTGRAKLGGIPVGVIAVETQYMXQIIPADPGQLDSHERSVPRA
GQVNFPDSATKTAQALLDFNREGLPLFTLANWRGFSGGQRDLFEGILQAGSTIVENLRTSNQPAFVYIPMAGEL
RGGAWVVVDSKINPDRIECYAERTAKGNVLEPQGLIEIKFRSEELQDKMGRLDPSLINILKAKLQDVNHGNGSLP
DIEGIRKSIEARTKQLLPLYTQIAIRPAELHDTSLRMAAKGVIKRVVDWSEESRSPFYKRLRRRIARDVLAKEIR
QIVGDKFTHQLAMELIREWYLASQATTGSTGWDDDDAFVAWKDSPENYKSHIQKLRAQKVSHSLSDLADSSSDI
QAFSQGLSTLLDKMDPSQRAKPVQRVKKVLU
```

FIGURE 9A

```
>AY312171_Zea_mays
ATGTCACAGCTTGGATTAGCCGCAGCTGCCTCAAAGGCCTTGCCACTACTCCCTAATCGCCAGAGAAGTTCAGCTGG
GACTACATTCTCATCATCTTCATTATCGAGGCCCTTAAACAGAAGGAAAAGCCGTACTCTTCACTCCGTGATGGCG
GAGATGGGTATCAGATGCCAAAAGGCACAGCCAGTCTGTTCGTCAAGGTCTTGCTGGCATTATCGACCTCCCAAGT
GAGGCACCTTCCGAAGTGGATATTTCACATGGATCTGAGGATCCTAGGGGGCCAACAGATTCTTATCAAATGAATGG
GATTATCAATGAAACACATAATGGAGGACATGCCTCAGTGTCCAAGGTTGTTCAATTTTGTGCGCCACTAGGTGGCA
AACACCAATTCACAGTATATTAGTTGGCCAACAATGGAATGGCAGCAGCAAAATTTTATGAGGAGTGTCCGGACATGG
GCTAATGATACTTTTGGATCTGAGAAGGCAATTCAACTCATAGCTATGGCAACTCCGGAAGACATGAGGATAAATGC
AGAACACATTAGAATTGCTGACCAATTCGTAGAGGTGCCTGGTGGAACAAACAATAATAACTACGCCAATGTTCAAC
TCATAGTGGAGATGGCACAAAACTAGGTGTTTCTGTTGGCCTGGTTGGGTCATGCTTCTGAGAATCCTGAA
CTGCCAGATGCATTGACCGCAAAGGCATCTTTTCTTGGCCCACCTGCATCATCAATGAATCCTTGGGAGATAA
GGTCGGCTCAGCTCTCATGCTCAAGCAGCCGGGTCCCAACTCTTGCTTGGAGTGGATCACATGTCAAGTTCTAT
TAGAGTGCTGCTTAGACGCGATACCTGAGGAGATGTATAGAAAAGCTTGCGTTACTACCACAGAGGAAGCAGTTGCA
AGTTGTCAAGTTGTTGGTTATCCTGCCATGATTAAGGCATCCTGGGGAGGTGTTGGTAAAGGAATAAGAAAGGTTCA
TAATGATCATGAGGTTACAGCGCCTGTTTAAGCAAGTACAAGGTGAAGTCCCTGGCTCCCAATATTTGTCATGAGGC
TTGCATCCCAGAGTCGGCATCTTCAACTTCACTTGCCTTCTTCATCAATATGCTAATCTAGCAGCACTTCACAGTCGT
GATTGCASTGTCCAACGGCGACACCAGAAGAATATTGAAGAAGGTCCAGTTACTGTTGCTCCTCGTGAGACAGTTAA
AGCACTTGAGCAGGCAGCAAGGAGGCTTGCTAAGGCTGTGGGTTATGTTGGTGCTGCTACTGTTGAGTATCTTTACA
GCATGGAAACTGGAGACTACTATTTCTGGAACTTAATCCCGACTACAGCTTGAGCATCCAGTCACCGAGTGGATA
GCTGAAGTAAATCTGCCTGCAGCTCAAGTTGCTGTTGGAATGGGCATACCTCTTGGCAGATTCAGAAATCAGACG
TTTCTATGGAATGGACTATGGAGGAGGGTATGACATTTGCAGGGAAAACAGCAGCTCTTGCTACACCATTAATTTTG
ATGAAGTAGATTCTCAATGGCCAAAGGGCCATTGTGTAGCAGTTAGAATTACTAGTGAGAGCCCAGATGATGGTTTC
AAACCTACTGGTGGGAAAGTGAAGGAGAAGTTTTTAAAAGCAAGCCTAATGTTTGGGCCTACTTCTCAGTAAAGTC
TGGTGGAGGCATTCATGAATTTGCTGATTCTCAGTTCGGACATGTTTTTGCATATGGGCTCTCTAGATCAGCAGCAA
TAACAAACATGACTCTTGCATTAAAAGAGATTCAAATCGTTGGAGAAATTCATTCAAATGTTGATTACACAGTTGAC
CTCTTAAATGCTTCAGACTTTAGAGAAAACAAGATTCATACTTGGTTGCCTCAACACCAAAATACCATTGCGTGTTCA
AGCTGAGAGGCCCCCATGGTATATTCAGTGGTTGGGGGTGCTTTATATAAAACAGTAACCACCAATCCAGCCACTG
TTTCTGAATATGTTAGTTATCTCACCAAGGGCCAGATTCCACCAAAGCATATATCCCTTGTCAATTCTACAGTTAAT
TTGAATATAGAAGGCAGCAAATACACAATTGAAACTGTAAGGACTGGACATGGTAGCTACAGGTTGAGAATAATGA
TTCAACAGTTGAAGCGAATGTACAATCTTTATGTGATGGTGGCTCTTAATGCAGTTGGATGGAAACAGCCATGTAA
TTTATGCAGAAGAAGAAGCTGGTGGTACACGGCTTCAGATTGATGGAAAGACATGTTTATTGCAGAATGACCATGAT
CCATCAAAGTTATTAGCTGAGACACCCTGCAAACTTCTTCCTTTCTTGGTTGCTGATGGTGCTCAGGTGATGCGGA
TGTACCATACGCGGAAGTTGAGGTTATGAAGATGTGCATGCCTCTCTTGTCGCCTGCTTCTGGTGTCATTCATTGTA
TGATGTCTGAGGGCAGGCATTGAGGCTGGTGATGTTATAGCAAGGTTGGATCTTCATAGCCCTTCTGCTGTGAAA
AGACGTGAGCCATTTGATGGAATATTTCCACAAATGGAGCTCCCTGCTGCTGCTGCTAGTCAGCTACACAAAAGATA
TGCTGCAAGTTTGAATGCTGCTCGAATGGTCCTTGCAGGGATATGAGCCACAATATTAATGAAGTCGTTCAAGATTTGG
TATGCTGCCTGGACAACCCTGAGCTTCCTTTCCTACAGTGGGATGAACTTATGTCTGTTCTAGCAACGAGGCTTCCA
AGAAATCTCAAGAGTCAGTTAGAGGATAAATACAAGGAATACAAGTTGAATTTTTACCATGGAAAAACGAGGACTT
TCCATCCAAGTTGCTAACAGACATCATTGAGCGAAAATCTTTCTTATCGTTCAGAGAAGGAAAAGGCTACAAATGAGA
GGCTTGTTGAGCCTCTTATGAACCTACTGAAGTCATATGAGGGTGGGAGAGAGAGCCATGCACATTTCTTCTCAAG
TCTCTTTTCGAGGAGTATCTTACAGTGGAAGAACTTTTAGTGATGGCATTCAGTCTGACGTGATTGAAACATTGCG
GCATCAGCATAGTAAAGACCTGCAGAGGTGTAGACATTGTGTTGTTTACTAGGGTGTGAGGAACAAAGCTAAGC
TTGTAACGGCACTTATGGAAAAGCTGCTTTATCCAAATCCTGGTGCTTACACGGGATCTGTTAGTTCGGTTTTCTTCC
CTCAATCATAAAAGATATTATAAGTTGGCCCTTAAAGCAGTGGACTAAGCCTTCTTGAACAAACCAAACTAAGTGAACTCCG
TGCAAGCGTTGCAAGAAGCCTTTCGGATCTGGGGATGCATAAGGGAGAAATGAGTATTAAGGATAACATGGAAGATT
TAGTCTCTGCCCCGTTACCTGTTGAAGATGCTCTGATTTCTTTGTTTGATTACAGTGATCGACTGTTCAGCAGAAA
GTGATTGAGACATACATATCACGGATTGTACCAGCCTCATCTTGTAAAGGATAGCATCCAAATGAAATTCAAGGAATC
TGGTGCTATTACTTTTTGGGAATTTATGAAGGGCATGTTGATACTAGAAATGGACATGGGGCTATTATTGGTGGCA
AGCGATGGGTGCCATGGTCGTTCTCAAATCACTTGAATCTGCGTCAACAGCCATTGTGGCTGCATTAAAGGATTCG
GCACAGTTCAACAGCTCTGAGGCAACATGATGCACATTGCATTATTGATGCTGAAAATGAAAGTAATATAAGTGG
AATAGTGATGATCAAGCTCAACATAACATGGAAAAGCTTAGCAAGATACTCAAGGATACTAGCCTTGCAAGTGATC
TCCAAGCTGCTGGTTTGAAGGTTATAAGTTGCATTGTTCAAAGAGAATGAAGCTCGCATGCCAATGCGCCACACATTC
CTCTGGTTGGATGACAACAGTTGTTATGAAGAAGAGCAGATTCTCCGGCATGTGGAGCCTCCCTCTCTATACTTCT
TGAATTGGATAAGTTGAAGGTGAAAGGATACAATGAAATGAAGTATACTCCTTCGCGTGACTGCCAATGGCATATCT
ACACACTAAGAAATACTCGAAAACCCCAAAATGTTGCATAGCGTGTTTTCCGAACTATTGTCAGGCAACCCAATGCA
```

```
>AAP78896_Zea mays
MSQLGLAAAASKALPLLPNRQRSSAGTFFSSSSLSRPLNRRKSRTRSLRDGGDGVSDAKKHSQSVRQGLAGIID
LPSRAPSEVDISHGSEDPRGPTDSYQMNGTINETHNGRSASVSKVVEFCAALGGRTPTHSILVANNGMAAAKFM
RSVRTWANDTFYGSEKAIQLIAMATPEDMRINAEHIRIADQFVEVPGGTNNNNYARVQLIVEMAQKLGVSAVWPG
WGHASENPELFDALTAKGIVFLGPPASSMNALGDKVGSALIAQAAGVPTLAWSGSHVEVELECCLDATPEEMYR
KACVTTFEEAVASCQVVGYPAMIKASWGGGGKGIRKVENDDEVRALFKQVQGEVPGSPIFVMRLASQSRHLEVQ
LLCDQYGNVAALHSRDCSVQRRHQKIIEEGPVTVAPRETVKALEQAARRLAKAVGYVGAATVEYILYSMETGDYY
FLELNPRLQVEHPVTEWIAEVNLPAAQVAVGMGIPLWQIPEIRRFYGMDYGGGYDIWRKIAALATPFNFDEVSS
QWPKGRCVAVRITSEDPDDGFKPTGGKVKEISFKSKPNVWAYFSVKSGGIHSFADSQFGHVFAYGLSRSAAIT
NMTIAIKEIQIRGEIHSNVDYFVDLLMASDFRRNKIHTGWLDTRIAMRVQAERPPWYISVVGGALYKTVTTHAA
TVSEYVSYLTEGQIPPKHISLVNSTVNLNIEGSKYTIETVRTGHGSYRLPMNDSTVEANVQSLCDGGLLMQLDG
NSHVIYAEEEAGGTRLQIDGKTCILQNDHDPSKLLAETPCKLLRFLVADGAHVDADVPYAEVEVMKNCMPLLSF
ASGVIHCMMSEGQALQAGDLIARLDLDDPSAVKRAEPFDGIFPQMELFVAVSSQVHKRYAASLNAARMVLAGYE
HNINEVVQDLVCCLINPELPFLQHELMSVLRTRLPRNLKSELEDKYKEYKLNFYHGKNEDFPSKILRDIIEEN
LSYGSEKEKATNERLVEPLMNLLKSYEGGRESRAHPVVKSLFEEYLTVEELFSDGIQSDVISTLRHQHSKDLQK
VVDIVLSHQGVRNKAKLVTAIMEKLVYPNPGGYRDLLVRFSSINHKRYYKIALKASELLEQTKLSELRASVARS
LSDLGMHKGEMSIKDNMEDLVSAPLPVEDALISLFDYSDRTVQQKVIETYISRLYQPHLVKDSIQMKFKESGAI
TFWEFYEGHVDTRNGHGAIIGGKRWGAMVVLKSLESASTAIVAALKDSAQFNSSEGNMMHIALLSAENESNISG
ISDDQAQHKMEKLSKILKDTSVASDLQAAGLFVISCIVQRDEARMPNRHTFLNLDDKSCYEEEQIIRHVEPSLS
TLLELDKLKVKGYNEMKYTPSRDRQWHIYTLRNTENPKMLSRVFFRTIVRQPNAGNKFTSAQISDAEVGCPEES
LSFTSNSILRSLMTAIEELELHAIRTGHSHMYLCILKEQKLLDLIPFSGSTIVDVGQDEATACSLLKSHALKIE
ELVGARMEHLSVCQNEVKLKLDCDGPASGTWRVVTENVTGHTCTIDIYREVEEIESQKLVYESATSSAGPLRGV
ALNKPYQPLSVIDLKRCSARNNRTTYCYDFFLAFETALQKSWQTNGSTVSEGNENSKSYVKATELVFAEKHGSW
GTFIIPMERPAGLNDIGMVANIMEMSFPEFFNGRQIIVVANDITFRAGSFGPREDAFFETVTNLACERKLPLIY
LAANSGARIGIADEVKSCFRVGWSDEGSPERGFQYIYLTEEDYARISSSVIASKLELDSGEIRNIIDSVVGRED
GLGVENIHGSAAIASAYSRAYEETFTLTFVTGRTVGIGAYLARLGTRCIQRLSQPIILTSFSALNKLLGRSVYS
SRMQLGGPKIMATNGVELTVPDDLEGVSNILRWLSYVPANIGGSPLPITKPLDEPDRPVAYIPENTCDPRAALC
GVDDSQGKWLGGMFDKDSFVETFEGWAKTVVTGRAKLGGIPVGVIAVETQTMMQIIPADFGQLDSHERSVPRAG
QVWFPDSATKTAQALLDFNREGLFLFILANWRGFSGGQRDLFEGILQAGSTIVENLRTYNQPAFVYIPMAGELR
GGAWVVVDSKINPDRIECYAERTAKGNVLSPQGLTEIKFRSEELQDMGRLDPELINLKAKLQDVNHGNGSLPD
IEGIRKSIEARTNQLLPLYTQIAIRFAELHDTSLRMAAKGVIKMVVDWEESRSFFYKRLRRRIAEDVLAKEIRQ
IVGDKFTHQLAMELIKEWYIASQATTGSTGWHDDDAFVAWKDSPENYKGHIQKLRAQKVSHSLSDLADSSSDLQ
AFSQGLSTLLDKNDPSQRAKFVQEVKKVLD
```

FIGURE 10A

>AF029895 Triticum aestivum
ATGCGATCCACACATTTGCCCAGTCTCGGCCTTAATGCCTGGACAACACCATGGCTATCCACTATTCGCCCGGTAAA
TTCAGCCGGTGCTGCATTCCAACCATCTGCCCCTTCTAGAACCTCCAAGAAGAAAAGTGGTGGTGTTCAGTCATTAA
GGGATGGAGGCGATGGAGGCGTGTCAGACCCTAACCAGTCTATTCGCCAAGGTCTTGCCGGCATCATTGACCTCCCA
AAGGAGGGCACATCAGCTCCCGGAAGTGGGATATATTTCACATGGGTCCGGAGAACCCAGGGGCTCCTACCAAATGAATGG
CATACTGAATGAACGACATAATGGGAGGCATGCTTCGCTGTCTAAGGTTGTCGAATTTTGTATGGCATTGGGCGGCA
AAACACCAATTCACAGTGTATTAGTTGCGAACAATGGAATGGCAGCAGCTAAGTTCATGCGGAGTGTCCGACATGG
GCTAATGAAACATTTGGGTCAGAGAAGGCAATTCAGTTGATAGCTATGGCTACTCCAGAAGACATGAGGATAAATGC
AGAGCACATTAGAATTGCTGATCAATTTGTTGAAGTACCCGTGGAACAAACAATAACAACTATGTAATGTCCTAC
TCATAGTGCAGATACCAGTGACAACCGGTGTTCTGCTCTTTGCCCTCGTTGCGGCCATGCATCGAGAATCCTGAA
CTTCCAGATGCACTAAATGCAAACGGAATTGTTTTCTTGGGGCACCATCATCATCATGAACGCACTAGGTGACAA
GGTTGGTTCAGCTCTCATTGCTGAAGCAGCAGGGGTTCCGACTCTTCCTTGGAGTGGATCACAGGTGGAAATTCCAT
TAGAAGTTGTTGGACTCGATACCCGCGGAGATGTATAGGAAAGCTGCGTTAGTACTACGGAGGAAGCACTTCCG
AGTTGTCAGATCATTGGGTATCCCCCATGATTAAAGCATCATCGCCTCCTGCCTAAACGGATCCCGAAAGCTTAA
TAATGACGATGATGTCAGAGCACTGTTTAAGCAAGTGCAAGGTGAAGTTCCTGGCTCCCCAATATTTATCATGAGAC
TTGCATCTCAAGTCTGACATCTTGAAGTTCAGTTGCTTTGTGATCAATATGGCAATGTAGCTGCCGCTTCACAGTCGT
GACTGCAGTGTGCAACGGCGACACCAAAAGATTAGTTGAGGAACGACCAGTTGCTGTTGCTCTGGCACATAGTCAA
AGAGCTAGAGCAGCCAGCAAGCGAGCCTTGCTAAGGCTGTGGGTTATGTTGGTGCTGCTACTGTTGAATATCTCTACA
GCATGGAGACTGGTGAATACTATTTTCTGGAACTTAATGCCACGGTTGCAGGTTGAGCCATCCAGTCACCGAGTGGATA
GCTGAAGTAAACTTGCCTGCAGCTCAAGTTGCAGTTGGAATGGGTATACCCCTTTGGCAGGTTCCAGAGATCAGACG
TTTCTATGTAATGGACAATGGAGCTACGCTATGACATTTGGAGGAAAACAGCAGCTCTTGCTACTCCATTTAACTTCG
ATGAAGTGGATTCTCAATGGCCAAAGGGTCATTGTGTAGCAGTTAGGATAACCAGTGAGGGATCCAGATGAGGGATTC
AAGCCTACCCGGTGGAAAAGTAAAGCAGATCATTTGTAAAAGCAGCGCAAATGTTTGGGCCTATTTGTGTTAACTC
CGGTGGAGGCATTCATGAATTTGCTGATTCTCAGTTTGGACATGTTTTTGCATATGGAGTGTCTAGAGCAGCAGCAA
TAACCAACATGTCTCTTGCGCTAAAGAGATTCAAATTCGTGGAGAAATTCATTCAAATGTTGATTACACAGTTGAT
CTCTTGAATGCCTCAGACTTCAAAGAAAACAGGATTCATACTGGCTGGCTGGATAACAGAATAGCAATGCGAGTCCA
AGCTGACAGACCTCCGTGGTATATTTCAGTGGTTGGAGGCAGCTCTATATAAACAATAACCAGCAACACGACACTG
TTTCTGAATATGTTAGCTATCTCGTCAAGGGTCAGATTCCACCGAAGCATATATCCCTTGTCCATTCAACTGTTTCT
TTCAATATGACAAAAGCGAAATATACAATTGAAACTATAAGCAGCCCACACCCTACCTACAGATTGCGAATGAATGG
ATCAGTTATTGAAGCAAATGTCCAAACATTATGTGATGGTGGACTTTTAATGCAGTTGGATGGAAACAGCCATGTAA
TTATGCTGAAGAACAGCCGGTTCTACACGCCTTCTAATTGATGCAAAGACATGCTTCTTACAGAATGATCACGAT
CCTTCAAGGTTATTAGCTGAGACACCGTGCCAAACTTCTTCGTTCGTTGGTTCCCGGATGGTCCTCATGTTGAAGCTGA
TGTACCATATGCCGAAGTTGAGGTATGAAGATGTGCATGCCCCTCTTGTCACCTGCTGCTGGTGTCATAATGTTT
TGTTGTCTGAGGGCCAGCCTATGCAGGCTGGTGATCTTATAGCAAGACTTGATCTTGATGACCCTTCTGCTGTGAAG
AGAGCTGAGCCATTTAACGGATCTTTCCAGAAATGAGCCTTCCTATTGCTGCTTCTGGCCAAGTTCACAAAAGATG
TGCCACAAGCTTGAATGCTGCTGGGATGGTCCTTGCAGGATATGATCACCGGATCAACAAAGTTGTACAAGATCTGG
TATCCTGTCTAGATGCTCCTGAGCTTCCTTTCCTACAATGGAAGAGCTTATGTCTGTTTAGCAACTAGACTTCCA
AGGCTTCTTAAGACCGAGTTGGAGGGTAAATACAGTCAATATAAGTTAAATGTTGGCCATGGGAGAGCAAGGATTT
CCCTTCCAAGATGCTAAGAGACAGAATCGAGGCAAAATCTTGCACATGGTTCTCAGAAGCAAATTGCTACAAATGAGA
GGCTTGTTGAGCCTCTTATGAGCCTACTGAAGTCATATGAGGGTGGCAGAGAAAGCCATGCACACTTTATTGTGAAG
TGCCTTTTCGAGCGACTATCTCGGGTTGAGGAACTATTCAGTGATGGCATTCAGTCTGATGTGATTGAACGCCTGCA
CCAACAACATAGTAAAGATCTCCAGAAGGTTGTAGACATTTGTGTTGTCTCACCCAGGTGTGAAGAACAAACTAAGC
TGATACTAACACTCATGGAGAAACTGGTCTATCCAAACCCTGCTGTCTACAACGGATCAGTTGACTCGCTTTCCTCC
CTCAATGACAAAAGATATTATAAGTTGGCCCTTAAAGCTAGCGAGCTTCTTGAACAAACCAAGCTTAGTGAGCTCCG
CACAAGCATTGCAAGGAGCCTTCAGAGACTTGAGATCTTTACTGAAGAAAGGACGGCCATTAGTGAGATCATGGCAG
ATTAGTGACTGCCCACTGCCAGTTGAAGATGCACTGGTTTCTTGTTTGATTGTAGTGATCAAACTCTTCAGCAG
AGCCTGATCCAGACCTACATATCCGATTATACCAGCCCTCATCTTCTCAAGGATAGTATCCAGCTGAAATATCAGGA
ATCTGGTGTTATTCCTTTATGGGAATTCGCTGAAGCGCATTCAGAGAAGAGATTGGTGCTATGGTTATTGTGAAGT
CGTTAGAATCTGTATCAGCAGCGATGGAGCTGCACTAAAGGGTACATCACGCTATGCAAGCTCTGAGGGTAACATA
ATGCATATTGCTTTATTGGGTGCTGATAATCAAATGCATGGAACTGAAGACAGTGGTGATAACGATCAAGCTCAAGT
CAGGATAGACAAACTTTCTGCGACACTGGAACAAAATACTGTCACAGCTGATCTCCGTGCTGCTGGTGTGAAGGTTA

FIGURE 10A (continued)

```
TTACTTGCATTCTTCAAAGGGATGCACCACTCATGCCTATGCGCCATACCTCCTCTTGTCGGATGAAAAGCTTTGT
TATGAGGAAGAGCCGGTTCTCCGGCATGTGGAGCCTCCTCTTTCTGCTCTTCTTGAGTTGGGTAAGTTGAAAGTGAA
AGGATACAATGAGGTGAAGTATACACCGTCACCTGATGGTCAGTGGAACATATACACACTTAGAAATACAGAGAACC
CCAAAATGTTGCACAGGGTGTTTTTCCGAACTCTTGTCAGGCAACCCGGTGCTTCCAACAAATTCACATCAGGCAAC
ATCAGTCATGTTCAACTGCCAGCAGCTGAGGAAATCTCTTTCATTTACATCGAGCAGCATATTAAGATGGCTGATGAC
TGCTATAGAAGAGTTGGAGCTTCACGCCGATTAGGACAGGTCACTCTCATATGTTTTTGTGCATATTGAAAGAGCAAA
AGCTTCTTGATCTTGTTCCCGTTTCAGGGAACAAAGTTGTGGATATTGGCCAAGATGAAGCTACTGCATGCTTGCTT
CTGAAAGAAATGGCTCTACAGATACATGAACTTGTGGGTGCAAGGATGCATCATCTTTCTGTATGCCAATGGCAGTT
GAAACTTAAGTTGTACAGCCGATGGCCTGCCAGTGGTACCTGTAGAGTTGTAACACCCAATGTTACTAGTCACACCT
GCACTGTGGATATCTACCCTGAGGTCGAAGATACAGAATCACAGAAACTAGTCTACCACTCTGCCTCCATCGTCATCT
GGTCCTTTGCATGGCGTTGCACTGAATACTCCATATCAGCCTTTGAGTGTTATTGATCTGAAACGTTGCTCCGCTAG
AAATAACAGAACTACATACTGCTATGATTTTCCGTTGGCATTTGAAACTGCAGTGCAGAAGTCATGGTCTAACATTT
CTAGTCACACTAACCCATGTTATCTTAAAGCGACCGACCTGGTCTTTCCTCACAAGAACGGGTCATGGGCACTGCT
GTAATTCCTATGGAGCGTCCTGCTGGGCTCAATGACATTGGTATGGTAGCTTGGATCTTGGACATGTCCACTCCTGA
ATATCCCAATGGCAGGCAGATTGTTGTCATCGCAAATGATATTACTTTTAGAGCTGGATCGTTTGGTCCAAGGGAAG
ATGCATTTTTGAAACTGTTACCAACCTAGCTTGTGAGACGAAGCTTCCTCTCATCTACTTGCAGCAAACTCTGGT
GCTCGGATCGGCATAGCACATGAAGTAAAATCTTGCTTCCGTGTTGGATGGTCTGATCATGCCAGCCCTGAACGTGG
GTTTCAATATATTTATCTGACTGAAGAAGACCATGCTCCTATTAGCGGTTCGTTATAGCGCACAACATGCACCTTG
ATAATGGTGAAATTAGGTGGGTTATTGATTCTGTTGTAGGGAAGGAGGATGGGGTAGGTGTGGAGAACATACATGGA
AGTGCTCTATTGCCAGTGCCTATTCTAGGGCCTATGAGGAGACATTTACGCTTACATTTGTGACTGGAAGGACTGT
TGGAATAGGAGCATATCTTGCTCGACTTGGCATACGGTGCATACAGCGTACTGACCAGCCCATTATCCTAACTGGGT
TCTCTGCCTTGAACAAGCTTCTTGGCCGGGAAGTTACAGCTCCCACATGCAGTTGGGTGGCCCAAAATTATGCCG
ACAAACGGTGTTGTCCATCTGACAGTTTCAGATGACCTTGAAGGTGTATCTAATATATTGAGGTGGCTCAGCTATGT
TCCTGCCAACATTGGTGGACCTCTTCCTATTACAAAATCTTTGGACCCACCTGACAGACCCGTTGCTTACATCCTG
AGAATACATGCGATCCTCCTGCTGCCATCAGTGGCATTGATGATAGCCAAGGCAAATGGTTCCCGGGATGTTCGAC
AAAGACAGTTTGGTGGAGACATTTGAAGGATGGCCAAGTCAGTTGTTACTGGCAGAGCGAAACTCGGAGGGATTCC
GGTGGGTGTTATAGCTGTGGGAGACACAGGACTATGATGCAGTCCATCCCTGCTGATCCAGCGCCAGCTTGATTCCCATG
AGCGATCTGTTCCTCGTGCTTGGGCAAGTCTGGTTTCCAGATTCAGCTACTAAGACAGCGCAGGCAAGGCTGGACTTG
AACCGTGAAGCATTACCTCTGTTCATGCTTCCTAACTGCAGAGCCTTCTCTCGTGGCAAAGACATCTTTTCGAACG
AATCCTTCAGGCTGGGTCAACAATTGTTGAGAACCTTAGGACATACAATCAGCCTGGCCTTTGTATATATCCCGAAGG
CTGCAGAGCTACGGGAGGGCCTTGCGTCCTGATTCATACCAACATAAATCCAGATGCCATTCAGTTCTATGCTGAG
AGGACTGCAAACGGCAATGTTCTGCCAACCTCAAGGCTTGATGAGATCAACTTCAGGTCAGGAACTCCAAGACTG
CATCCCTAGCCTTCATCCACAATTCATAAATCTGAAGGCAAAGCTCCACCGACTAAACCATGAAAATGCACGTCTAC
CTGAGTCAGAATCCCTTCAGAAGAGCATAGAAGCCCGGAAGAAACAGTTGTTGCCTTTGTATACTCAAATTGCGGTA
CGGTTCGCTGAATTGCATGACACTTCCCTTAGAATGGCTGCTAAGGGTGTGATTAAGAAGCTTGTAGACTGGGAAGA
TTCTAGGTGGTTCTTCTACAAGAGGATTACGGAGGAGGATATCCGAGGGATGTTCTTGCGAAGCGAAATTAGAGGTGTAA
GTGGCAAGCAGTTTTCTCACCAATCGGCAATCGAGCTGATCCAGAAATCGTACTTGCCCTCTAACGGAGCTGAAACA
GGAAGCACTGAATGGGATGATGACGATGCTTTTGTTGCCTGGACGGAAAACCCTGAAAACTACCAGGAGTATATCAA
AGAACTCAGGCTCAAAGGGTATCTCAGTTGCTCTCAGATGTTGCAGACTCCAGTCCAGATCTACAAGCCTTGCCAC
AGGGTCTTTCTATGCTATTAGAGAAGATGGATCCCTCAAGGAGAGCACAGTTTGTTGAGGAAGTCAAGAAAGTCCTT
AAATGA
```

FIGURE 10B

```
>AAC39330_Triticum_aestivum
MGSTHLPIVGLNASTTPSLSTIRPVNSAGAAFQPSAPSRTSKKKSRRVQSLRDGGDGGVSDPNQSIRQGLAGII
DLPKEGTSAPEVDISHGSEEPRGSYQMNGILNEARNGRHASLSKVVEFCMALGGKTPIHSVLVANNGMAAAKEM
RSVRTWANETFGSEKAIQLIAMATPELMRINAEHIRIADQFVEVPGGTNNNNYARVQLIVEIAVRTGVSAVWPG
WGHASENPELPDALNANGIVPLGPPSSSMNALGDKVGSALIAQAAGVPTLPWSGSQVEIPLEVCLDSIPAEMYR
KACVSTTEEALASCQMIGYSAMIKASWGGGKGIRKVNNDDDVRALFKQVQGEVPGSPIFIMRLASQSRHLEVQ
LLCDQYGNVAALHSRDCSVQRRHQKTIESGPVTVAPRETVKELEQAARRLAKAVGYVGAATVEYLYSMETGEYY
FLELNPRLQVEHPVTEWIAEVNLPAAQVAVGMGIPLWQVPEIRRFYGMDNGGGYDIWRKTAALATPFNFDEVDS
QWPKGHCVAVRIFSEDPGDGFKPTGGKVKEISFKSKPNVWAYFSVKSGGGIRRFADSQFGHVFAYGVSRAAAIT
NMSLALKEIQTRGEIHSNVDYTVDLLNASDFKENRIHTGWLDNRIAMRVQAERPPWYISVVGGALYKTITSNTD
TVSEYVSYLVKGQIPPKHISLVISTVSLNIEESKYTIFTIRSGQGSYRLRMNGSVIEANVQTLCDGGLLMQLDG
NSHVIYAEEEAGGTRLLIDGKTCLLQNDHDPSRLLAETPCKLLRFLVADGARVEADVEVAEVEVMKMCMPLLSP
RAGVINVLLSEGQFMQAGDLIARLDLDDPSAVKRAEPFNGSFPEMSLPIAASGQVHKRCATSLNAARMVLAGYD
HPINKVVQDLVSCLDAPELPFLQWEELMSVLATRLPRLLKSELEGKYSEYKINVGHGKSKDFPSKMLREITERN
LAHGSEKRIATNERLVEPIMSLLKSYEGGRESHAHFIVKSLFEDYLSVEELPSDGIQSDVIERLRQQHSKDLQK
VVDIVLSHQGVRNKTKLILTIMEKLVYSNPAVYKDQLTRFSSLNSKRYYKLALKASELLEQTKLSELRTSIARS
LSELEMFTEERTAISEIMGDLVTAPLPVEDALVSLFDCSRQTLQQRVIETYISRLYQFHLVKDSIQLKYQESGV
IALWEFAEAHSEKRLGAMVIVKSLESVSAAIGAALKGTSRYASSEGNIMRIALLGADNQMHGTEDSGDNDQAQV
RIDKLSATLEQNTVTADLRAAGVKVISCIVQRDGALMPNREFPLLSDEKLCYEEEPVLRHVEPPLSALLELGKL
KVKGYNEVKYTPSRDRQWHIYTLRNTENPRMLHRVFFRTLVRQPGASNKFTSGNISDVEVGGAERSLSFTSSSI
LRSLMTAIRRLELHAIRTGHSHMFLCILKEQRLLDLVPVSGNKVVDIGQDEATACLLIKSMAIQIHELVGARMH
HLSVCQNEVKLKLDSDGPASGTWRVVTTNVTSHTCTVDIYREVEDTESQKLVYHSAPSESGFLHGVALNTPYQP
LSVIDLKRCSARNNRPTYCYDFFLAFETAVQKSWSNISSDTNRCYVKATELVFARKNGSWGTPVIPMERPAGLN
DIGMVAWILDMSTPEYSNGRQIVVIANDITPRAGSEGPREDAFFETVTNLACERMLPLIYLAANSGARIGIADE
VKSCFRVGWSDDGSPERGFQYIYLTEEDHARISASVIAHKMQLDNGETRWVIDSVVGKEDGLGVENIHGSAAIA
SAYSRAYEETFTLTFVTGRTVGIGAYLARLGIRCIQRTDQPIILTGFSALNKLLGREVYSSHMQLGGPKIMAYN
GVVSLTVSDDLEGVSRILRWLSYVPANIGGPLPIFKSLDPPDRPVAYIPENTCDPRAAISGIDDSQGKWLGGMF
DKDSFVETFEGWAKSVVTGRAMLGGIPVGVIAVEFQTMMQLIPADPGQLDSHERSVPRAGQVWFFDSAIKTAQA
MLDFNREGLPLFILANWRGFSGGQRDLFEGILQAGSTIVENLRTYNQPAFVYIFKAAELRGGAWVIDSKINPD
RIEFYAERTAKGNVLEPQGLIEIKFRSEELQECMGRLDPELINLKAKLQGVKHERGSLPESESLQKSIEARKKQ
LLPLYTQIAVRFAELRDTSLRMAAKGVIKKVVDWEDSRSFYYKRLRRRISEDVLAKEIRGVSGKCFSHQSAIEL
IQHWYLASKGAETGSTEWDDDDAFVAWRENPENYQEYIKELRAQRVSQLLSDVADSSPDLSALPQGLSMLLEKM
DPSRRAQFVEEVKKVLK
```

FIGURE 11A

```
>AY219174_Setaria italica (foxtail millet)
ATGTCCAACTTGGATTAGCTGCAGCTGCCTCAAAGGCGCTGCCACTACTTCCTAATCGCCATACAAACTTCAGCTGG
AACTACATTCCACATCACCTGTATCATCGCGGCCCTCAAACCGAAGGAAAAAGCCGCACTCGTTCACTTCGTCATGGAG
GAGATGGGTATCATATGCCAAAAAGCACAACCAGTCTGTCCGTCAAGGTCTTGCTGGCATCATGGACCTCCCAAAT
GAGGCAACATCGGAAGTGGATATTTCTCATGGATCCGAGGATCCCAGGGGGCCAACCGATTCATATCAAATGAATGG
GATTGTAAGTGAAGCACATAATGCCAGACATGCCTCACTGTCCAAGGTTGTTGAATTTTGTGCGGCGCTAGGTGGCA
AAACACCAATCACAGTATACTAGTGGCCAACAATGGAATGGCAGCAGCAAAGTTCATGAGCAGTGTCCGGACATGG
GCTAATGATACTTTGGATCGGAGAAGGCCATTCACCTCATAGCTATGGCAACTCCAGAAGACATGAGGATAAATGC
AGAACACATTAGAATTGCTGATCAATTTGTGGAGCTGCCTGGTGGAACAAACAATAAGAACTATGCAAATGTTCAAC
TCATAGTGGAGGTAGCAGAAAGAATAGCGTGTTTCTCCTGTTTGCCCTGCTTGGGGTCATGCTTCTCAGAATCCTGAA
CTTCCAGATGCATTCACTGGCAAAAGGAGTTGTTTTGCTTGGGCCCACATGCGGCATCAATGAATGCATTGGCAGATAA
GGTGCGTTCAGCTCATTGCTCAAGCCGTTGGGGTCCCGACCCTTTCGTGGAGTGGATCACATGTTGAAGTTCCAT
TAGAGTGCTGCTTAGATGCGATACCTGAGGAAATGTATACAAAAGCTTGTGTTACTACCACAGAAGAAGCTGTTGCG
AGTTGTCAGGTGGTTGGTTATCCTGCCATGATTAAGGCATCCTGGGGAGGTGGTCGTAAAGCAATAAGAAAGGTTCA
TAATGACGATGACGGTAGAGGCACTGTTTAAGCAAGTACAAGGTGAAGTCCCTGGCTCCCCAATATTTAGCATGAGGC
TTGCATCCAGAGTCGTCATCTTGAGGTTCAGTTGCTTTGTGATCAATATGGCAATGTGGCAGCACTTCACAGTCGT
GATTGCAGTGTGCAACGGCGACACCAAAAGATTATTGAGGAAGCCCCAGTTACTGTTGCTCCTGGTCAGACAGTTAA
AGCGCTTGAGCAGGCAGCAAGGAGCCTTGCTAAGGCTGTGGTTAGTTGGTGCTGCTACTGTTCAATACCTTTACA
GCATGGAGACTGGGGAATACTATTTTCTGGAGCTTAATCCCAGATTACAGGTCAGCATCCAGTCACTGAGTGGATT
GTTGAAGTAAATTCTTGGAAATGAACAAGTAGCATTGAGAATGGGATACCTCTTTGCCAGATTCCAGAAATCAGCCG
TTCCATGCAATGCACTATGCAGCCAGGCATATGACATTTGGAGGAAAACAGCACAGTCTTGCCACACCATTTAATTTTG
ATGAAGTAGATTCTCAATGGCCAAAGGGCCATTGTGTAGCAGTTAGAATTACTAGCGAGGATCCAGATGATGCTTTC
AAACCTACTGGTGGGAAAGTGAAGGAGATAAGTTTTAAAAGCAAGCCTAATGTTTGGGCCTACTTCTCAGTAAAGTC
TGGTGGAGGCATTCATGAATTTGTTGATTCTCAGTTTGCGCATGTTTTTGCATATGGCCTCTAGATCAGCAGCAA
TAACGAACATGGCTCTTGCGTAAAACAGATTCAAATTCCTCGAGAAATTCATTCAAATCTTCATTACACAGTTGAT
CTCTTAAATGCTTCAGACTTCAGAGAAAATAAGATTCATACTGGCTGGCTTGATACCAGAATAGCTATGCGTGTTCA
AGCTGAGAGGCCCCATGGTATATTCCAGTGGTTGGAGGAGCTCTATATAAAACATAACTGCCAATGTAGCCACTG
TTTCTGATTATGTCAGTTATGTCACCAGGCCAGATTCACCAAAATATATCCCTTGTCAGTTCAACAGTTAAT
CTGAATATCGAAGGCAGTGAAATACACAGTTGAAACGTAAGGACTGGACATGGTAGCTACAGATTACGAATGAATGA
TTCAGCAATGGAAGGCGAATGTACAATGTTATGTGATGGAGGCCCTTAATGCACTTGGATGCAAATAGCCATGGAA
TTTACGCGGAAGAAGAAGCTGGTGGTACACGACTTCTGATTGATGGAAAGACATGCTTGTTACAGAATGATCATGAT
GCATCAAAGTTATTAGCTGAGACACCCTGCAAACTTCTTCGGTTCTTGGTTGCTGATGGTGCCCATGTTGATGCTGA
TGTACCATATGCCGAAGTTGAGGTTATGAAAATGTGCATGCCTCTCTTGTCGCCTGCTTCTGGTGTCATTCATGTTA
TGATGTCTGAGGGCCAGGCATTGCAGGCTGGTGATCTTATAGCAACGCTCGATCTTGATCACCTTCTGCTGTGAAA
AGAGCTGAACCATTTCATGGAATATTTCCACAAATGGACCTTCCTGTTGCTGCCTCTAGCCAAGTACACAAAGATA
TGCTGCAAGTTGGAATGCTGCTCAATGGTCCTTGCAGGATACGAGCATAATATCAATGAAGTTGTACAAGATTTGG
TATGCTGCCTGGATGATCCGGCTTCCTCTACAGTGGATGAACTTATGTCAGTTCTAGCAACTAGGCTTCCA
AGAAATCTTAAGAGTGAGTTAGAGGATAAATACATGGAATACAAGTTGAACTTTTACCATCGGAAAACAAGGACTT
CCCGTCCAAGCTGCTGAGAGACATCATTGAGGCAAATCTTGCATATGGTTCAGAGAAGGAAAAGCTACGAATGAGA
GGCTTATTGAGCCTCTTATGAGCCTACTTAAGTCATATGAGGGTGGAGAGAAAGCCATGCTCATTGTTGTCAAG
TGCCTTTTCAAGCAGTACCTTGCTGTGGAAGAACTTTCAGTGATGGGATTCAGTCTGATGTGATTGAAACCCTGCG
TCATCAGCACAGTAAAGACTTCGAGAAGGTTGTAGACATTGTGTTGTCTCACCAGCGTGTGAGGAACAAAGCTAAGC
TTGTAACAGCACTTATGGAAAAGCTGGTTTATCCAAATCCTGCTGCTTACAGGGATCTGTTGGTTGCTTTTCTTCA
CTCAATCATAAAAGATATTATAAGTTGGCCCTTAAAGCAAGCGAACTTCTTGAACAAACTAAGCTAAGTGAACTCCG
TGCAAGCATCGCAAGAAGCCTTTCTGATCTGGGAGGCATAAGGCAGAAATGACTATTGAAGATAGCATGGAAGATT
TAGTCTCTGCCCCATTACCTGTCGAAGATGCACTTTATTTCTTTCTTTGATTACAGTGATCCAACTGTTGAGCAGAAA
GTGATCGAACATACATATCTCGATTGTATCAGCCTCTTCTTGTGAAAGATAGCATCAAGTGAAATTAAGGAATC
TGGTGCCTTGCTTATGGAATTTTCTGAAGGGCATGTTGATACTAAAAATGGACAAGGACCGTTCTTGGTCCAA
CAAGATGGGGTGCCATGGTAGCTGTCAAATCAGTTGAATCTGCACGAACAGCCATTGTAGCTGCATTAAAGGATCCG
GCACAGCATGCCAGCTCTGAGGGCAACATGATGCACATTGCCTTATTGAGTGCTGAAAATGAAATAATATCAGTGA
GGATCAAGCTCAACATAGGATGGAAAACTTAACAAGATACTCAAGGATACTAGTGTCGCAAATGATCTTCGAGCTG
CTGGTTTGAAGGTTATAAGTTGCATTGTTCAAAGAGATGAAGCATGCATGCCAATGGACACAATTACCTGGTCA
GATGAAAACATTGTTATGAGGAAGAGCAGAATCTTCGGCATGTGCAGCCTCCCCTCTTCATGCTTCTTGAAATGGA
TAAGTTGAAAGTGAAAGGATACAATGAAATGAAGTATACTCCATCACGTGATCGTCAATGGCATATCTACACACTAA
```

FIGURE 11A (continued)

```
GAAATACTGAAAACCCCAAAATGTTGCATAGGGTATTTTTCCGAACTATTGTCAGGCAACCCAATGCAGGCAACAAG
TTTATATCAGCCCAAATTGGCGACACTGAAGTAGGAGGTCCTGAGGAATCTTTGTCATTTACATCTAATAGCATTTT
AAGAGCCTTGATGACTGCTATTGAAGAATAGAGCTTCATGGAATTAGGACTGATCATTCTCACATGTATTTGTGCA
TATTGAAAGAACAAAAGCTTCTTGATCTCATTCCGTTTTCAGGGAGCACAATCGTCGATGTTGTCCAAGACGAAGCT
ACTGCTTGTTCACTTTTAAAATCAATGGCTTTGAAGATACACGAACTTGTTGGTGCACAGATGCATCATCTTTCTGT
ATGCCAGTGGGAGGTGAAACTCAAGTTGTACTGCGATGGGCCTGCCAGTGGCACCTGGAGAGTTGTAACTACAAATG
TTACTAGTCACACTTGCACCGTTGATATCTACCGGGAAGTGGAAGATACTGAATGGCAGAAGTTAGTATACCATTCA
GCTTCTCCGTCAGCTAGTCCTTTGCATGGTGTGGCCCTGGATAATCCGTATCGACCTTTGAGTGTCATTGATCTAAA
ACACTGCTCTGCTAGGAACAACAGAACTACATAGTTGCTATGATTTTCCACTGGCATTTGAAACTGCCCTGCAGAAGT
CATGGCAGTCCAATGGCTCCAGTGTTTCTGAAGGCAGTGAAAATAGTAGGTCTTATGTGAAAGCAACAGAGCTGGTG
TTTGCTGAAAAACATGGGTCCTGGCGTCACTCCTATAATTTCCATGGAGCGTGCCGCTGGGCTCAATGACATTGGCAT
CCTAGCTTCGATCTTACAGATCTCCACTCCTGAATTTCCCAATGGCAGGCAGATTATTGTCATAGCAAATGATATTA
CTTTCAGAGCTGGATCATTTGGCCCAAGGGAAGATGCGTTTTTTGAAGCTGTCACGAACCTGGCCTGCCGAGAGGAAC
CTTCCTCTTATATACTTGGCAGCAAACTCCGGTGCTAGGATTGGCATAGCCGATGAAGTGAAATCTTGCTTCCGTGT
TGGGTGGTCCGATGAAGGCAGCCCTGAACGGGGTTTTCAGTACATTTATCTGACTGACGAAGACTATGCCGGTAGTA
GCTTGTCGTTATAGCACACAAGCTGCACCTGGATAATGGTGAAATTAGGTGGATTATTGACTCTGTTGTGGGCAAG
GAGGATGGGCTTGGTGTTGAGAATATACATGGAAGTGCTGCTATTGCCAGTGCTTATTCTAGGGCATATGAGCAGAC
ATTTACACTTACATTTGTGACTGGCGGACTGTTGGAATAGGAGCATATCTTGCTCGGCTCGGTATACGGTGCATAC
AGCGTCTTGACCAGCCTATTATTTTAACTGGGTTTTCTGCCCTGAACAAGCTTCTTGGCGGGGAAGTGTACAGCTCC
CACATGCAGTTGGGTCGTCCTAAGATCATGGCGACCAATGGTCTTGTCCACTTGACTGTTTCAGATGACCTTGAAGG
TGTTTCCAATATATTCAGGTGGCTCAGCTATGTTCCTGCCAACATTGGTGGACCTCTTCCTATTCAAAACCCTTTGG
ACCCACCAGACAGACCTGTTGCATACATCCCTGAGAACACATGTGATCCGCGCAGCCATTCCTGGTGTAGATGAC
AGCCAAGGGAATTGTTTGGTGGTATGTTTGACAAAGACAGCTTTGTCGAGACATTTGAAGGATGGCGAAAACAGT
GGTTACGGGCAGAGCAAAGCTTGGAGGAATTCCTGTTGCCGTCATAGCCGTCGAGACACAAACCATGATGCAGCTTA
TCCCTGCTGATCCAGGCCAGCTTGATTCCCATGAGCGATCTGTTCCTCGGGCTGGACAAGTGTGGTTCCCAGATTCT
GCAACCAAGACAGCTCAGGCATTGTTTGGACTTCAACCGTGAAGGATTGCCGCTGTTCATCCTTGCTAACTGGAGAGG
ATTCTCTGGTGGACAAAGAGATCTGTTTGAAGGAATTCTTCAGGCTGGGTCAGCAATTGTTGAGAACCTTAGGACAT
ACAATCAGCCTGCTTTTTCTACATTCCTATGCTGGAGAGCTGCGTGGAGGAGCTTGGTTGTGGTTGATAGCAAA
ATAAATCCAGACCGAATTGAGTGTTATCCTGAGAGGACTGCTAAAGGCAATGTTCTGGAACCCCAAGGGTTAATTGA
AATCAAATTCAGATCAGAGGAGCTCCAGAGCTGTATGGGTAGGCTTGACCCCAGGCGTTTGATAAAATCTGAAAGCAAAAC
TCCAAGGTGCAAAGCTTGGAAATGGAAGCCTAACGATGTAGAATCCCTTCAGAAGAGTATAGATGCTCGTACGAAA
CAGTTGTTGCCTTTATACACCCAGATTGCAATACGGTTTGCTGAATTGCATGATACTTCCCTCAGAATGGCAGCTAA
AGGTGTGATTAAGAAAGTTGTAGATTGGGAAGAATCACGTTCTTTCTTCTACAGAAGGCTACGGAGGAGGATCTCTG
AAGATGTTCTTGCAAAAGAAATAAGAGGAATAGCTGGTGACCACTTCACTCACCAATCAGCAGTTGAGCTGATCAAG
GAATGTACTTGGCTTCTCAAGCCACAACAGGAAGCACTGAATGGGATGATGATGCTTTTGTTGCCTGGAAGCA
GAATCCTGAAAACTATAAGGGATATATCCAAGAGTTAACGGCTCAAAAGGTGTCTCAGTGGCTCTCCGATCTTGCAG
ACTCCAGTTCAGATCTAGAAGCATTCTCACAGGGTCTTTCCACATTATTAGATAAGATGGATCCCTCTCAGAGAGCC
AAGTTCATTCAGGAAGTCAAGAAGGTCCTGGGTTGA
```

FIGURE 11B

```
>AAO62902_Setaria italica (foxtail millet)
MSQLGLAAAASKALPLLPNRHRTSAGTTFPSPVSSRPSNRRKSRTRSLRDGGDGVSDAKKSNQSVRQGLAGIID
LPNEATSEVDISHGSEDPRGPTDSYQMNGIVSEAHNGRHASVSKVVEFCAALGGKTPIESILWANNGMAAAKFM
RSVRTNANDTFGSEKAIQLIAMATPEDMRINAEHIRIADQFVEVPSGTNNNNYANVQLIVEVAERIGVSAVWPG
WGHASENPELPDRLTAKGVVFLGPPAASMNALGDRVGSALIAQAAGVPTLSWSGSHVEVPLECCLDAIPEEMYR
KACVFTTEEAVASCQVVGYPAMIKASWGGGGKGIERVSNDDEVRALEKQVQGEVPGSPIFIMRLASQSRHLEVQ
LLCDQYGNVAALSSRDCSVQRREQKIIEESPVTVAPRETVKALEQAARRLAKAVGYVGAATVEYLYSMETGEYY
FLELNPRLQVEHPVTEWIAEVNLPAAQVAVGMGIPLMQIPEIRRFDGMDYGGYDIWRKTAALATPFNFDEVDS
QNPKGHCVAVRITSEDPDDGPKFTGGKVKEISFKSKPNVWAYFSVKSGGGIREPVDSQFGEVFAYGLSRSAAIT
NMALALREIQIRGEIRSNVDYTVDLLNASDFRENKIHTGNLDTRIAMRVQAERPPWYISVVGGALYKTVTANAA
TVSDYVSYLTKGQIPPKHISLVSSTVNLNIECSKYTVETVSRTCHGSYRLPMNDSAIEANVQSLCDGGLLMQLSG
NSHVIYAEEEAGGTRLLIDGKTCILQNDHDPSKLIAETPCKLLRFLVADGAHVDADVFYARVEVMKMCMPLLSP
ASGVIHVMMSEGQALQAGDLTARLDLDDPSAVKRAEFFNGIFPQMDLPVAASSQVNKRYAASWNAARMVLAGYE
HNINEVVQDLVCCLEDPELPPTQWDELMSVLATRLPRNLKSELEDKYMEYKLNPYNGKNHDFPSKLLRDYIEAN
LAYGSEKEKATNERLIEPLMSILKSYEGGRESHAHPVVKSLFKEYLAVEKLFSDGIQSDVIETLRHQHSKDLQK
VVDIVLSHQGVRNKAKLVTALMEKLVYPNPAAYRDLLVRFSSLNEKRYYKLALKASELLEQTKLSELRASIARS
LSDLGMHKGKMTIRDSMEDLVSAPLPVEDALISLFDYSDPTVQQKVIETYISRLYQPLLVKDSIQVKFKESGAF
ALWSFSEGHVDTKNGQGTVLGRTRWGAMVAVKSVESARTAIVAALKDSAQHASSEGNMMHIALLSAENENNISD
DQAQHRMEKLNKILRDTSVANDLRAAGLRVISCIVQRDEARMPKRHTLLWSDEKSCYEEQILRHVEPPLSMLL
EMDRLKVKGYNEMRYTESRDRQWHIYTLRNTENPRMLSRVFFRTIVRQPNAGNKFISAQIGDTEVGGPEESLSF
TSNSILRAINTAIEELELHAIRTDRSHMYLCILKEQKLDLIPFSGSTIVDVVQDEATACSILKSMALKIHELV
GAQMRHLSVCQWEVKLRLYCDGPASGTWRVVTINVTSHTCTVDIYREVEDTESQKLVYHSASPSASPLHGVALD
NFYQFLSVIDLKHCSARNNRTTYCYDFPLAFETALQKSWQSNGSSVSEGSENSRSYVKATELVFAEKHGSWGTP
IISMERPAGLNDIGMVAWILSMSTPKFPNGRQIIVIANDITFRAGSFGPREDAFPEAVTNLACERKLPLIYLAA
MSGARIGIADEVKSCFRVGWSDEGSPERGFQYIYLTDEDYARISLSVIAHRIQLLNGEIRWIIDSVVGKEDGLG
VENIHGSSAATASAYSRAYEETFTLTFVTGRTVGIQAYLARLGIRCIQRLDQPIILTGFSALNKLLGREVYSSRM
QLGGPKIMATNGVVRLTVSDDLEGVSNILRWLSYVPANIGGPLFITKPLDPPDRPVAYIPENTCDPRAAIRGVD
DSQGKNLGGMFDKDSFVETFEGWAKTVVTGRAKLGGIPVGVIAVETQTMMQLIPADPGQLDSHERSVPRAGQVW
FPDSATKTAQALLDFNREGLPLFILANWRGFSGGQRDLFEGILQAGSTIVEMLRTYNQPAFVYIPMAGELRGGA
WVVVDSKINPDRIECYAERTAKGNVLEPQGLIEIKFRSEELQDCMGKLDPGLINLKAKLQGAKLGNGSLTDVES
LQKSIDARTKQLLPLYTQIAIRFAELRDTSLRMAAMGVIRKVVDWERSRSFFYRRLRRRISEDVLAKEIRGIAG
DNFTHQSAVELIKEWYIASQATTGSTENDDODAFVAWKENPENYKGYIQELRAQKVSQSLSDLADSSSDLEAFS
QSISTLLDKMDPSQRAKFIQKVKKVLG
```

```
>AAO62903_Setaria italica (foxtail millet)
MSQLGLAAAASKALFLLPNRHKTSAGTTFPSPVSSRPSNRRKSRTRSLRDGGDGVSDAKKHNQSVPQGLAGIID
LPNEATSEVDISHGSEDPRGPTDSYQMNGIVNEAHNGREASVSKVVEFCAALGGETPIHSILVANNGMAAAKFM
NSVRTWANDTFGSEKAIQLIAMATFEDMRINAEHIRIADQFVEVPSGTNNNNYANVQLIVEVAERIGVSAVWPG
NGHASENPELPDALTANGIVFLGPPAASMNAIGDKVGSALIAQAAGVPTLSWSGSHVEVPLECCLDAIPERMYR
KACVTTTEEAVASCQVVGYPAMIKASWGGGGKGIRKVRHDDEVRALFKQVQGEVPGSPIFIMRLASQSRHLEVQ
LLCDQYGNVAALHSRECSVQRRHQKIIEEGPVTVAPRETVKALEQAARRLARAVGYVGAATVEYLYSMETGEYY
FLELNFRLQVEHPVTEWIAEVNLPAAQVAVGMGIPLNQIPEIRRFYGMDYGGGYDIWRKTAALATPFNFDRVDS
QWPKGECVAVRITSEDPDDGFKPTGGKVHSISFKSKPNVWAYFSVKSGGGIHEFADSQFGHVFAYGLSRSAAIT
NMALALKEIQIRGEIHSNVDYTVDLLNASDFRENKIWTGWLDTRIAMRVQAERPPWYISVVGGALYKTVTANAA
TVSDYVSYLTKGQIFPRHISLVSSTVNLNIEGSKYPVETVRTGNGSYRLRMNDSAIEANVQSLCDGGLLMQLDG
NSRVIYAREEAGGTRLLIDGKTCLLQNDHEPSKLLAETPCKLLRFLVADGAHVDADVPYAREVEVMKNCMPLLSP
ASGVIHVMESEGQALQAGDLIARLDLDDPSAVKRAEPFRGIFPQMDLPVAASSQVHKRYAASLNAARMVLAGYE
HNINEVVQDLVCCLDDPELPFLQWDELMSVLATRLPRNLKSELEDRYMEYKLNFYRGKNKDFPSKLLRDIIEAN
LAYGSEKEKATNERLIEPLMSLLKSYEGGRESHAHPVVKSLFKEYLAVEELFSDGIQSINVIETLRHQHSKDLQK
VVDIVLSHQGVRNKAKLVTALMEKLVYPNPAAYRDLLVRFSSLNHKRYYKIALKASELLEQTKLSELRASIARS
LSDLGMHKGEMTIEDSMEDLVSAPLPVEDALISLFDYSDPTVQQKVIETYISRLYQPLLVKDSIQVKFKESGAF
AIWEFSEGHVDTKNQQCTVLGHTRWGAMVAVKSVESARTAIVAALKDSRQHASSEGNMMRIALLSAENENNISD
DQAQHRMEKLNKILKDTSVANDLRAAGLEVISCIVQRDEARMPMRHTLLNSDEKSCYEEEQILRHVEPPLSMLL
EMDKLKVKGYNEMKYTESRDRQWHIYTLRNTENPKMLHRVFFRTIVRQPNAGNKFISAQIGDFEVGGPSESLSF
TPSNSILRALNTAIKELELHAIRTGHSRMYLCILKEQKLIDLIPFSGSTIVDVGQDEATACSLLKSMALKIRELV
GAQMHRILSVCQWEVRLKLYCDGPASGTWRVVTTNVTSHTCTIDIYREVEDTESQKLVYRSASPSASPLHGVALD
NPYQPLSVIDLKRCSARNNRTTYCYDFPLAPETALQKSWQSNGSSVSEGSENSRSYVKATELVFAEKHGSWGTP
IISMERFAGLNDIGMVAWILEMSTPEFPNGRQIIVIANDITFRAGSFGPREDAFFEAVTNLACERKLPLIYLAA
NSGARIGIADEVKSCFRVGWSDEGSPERGPQYIYLTDEDYARISLSVIAHKQLDNGEIRWIIDSVVGKEDGLG
VENLHGSAAIASAYSRAYEETFTILTPVTGRTVGIGAYLAPLGIRCIQRLDQPIILTGFSALNKLLGREVYSSHM
QLGGPKIMATNGVVRLTVSDNLEGVSNILRWLSYVPANIGGPLPTTKPLDPPDRPVAYIPENTCDPRAAIRGVD
DSQQKWLGGNFDKDSFVETFEQWAKTVVTGRAKLGGIPVGVIAVETQTMNQLIPADSGQLDSHERSVPRAGQVW
FPDSATKPAQALLDFNREGLPLFILANNRGPSGGQRDLFEGIILQAGSTIVERLRTYNQPAFVYIPMAGELRGGA
WVVVDSKINPDRIECYAERTAKGNVLEPQGLIEIKPRSEELQDCMGRLDPELINLKAKLQGAKLGNGSLTDVES
LQESIDARTKQLLPLYTQIAIRFAELHDTSLRMAAKGVIKKVVDWEEESRSFFYRRIRRRISEDVLAKEIRGIAG
DHFTRQSAVELIKEWYLASQATTGSTEWDEDDAFVAWKENFENYKGYIQELRAQNVSQSLSDLADSSSDLEAFS
QGLSTLLDKMDPSQRAKFIQEVKNVLG
```

FIGURE 13A

```
>AF294805 Setaria italica (foxtail millet)
ATGTCGCAACTTGGATTAGCTGCAGCTGCCTCAAAGGCGCTGCCACTACTTCCTAATCGCCATAGAACTTCAGCTGG
AACTACATCCCATCACCTGTATCATCGCGGCGCTCAAACGAAGGAAAAGCCGCACTCGTTCACTTCGTGATGGAG
GAGATGGGGTATCAGATGCCAAAAAGCACAACCAGTCTGTCCGTCAAGGTCTTGCTGGCATCATCGACCTCCCAAAT
CAGGCAACATCGGAAGTGGATATTTCTCATCGATCCGAGGATCCCAGGGGGCCAACCGATTCATATCAAATCAATGG
GATTGTAAATGAAGCACATAATGGCAGACATGCCTCAGTGTCCAAGGTTGTTGAATTTGTGCGGCGCTAGGTGGCA
AAACACCAATTCACAGTATACTACTGGCCAACAATGGAATGGCAGCAGCAAAGTTCATGACGAGTGTCCGGACATGG
GCTAATGATACTTTTGGATCGGAGAAGGCGATTCAGCTCATAGCTATGCCAACTCCAGAAGACATCAGGATAAATGC
AGAACACATTAGATTGCTGATCAATTTGTAGAGGTGCCTGGTGGAACAAACAATAACAACTATCCAAATGTTCAAC
TCATAGTGGAGGTAGCAGAAAGAATAGGTGTTTCTGCTGTTTGGCCTGGTTGGGGTCATGCTTCTGAGAATCCTGAA
CTTCCAGATGCATTGACCGCAAAGGAATTGTTTTCCTTGGGCCACCTGCGGCATCAATGAATGCATTGGGAGATAA
GGTCGGTTCAGCTCTCATTGCTCAAGCAGCTGGGGTCCCGACCCTTCGTGGAGTGGATCACATGTTGAAGTTCCAT
TAGAGTGCTGCTTAGATGCGATACCTGAGGAAATGTATAGAAAAGCTTGTGTTACTACCACGAAGAAGCTGTTGCG
AGTTGTCAGGTGGTTGGTTATCCTGCCATGATTAAGGCATCCTGGGGAGGTGGTGGTAAAGGAATAAGAAAGGTTCA
TAATGACGATGAGGTTAGAGCACTGTTTAAGCAAGTACAAGGTGAAGTCCCTGGCTCCCCAATATTTATCATGAGGC
TTGCATCCAGAGTCGTCATCTTGAGTTCAGTTGCTTTGTGATCAATATGGCAATGTGGCAGCACTTCACAGTCGT
GATTGCAGTGTCAACGGCGACACCAAAGATTATTGAGGAAGGCCCAGTTACTGTTGCTCCTCGTGAGACAGTTAA
AGCGCTTGAGCAGGCAGCAAGGAGGCTTGCTAAGGCTGTGGGTTATGTTGGTGCTGCTACTGTTGAATACCTTTACA
GCATGGAGACTGGGGAATACTATTTCTGGAGCTTAATCCCAGATTACAGGTCGAGCATCCAGTCACTGAGTGGATT
GCTGAAGTAAATCTTCCTGCAGCTCAGTTGCAGTTGGAATGGGCATACCTCTTTGGCAGATTCCAGAAATCAGACG
TTTCTATGGAATGGACTATGGAGGACGATATGACATTTCGAGGAAAACAGCAGCGTCTTGCCACACCATTTAATTTTG
ATGAAGTAGATTCTCAATGCCAAAGGGCCATTGTGTACCAGTTAGAATTACTAGCGAGGATCCAGATGATGGTTTC
AAACCTACTGGTGGGAAAGTGAAGGAGATAAGTTTTAAAAGCAAGCCTAATGTTTGGGCCTACTTCTCAGTAAAGTC
TGGTGGAGGCATTCATGAATTGCTCGATCTCACTTTCGGCATCTTTTGCATATCGCGCTCTAGATCAGCAGCAA
TAACGAACATGGCTCTTGCATTAAAAGAGATTCAAATTCGTGGAGAAATTCATTCAAATGTTGATTACACAGTTGAT
CTCTTAAATCCTTCAGACTTCAGAGAAAATAAGATTCATACTGGCTGGCTTGATACCAGAATAGCTATGGTGTTCA
AGCTGAGAGGCCCCATGGTATATTTCAGTGGTTGGAGGAGCCTCTATATAAACAGTAACTGCCAATGCAGCCACTG
TTTCTGATTATGTCAGTTATCTCACCAAGGGCCAGATTCCACCAAGCACATATATCCCTTGTCAGTCCAACAGTTAAT
CTGAATATCGAAGGAGCAAATACACAGTTGAAACTGTAAGGACATGCACATCGTAGCTACACATTACCGAATGAATGA
TTCAGCAATTGAAGCGAATGTACAATCTTTATGTGATGGAGGCCTCTTAATGCAGTTGGATGGAAATAGCCATGTAA
TTTACGCCGGAGAAGAAGCTGGTGGTACACGACTTCTGATTGATGGAAAGACATGCTTGTTACAGAATGATCATGAT
CCATCAAAGTTATTAGCTGAGACACCCTGCAAACTTCTTCGGTTCTTGGTTGCTGATGGTGCTCATGTTGATGCTGA
TGTACCATATGCGGAAGTTGAGGTTATGAAAATGTGCATGCCCTCTTGTCGCCTGCTTCTGGTGTCATTCATGTTA
TGATGTCTGAGGCCAGGCATTGCAGGCTGGTGATCTATAGCAAGGCTGGATCTTGATGACCCTTCTGCTGTGAAA
AGAGCTGAACCATTCATGGAATATTTCCACAAATGGACCTTCCTGTTGCTGCCTCTAGCCAAGTACACAAAAGATA
TGCTGCAAGTTTCAATGCTGCTCGAATGCTCCTTGCACCATACGAGCATAATATCAATGAACTTGTACAAGATTCG
TATGCTCCCTGCATGATCCCCGAGCTTCCCTTCCTACACTGGGATGAACTTATGTCAGTTCTTGCAACTAGGGCTTCCA
AGAAATCTTAAGAGTGAGTTAGAGGATAAATACATGGAATACAAGTTGAACTTTTACCATGCGAAAAACAAGGACTT
CGGTTCCAGCTGCTGAGGAGAATCATGAGCCAAATCTTGCATATGGTTCAGAAGGAAAAGCTACGAATGAGA
GGCTTATTGAGCCTCTTATGAGCCTACTTAAGTCATATGAGGGTGGGACAGAAAGCCATGCTCATTTGTTGTCAAG
TCCCTTTTCAAGGAGTACCTTGCTGTGGAAGAACTTTTCAGTGATGGATTCAGTCTGATGTGATTGAAACCCTGCG
TCATCAGCACAGTAAAGACTTGCAGAAGGTTGTAGACATTGTGTTGTCTCACCAGCGTGTGAGGAACAAAGCTAGGC
TTGTAACAGCACTTATGGAAAAGCTGGTTTATCCAAATCCTGCTGCTACAGGGATCTGTTGGTTCCGTTTTCTTCA
CTCAATCATAAAAGATATTATAAGTTGGCCCTTAAAGCAAGCGAACTTCTTGAACAAACTAAACTAAGTGAACTCCG
TGCAAGCATCGCAAGAAGCCTTTCTGATCTGGGGATGCATAAGGGAGAAATGACTATTGAACATAGCATGGAAGATT
TAGTCTCTGCCCCATTACCTGTCGGAAGATGCACTTATTTCTTTGTTTGATTACAGTGATCCAACTGTTCAGCAGAAA
GTGATCGAGACATACATATCTCGATTGTATGATCAGCCTCTTCTTGTGAAAGATAGCATCCAAGTGAAATTAAGGAATC
TGGTGCCTTTGCTTTATGGCAATTTTCTCAAGGGCATGTTGATACTAAAAATGGACAAGGGACCGTTCTTGGTCGAA
CAAGATGGGGTGCCATGGTAGCTGTCAAATCAGTTGAATCTGCACGAACAGCCATTGTAGCTGCATTAAGGATTCG
GCACAGCATGCCAGCTCTGAGGGCAACATGATGCACATTGCCTTATTGAGTGCTGAAAATGAAATAATATCAGTGA
TGATCAAGCTCAACATAGGATGGAAAACTTAACAGAGATACTCAAGGATACTAGTGTCCCAAATGATCTTCGAGCTG
CTGGTTTGAAGGTTATAAGTTGCATTGTTCAAAGAGATGAAGCACGCATGCCAATGCGCCACACATTACTCTGGTCA
```

FIGURE 13A (continued)

```
GATGAAAAGAGTTGTTATGAGGAAGAGCAGATTCTTCGGCATGTGGAGCCTCCCCTCTCCATGCTTCTTGAAATGGA
TAAGTTGAAAGTGAAAGCATACAATGAAATGAACTATACTCCATCACCTGATCCTCAATGGCATATCTACACACTAA
GAAATACTGAAAACCCCAAAAGTTGCATAGGGTATTTTTCCGAACTATTGTCAGGGCAACCCAATGCAGGCAACAAG
TTTATATCAGCCCAAATTGGCGACACTGAAGTAGGAGGTCCTGAGGGATCTTTGTCATTTACATCTAATAGCATTTT
AAGAGCCTTGATGACTGCTATTGAAGAATTAGAGCTTCATGCAACTTAGGACTGGTCATTCTCACATGTATTTGTGCA
TATTGAAAGAACAAAAGCTTCTTGATCTCATTCCGTTTTCAGGGAGCACAATCGTCGATGTTGGCCAAGACGAAGCT
ACTGCTTGTTCACTTTTAAAATCAATGGCTTTGAAGATACACGAACTTGTTGGTGCACAGATGCATCATCTTTCTGT
ATGCCAGTGGGAGGTGAAACTCAAGTTCTACTGCGATGGGCCTGCCAGTGGCACCTGGAGAGTTGTAACTACAAATG
TTACTAGTCACACTTGCACCGTTGATATCTACCGGGAAGTGGAAGATACTGAATCGCAGAAGTTAGTATACCATTCA
GCTTCTCCGTCAGCTAGTCCTTTGCATGGTGTGGCCCTGGATAATCCGTATCAACCTTTGAGTGTCATTGATCTAAA
ACGCTGCTCTGCTAGGAACAACAGAACTACATATTGCTATGATTTTCCACTGGCATTGAAACTGCCCTGCAGAAGT
CATGGCAGTCCAATGGCTCCAGTGTTCTGAAGGACAGTGAAAATAGTAGGTCTTTATGTTGAAAGCAACAGAGCTGGTG
TTTGCTGAAAAACATGGGTCCTGGGGCCACTGGTATAATTCCATGGAGCGTCCCGCTGCGTCTCAATGACATTGGCAT
GGTAGCTTGCATCTTACAGATGTCCACTCCTGAATTTCCCAATGGCAGGCACATTATTGTCATAGCAAATGATATTA
CTTTCAGAGCTGGATCATTTGGCCCTAAGGGAAGATGCTTTTTTTGAAGCTGTCACGAACCTGGCCTGCGAGAGGAAG
CTTCCTCTGATATACTTGGCAGCAAACTCCGGTGCTAGGATTGGCATAGCCGATGAAGTGAAATCTTGCTTCCGTGT
TGGGTGGTCCGATGAAGGCAGCCCTGAACGGGGTTTTCAGTACATTATCTCACTGACGAAGACTATGCCCGTATTA
GCTTGTCTGTTATAGCACACAAGCTGCAGCTGCATAATGCTGAAATTACGTCCATTATTCACTCTGTTGTGGGCAAG
GAGGATGGGCTTGGTGTTGAGAATATACATGGAAGTGCTGCTATTGCCAGTGCTTATTCTAGGGCATATGAGGAGAC
ATTTACACTTACATTTGTGACTGGGGGGACTGTTGGAATAGGAGCATATCTTGCTCGGCTGGTTATACGGTGCATAC
AGCGTCTTGACCAGCCTATTATTTTAACTGGGTTTTCTGCCCTGAACAAGCTTCTTGGGCGGGAAGTGTACAGCTCC
CACATGCAGCTGCGCTGCCTCCTAAGATCATGCTGACCAATGGTGTCTCCACTTGACTGTTCAGATGACCTTGAACG
TGTTTCCAATATATTGAGGTGGCTCAGCTATGTTCCTGCCAACATTGGTGGACCTCTTCCTATTACAAAACCTTTGG
ACCCACCAGACAGACCTGTTGCATACATCCCTGAGAACACATGTGATCCGCGCGCAGCCATTCGTGGTGTAGATGAC
AGCCAAGGGAAATGGTTGGGTGGTATGTTTGACAAAGACAGCCTTTGTCGAGACATTTGAAGGATGGGCGAAAACAGT
GGTTACGGGCAGAGCAAAGCTTGGAGGAATTCCTGTTGGTGTCATAGCTGTGGAGACACAACCATGATGCAGCTTA
TCCCTGCTGATCCAGGCCAGCTTGATTCCATGAGCGATCTGTTCCTCGGGCTGGACAAGTGGTTCCCAGATTCT
GCAACCAAGACAGCTCAGGCATTGTTGGACTTCAACCGTGAAGGATGCCGCTGTTCATCCTTGCTAGCTGGAGAGG
ATTCTCTGGTGGACAAAGAGATCTGTTTGAAGGAATTCTTCAGGCTGGCTCAACAATTGTTGAGAACCTTAGGACAT
ACAATCAGCCTGCTTTTGTCTACATTCCTATGGCTGGAGAGCTGCGTGGAGGAGCTTGGTTGTGGTGATAGCAAA
ATAAATCCAGACCCAATTGAGTGTTATGCTGAGAGGACGCTAAAGGCAATGTTCTGGAACCCTCAAGGGTTAATTGA
AATCAAATTCAGATCAGAGGACCTCCTAGACTGTATGGGTAGGCTTGACTTCACGTTGATAAATCTGAAAGCAAAAC
TCCAAGGTGCAAAGCTTGGAAATGGAACCCTAACAGATGTAGAATCCCTTCAGAAGAGTATAGATGCTCGTACGAAA
CAGTTGTTGCCTTTATACACCCAGATTGCAATACGGTTTGCTGAAATTGCATGATACTTCCCTCACAATGGCAGCTAA
AGGTGTGATTAAGAAAGTTGTAGATTGGGAAGAATTACGTTCTTTCTTCTACAGAAGGCTACGGAGGAGGATCTCTG
AAGATGTTCTTGCAAAAGAAATAAGAGCAATAGCTGGTGACCACTTCACTTACCCAATGCAGCAGTTGAGCTGATCAAG
GAATGGTACTTGGCTTCTCAAGCCACAACAGGAAGCACTGAATGGGATGATGATGATGCTTTTGTTGCCTGGAAGGA
GAATCCTGAAAACTATAAGCGGATATATCCAAGAGTTAAGGGCTCAAAAGGTCTCTGAGTCGCTCTCCGATCTTGCAG
ACTCCAGTTCAGATCTAGAAGCATTCTGACAGGGTCTTTCCACATTATTAGATAAGATGGATCCCTCTCAGAGAGCC
AAGTTCATTCAGGAAGTCAAGAAGGTCCTGGGTTGA
```

FIGURE 13B

```
>AAL02056_Setaria italica (foxtail millet)
MSQLGLAAAASKALPLLPNREPTSAGTTFPSPVSSRPSNRRKSRTRSLRDGGDGVSDARKHNQSVRQGLAGIID
LPNEATSEVDISHESEDPRGPTDSYQMNGIVNEAHNGRRASVSKVVEFCAALGGKTPIHSILVANNGMAAAKFM
RSVRTWANDTFGSEKAIQLIAMATPEDMRINAEHIRIADQFVEVPGGTNNNNYANVQLIVEVAERIGVSAVWPG
WGHASENPELPDALTARGIVFLGPPAASMNALGDKVGSALIAQAAGVPTLSWSGSHVEVPLECCLDAIPEEMYR
KACVTTTEEAVASCQVVGYPAMIKASWGSGGKGIRKVENDEVRALFKQVQGEVPGSPIFIMRLASQSRHLSVQ
LLCDQYGNVAALHSRDCSVQRREQKIIEEGPVTVAPRETVKALEQAARRLAKAVGTVGAATVEYLYSMETGEYY
FLELNPRLQVESPVTEWIAEVNLPAAQVAVGMGIPLRQIPEIRRFYGMDYGGGYDIWRKTAALATPPNFGEVDS
QWPKGRCVAVRITSEDPDDGFKPTGGKVKEISFKSRPNVWAYFSVRSGGGIHEFADSQFGHVFAYGLSRSAAIT
NMALALKEIQIRGEIHSNVDYTVDLLMASDFRENKIHTGWLDTRIAMRVQAERPPWYISVVGGALYKTVTAKAA
TVSDYVSYLTKGQIPERHISLVSSTVNLNIEGSKYTVETVRTSHGSYRLRMNDSAIEANVQSLCDGGLLMQLDG
NSHVIYAERKAGGTRLLIDGKTCLLQNDHDFSKLLAETPCKLLRFLVADGAHVEADVEYAEVEVNKMCMPLLSP
ASGVISWMMSEGQALQAGDLIARLDLDDFSAVKRAEPFHGIFPQMDLPVAAESQVHKRYAASLNAARMVLAGYE
SNINEVVQDLVCCLDDPELPFLQWDELMSVLATRLPRNLKSELEDKYMEYKLNFYHGKNRDFPSKLLRDIIEAN
LAYGSEKEKATNERLIEPLMSLLKSVEGGRESEAHFVVKSLFKEYLAVEELFSDGIQSDVIETLRHQRSKDLQK
VVDIVLSHQGVRNKAKLVTALMERLVYPNPAAYRDLLVRFSSINHKRYYKLALKASELLBQTKLSELRASIARS
LSDLGMRKGEMTIEDSMEDLVSAPLPVEDALISLFDYSDPTVQQKVIETYIERLYQPLLVKDSIQVKFKESGAF
ALWEFSEGHVDIKNGQGTVLGSTRNGAMVAVKSVESARTAIVAALKDSAQHASSEGNMMRIALLSAENENNISD
DQAQHRMERLNKILKDTSVANDLRAAGLKVISCIVQRDRARMPMRETLLWSDEKSCYEEEQILRHVEPPLSMLL
EMDKLRVKGYNEMKYTPSRDRQWRIYTLRNTENPKMLERVPFERTIVRQPNAGNKFISAQIGDTEVGGPESSLSF
TSNSILRALMTATEELELHAIPTGRSEMYLCILKRQKLDLIPFSGSTIVDVGQDEATACSLLKSMALKIHELV
GAQMSHRLSVCQWEVLKLYCDGFASGTWRVVTTNVISHTCTVDIYREVEDTESQKLVYHSASPSASPLEGVALD
NFYQPLSVIDLKRCSARNNRTTYCYDFPLAFETALQKSWQSNGSSVSEGSENSRSYVKATELVFAERHGSWGTP
IISMERPAGLNDIGMVAWILEMSTPEFPNGRQIIVIAMDITFRAGSFGPREDAFFEAVTNLACERKLPIYLAA
NSGARIGIADEVKSCFRVGWSDEGSPERGFQYIYLTDEDYARISLSVIASKLQLDNGEIRWIIDSVVGKEDGLG
VENIRGSAAIASAYSRAYEETFTLTFVTGRTVGIGAYLARLGIRCIQRLDQPIILTGFSALNKLLGREVYSSHM
QLGGPKIMATNGVVHLTVSDDLEGVSNILRWLSYVPANIGGPLPITKPLDPPDRPVAYIPENTCDPRAAIRGVD
DSQGKWLGCMFDKDSFVETFEGWAKTVVTGRAKLGKIPVGVIAVRTQTMMQLIPADPGQLDSRERSVPRAGQVW
FPDSATKTAQALLDFNREGLPLFILANWRGFSGGQRDLFEGILQAGSTIVENLRTYNQEAFVYIPMAGELRGGA
NVVVDSKINPDRIECYAERTAKGNVLEPQGLIEIKFRSEELQDCMGSLDPELINLKAKLQGAKLGNGSLTDVES
LQKSIDARTKQLLPLYTQIAIRFAELHDTSLRMAARGVTKKVVDWSELRSFPYRRLRRRISEDVLAKEIRGIAG
DHFTHQSAVELIKEWYLASQAFTGSTEWDDDDAFVAWRENPENYKGYIQELRAQKVSQSLSDLADSSSDLEAFS
QGLSTLIDRMDPSQRAKFIQEVRKVLG
```

FIGURE 14A

```
>AJ310767 Alopecurus myosuroides (black-grass)
ATGGGATCCACACACATCTGCCCATTGTCGGGTTTAATGCATCCACAACACGATCGCTATCCACTCTTCGCCAGATAAA
CTCAGCTGCTGCTGCATTCCAACTTCGTGCCCTTCAAGGTCATCCAAGAAGAAAGCCGACGTGTTAAGTCAATAA
GGGATGATGGCGATCGAAGCGTGTCAGACCCTGCAGGCATGCCGTCTATTCGCTAACGTCTCGCTGGCATCATC
GACCTCCCAAAGGAGGGGCGCATCAGCTCCAGATGTGGACATTTCACATGGGTCTGAAGACCACAAGCCTCCTACCA
AATGAATGGGATACTGAATGAATCACATAACGGGAGGCACGCCTCTCTGTCTAAAGTTTATGAATTTTGCACGGAAT
TGGGTGGAAAAACACCAATTCACAGTGTATTAGTCGCCAACAATGGAATGGCAGCAGCTAAGTTCATGCGGAGTGTC
CGGACATGGCTAATGATACATTTGGGTCAGAGAAGGCGATTCAGTTGATAGCTATGGCAACTCCGGAAGACATGAG
AATAAATCCACACCACATTACAATTCCTCATCAGTTTGTTGAAGTACCTGGTGGAACAAACAATAACAACTATGCAA
ATGTCCAACTCATAGTGGAGATAGCACAGAGAACTGGTGTCTCCGGCCGTTTGGCCTGGTTGGGGCCATGCATCTCAG
AATCCTGAACTTCCAGATGGCACTAACTGCAAAAGGAATTGTTTTCTTGGGCCACCAGCATCATCAATGAACGCACT
AGGCGACAAGGTTGGTTCAGCTCTCATTGCTCAAGCAGCAGGGGTTCCCACTCTTGCTTCGAGTCGATCACATGTGG
AAATTCCATTAGAACTTGTTTGGACTCGATACCTCAGGACATGTATAGGAAAGCCTGTGTTACAACGCTGATGAA
GCAGTTGCAAGTTGTCAGATGATTGGTTACCCTGCCATGATCAAGGCATCCTGGGGTGGTGGTAAAGGGATTAG
AAGGTTAATAATGATGACGAGGGTGAAGCACTGTTTAAGCAAGTACAGGGTGAAGTTCCTGGCTCCCGATATTTA
TCATGAGACTTGCATCTCAGAGTCCTCATCTTGAAGTCCAGCTGCTTTGTGATGAATATGGCAATGTAGCAGCACTT
CACAGTCGTGATTGCAGTGTGCAACGACGACACCAAAAGATTATCGAGCAACGACCAGTTACTGTTGCTCCTCGTCA
AACAGTGAAAGAATAGAAGCAAACAGCAAGGAGGCTTGCTAAGGCCGTGGGTTACGTCGGTGCTGCTACTGTTGAAT
ATCTCTACAGCATGGAGACTTCATGAATACTATTCTCTGCCAGCTTAATCCACGGTTGCAGGTTGAGCACCCAGTCACC
GAGTCGATAGCTGAACTAAATTTGCCTGCAGCCCAAGTTGCCAGTTGGATGGTATACCCTTTGCAGATTCCAGA
GATCAGACGTTTCTACGGAATGGACAATGGAGGAGCCTATGATATTTGGAGGAAAACAGCAGCTCTCGCTACTCCAT
TCAACTTTGATGAAGTAGATTCTCAATGGCCGAAGGGTCATTGTGTGGCAGTTAGGATAACCAGTGAGAATCCAGAT
GATGGATTCAGCCTACTGGTGGAAAGTAAGGCACATAAGTTTTAAAAGTAAGCCCAAATGTCTGGGGATATTTCTC
AGTTAAGTCTGGTCGAGCCCATTCATCGATTTGCGCATTCTCACTTTCGACACGTTTTTGCCTATGGAGAGACTAGAT
CAGCAGCAATAACCAGCATGTCTCTTGCACTAAAGAGATTCAAATTCGTGGAGAAATTCATACAAACGTTGATTAC
ACGGTTGATCTCTTGAATGCCCAGACTTCAGAGAAAACACGATCCATACCGGTTGGCTGGATACCAGAATAGCTAT
GGGTGTTCAAGCTGAGAGGCCTCCTGGTATATTCAGTGGTTGGAGGAGCTCTATATAAACAATAACCACCAATG
CGGAGACCGTTTCTGAATATGTTAGCTATCTCATCAAGGGTCAGATTCCACCAAAGCCACAGATCCCTTGTTATTCA
ACTATTTCTTTGAATATAGAGCAAACCAAATATACAATTGAGATTGTCAGGAGTGGACAGGTAGCTACAGATTGAG
ACTGAATGGATCACTTATTGAAGCCAATGTACAAACATTATGTGATGGAGGCCTTTTAATGCAGCTGGATGGAAATA
GCCATGTTATTTATGCTGAAGAGGAAGCCGGGTGGTACACGGCTTCTTATTGATGGAAAAACATGCTTGCTACAGAAT
GACCATGATCCGTCAAGGTTATTAGCTGAGACACCCTGCAAACTTCTTCGTTTCTTGATTGCCGATGGTGCTCATGT
TGATCCTGATCTACCATACGCCGGACTTGAGGTTATGAAGATGTGCATGCCCCTCTTGTCGCCTGCTGCTGGTGCCA
TTAATGTTTTGTTGCTCGAGGGCCAGGCGATGCAGGCTGGTGATCTTATAGCGAGACTTGATCTCGATGACCCTTCT
GCCTGTGAAGAGAGCCGAGCCATTTGAAGGATCTTTTCCAGAAATGAGCCTTCCTATTGCTGCTTCTGGCCAAGTTCA
CAAAAGATGTGCTCAAGTTTGAACGCTGCTCGAATGGTCCTTGCAGGATATGACCATGGCCAACAAAGTTGTGC
AAGATTTGGTATCGTGCCTTGATACACCTGCTCTCCTTCCTACAATGGAAGACACGCTTATGTCTCTTTTAGCAACT
AGACTTCCAAGACGTCTTAAGACGCCATGGAGGGCAAATACAATGAATACAAGTTAAATGTTGACCCATGTGAAGAT
CAAGGATTTCCCTACCGAGATGCTTAGAGAGACAATCGAGGAAAATCTTGCATGTGTTTCCCAGAAGGAAATGGTGA
CAATTGAGAGGCTTGTTGACCCTCTGATGACCCTGCTGAAGTCATACGAGGGTGGGAGAGAAAGCCATGCCCACTTT
ATTCTCAAGTGCCTTTTTCGAGGAGTATCTCTCGCTTCACGAACTATTCAGTGATGCCATTCAGTCTGACGTGATTGA
ACGCCTGCGCCTACAATATAGTAAGACCTCCAGAAGGTTGTAGACATTGTTTTGTCTCACCAGGGTGTGAGAAACA
AAACAAAGCTGATACTGGCGCTCATGGAGAAACTGGTCTATCCAAACCCTGCTGCCTACAGAGATCAGTTGATTCGC
TTTTCTTCCCTCAACCATAAAAGATATTATAAGTTGCCTCTTAAAGCTAGTGAACTTCTTGAACAAACCAAGCTCAG
CGAACTCCGCACAAGCATTGCAAGGAACCTTTCAGCGCTGGATATGTTCACCGAGGAAAAGGCAGATTCTCCTTGC
AAGACAGAAAATTGGCCATTAATGAGAGCATGGAGATTTAGTCACTGCCCCACTGCCAGTTGAAGATGCACTTGTT
TCTTTGTTTGATTGTACTGATCAATCTTCAGCAGAGATGATCAGACATACATATCCTCATTATACCGCCCTCA
ACTTGTGAAGGATAGCATCCAGCTGAAATCAGGATTCTGGTGTTATTGCTTATGGGAATTCACTGAAGGAAATC
ATGAGAAGAGATTGGGTGCTATGGTTATCCTGAAGTCACTAGAAACTGTGTCAACAGCCATTGGAGCTGCTCTAAAG
GATGCATCACATTATGCAAGCTCTGCGGGCAACACGGTGCATATTGCTTTGTTGGATGCTGATACCCAACTGAATAC
AACTGAAGATAGTGGTGATAACACCCAAGCTCAAGACAAGATGGATAAACTTTCTTTTGTACTGAAACAAGATGTTG
TCATGGCTGATCTACCTGCTGCTGATGTCAAGGTTGTTAGTTCCATTGTTCAAAGAGATGGCAGCAATCATGCCTATG
CGCCGTACCTTCCTCTTGTCAGAGCAAAACTTTGTTACGAGGAAGAGCCGATTCTTCGGCATGTGGAGCCTCCACT
TTCTGCACTTCTTGAGTTGGATAAATTCAAAGTCAAGGATACAATGAGATGAAGTATACACCGTCACGTGATCGTC
```

FIGURE 14A (continued)

```
AGTGGCATATATACACACTTAGAAATACTGAAAATCCAAAAATGCTGCACAGGGTATTTTCCGAACACTGTCAGA
CAACCCAGTGCAGGCAACAGGTTTACATCAGACCATATCACTGATGTTGAAGTAGGACACGCAGAGGAACCTCTTTC
ATTTACTTCAAGCAGCATATTAAAATCCTTGAAGATTGCTAAACAACAATTGGAGCTTCACGCCATCAGGACTGGCC
ATTCTCATATGTACTTGTGCATATTGAAAGAGCGAAAAGCTTCTTGACCTTCTTCCTGTTTCAGGGAACACTGTTGTG
GATGTTGGTCAAGATGAAGCTACTGCATGCTCTCTTTGAAAGAAATGGCTTTAAAGATACATGAACTTGTTGGTGC
AAGAATGCATGATCTTTCTGTATGCCAGTGGGAAGTGAAACTTAAGTTGGTGAGCGATGGCCTGCCAGTGGTAGCT
GGAGAGTTGTAACAACCAATGTTACTGGTCACACCTGCACTGTGGATATCTACCGGCAGGTCGAAGATACAGAATCA
CAGAAACTACTATACCACTCCACCCCATTGCCATCTCCTCCTTTCCATCGTCTTCCACTGAATACTTCGTATCAGCC
TTTGAGTGTTATTGATTTAAAACGTTGCTCTGCCAGGAACAACAAAACTACATACTGCTATGATTTCCATTGACAT
TTGAAGCTGCACTGCAGAAGTCGTGGTCGAACATTTCCAGTGAAAACAACCAATGTTATGTTAAAGCGACAGAGCTT
GTCTTTGCTGAAAAGAATGGGTCGTGGGGCACTCCTATAATTCCTATGCAGCGTGCTGCTGGCTGAATGACATTGG
TATGGTAGGCTGGCATCTTGCACATGTCCCACTCCTGAATTCCAGCGGCACACACATCATTCTTATCCAAATGATA
TTACATTTAGAGCTGGATCATTTGGCCAAGGGAAGATGCATTTTCGAAGCTGTAACGAACCTGGCTTGTGAGAAG
AAGCTTCCACTTATCTACTTGGCTGCAAACTCTGGTGCTCGGATTGGCATTGCTGATGAAGTAAAATCTTGCTTCCG
TGTTGGATGGACTGATGATAGCAGCCCTGAACGTGGATTTAGGTACATTTATATGACTGACGAAGACCATGATCGTA
TTGGCTGTTCAGTTATAGCACACAAGATGCAGCTAGATAGTGGCGACATCACGTGCGTTATTCATTCTGTTGTGCGA
AAAGAGGATGGACTAGGTGTGGAGAACATACATGGAAGTGCTGCTATTGCCAGTGCCTATTCTAGGGCGTACGAGGA
GACATTTACACTTACATTCGTTACTGGACGAACTGTTGGAATCGGAGCCTATCTTGCTCGACTTGGCATACGGTGCA
TACAGCGTATTGACCAGCCCATTATTTTGACCGGGTTTTCTGCCCTGAACAAGCTTCTTGGCGGGAGGTGTACAGC
TCCCACATGCAGTTGGGTGGTCCCAAAATCATGGCCACGAATGCTGTTGTCCATCTCACTCTTCCAGATGACCTTGA
AGGTGTTTCTAATATATTGAGGTGGCTCAGCTATGTTCCTGCAAACATTGGTGGACCTCTTCCTATTACAAAATCTT
TGGACGCCAATAGACAGACCCGTTGCTACATCCCTGAGAATACATGTGATCCTCGTGCAGCCATCAGTGGCATTGAT
GACAGCCAAGGGAAATGGTTGGGTGGCATGTTTGACAAAGACAGTTTTGTGGAGACATTTGAAGGATGGGCGAAGAC
AGTAGTTACTGGCACACCAAAAACTTGGAGGCATTCCTCTTGGTGTTATAGCTGTGCACACACAGACCATCATCCACGC
TGGTGCCGCTGATCCAAGGCCAGCCTGATTCCCACGAGCGGTCTGTTCCTCCTGCTGGCAAGTTTGGTTTCAGAT
TCTGCTACCAAGACAGCGCAGGCATGTTGGACTTCAACCGTGAAGGATTACCTCTGTTCATACTTGCTAACTGGAG
AGGCTTCTCTGGAGGGCAAAGAGATCTTTTTGAAGGAATTCTGCAGGCTGGGTCAACAATTGTTGAGAACCTTAGGA
CATACAATCAGCCTGGCTTTGTATATATCCCGAAGCCTCCAGAGCCTACGTGCAGCAGCCTGGCTCCTCATTCATAGC
AAGATAAACCCAGATCGCATCGATGCTATGCTGAGAGGACTGCAAAGGGTAATGTTCTCGAACCTCAAGGGTTGAT
TGAGATCAAGTTCAGGTCAGATAAACTCAAAGAATGCATGGGTAGGCTTGATCCAGAATTCATAGATCTGAAAGCAA
GACTCCAGGGAGCAAATGGAAGCCTATCTGATGGACAATCCCTTCAGAACAGCATAGAAGCTGGGAAGAAACAGTTG
GTCCCTCTGTACACCCAAATGCCGGCTACGTTTTGCGGAATTGCACGGACACTTCCCTTAGAATGGCTGCTAAAGGTGT
GATCAGGAAAGTTGTAGACTGGGAACACTCTCGGTCTTTCTTCTACAAGAGATTACGGAGCAGGCTATCCGAGGACG
TTCTGGCAAAGGGAGATTAGAGGTGTAATTGGTGAGAAGTTCCTCACAAATCAGCGATCCGCCTGATCAAGAAATGG
TACTTGGCTTCTGAGGCAGCTGTAGCAGGAAGCACCGACTGGGATGACGACGATGCTTTTGTCGCCTGGAGGGAGAA
CCCTGAAAACTATAAGGAGTATATCAAAGAGCTTAGGCTCAAAGGGTATCTCGGTTGCTCTCAGATGTTGCAGGCT
CCAGTTCGGATTACAAGCCTTGCCCGCAGGGTCTTCCATGCTACTAGATAAGATGGATCCCTCTAAGAGAGCACAG
TTATCGAGGAGGTCATGAAGGTCCTGAAATGA
```

FIGURE 14B

```
>CAC84161 Alopecurus myosuroides (black-grass)
MGSTELPIVGFNASTTPSLSTLRQINSAAAAFQSSSPSRSSKKKSRRVKSIRDDGDGSVPDPAGHGQSIRQGLA
GIIDLPKRGASAPDVDISHGSEDHKASYQMNGILNESHNGRHASLSKVYEFCTELGGKTPIRSVLVANNGMAAA
KFMRSVRTWANDTFGSEKAIQLIAMATPRDMRINAEHIBIADQFVEVPGGTNHNNYANVQLIVEIAERTGVSAV
WPGWGHASENPELFDALTAKGIVFLGPPASSMNALGDKVGSALIAQAAGVPTLAWSGSHVEIPLELCLDSIPEE
MYRKACVTTADEAVASCQMIGYPAMIKASWGGGGKSIRKVNNDDEVKALFKQVQGRVPGSPIFIMRLASQSREL
RVQLLCDKYGNVAALHSKDCSVQRRHQKIIEKGPVTVAPRETVKELEQAARRLAKAVGYVGAATVEYLYSMETG
RYYFLELNPRLQVEHFVTESTAEVNLPAAQVAVGMGIPLWQIPEIRRFYGMDNGGGYDIWRRKTAALATPSNFDE
VDSQWFKGHCVAVRITSENPODGFKPTGGRVKEISFKSKPNWGYFSVKSGGGIHEFADSQFGHVFAYGETRSA
AITSMSLAIKEIQIRGRIHTNVDYTVDLINAPDFRENTIETGWLDTRIAMRVQAERPPWYISVVGGALYKTITT
NAETVSEYVSYLIKGQIFPKHISLVESTISLNIEESKYTIEIVRSGQSYRLRLMGSLIEANVQTLCDGGLIMQ
LDGNSHVIYAEEEAGGTRLLIDGKTCLLQNDHDPSRLLAETPCKLLRFLIADGAHVDADVPYAEVEVMRMCMPL
LSPAAGVINVLLSEGQAMQAGDLIARLDLCDPSAVKRAEPFFEGSFPEMSLPTAASGQVEKRCAASLNAARMVLA
GYDRAANKVVQDLVWCLDTPALPFLQWEELMSVLATRLPRRLKSELEGKYNEYRLNVDHVKIKDEPTEMLRETI
EENLACVSEKEMVTIERLVDPIMSLLKSYEGGRESHAEFIVKSLFEEYLSVEELFSDGIQSDVIERLRLQYSKD
LQKVVDIVLSHQGVRNKTKIILALMEKLVYPNPAAFRDQLIRFSSLNEKRYYKLALKASELLEQTKLSELETSI
ARNLSALEMFTEEKADFSLQDRKLAINESMGDLVTAPLFVEDALVSLFDKTDQTLQQRVIQTYISRLYQPQLVK
DSIQLKYQDSGVIALHRFTEGNHEKRLGAMVILKSLESVSTAIGAALKDASHYASSAGNTVHIALLDADTQLNT
TEDSGDNDQAQDKMDKLSFVLKQDVVMADLRAADVKVVSCIVQRDGAINPMRRTFLLSEEKLCYREEPILRHVE
PPLSALLELDKLKVKGYNEMKYTPSRDRQWHIYTLRNTENPKMLSSVFFRTLVRQPSAGNRFTSDHITDVEVGR
AEEPLSFTSSSILKSLKIAKEELELRAIRTGHSRMYLCILKEQKLLDLVPVSGNTVVDVGQDEATACSLLKEMA
LRIRRLVGARMHHLSVCQWEVRLKLVSDGFASGSWRVVTTNVTGETCTVDIYREVEDTESQKLVYHSTALSSGP
LHGVALNTSYQFLSVIDLKRCSABNNKTTYCYDFPLTFEAAVQKSWSNISSENNQCYVKATELVEAERNGSWGT
PIIPMQRAAGLSNDIGMVAWILDMSTPEFPSGRQIIVIANDITFRAGSFGPREDAFFEAVTNLACEKKLPLIYLA
ANSGARIGIADEVRSCFRVGNTDDSSPERGFRYIYMTDEDHDRTGSSVIARKMQLDSGEIRNVIDSVVGREDGL
GVENIHGSAAIASAYSRAYEETFTLTFVTGRTVGIGAYLARLGIRCIQRIDQPIILTGFSALNKLLGREVYSSR
MQLGGPKIMATNGVVHLTVPODLEGVSNIIRWLSYVPANIGGPLFITKSLDPIDKPVAYIPENTCDPRAAISGI
DDSQGKWLGGMFDKDSFVETFRGWAKTVVTGRAKLSGIPVGVIAVETQTMMQLVPADFGQPDSHERSVPRAGQV
WFPDSAPKTAQAMLDFNREGLPLFILANWRGFSGGQRDLFEGILQAGSTIVENLRTYNQPAFVYIPKAAELRGG
AWVVIDSKINFDRIECYAERTAKGNVLRPQGLIEIKFRSEELKECMGRLDPELIDLKARLQGANGSLSDGESLQ
KSIEARKKQLLPLYTQIAVRFAELHDTSLRMAAKGVIRRVVDWEDSRSFFYKRLRRHLSEDVLAKETRGVIGEK
FPHKSAIELIKKWYLASEAAAAGSTDWDDCDAFVAWFRENPENYKRYIKELRAQRVSRLLSDVAGSSSOLQALFQ
GLSMLIDKMDPSKRAQFIEEVMKVLK
```

FIGURE 15A

```
>EU660887_Aegilops tauschii (jointed goatgrass)
ATGGGATCCACACATTTGCCCATTGTCGGCCTTAATGCCTCGACAACACCATCGCTATCCACTATTCGCCCGGTAAA
TTCAGCCGGTGCTGCATTCCAACCATCTGCCCCTTCTAGAACCTCCAAGAAGAAAAGTCGTCGTGTTCAGTCATTAA
GGGATGGAGGCGATGGAGGCGTGTCAGACCCTAACCAGTCTATTCGCCAAGGTCTTGCCGGCATCATTGACCTCCCA
AAGGAGGGCACGTCAGCTTCGGAAGTGGATATTTCACATGGGTCGAAGGACCCAGGGCCTCCTACCGAATGAATGG
GATACTGAATGAAGCACGTAATCGGAGGCATGCTTCGCTGTCTAAGGTTGTCGAATTTGTATGGCATTGGCCGGCA
AAACACCAATTCATAGTGTATTAGTTGCGAACAATGGAATGGCAGCAGCTAAGTTCATGCCGAGTCTCCGAACATGG
GCTAATGAAACATTTGGGTCAGCGAAGGCAATTCAGTTGATAGCTATGGCTACTCCAGAAGACATGAGGATAAATGC
AGAGCCATTAGAATTGCTGATCAATTTGTTGAAGTACCCGGTGGAACAACAATAACAACTATGCAAATGTCCAAC
TCATAGTGGAGATAGCAGTGAGAACCCGGTGTTTCTGCTGTTTGGCCTGGTTGCGGCCATGCATCTGAGAATCTCAA
CTTCCAGATCCACTAAATCCAAACCCAATTCTTCCGCCACCATCATCATCAATGAACCACTAGGTGACAA
GGTTCGTTCAGCTCTCATTGCTCAAGCAGCAGGGGTTCCGACTCTTCCTTGGAGTGGATCACACGGTGGAAATTCCAT
TAGAAGTTTGTTTGGACTCGATACCTGCGGATATGTATAGGAAAGCTTGTGTTAGTACTACGGAGGAAGCACTTGCG
AGTTGTCAGATGATTGGGTATCCAGCCATGATTAAAGCATCATGGGGTGGTGGTGGTAAAGGATCCGAAGGTTAA
TAACGACGATGATGTCAGAGCACTGTTTAAGCAAGTGCAAGGTGAAGTTCCTGGCTCCCCAATATTTATCATGAGAC
TTGCATCTCAGAGTCGACATCTTGAAGTTCAGTTGCTTTGTGATCAATATGGCAATGTAGCTGCGCTTCACAGTCGT
GACTGCAGTGTGCAACGGCGACACCAAAAGATTATTCAGGAAGGACCAGTTACTGTTGCTCCTCGCGAGACAGTGAA
AGAGCTAGAGCAAGCAGCAAGGAGGCTTGCTAAGGCTGTGGGTTATGTTGGTGCTGCTACTGTTGAATATCTCTACA
GCATGCAGACTGCTGAATACTATTTCTGGACTTAATCCACCGGTTGCAGGTTGCAGCATCCCACGTCACCAGTGGATA
GCTGAAGTAAACTTGCCTGCAGCGCAAGTTGCAGTTGGAATGGGTATACCCCTTTGGCAGGTTCCAGAGATCAGACG
TTTCTATGGAATGGACAATGGAGGAGGCTATGACATTGGAGGGAAAACAGCAGCTCTTGCTACCCCATTAACTTTG
ATGAAGTGGATTCTCAATGGCCAAAGGGTCATTGTGTAGCAGTTAGGATAACCAGTGAGGATCCAGATGACGGATTC
AACCCTACCGGTGGAAAAGTAAAGGAGATCAGTTTTAAAAGCAAGCCAAATGTTTCGGCCTATTCTCTCGTTAAGTC
CGGTGGAGGCATTCATGAATTTGCTCGATTCTCAGTTTGGACATGTTTTTGCATACGGAGTGTCTAGAGCAGCAGCAA
TAACCAACATGTCTCTTGCGCTAAAGAGATTCAAATTCGTGGAGAAATTCATTCAAATGTTGATTACACAGTTGAT
CTCTTCAATGCCTCGACTTCAAAGAAAACAGGATTCATACTGGCTGGCTGGATAACAGAATAGCAATGCCAGTCCA
AGCTCAGAGACCTCCCTGGTATATTCAGTGGTTGCAGGAGCCTCTATATAAAACAATAACGACCAACACAGACACTG
TTCTGAATATGTTAGCTATCTCCTCAAGGGTCAGATTCCACCGAAGCATATATCCCTTGTCCATTCAACTGTTTCT
TTGAATATAGAGGAACAAAATACAATTGAACCTATAAGGAGCGGACGGAGTAGCTACAGATTGCGAATCAATGG
ATCAGTTATTGAAGCAAATGTCCAAACATTATGTGATGGTGGACTTTTAATGCACTGTGGATGGAAACAGCCATGTAA
TTTATGCTGAAGAAGAGGCCGGTGGTACACGGCTTCTAATTGATGGAAAGACATGCTTGTTACAGAATGATCACGAT
CCTTCAAGGTTATTAGCTGAGACACCCTGCAAACTTCTTCGTTTCTTGGTTGCGATGTGCTCATGTTGAAGCTGA
TGTACCCATATGCCGAAGTTGAGGTTATGAAGATGTGCATGCCCCTCTTGCCACCTGCTGCTGGTGTCATTAATGTTT
TGTTGTCTGAGGGCCAGCCTATGCAGGCTGGTGATCTTATAGCAAGACTTGATCTTGATGACCCTTCTGCTGTGAAG
AGAGCTGAGCCGTTAACGGATCTTTCCCAGAAATGAGCCTTCCTATTGCTGCTTCTGCCAAGTTCACAAAAGATG
TCCCACAAGCTTGAATGCTGCTGCGATCGTCCTTGCAGGATATGATCACCCGATCAACAAATTCGTACAACATCCTGG
TATCCTGTCTAGATGCTCCTGAGCTTCCTTTCCTACAATGGGAAGAGCTTATGTCTGTTTAGCAACTAGACTTCCA
AGGCTTCTTAAGAGCGAGTTGGAGGGTAATACAGTGAATTACAGTCCATCTTGCCGAGGATAGTATCCAGCTGAAATATCAGGA
CCCTTCCAAGATCTTAAGAGGAGATAATCAGGCAAAATCTTCCACATGGTTCTCAGAGGCAAATTGCTACAAATGAGA
GGCTTCTTGAGCCTCTTATGAGCCTACTGAAGTCATATGAGGGTGGCAGGCAAAGCCATGCACACTTTATTGTGAAG
TCCCCTTTTTCGAGGACTATCTCTCGGTTGAGGAACTATTCAGTGATGGCATTCAGTCTGATGTGATTGAACGCCTGCG
GCAACAACATAGTAAAGATCTCCTAGAAGGTTCTAGACATTCTGTTGTCTCACCAGGGTGTGGAAACAAAACTAAGC
NGATACTAACACTCATGGAGAAACTGCTCTATCCAAACCCTGCTCCTACAAGGATCGTTGACTCGCTTTTCCTCC
CTCAATCGCAAAAGATAGTATAAGTTGGCCCTTAAAGCTAGCGAGCTTCTTGAACAAACCAAGCTTAGTGACCTCCG
CACAAGCATTGCAAGGAGCCTTTCAGAACTTGAGATGTTTACTGAAGAAAGGACGGCCATTAGTGAGATCATGGGAG
ATTAGTGACTGCCCCACTGCCAGTTGAAGATGCACTGGTTTCTTTGTTTGATTGTAGTGATCAAACTCTTCAGCAG
AGGGTGATCGAGACGTACATATATCCGATTATACGAGCCTCATCTTGCCAAGGATAGTATCCAGCTGAAATATCAGGA
ATCTGGTGTTATTGCTTTATGCGAATTCGCTCAAGCCCATTCAGAGAACAGATTCGGTCCTATGGTTATTGTGAAGT
CGTTAGAATCTGTATCAGCAGCAATGGAGCTGCACTAAAGGGTACATCACGCTATGCAAGCTCTGAGGGTAACATA
ATGCATATTGCTTTATTGGGTGCTGATAATCAAATGCATGGAACTGAAGCACTGGTGATAACGATCAGGCTCAAGT
CAGGATAGACAAACTTTCTGCGACACTGGAACAAAATACTGTCACAGCTGATCTCCGTGCTGCTGGTGTGAAGGTTA
TTAGTTGCATTGTTCAAAGGGATGGAGCACTCATGCCTATCGCCATACCTTCCTCTGTCGGATGAAAGCTTTGT
TATGAGGAAGAGCCGGTTCTCCGGCATGTGGAGCCTCCTCTTTCTGCTCTTCTTGAGTTGGGTAAGTTGAAAGTGAA
AGGATACAATGAGGTGAAGTATACACCGTCACGTGATCGTCAGTGGAACATATACACACTTAGAAATACAGAGAACC
```

FIGURE 15A (continued)

```
CCAAAATGTTGCACAGGCTGTTTTTCCGAACTCTTGTCAGGCAACCCGGTGCTTCCAACAAATTCACATCAGGCAAC
ATCACTCATCTTCAACTCCCAGCAGCTCAGGAATCTCTTTCATTTACATCCACCACCATATTAACATCCCTCATCAC
TGCTATAGAAGAGTTGGAGCTTCAGCCGATTAGGACAGGTCACTCTCATATGTTTTTGTGCATATTGAAAGAGCAAA
AGCTTCTTGATCTTGTTCCCGTTTCAGGGAACAAAGTTGTGGATATTGGCCAAGATGAAGCTACTGCATGCTTGCTT
CTGAAAGAAATGGCTCTACAGATACATGAACTTGTCGGTGCAAGGATGCATCATCTTTCTGTATGCCAATGGCAGGT
GAAACTTAACTTCGACAGCGATGGCCCTGCCAGTGGTACCTGGAGAGTTCTAACAACCAATGTTACTACTCACACCT
GCACTGTGGATATCTACCGTGAGGTTCAAGATACAGAATCACAGAAACTAGTGTACCACTCTGCTCCATCGTCATCT
GGTCCTTTGCAGGCCTTGCACTGAATACTTCATATCAGCCTTTGAGTGTTATTGATCTGAAACGTTGCTCCGCTAG
AAATAACAGAACTACATACTGCTATGATTTTCCGTTGGCATTTGAAACTGCAGTGCAGAAGTCATGGTCTAACATTT
CTAGTGACACTAACCGATGTTATGTTAAAGCGACGGAGCTGGTGTTTGCTCACAAGAACGGGTCATGGGCACTCCT
GTAAATCCTATGGACCGTCCTGCTGGCTCAATGACATTGGTATGGTAGCTTGGATCTTGGACATGTCCACTCCTGA
ACATCCCAATGGCAGCCAGATTGTTGTCACGCAAATGATATTACTTTAGAGTGCATCGTTTGCTCCAAGGGAAG
ATGCATTTTTGAAACTGTTACCAACCTAGCTTGTGCACAGGAAGCTTCCTCTCATCTACTTGGCAGCAAACTCTGGT
GCTCGGATCGGCATAGCAGATGAAGTAAAATCTTGCTTCCGTGTTGGATGGTCTGATGATGGCAGCCCTGAACGTGG
GTTCAATATATTATCTGACTGAAGAAGACCATGCTCGTATTAGCGGCTTCTGTTATACGGCACAAGATGCAGCTTG
ATAATGGTGAAATTAGGTGGGTTATTCATTCTGTTGTAGGGCAAGGAGGATCGGCTACGTGTGGAGAACATACATGGA
AGTGCTGCTATTGCCAGTGCCTATTCTAGGGCCTATGACGAGACACATTTACCGCTTACATTCGACTGGAAGGACTCT
TGGAATAGGAGCATATCTTGCTCGACTTGGCATACGGTGCATTCAGCGTACTGACCAGCCCATTATCCTAACTGGGT
TCTCTGCCTTGAACAAGCTTCTTGGCCGGGAAGTGTACAGCTCCCACATGCAGTTGGTGGCCCAAAATTATGGCC
ACAAACGGTGTTGTCCATCTGACAGTTTCAGATGACCTTGAAGGTGTATCTAATATATTGAGGTGGCTCAGCTATGT
TCCTGCCAACATTGCTGGACCTCTTCCTATTAGAAAATCTTTGCACCCACCTCACAGACCCGTTGCTTACATCCCTG
AGAATACATGTGATCCTCCTGCAGCCATCAGTGGCATTGATGATACCCAAGCGAAATGGTTGGCGGCTATGTTCGAC
AAAGACAGTTTTGTCGAGACATTTGAAGGATGGGCGAAGTCAGTAGTTACTGGCAGAGCGAAACTCGGAGGGATTCC
GGTGGGTGTTATAGCTGTGGAGACACAGACTATGATGCAGCTCATCCCTGCTGATCCAGGTCAGCTTGATTCCCATG
AGCGGTCTGTTCCTCGTGCTGGGCAAGTCTGGTTTCCAGATTCAGCTACTAAGACAGCGCAGGCAATGCTGGACTTC
AACCGTGAAGGATTACCTCTGTTCATCCTTGCTAACTGGAGAGGCTTCTCTGGTGGGCAAAGAGATCTTTTGAAGG
AATCCTTCAGGCTGGGTCAACAATGTTGAGAACCTTAGGACATACAATCAGCCTGCCTTTGTATATATCCCCAAGG
GTGCAGAGCTACGTGGAGGGCTTGGGTCGTGATTGATAGCAAGATAAATCCAGATCGCATTCAGTTCTATGCTGAG
AGGACTGCAAAGGGCAATGTTCTTCAACCTCAACGGTTGATTCAGATCAACTTCACCTCACAGCAACTCCAACAGTG
CATGGGCAGGCTTGACCCAGAATTCATAAATTTGAAGCCAAAACTCCTGGCAGCAAAGCATGAAAATGGAAGTCTAT
CTGAGTCAGAATCCCTTCAGAAGAGCATAGAAGCCCGGAAGAAACAGTTGTTGCCTTTGTATACTCAAATTGCGGTA
CGGTTCGCTGAATTGCATGACACTTCCCTTAGAATGGCTGCTAAGGGTGTGATTAAGAAGGTTGTAGACTGGGAAGA
TTCTAGGTCTTTCTTCTACAAGAGATTACGGAGCACGATATCCAGGGTGTTCTTGCAAAGCAAATTAGAGCTGTAA
GTGGCAAGCAGTTTCTCACCAATCGGCAATCGAGCTGATCCAGAAATGGTACTTGGCCTCTAAGGGAGCTGAAACG
GGAAACACTGAATGGGATGATGACCGATCCTTTTGTTGCCTGGAGGGAAAACCCTCAAAACTACCGGAGTATATCAA
AGAACTCAGGGCTCAAAGGGTACCTCAGTTGCTCTCAGATGTTGCAGACTCCAGTCCAGATCTAGAAGCCTTGCCAC
AGGGTCTTTCTATGCTACTAGAGAAGATGGATCCCTCAAGGAGAGCAGTTTGTTCAGGAAGTCAACAAGGCCCTT
AAATGA
```

FIGURE 15B

```
>ACD46679_Aegilops tauschii (jointed goatgrass)
MGSTRLPIVGLNASTTPSLSTIRPVNSAGRAFQPSAPSRTSRKKSRRVQSLRDGGDGGVSDPNQSIRQGLAGII
DLPKEGTSAPEVDISHGSERPRGSYQMNGILNKAHNGRHASLSKVVEPCMALGGKTPIHSVLVANNGMAAAKEM
RSVRTWANETFGSEKAIQLIAMATPEDMRINAERIRIADQFVEVPGGTNNNKYANVQLIVEIAVRTGVSAVWFG
WGHASENFELPDALNANGIVFLGPFSSSMNALGDRVGSALIAQAAGVPTLFWSGSQVEIPLRVCLDSIPADMYR
KACVSTTBEALASCQMIGYPAMIKASWGGGGKGIRRVNNDDDVRALFKQVQGEVFGSPIFIMRLASQSRHLEVQ
LLCDQYGNVAALHSRDCSVQRRHQKIIERGPVTVAPRETVKELRQAARRLAKAVGYVGAATVEYLYSMETGEYY
FLELNPKLQVEHPVTEWIAEVNLPAAQVAVGMGIFLNQVPEIRRFYGMDNGGGYDIWRKTAALATPPNFDEVDS
QWPKGHCVAVRITSEDPDDGFKPTGGKVKEISFKSKPNVWAYFSVKSGGGIHEFADSQFGRVFAYGVSRAAAIT
NMSLALKEIQIRGEIHSNVDYTVDLLNASDFRENRIHTGWLDNRIAMRVQAERPPWYISVVGGALYKTITSNTD
TVSEYVSYLVKEQIPPRHISLVHSTVSLNIERSKYTIETIRSGQGSYRIRMNCSVIEANVQTLCDGGLLMQLDG
NSHVIYAEERAGGTRLLIDGKTCLLQNDHDPSRLLAETPCKLLAFLVADGAHVEADVPYAEVEVMHMCMPLLSP
AAGVINVLLSEGQPMQAGDLIARLDLDDFSAVKRAEFFNGSSFEMSLPIAASGQVHRKRCATSLNAARMVLAGYD
HPINKVVQDLVSCLDAPELPFLQWEELMSVLATRLPRLLKSELEGKYSEYKLNVGHGKSKDFPSKMLREITERN
LARGSEKEIATNERLVEPLMSLLKSYEGGRESHAHFIVKSLFEDYLSVEELFSDGIQSDVIERLRQQHSKDLQK
VVDIVLSHQGVRNKTRLILTIMEKLVYPNPAAYKDQLTRFSSLNHKRYYKLALKASELLEQTKLSELRTSIARS
LSRLEMFTEERTAISEIMGDLVTAPLPVEDALVSLFDCSDQTLQQRVIETYISRLYQPHLVKDSIQLKYQESGV
IALWEFAEAHSERRLGAMVIVKSLESVSAAIGAALRGTSRYASSEGNIMSIALLGADNQMHGFEDSGDNDQAQV
RIDKLSATLEQNTVTADLRAAGVKVISCIVQRDGALMPMRHTFLLSDEKLCYEEEPVLRRVEPPLSALLELGKL
KVKGYNEVKYTPSRDRQWNIYTLRNTRNFKMLHRVFFRTLVRQPGASNKFTSGNISCVEVGQAEESLSFTPSSSI
LRSLMTAIEELELRAIRTGHSRMFLCILKEQKLLDLVPVSGNKVVDIGQDEATACLLLREMALQIHELVGARMH
HLSVCQWEVKLKLDSDGFASGTWRKVVTTNVTSHTCTVDIYREVEDTESQKLVYHSAPSSSGPLHGVALNTPYQF
LSVIDLKRCSARNNETTYCYDFFLAFETAVQKSWSNISSDTNRCYVKATELVFARKNGSWGTPVIFMERPAGLN
DIGMVAWILDMSTPEYPNGRQIVVIANDITFRAGSFGPREDAFFETVINLACERRLFLIYLAANSGARIGIADE
VKSCFRVGWSDDGSPRRGFQYIYLTEEDHARISASVIAHKMQLINGEIRWVIDSVVGKEDGLGVENIHGSAAIA
SAYSRAYREFFFTLTFVTGRTVGTGAYLARLGIRCIQRFDQPIILTGFSAINKLLGREVYSSHMQLGGPKIMATN
GVVHLTVSDDLEGVSNILRWLSYVPANIGGPLPITKSLDPPDRPVAYIPENTCDPRAAISGIDESQGKWLGSMF
DKDSFVETFEGWAKSVVTGRAKLGGIPVGVIAVETQTMMQLIPADFGQLDSHERSVPRAGQVWFPDSATKTAQA
MLDFNREGLPLFILANWRGFSGGQRDLFEGILQAGSTIVENLRTYNQPAFVYIFKAAELRGGANVVIDSKINFD
RIEFYAERTAKGNVLEPQGLIEIKFRSEELQECMGRLDPEIINLRAKLLGARHNGSLSESESLQRSIEARKKQ
LLPLYTQIAVRFAELHDTSLRMAAKGVIRKVVDWEDSRSFFYKRLRRRYSEDVLAKEIRGVSGKQFSRQSAIEL
IQKWYLASKQAETGRTRWDDDDAFVAWRENPENYQRYIKELRAQRVSQLLSDVADSSPDLEALPQGLSMLLEKN
DFSRRAQFVEEVKKALK
```

FIGURE 16

| ACCase Mutation | Selections Agent | #exp | # lss | # Putative events | Putative TE | # Confirmed events | Confirmed TE | % escapes |
|---|---|---|---|---|---|---|---|---|
| RLM183 | pursuit | 2 | 27 | 15 | 56% | 14 | 52% | 4% |
| | cycloxydim | 2 | 29 | 0 | 0% | 0 | 0% | 0% |
| | tepraloxydim | 2 | 29 | 0 | 0% | 0 | 0% | 0% |
| I783L | pursuit | 2 | 40 | 22 | 55% | 21 | 53% | 3% |
| | cycloxydim | 2 | 50 | 16 | 32% | 15 | 30% | 2% |
| | tepraloxydim | 2 | 50 | 0 | 0% | 0 | 0% | 0% |
| I1781L, W202C | pursuit | 2 | 40 | 10 | 25% | 9 | 23% | 3% |
| | cycloxydim | 2 | 50 | 20 | 40% | 20 | 40% | 0% |
| | tepraloxydim | 2 | 50 | 11 | 22% | 11 | 22% | 0% |
| I1781L, D1041N | pursuit | 2 | 40 | 10 | 25% | 9 | 23% | 3% |
| | cycloxydim | 2 | 50 | 12 | 24% | 12 | 24% | 0% |
| | tepraloxydim | 2 | 50 | 14 | 28% | 14 | 28% | 0% |
| I783A | pursuit | 2 | 35 | 16 | 46% | 14 | 40% | 6% |
| | cycloxydim | 2 | 50 | 0 | 0% | 0 | 0% | 0% |
| | tepraloxydim | 2 | 50 | 0 | 0% | 0 | 0% | 0% |
| Wild Type | pursuit | 2 | 30 | 16 | 53% | 15 | 50% | 3% |
| | cycloxydim | 2 | 50 | 0 | 0% | 0 | 0% | 0% |
| | tepraloxydim | 2 | 50 | 0 | 0% | 0 | 0% | 0% |

FIGURE 18

```
   1 MGSTHLPIVG PWASTTPSLS TLRQINSAAA APQSSSPSRS SKKKSRRVKS IRDDGDGSVP
  61 DPAGHGQSIR QGLAGIIDLP KEGASAPDVD ISKGSEDHKA SYQMNGILNE SHNGRHASLS
 121 KVYEPCTELS GKTPIHSVLV ANNGMAAAKF MRSVRTWAND TPGSEKAIQL IAMATPEDMR
 181 INAEHIRIAD QPVEVPGGTN NNNYANVQLI VEIAERTGVS AVWPGWGHAS ENPSLPDALT
 241 AKGIVFLGPP ASSMNALGDK VGSALIAQAA GVPTLAWSGS HVEIPLELCL DSIPEEMYRK
 301 ACVTTADEAV ASCQMIGYPA MIKASWGGGG KGIRKVNNDD EVKALFKQVQ GEVPGSPIFI
 361 MRLASQSRHL EVQLLCDEYG NVAALHSRDC SVQRRHQKII EEGPVTVAPR STVKELEQRA
 421 RRLAKAVGYV GAATVEYLYS METGEYYFLE LNPRIQVEHP VTESIAEVNL PAAQVAVGMG
 481 IPLWQIPEIR RFYGMDNGGG YDIWRKTAAL ATPFNFDEVD SQWPKGHCVA VRITSENPDD
 541 GFKPTGGKVK EISFKSKPNV WGYFSVKSGG GIHEFADSQF GHVFAYGETR SAAITSMSLA
 601 LKRIQIRGEI HTNVDYTVDL LNAPDFRENT IHTGWLDTRI AMRVQAERPP WYISVVGGAL
 661 YKTIPTNAST VSEYVSYLIK GQIPPKHISL VHSTISLNIR ESKYPIEIVR SGQGSYRLRL
 721 NGSLIEANVQ TLCDGGLLEQ LDGNSHVIYA SSEAGGTRLL IDGKTCLLQN DHDPSRLLAS
 781 TPCKLLRFLI ADGAHVDADV PYAEVEVMSM CMPLLSPAAG VTNVLLSEGQ AMQAGDLIAR
 841 LDLDDPSAVK RAEPFEGSFP SMSLPIAASC QVRKRCAASL NAARMVLAGY DHAANKVVQD
 901 LVWCLDTFAL PFLQWEELNS VLATRLPRRL KSELEGRYNR YKLNVDSVKI KDFPTEMLRE
 961 TIEENLACVS EKEMVTIRRL VDPLMSLLKS YEGGRESHAH FIVKSLFEEY LSVEELFSDG
1021 IQSDVIERLR LQYSKELQKV VDIVLSHQGV RNKTKLIIAL MEKLVYPNPA AYRDQLIRFS
1081 SLNHKRYYKL ALKASELLEQ TKLSELRTSI ARNLSALDMF TEEKADFSLQ DRKLAINESM
1141 GDLVTAPLPV SDALVSLFDC TDQTLQQRVI QTYISRLYQP QLVKDSIQLK YQDSGVIALW
1201 EPTEGNHEKR LGAMVILKSL RSVSTAIGAA LKDASHYASS AGNTVHIALL DADTQLNTTE
1261 DSGDNDQAQD KMDKLSFVLK QDVVMADLRA ADVK/VSCIV QRDGAIMPMR RTFLLSEEKL
1321 CYREEFILRH VSPPLSALLE LDKLKVKGTN SMKYTPSRDR QWHIYTLRNT ENPKKLHRVF
1381 FRTLVRQPSA GNRFTSDHIT DVSVGHASEP LSFTSSSILK SLKIAKEELE LHAIRTGHSH
1441 MYLCILKEQK LLDLVPVSGN TVVDVGQDEA TACSLLREMA LKIHELVGAR MHRLSVCQWE
1501 VKLKLVSDGP ASGSWRVVPT NVTGHTCTVD IYREVEDTES QKLVYHSTAL SSGPLHGVAL
1561 NTSYQPLSVI DLKRCSARNN KPTYCYDFPL TFEAAVQKSW SNISSENNQC YVKATELVFA
1621 EKNGSWGTPI IPNQRAAGLN DIGMVAWILD MSTPEFPSGR QIIVIANDIT FRAGSPCPRE
1681 DAFFEAVTNL ACEKKLPLIY LAANSGARIG IADEVKSCFR VGWTDDSSPS RGFRYIYMTD
1741 SDHSRIGSSV IAHKMQLDSG RIBWVIDSVV GKEDGLGVEN IHGSAAIASA YSRAYEETFT
1801 LTFVTGRTVG IGAYLASLGI RCIQRIDQPI ILTGFSALMK LLGRRVYSSH MQLGGPKIMA
1861 TNGVVHLTVP DDLSGVSNIL RWLSYVPANI GGPLPITKSL DPIDRPVAYI PENTCDPRAA
1921 ISGIDDSQGK WLGGMFDKDS FVETFEGWAK TVVTGRAKLG GIPVGVIAVE TQTMMQLVPA
1981 DPGQPDSHER SVPRAGQVWF PDSATKTAQA MLDFNREGLP LFILANWRGF SGGQRDLFEG
2041 ILQAGSTIVE NLRTYNQPAF VYIPKAAELR GGAWVIDSK INPDRIECYA ERTAKGHVLE
2101 PQGLIEIKFR SSELKECMGR LDFELIDLKA RLQGANGSIS DGESLQKSIE ARKKQLLPLY
2161 TQIAVRFAEL HDTSLRMAAK GVIRKVVDWE DSRSFFYKRL RRRLSEDVLA KEIRGVIGEK
2221 FPHKSAIELI KKWYLASEAA AAGSTDWDDD DAFVAWRENP ENYKEYIKEL RAQRVSRLLS
2281 DVAGSSSDLQ ALPQGLSMLL DKMDPSKRAQ FIEEVMKVLK
```

FIGURE 19

|  |  |  | 1 |  | 60 |
|---|---|---|---|---|---|
| AmACCI | [CAC84161] | (1) | MGSTHLPTVGFNASTFPSLSTLRQINSAAAAPQSSPSRSSKKSSRRVKSIRDDGDGSVP |  |  |
| OsIACCI | [BGIOSIBCE018385] | (1) | MTSTHVATLGVGAQAFPRKQ-KKSAGTAFVSSGGSRFSYRKGGQRFSLREESNGGVS |  |  |
| OsJACCI | [EAZ33685] | (1) | MTSTHVATLGVGAQAFPRKQ---KKSAGTAFVSSGGSRFSYRKNGQRFSLREESNGGVS |  |  |

|  |  |  | 61 |  | 120 |
|---|---|---|---|---|---|
| AmACCI | [CAC84161] | (61) | DPAGHSQSIRQGIAGIIDLPKEGASAPDVOIEKGSEDREA------SQHNGILNSSRNGR |  |  |
| OsIACCI | [BGIOSIBCE018385] | (58) | DSKKLNSSIRQGIAGIIDLPNDAAS-EVDISKGSEDPRGPTVPGSYQHNGIINETENGR |  |  |
| OsJACCI | [EAZ33685] | (58) | DSKKLNKSIRQGIAGIIDLPNDAAS---EVDISKGSEDPRGPTVPGSYQHNGIINETENGR |  |  |

|  |  |  | 121 |  | 180 |
|---|---|---|---|---|---|
| AmACCI | [CAC84161] | (116) | EASLSKVYEPCTELGGKTPIHSVLVANNGMAAAKFMRSYRTWANDTFGSEEAIQLIAMAT |  |  |
| OsIACCI | [BGIOSIBCE018385] | (116) | EASVSKVVEFCTALGGKTPIHSVLVANNGMAAAKFMRSVRTWANDTFGSEEAIQLIAMAT |  |  |
| OsJACCI | [EAZ33685] | (116) | EASVSKVVEFCTALGGKTPIHSVLVANNGMAAAKFMRSVRTWANDTFGSEEAIQLIAMAT |  |  |

|  |  |  | 181 |  | 240 |
|---|---|---|---|---|---|
| AmACCI | [CAC84161] | (176) | PEDMRINAESIRIADQFVEVPGGTNNNYANVQLIVEIAERTGVSAVWPGWGHASENPEL |  |  |
| OsIACCI | [BGIOSIBCE018385] | (176) | PEDLRINAESIRIADQFVEVPGGTNNSNYANVQLIVEIAERTGVSAVWPGWGHASENPEL |  |  |
| OsJACCI | [EAZ33685] | (176) | PEDLRINAESIRIADQFVEVPGGTNKGSYANVQLIVEIAERTGVSAVWPGWGHASENPEL |  |  |

|  |  |  | 241 |  | 300 |
|---|---|---|---|---|---|
| AmACCI | [CAC84161] | (236) | PDALTAKGIVFLGPPASSMNALGDKVGSALIAQAACVPTLAWSGSHVEIPLELCLDSIPS |  |  |
| OsIACCI | [BGIOSIBCE018385] | (236) | PDALTAKGIVFLGPPASSMHALGDKVGSALIAQAAGVPTLAWSGSHYEVPLEDCLASIPS |  |  |
| OsJACCI | [EAZ33685] | (236) | PDALTAKGIVFLGPPASSMHALGDKVGSALIAQAAGVPTLAWSGSHYKVPLEDCLASIPS |  |  |

|  |  |  | 301 |  | 360 |
|---|---|---|---|---|---|
| AmACCI | [CAC84161] | (296) | EMYRKACVTTADEAVASCQMIGYPAMIKASWGGGGKGIRKVNNDDEVSALFRQVQGEVPG |  |  |
| OsIACCI | [BGIOSIBCE018385] | (296) | EMYRKACVTTSEEAVASCQVVGYPAMIKASWGGGGKGIRKVNDDEVRTLFRQVQGEVPG |  |  |
| OsJACCI | [EAZ33685] | (296) | EMYRKACVTTSEEAVASCQVVGYPAMIKASWGGGGKGIRKVNDDEVRTLFRQVQGEVPG |  |  |

|  |  |  | 361 |  | 420 |
|---|---|---|---|---|---|
| AmACCI | [CAC84161] | (356) | SPIFIMRLASQSRHLEVQLLCDRYGNVAALHSRDCSVQRRHQKIIEEGPVTVAPRETVKS |  |  |
| OsIACCI | [BGIOSIBCE018385] | (356) | SPIFIMRLAAQSRHLEVQLLCDQYGNVAALHSRDCSVQRRHQKIIEEGPVTVAPRETVKS |  |  |
| OsJACCI | [EAZ33685] | (356) | SPIFIMRLAAQSRHLEVQLLCDQYGNVAALHSRDCSVQRRHQKIIERGPVTVAPRETVKS |  |  |

|  |  |  | 421 |  | 480 |
|---|---|---|---|---|---|
| AmACCI | [CAC84161] | (416) | LEQAARRLAKAVGYVGAAFVEYLYSMETGEYYFLELNPRLQVEHPVTEWIASVHLEAAQV |  |  |
| OsIACCI | [BGIOSIBCE018385] | (416) | LEQAARRLAKAVGYVQAATVEYLYSMETGEYYFLELNPRLQVEHPVTEWIASVHLEAAQV |  |  |
| OsJACCI | [EAZ33685] | (416) | LEQAASRLAKAVGYVQAATVEYLYSMETGEYYFLELNPRLQVEHPVTEWIASVHLPAAQV |  |  |

|  |  |  | 481 |  | 540 |
|---|---|---|---|---|---|
| AmACCI | [CAC84161] | (476) | AVGMGIPLWQIPEIRRFYGNDSGGYDIWRKTAALATPFNFDEVDSQRPKGHCVAVRITS |  |  |
| OsIACCI | [BGIOSIBCE018385] | (476) | AVGKGIPLWQIPEIRRFYGMNEGGGKDLWRKTAALATPFNFDEVDSPWPKGHCVAVRITS |  |  |

| | | 1081 1140 |
|---|---|---|
| AmACC1 (CAC84161) | (1076) | LIRFSSLNHKKYYKLALKASELLEQTKLSELRTSIARNLSALDMFTEKKADFSLQDRKLA |
| OsIACC1 (BGIOSIBCE018385) | (1076) | LIRFSSLNHKAYYKLALKASELLEQTKLSELRARIARSLSELEMFTEESKGLSMHKREIA |
| OsJACC1 (EAZ33685) | (1076) | LIRFSSLNHKAYYKLALKASELLEQTKLSELRARIARSLSELEMFTEESKGLSMHKREIA |
| | | 1141 1200 |
| AmACC1 (CAC84161) | (1136) | IRESMEDLVTAPLPVEDALVSLFDCSDQTLQQRVIQTYISRLYQPQLVKDSIQLKYQESG |
| OsIACC1 (BGIOSIBCE018385) | (1136) | IKESMEDLVTAPLPVEDALISLFDCSDTTVQQRVIETYIARLYQPHLVKDSIKMKWIESG |
| OsJACC1 (EAZ33685) | (1136) | IKESMEDLVTAPLPVEDALISLFDCSDTTVQQRVIETYIARLYQPHLVKDSIKMKWIESG |
| | | 1201 1260 |
| AmACC1 (CAC84161) | (1196) | VIALWEFSEGNHEKR----------LGAMVILKSLESVSTAIGAALKDASHYASSAGNTV |
| OsIACC1 (BGIOSIBCE018385) | (1196) | VIALWEFPEGHFDARNGGAVLGDKRWGAMVIVKSLESLSMAIRFALKETSHYTSSEGNMM |
| OsJACC1 (EAZ33685) | (1196) | VIALWEFPEGHFDARNGGAVLGDKRWGAMVIVKSLESLSMAIRFALKETSHYTSSEGNMM |
| | | 1261 1320 |
| AmACC1 (CAC84161) | (1246) | HIALLDADTQLNTTEDSGDNDQAQDKMDKLSFVLKQDVVMADLRAADVKVVSCIVQRDGA |
| OsIACC1 (BGIOSIBCE018385) | (1256) | HIALLGADNKMHLIQESG---DDADRIAKLPLILKDN--VTDLHASGVKTISFIVQRDEA |
| OsJACC1 (EAZ33685) | (1256) | HIALLGADNKMHLIQESG---DDADRIAKLPLILKDN--VTDLHASGVKTISFIVQRDEA |
| | | 1321 1380 |
| AmACC1 (CAC84161) | (1306) | IMPMRRTFLLSEEKLCYEEEPILRHVEPPLSALLELDKLKVKGYNEMKYTPSRDRQWHIY |
| OsIACC1 (BGIOSIBCE018385) | (1311) | RMTMRRTFLWSDEKLSYEEEPILRHVEPPLSALLELDKLKVKGYNEMKYTPSRDRQWHIY |
| OsJACC1 (EAZ33685) | (1311) | RMTMRRTFLWSDEKLSYEEEPILRHVEPPLSALLELDKLKVKGYNEMKYTPSRDRQWHIY |
| | | 1381 1440 |
| AmACC1 (CAC84161) | (1366) | TLRNTENPKMLHRVFFRTLVRQPSASNRFTSDHITDVEVGHAEEPLSFTSSSILKSLKIA |
| OsIACC1 (BGIOSIBCE018385) | (1371) | TLRNTENPKMLHRVFFRTIVRQPSVSNKFSSGQIGDMEVGSAEEPLSFTSTSILRSLMTA |
| OsJACC1 (EAZ33685) | (1371) | TLRNTENPKMLHRVFFRTLVRQPSVSNKFSSGQIGDMEVGSAEEPLSFTSTSILRSLMTA |
| | | 1441 1500 |
| AmACC1 (CAC84161) | (1426) | KEELELHAIRTGHSHMYLCILKEQKLLDLVPVSGNTVVDVGQDEATACSLLKEMALKIHE |
| OsIACC1 (BGIOSIBCE018385) | (1431) | IEELELHAIRTGHSHMYLHVLKEQKLLDLVPVSGNTVLDVGQDEATAYSLLKEMAMKIHE |
| OsJACC1 (EAZ33685) | (1431) | IEELELHAIRTGHSHMYLHVLKEQKLLDLVPVSGNTVLDVGQDEATAYSLLKEMAMKIHE |
| | | 1501 1560 |
| AmACC1 (CAC84161) | (1486) | LVGARMHHLSVCQWEVKLKLVSDGPASGSWRVVTTNVTGHTCTVDIYREVEDTESQKLVY |
| OsIACC1 (BGIOSIBCE018385) | (1491) | LVGARMHHLSVCQWEVKLKLDCDGPASGTWRIVTTNVTSHTCTVDIYREMEDKESRKLVY |
| OsJACC1 (EAZ33685) | (1491) | LVGARMHHLSVCQWEVKLKLDCDGPASGTWRIVTTNVTSHTCTVDIYREMEDKESRKLVY |
| | | 1561 1620 |
| AmACC1 (CAC84161) | (1546) | HSTALSSGPLHGVALNTSYQPLSVIDLKRCSARNNKTTYCYDFPLTFEAAVQKSWSNISS |
| OsIACC1 (BGIOSIBCE018385) | (1551) | HPATPAAGPLHGVALNNPYQPLSVIDLKRCSARNNRTTYCYDFPLAFETAVRKSWSSSTS |
| OsJACC1 (EAZ33685) | (1551) | HPATPAAGPLHGVALNNPYQPLSVIDLKRCSARNNRTTYCYDFPLAFETAVRKSWSSSTS |
| | | 1621 1680 |
| AmACC1 (CAC84161) | (1606) | ------ENNQCYVKATELVFAEKNGSWGTPIIPMQRAAGLNDIGMVAWILDMSTPEFPSG |

FIGURE 19 (continued)

```
OsIACCI [BGIOSIBCE018385]   (1611)  GASKGVENAQCKVKATELVPADREGGWGTPLVQSDRPAGLNDIGNVANTLKMSTPPSPSG
OsJACCI [EAZ33685]          (1611)  GASKGVENAQCKVKATELVPADEDGGNWTPLVQSDREAGLNDIGNVANWLKMSTPPPTPGC 1681                                                        1740
AaACCI  [CAC84161]          (1660)  RQIIVIANDITPRAGSFGPREDAFFEAVTRLACERKLPLIYLAANSGARIGIACEVKSCF
OsIACCI [BGIOSIBCE018385]   (1671)  REIIVVANDITPRACSFGPREDAFFEAVTRLACERKLPLIYLAANSGAPIGIADEVKSCF
OsJACCI [EAZ33685]          (1658)  RETIVVPNDITPRAGSFGPREDAFFEAVTPLACRPKLPLIYLAANSGARIGIADEVKSCF 1741                                                        1800
AaACCI  [CAC84161]          (1720)  SVGWPDIGSPEKGPRVYMPDSBBDRIGSSVIAHENQLDSGEIRSVIDSVVGKEDGLAVS
OsIACCI [BGIOSIBCE018385]   (1731)  RVGWSDKGSPEKGPQVYYLSEEDYARIGTSVIAHENQLDSGETRSVIDSVVGKEDGLGVS
OsJACCI [EAZ33685]          (1718)  SVGWSDKGSPEKGPQKIYLSREDYARIGTSVIAHRKQLDSGEIRSVIDSVVGKEDGLGVS 1801                                                        1860
AaACCI  [CAC84161]          (1780)  NIEGSAAIASAYSRAYEETPTLSFVIGRTVSIGAYLARIGIRCIQRLDQPIILPSPSALS
OsIACCI [BGIOSIBCE018385]   (1791)  NIEGSAAIASAYSRAYEETPTLSFVIGRTVGIGAYLARLGIRCIQRLDQPIILEGYSALS
OsJACCI [EAZ33685]          (1778)  NIEGSAAIASAYSRAYEETPTLSFVIGRTVGIGAYLARLGIRCIQRLDQPIILPGYSALS 1861                                                        1920
AaACCI  [CAC84161]          (1840)  KLLGRKVYSSSMQLGGPKIMATRGVVHLPVPDIEGVSNILRSLSYVPANIGGPLPITPS
OsIACCI [BGIOSIBCE018385]   (1851)  KLLGRSVYSSNMQLGGPKIMATRGVVHLPVSDDLEGVSNILRSLGYVPANIGGPLPVTSP
OsJACCI [EAZ33685]          (1838)  KLLGRSVYSSNMQLGGPKIMATRGVVHLPVSDDLEGVSNILRSLGYVPANIGGPLPVESP 1921                                                        1980
AaACCI  [CAC84161]          (1900)  LDPIDRPVAYIPENTCDPGAAISGIDESQGKWLGGKFDKDSFVETFEGRAKTVVTGRAKL
OsIACCI [BGIOSIBCE018385]   (1911)  LDPPDRPVAYIPENSCDPRAAISGVDESQGKWLGSMFPKDSFVETFEGRAKTVVTGRAKL
OsJACCI [EAZ33685]          (1898)  LDPPDRPVAYIPFNSCDPRAAIRGVDESQGKWLAGNTDKDSFVETFEGNAKTVVTGRAKL 1981                                                        2040
AaACCI  [CAC84161]          (1960)  GGIPVGVIAVETQTMKQLVPADPGQPTGHEPSVPPAEQVWFPDSATKTAQAMLDFNSEGL
OsIACCI [BGIOSIBCE018385]   (1971)  GGIPVGVIAVETQTMKQTIPADPGQLTSREQSVPRAGQVWFPDSATKTAQALLDFNREGL
OsJACCI [EAZ33685]          (1958)  GGIPVGVIAVETQTMKQTIPADPGQLGGREQSVFRASQVWFPDSATKTAQALLDFNSEGL 2,041                                                       2100
AaACCI  [CAC84161]          (2020)  PLFILANWRGFSGKQRDLFEGILQAGSTIVENLRTYNQPAFVYIPKAAKLRSGAWVVIDS
OsIACCI [BGIOSIBCE018385]   (2031)  PLFILADWRGFSGKQRDLFEGILQAGSTIVDNLRTYNQPAFVYIPMAAKLRSGAWVVVDS
OsJACCI [EAZ33685]          (2018)  PLFILANWRGFSGKQRDLFEGILQAGSTIVDNLRTYNQPAFVYIPMAAKLRSGAWVVVDS 2101                                                        2160
AaACCI  [CAC84161]          (2080)  KINPURISCYAERTAKGNVLEPQGLIEIKFRSEELKECMGRLDPELIDIKARLQGAS--GS
OsIACCI [BGIOSIBCE018385]   (2091)  EINPIKIECYAERTAKGNVLEPQGLIEIKFPSEELQUCMSRLDPTLIDLKAKLEVANKRS
OsJACCI [EAZ33685]          (2,078) KINPIRRIECYAERTAKGNVLEPQGLIEIKFRSEELQDCMSRLDPTLIDLKAKLSVANES 2161                                                        2220
AaACCI  [CAC84161]          (2139)  LSIDGESLQKSIEARKKQLLPLYTQIAVRFAELDDTSLRMAAKGVIRSYVQSEDSSGFFYK
OsIACCI [BGIOSIBCE018385]   (2151)  SAPTESLQKSIEARTKQLSPLYTQIAIRFAELHDTSLRMAAKGVIKFYVRSCGSRUFFYK
OsJACCI [EAZ33685]          (2138)  SAPTESLQKSIEARTKQLSPLYTQIARRFAELHDTSLRMAAKGVIKKYVRSEESRSFFYK
```

FIGURE 19 (continued)

```
                              2321                                                   2380
     AtACCl [CAC84161]  (2199) RLRRRLSEDVLAREIPGVIGEKFPRKAIELIKKWYLASEAARAGSTWDCCDAFVARRE
  OsIACC1 [BGIOSIBCE013385]  (2213) RLRRRISEDVLAREIRAVAGRQFSHQPAIELIKKWYSASRAA------SHDEDDAFVARMD
     OsJACC1 [EAZ33685]  (2198) RLRRHISEDVLAREIRAVACEQFSBQPRIRLIKKWYCASRAA------SWDCRDAPVARNC 2281                                                   2340
     AtACC1 [CAC84161]  (2259) NPSNYKSYIKELRAQRVSRLLSDVAGSSSDLQALPQGLSMLLDRMDPSRRAQFIREVMRV
  OsIACC1 [BGIOSIBCE013385]  (2266) NPSNYKDYIQYLRAQRVSQSLSSLSDSGSDLQALPQGLSMLLDRMDFSRRAQLVRKIRRV
     OsJACC1 [EAZ33685]  (2253) NPSNYKDYIQYLRAQRVSQSLSSLSDRSSDLQALPQGLSMLLDRKDPSRRAQLVRKIRRV

2341
     AtACC1 [CAC84161]  (2319) LR
  OsIACC1 [BGIOSIBCE013385]  (2326) LG
     OsJACC1 [EAZ33685]  (2313) LG
```

METHOD FOR TREATING POST-EMERGENT RICE

RELATED APPLICATIONS

This application is a Continuation-in-Part of U.S. application Ser. No. 14/357,691, filed on May 12, 2014; which is a 35 U.S.C. 371 National Stage entry of PCT/US12/64831, filed on Nov. 13, 2012; which claims priority to U.S. Provisional Application Ser. No. 61/559,618, filed on Nov. 14, 2011; all of which are hereby incorporated herein in their entirety by reference. This application is a Continuation-in-Part of U.S. patent application Ser. No. 15/156,671, filed May 17, 2016; which is a Continuation of U.S. application Ser. No. 13/393,780, filed Jan. 7, 2013; which is a 35 U.S.C. 371 National Stage entry of PCT/US10/47571, filed on Sep. 1, 2010; which claims priority of U.S. Provisional Application Ser. No. 61/365,298, filed Jul. 16, 2010, and 61/238,906, filed Sep. 1, 2009; all of which are hereby incorporated herein in their entirety by reference.

FIELD

The present disclosure generally relates to treatment of domestic rice crop plants for the control of weeds.

BACKGROUND

Rice is one of the most important food crops in the world, particularly in Asia. Rice is a cereal grain produced by plants in the genus *Oryza*. The two most frequently cultivated species are *Oryza sativa* and *Oryza glaberrima*, with *O. sativa* being the most frequently cultivated domestic rice. In addition to the two domestic species, the genus *Oryza* contains more than 20 wild species. One of these wild species, *Oryza rufipogon* ("red rice" also referred to as *Oryza sativa* subsp. *rufipogon*) presents a major problem in commercial cultivation. Red rice produces red coated seeds. After harvest, rice seeds are milled to remove their hull. After milling, domestic rice is white while wild red rice appears discolored. The presence of discolored seeds reduces the value of the rice crop. Since red rice belongs to the same species as cultivated rice (*Oryza sativa*), their genetic makeup is very similar. This genetic similarity has made herbicidal control of red rice difficult.

Domestic rice tolerant to imidazolinone herbicides have been developed and are currently marketed under the tradename CLEARFIELD®. Imidazolinone herbicides inhibit a plant's acetohydroxyacid synthase (AHAS) enzyme. When cultivating CLEARFIELD® rice, it is possible to control red rice and other weeds by application of imidazolinone herbicides. Unfortunately, imidazolinone herbicide-tolerant red rice and weeds have developed.

Acetyl-Coenzyme A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homomeric protein, likely a homodimer.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

A number of ACCase-inhibitor-tolerance (AIT) mutations have been found in monocot weed species exhibiting tolerance toward one or more DIM or FOP herbicides. Further, an AIT maize has been marketed by BASF. All such mutations are found in the carboxyltransferase domain of the ACCase enzyme, and these appear to be located in a substrate binding pocket, altering access to the catalytic site.

DIMs and FOPs are important herbicides and it would be advantageous if rice could be provided that exhibits tolerance to these classes of herbicide. Currently, these classes of herbicide are of limited value in rice agriculture. In some cases, herbicide-tolerance-inducing mutations create a severe fitness penalty in the tolerant plant. Therefore, there remains a need in the art for an AIT rice that also exhibits no fitness penalty. This need and others are met by the present invention.

SUMMARY

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. In some further embodiments, the effective amount of quizalofop or an ester thereof is at least 14 g AI/Ha.

In even other embodiments, the aryloxyphenoxypropanoate herbicide is fluazifop or an ester thereof. In some further embodiments, the effective amount of fluazifop or an ester thereof is at least 56 g AI/Ha.

In some other embodiments, the aryloxyphenoxypropanoate herbicide is clodinafop or clodinafop-propargyl. In some further embodiments, the effective amount of clodinafop or clodinafop-propargyl is at least 11 g AI/Ha.

In still other embodiments, the aryloxyphenoxypropanoate herbicide is diclofop or diclofop-methyl. In some further embodiments, the effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona, Echinochloa crus-galli, Echinochloa crus-pavonis, Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis, Leptochloa fascicularis, Leptochloa panacea,* and *Leptochloa panicoides.*

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

BRIEF DESCRIPTION OF THE DRAWINGS

The present disclosure can be better understood by reference to the following drawings. The drawings are merely exemplary to illustrate certain features that may be used singularly or in combination with other features and the aspects of the present disclosure should not be limited to the embodiments shown.

FIG. 1A shows the results obtained with tepraloxydim, FIG. 1B shows the results obtained with sethoxydim, and FIG. 1C shows the results obtained with cycloxydim.

FIG. 5 provides the amino acid sequence of acetyl-coenzyme A carboxylase from *Alopecurus myosuroides* (GenBank accession number CAC84161) (SEQ ID NO. 24).

FIG. 6 provides the mRNA encoding acetyl-coenzyme A carboxylase from *Alopecurus myosuroides* (GenBank accession number AJ310767 region: 157 . . . 7119).

Figure 7A:
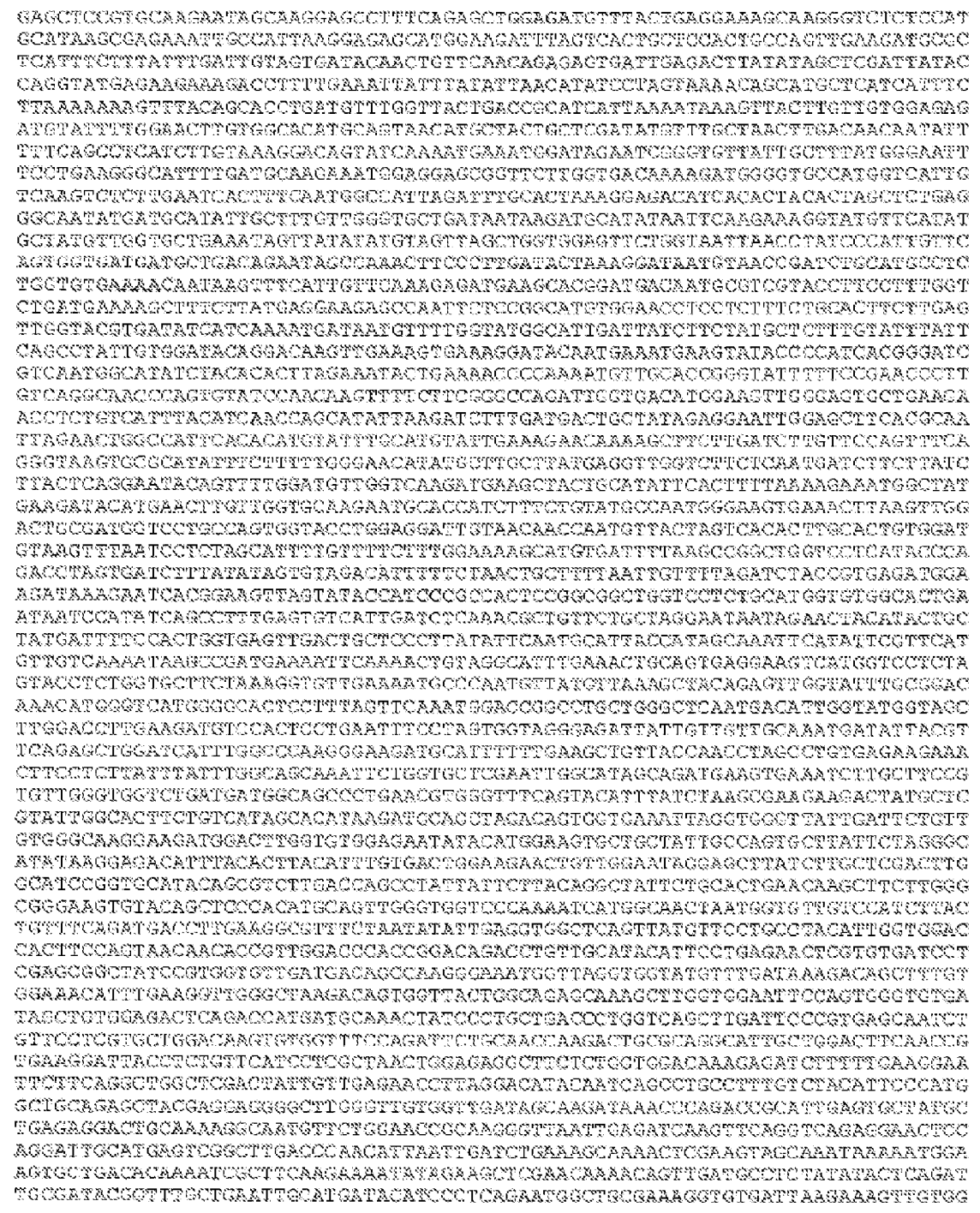

FIG. 7A provides the genomic nucleotide sequence for *Oryza sativa* Indica & Japonica acetyl-Coenzyme A carboxylase gene (SEQ ID NO:5).

FIG. 7B provides the nucleotide sequence encoding *Oryza sativa* Indica & Japonica acetyl-Coenzyme A carboxylase (SEQ ID NO:6).

FIG. 7C provides the amino acid sequence of *Oryza sativa* Indica acetyl-Coenzyme A carboxylase (SEQ ID NO:3).

Figure 8A:
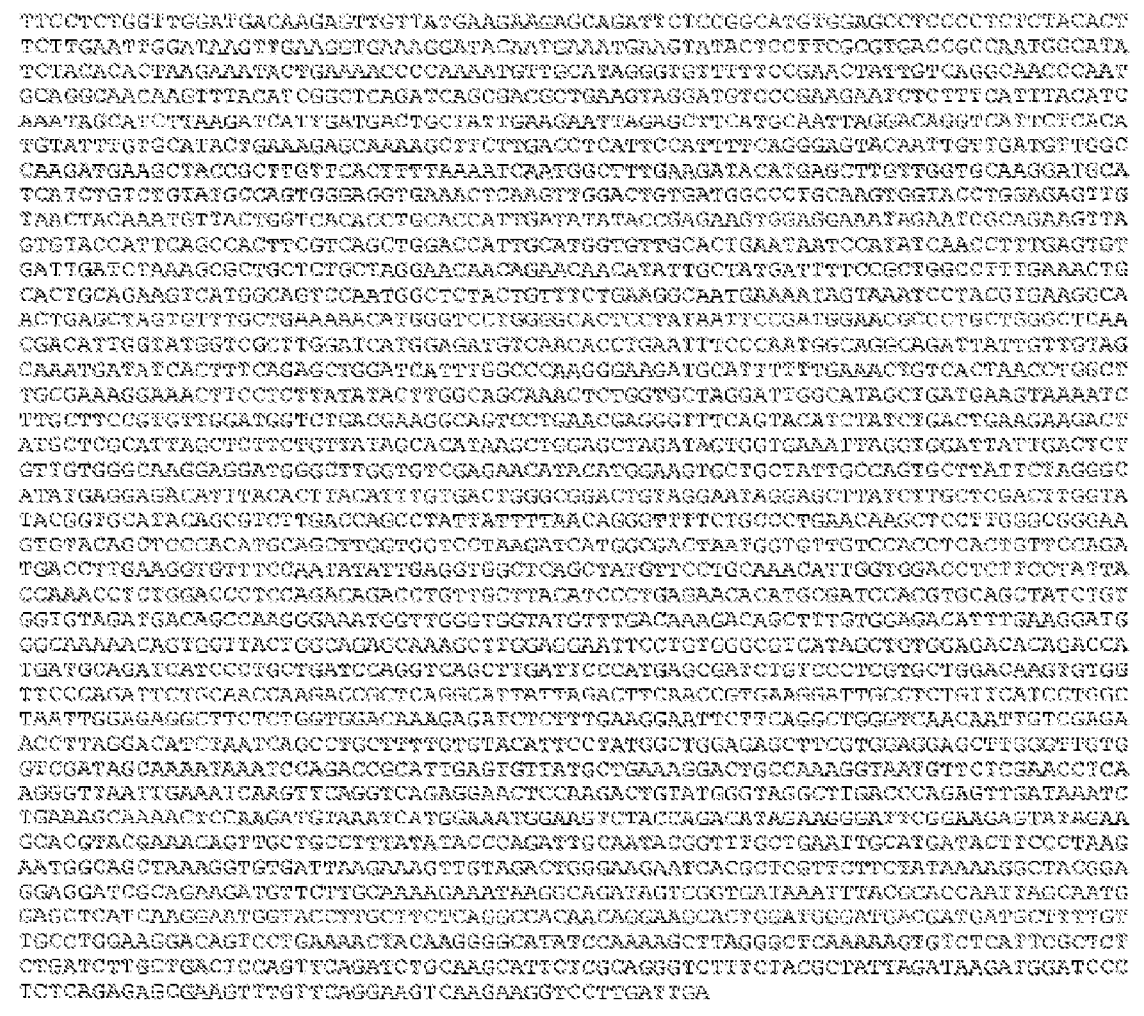

FIG. 8A provides the nucleotide sequence encoding *Zea mays* acetyl-Coenzyme A carboxylase (SEQ ID NO:11).

FIG. 8B provides the amino acid sequence of *Zea mays* acetyl-Coenzyme A carboxylase (SEQ ID NO:12).

Figure 9A:
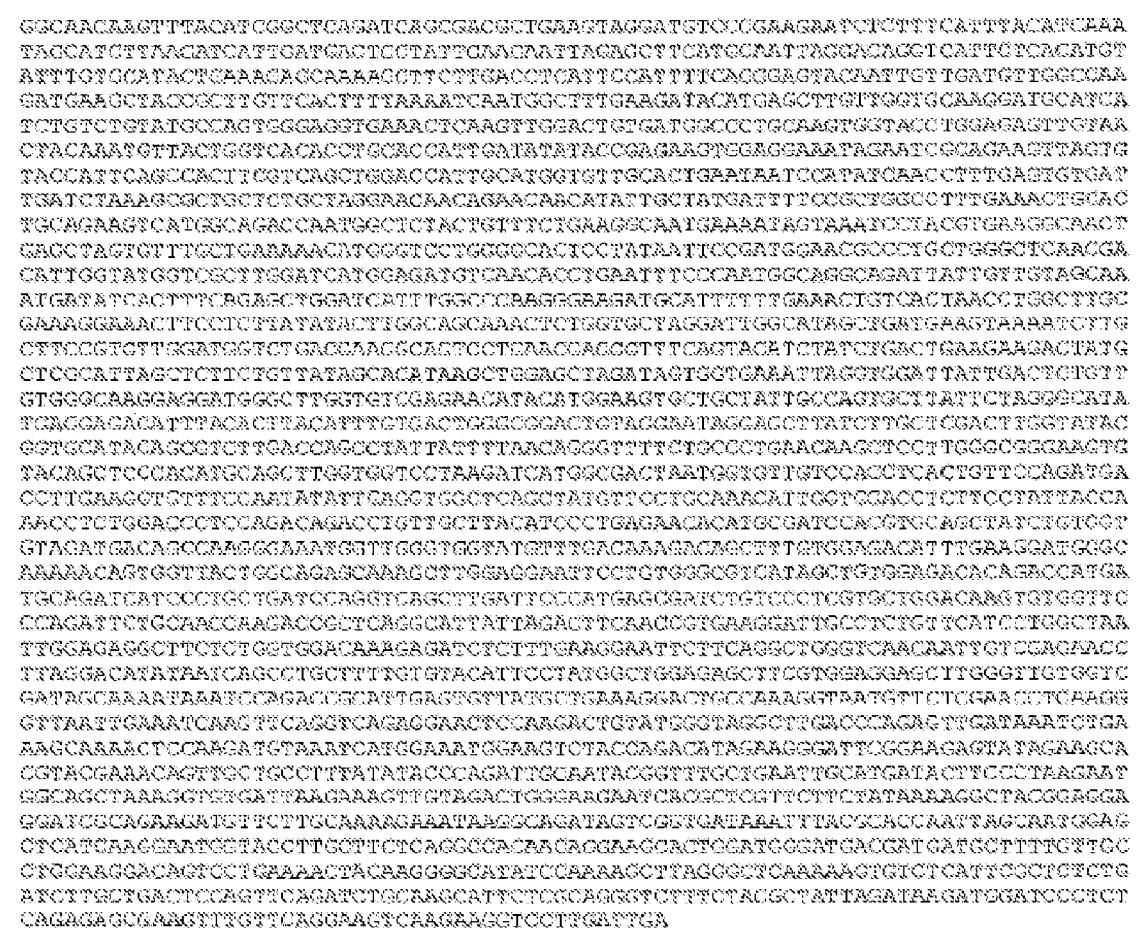

FIG. 9A provides the nucleotide sequence encoding *Zea mays* acetyl-Coenzyme A carboxylase (SEQ ID NO:13).

FIG. 9B provides the amino acid sequence of *Zea mays* acetyl-Coenzyme A carboxylase (SEQ ID NO:14).

FIG. 10A provides the nucleotide sequence encoding *Triticum aestivum* acetyl-Coenzyme A carboxylase (SEQ ID NO:15).

FIG. 10B provides the amino acid sequence of *Triticum aestivum* acetyl-Coenzyme A carboxylase (SEQ ID NO:16).

FIG. 11A provides the nucleotide sequence encoding *Setaria italica* acetyl-Coenzyme A carboxylase (SEQ ID NO:17).

FIG. 11B provides the amino acid sequence of *Setaria italica* acetyl-Coenzyme A carboxylase (SEQ ID NO:18).

Figure 12A:
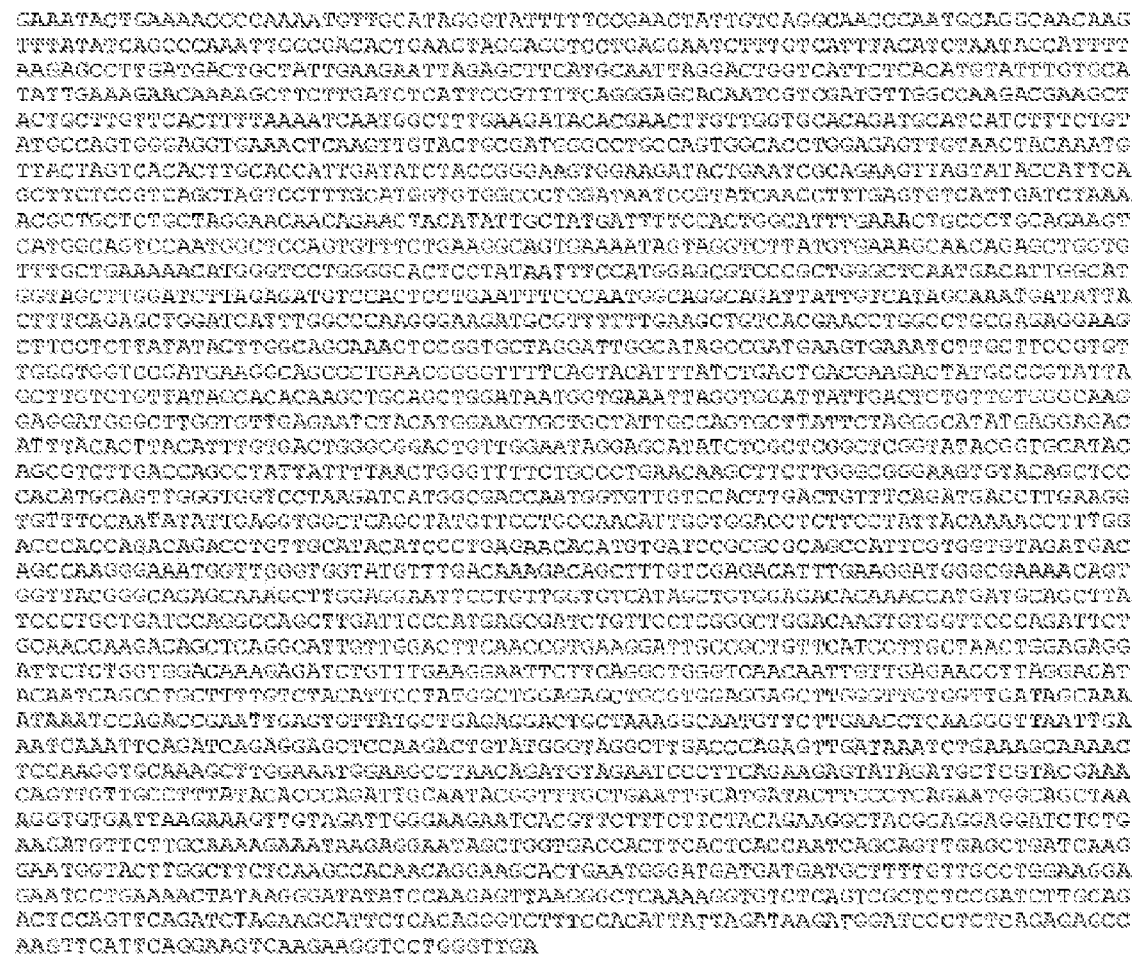

FIG. 12A provides the nucleotide sequence encoding *Setaria italica* acetyl-Coenzyme A carboxylase (SEQ ID NO:19).

FIG. 12B provides the amino acid sequence of *Setaria italica* acetyl-Coenzyme A carboxylase (SEQ ID NO:20).

FIG. 13A provides the nucleotide sequence encoding *Setaria italica* acetyl-Coenzyme A carboxylase (SEQ ID NO:21).

FIG. 13B provides the amino acid sequence of *Setaria italica* acetyl-Coenzyme A carboxylase (SEQ ID NO:22).

FIG. 14A provides the nucleotide sequence encoding *Alopecurus myosuroides* acetyl-Coenzyme A carboxylase (SEQ ID NO:23).

FIG. 14B provides the amino acid sequence of *Alopecurus myosuroides* acetyl-Coenzyme A carboxylase (SEQ ID NO:24).

FIG. 15A provides the nucleotide sequence encoding *Aegilops tauschii* acetyl-Coenzyme A carboxylase (SEQ ID NO:25).

FIG. 15B provides the amino acid sequence of *Aegilops tauschii* acetyl-Coenzyme A carboxylase (SEQ ID NO:26).

FIG. 16 provides a comparison of single and double mutants.

FIG. 18 provides *Alopecurus myosuroides* acetyl-Coenzyme A carboxylase amino acid sequence (GenBank accession no. CAC84161) (SEQ ID NO. 24). Amino acids that may be altered in the acetyl-Coenzyme A carboxylase enzymes of the disclosure are indicated in bold double underline.

FIG. 19 provides amino acid sequence of wild-type *Oryza sativa* acetyl-Coenzyme A carboxylases (SEQ ID NOs. 2, 3) aligned with *Alopecurus myosuroides* acetyl-Coenzyme A carboxylase (SEQ ID NO. 24) with some critical residues denoted.

DETAILED DESCRIPTION

Figure 1:
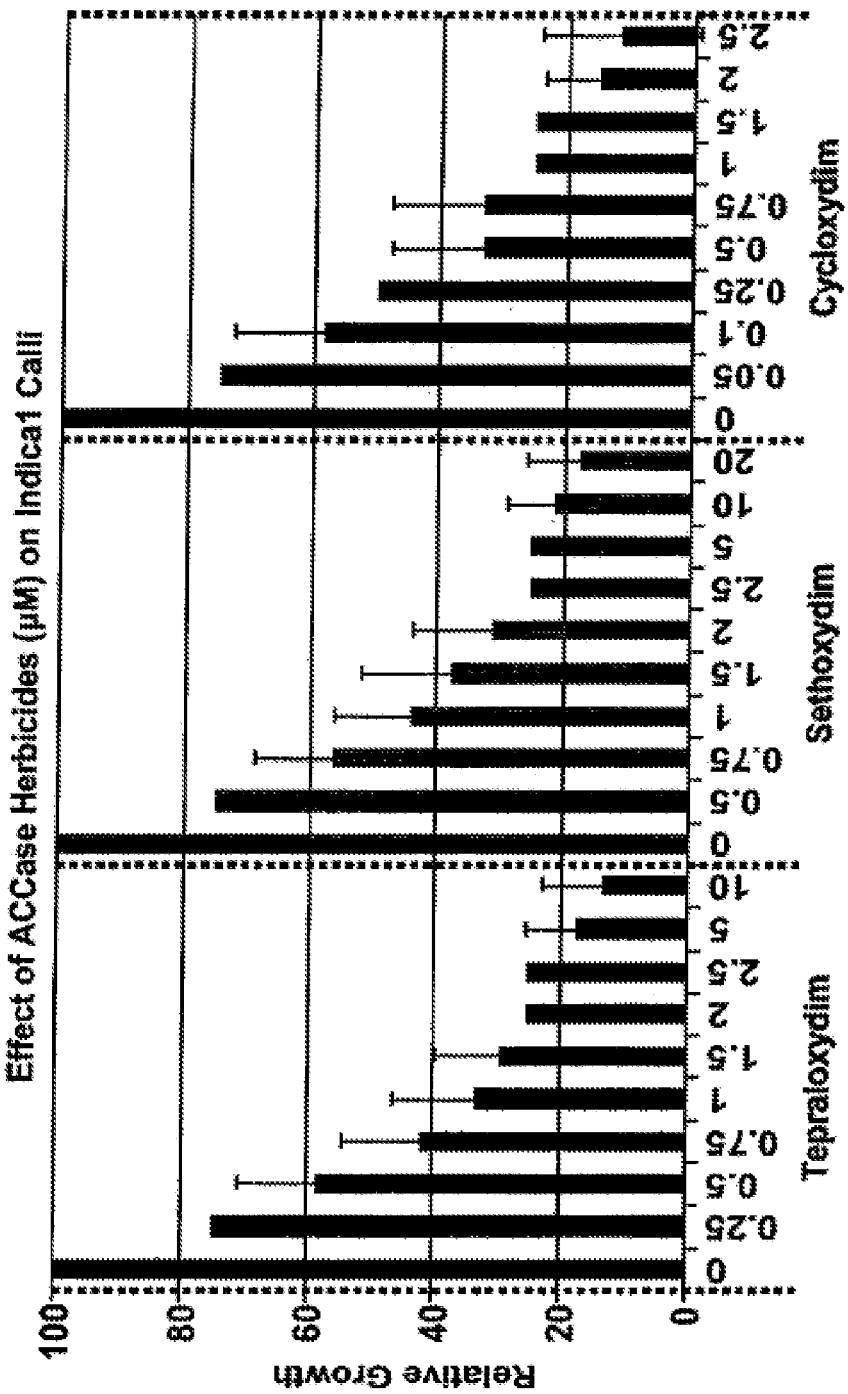
FIG. 1 is a bar graph showing relative growth rice calli derived from *Oryza sativa* subsp. *indica* grown in the presence of difference selection levels of herbicide.

The following detailed description is presented to enable any person skilled in the art to make and use the objectives of the present disclosure. For purposes of explanation, specific nomenclature is set forth to provide a thorough understanding of the objectives of the present disclosure. However, it will be apparent to one skilled in the art that these specific details are not required to practice the objectives of the present disclosure. Descriptions of specific applications are provided only as representative examples. The presently claimed disclosure is not intended to be limited to the embodiments shown, but is to be accorded the widest possible scope consistent with the principles and features disclosed herein.

Definitions

As used herein, "tolerant" or "herbicide-tolerant" indicates a plant or portion thereof capable of growing in the presence of an amount of herbicide that normally causes growth inhibition in a non-tolerant (e.g., a wild-type) plant or portion thereof. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant.

As used herein, "recombinant" refers to an organism having genetic material from different sources.

As used herein, "mutagenized" refers to an organism having an altered genetic material as compared to the genetic material of a corresponding wild-type organism, wherein the alterations in genetic material were induced and/or selected by human action. Examples of human action that can be used to produce a mutagenized organism include, but are not limited to, tissue culture of plant cells (e.g., calli) in sub-lethal concentrations of herbicides (e.g., acetyl-Coenzyme A carboxylase inhibitors such as cycloxydim or sethoxydim), treatment of plant cells with a chemical mutagen and subsequent selection with herbicides (e.g., acetyl-Coenzyme A carboxylase inhibitors such as cycloxydim or sethoxydim); or by treatment of plant cells with x-rays and subsequent selection with herbicides (e.g., acetyl-Coenzyme A carboxylase inhibitors such as cycloxydim or sethoxydim). Any method known in the art may be used to induce mutations. Methods of inducing mutations may induce mutations in random positions in the genetic material or may induce mutations in specific locations in the genetic material (i.e., may be directed mutagenesis techniques).

As used herein, a "genetically modified organism" (GMO) is an organism whose genetic characteristics have been altered by insertion of genetic material from another source organism or progeny thereof that retain the inserted genetic material. The source organism may be of a different type of organism (e.g., a GMO plant may contain bacterial genetic material) or from the same type of organism (e.g., a GMO plant may contain genetic material from another plant). As used herein, recombinant and GMO are considered synonyms and indicate the presence of genetic material from a different source whereas mutagenized indicates altered genetic material from a corresponding wild-type organism but no genetic material from another source organism.

As used herein, "wild-type" or "corresponding wild-type plant" means the typical form of an organism or its genetic material, as it normally occurs, as distinguished from mutagenized and/or recombinant forms.

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope.

As used herein in regard to herbicides useful in various embodiments hereof, terms such as auxinic herbicide, AHAS inhibitor, acetyl-Coenzyme A carboxylase (ACCase) inhibitor, PPO inhibitor, EPSPS inhibitor, imidazolinone, sulfonylurea, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide tolerant (HT) and herbicide tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to an AHAS enzyme, or AHASL polypeptide, it refers specifically to the ability to tolerate an AHAS-inhibitor. Classes of AHAS-inhibitors include sulfonylureas, imidazolinones, triazolopyrimidines, sulfonylaminocarbonyltriazolinones, and pyrimidinyloxy[thio]benzoates.

As used herein, "descendant" refers to any generation plant.

As used herein, "progeny" refers to a first generation plant.

As used herein, an "effective amount" refers to the amount of an herbicide required to achieve at least about 65% phytotoxicity of conventional rice (e.g., red rice) in field applications. In some embodiments, an effective amount may be further defined as an amount of an herbicide required to achieve at least about 70, 75, 80, 85, 90, 95 or 99% phytotoxicity of conventional rice (e.g., red rice) in field applications. In other embodiments, an effective amount may be further defined as an amount of an herbicide required to achieve at least about 65, 70, 75, 80, 85, 90, 95 or 99% phytotoxicity of *Echinochloa* or *Leptochloa* species weeds in field applications. Typically, an effective amount for post-emergent application will be at least 0.5× the standard application rate of a given herbicide. 1× rates of herbicides listed herein are within the knowledge of one of ordinary skill in the art and it understood herein that for any herbicide not having a published 1× application rate, a 1× rate is one that causes at least 90% phytotoxicity in *Echinochloa crus-galli*.

As used herein, the amino acid numbering, and the associated DNA sequence numbering are based on the numbering of the ACCase in *Alopercurus myosuroides* (blackgrass) (Genbank CAC84161.1) and denoted with an (Am). The reference positions cited within are intended to correspond to the actual recited positional equivalent in the ACCase of *Alopercurus myosuroides*.

As used herein, a "non-selective" or "rice-non-selective" ACCase-inhibiting herbicide relates to an herbicide of the DIM or FOP class that, at a given rate of application, of active ingredient causes both at least about 90% phytotoxicity in *Echinochloa crus-galli* and more than 10% phytotoxicity in domestic rice (*Oryza sativa*). Conversely, "selective" means any ACCase-inhibiting DIM or FOP herbicide that, at a given rate of application causes both at least 90% phytotoxicity in *Echinochloa crus-galli* and not more than 10% phytotoxicity in domestic rice (*Oryza sativa*).

As used herein, the terms "post-emergence" and "postemergent" refer to a time period encompassing the post-germination emergence of a seedling through the soil surface to the maturity of the plant.

As used herein in regard to mutant or mutagenized nucleic acids that encode herbicide-tolerant ACCase enzymes, the term "endogenous non-transfected" is defined to mean:
(1) that the nucleic acid is endogenous to the respective cell, seed, plant, or plant part and
(2) that its nucleotide sequence is "non-transfected" in that
  (a) it contains herbicide-tolerance mutation(s) produced randomly by a technique involving no step of introducing exogenous nucleic acid(s) or nucleic acid analog(s), into a plant cell or into other plant material, and
  (b) it contains no mutation(s) produced by a technique involving a step of introducing exogenous nucleic acid(s) or nucleic acid analog(s), into a plant cell or into other plant material.

Thus, techniques useful to produce such "non-transfected" nucleic acid sequences, as defined herein, include, e.g., traditional chemical mutagenesis using a chemical (i.e. non-nucleic-acid- or -analog-containing) mutagen, tissue culture mutagenesis involving somaclonal variation, radiation exposure, and other techniques for inducing mutations in endogenous plant gene(s) in a random or non-directed manner.

Accordingly, as defined herein, "endogenous non-transfected" nucleic acids exclude both those mutant or mutagenized nucleic acids whose mutation-containing sequences have resulted without an applied technique and those that were produced by use of a technique involving introduction into a plant cell or into other plant material of an exogenous nucleic acid or nucleic acid analog, whether per se or as part of a heteromolecular construct or complex. Examples of techniques excluded under this definition include: genetic engineering, oligonucleotide-directed mutagenesis, DNA mismatch-repair oligonucleotide-based mutagenesis, and other mutation-producing processes in which exogenous nucleic acid (or nucleic acid analog) has been transiently or stably introduced into a plant cell or other plant material.

As used in this definition of "endogenous non-transfected," the term "non-transfected" is analogous to the term "non-infected" used to describe a physician's patient who, not having been infected with or exposed to a pathogen, is not a carrier of it. Thus, by analogy, a "non-transfected" nucleic acid is one that is not a carrier of any "transfection product," i.e. of any mutation caused by a technique involving transient or stable introduction of exogenous nucleic acid or its analog.

One aspect of the present disclosure relates to a method for treating rice. The method comprises the steps of: providing a domestic rice crop plant and at least one ACCase-inhibiting aryloxyphenoxypropanoate herbicide selected from the group consisting of quizalofop or an ester thereof, haloxyfop, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence; thereby creating a treated rice plant; and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

In still other embodiments, the aryloxyphenoxypropanoate herbicide is quizalofop or an ester thereof. The 1× application rate for quizalofop or an ester thereof is 28 g AI/ha. In some further embodiments, an effective amount of quizalofop or an ester thereof is at least 14 g AI/Ha.

In even other embodiments, the aryloxyphenoxypropanoate herbicide is fluazifop or an ester thereof. The 1× application rate for fluazifop or an ester thereof is 112 g AI/ha. In some further embodiments, an effective amount of fluazifop or an ester thereof is at least 56 g AI/Ha.

In some other embodiments, the aryloxyphenoxypropanoate herbicide is clodinafop or clodinafop-propargyl. The 1× application rate for clodinafop or clodinafop-propargyl is 22 g AI/ha. In some further embodiments, an effective amount of clodinafop or clodinafop-propargyl is at least 11 g AI/Ha.

In still other embodiments, the aryloxyphenoxypropanoate herbicide is diclofop or diclofop-methyl. The 1× application rate for diclofop or diclofop-methyl is 452 g AI/ha. In some further embodiments, an effective amount of diclofop or diclofop-methyl is at least 226 g AI/Ha.

In some embodiments, the effective amount is effective for killing a weed of the genus *Echinochloa*. In some further embodiments, the weed of the genus *Echinochloa* is selected from the group consisting of *Echinochloa colona*, *Echinochloa crus-galli*, *Echinochloa crus-pavonis*, *Echinochloa oryzicola*, and *Echinochloa oryzoides*.

In other embodiments, the effective amount is effective for killing a weed of the genus *Leptochloa*. In some further embodiments, the weed of the genus *Leptochloa* is selected from the group consisting of *Leptochloa chinensis*, *Leptochloa fascicularis*, *Leptochloa panacea*, and *Leptochloa panicoides*.

In some embodiments, the method further comprises providing at least one cyclohexanedione herbicide and applying an effective amount thereof to the domestic rice crop plant.

Another aspect of the present disclosure relates to a method for treating rice comprising providing a domestic rice crop plant and at least one ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, the method further comprises comprising harvesting seed from the treated rice plant.

In some other embodiments, the domestic rice crop plant comprises and expresses an endogenous non-transfected mutant ACCase nucleic acid whose sequence encodes a multi-functional, plastidic ACCase containing a mutation that causes the ACCase to be tolerant to the herbicide, the nucleic acid thereby providing to the plant tolerance to the aryloxyphenoxypropanoate herbicide. In some further embodiments, the mutation is selected from the group consisting of I1781L, G2096S, and W2027C.

Yet another aspect of the present disclosure relates to a method for treating rice comprising providing a domestic rice crop plant and at least one rice-non-selective ACCase-inhibiting aryloxyphenoxypropanoate herbicide selected from the group consisting of quizalofop or an ester thereof, fluazifop or an ester thereof, clodinafop, clodinafop-propargyl, diclofop, and diclofop-methyl; applying an effective amount (measured in g AI/Ha) of the at least one aryloxyphenoxypropanoate herbicide to the domestic rice crop plant, post-emergence, wherein said effective amount is at least 0.5× of an amount that causes both at least about 90% phytotoxicity in wild type *Echinochloa crus-galli* and more than 10% phytotoxicity in wild-type *Oryza sativa*; thereby creating a treated rice plant, and growing the resulting treated rice plant.

In some embodiments, said effective amount is at least 0.5× and less than 1× of an amount that causes both at least about 90% phytotoxicity in wild type *Echinochloa crus-galli* and more than 10% phytotoxicity in wild-type *Oryza sativa*; thereby creating a treated rice plant.

In other embodiments, said effective amount is at least 0.5× and less than 0.95× of an amount that causes both at least about 90% phytotoxicity in wild type *Echinochloa crus-galli* and more than 10% phytotoxicity in wild-type *Oryza sativa*; thereby creating a treated rice plant.

In still other embodiments, said effective amount is at least 0.5× and less than 0.9× of an amount that causes both at least about 90% phytotoxicity in wild type *Echinochloa crus-galli* and more than 10% phytotoxicity in wild-type *Oryza sativa*; thereby creating a treated rice plant.

In yet other embodiments, said effective amount is at least 0.5× and less than 0.85× of an amount that causes both at least about 90% phytotoxicity in wild type *Echinochloa crus-galli* and more than 10% phytotoxicity in wild-type *Oryza sativa*; thereby creating a treated rice plant.

In even other embodiments, said effective amount is at least 0.5× and less than 0.8× of an amount that causes both at least about 90% phytotoxicity in wild type *Echinochloa crus-galli* and more than 10% phytotoxicity in wild-type *Oryza sativa*; thereby creating a treated rice plant.

In still even other embodiments, said effective amount is at least 0.5× and less than 0.75× of an amount that causes both at least about 90% phytotoxicity in wild type *Echinochloa crus-galli* and more than 10% phytotoxicity in wild-type *Oryza sativa*; thereby creating a treated rice plant.

In some embodiments, postemergent application of herbicides in the present methods can take place at the time of seedling emergence. In some embodiments, postemergent application of herbicides in the present methods can take place at the 2-, 3-, and/or 4-leaf stage. In some embodiments, postemergent application of herbicides in the present methods can take place at the 1st, 2nd, 3rd, and/or 4th tiller stage. In some embodiments, postemergent application of herbicides in the present methods can take place at the panicle initiation and/or panicle differentiation stage. In some embodiments, postemergent application of herbicides in the present methods can take place at the 2-, 3-, and/or 4-leaf stage. In some embodiments, postemergent application of herbicides in the present methods can take place at the heading, milk, or dough stages. In some embodiments, postemergent application of herbicides in the present methods can take place on mature plants.

Plants

The present disclosure provides herbicide-tolerant monocotyledonous plants of the grass family Poaceae. The family Poaceae may be divided into two major clades, the clade containing the subfamilies Bambusoideae, Ehrhartoideae, and Pooideae (the BEP clade) and the clade containing the subfamilies Panicoideae, Arundinoideae, Chloridoideae, Centothecoideae, Micrairoideae, Aristidoideae, and Danthonioideae (the PACCMAD clade). The subfamily Bambusoideae includes tribe Oryzeae. The present disclosure relates to plants of the BEP clade, in particular plants of the subfamilies Bambusoideae and Ehrhartoideae. Plants of the disclosure are typically tolerant to at least one herbicide that inhibits acetyl-Coenzyme A carboxylase activity as a result of expressing an acetyl-Coenzyme A carboxylase enzyme as described below. The BET clade includes subfamilies Bambusoideae, Ehrhartoideae, and group Triticodae and no other subfamily Pooideae groups. BET crop plants are plants grown for food or forage that are members of BET subclade, for example barley, corn, etc.

The present disclosure also provides commercially important herbicide-tolerant monocots, including Sugarcane (*Saccharum* spp.), as well as Turfgrasses, e.g., *Poa pratensis* (Bluegrass), *Agrostis* spp. (Bentgrass), *Lolium* spp. (Ryegrasses), *Festuca* spp. (Fescues), *Zoysia* spp. (*Zoysia* grass), *Cynodon* spp. (Bermudagrass), *Stenotaphrum secundatum* (St. Augustine grass), *Paspalum* spp. (Bahiagrass), *Eremochloa ophiuroides* (Centipedegrass), *Axonopus* spp. (Carpetgrass), *Bouteloua dactyloides* (Buffalograss), and *Bouteloua* var. spp. (Grama grass). In one embodiment, the present disclosure provides herbicide-tolerant plants of the Bambusoideae subfamily. Such plants are typically tolerant to one or more herbicides that inhibit acetyl-Coenzyme A carboxylase activity. Examples of herbicide-tolerant plants of the subfamily Bambusoideae include, but are not limited to, those of the genera *Arundinaria*, *Bambusa*, *Chusquea*, *Guadua*, and *Shibataea*.

In one embodiment, the present disclosure provides herbicide-tolerant plants of the Ehrhartoideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Erharta*, *Leersia*, *Microlaena*, *Oryza*, and *Zizania*.

In one embodiment, the present disclosure provides herbicide-tolerant plants of the Pooideae subfamily. Such plants are typically tolerant to one or more herbicides that inhibit acetyl-Coenzyme A carboxylase activity. Examples of herbicide-tolerant plants of the subfamily Ehrhartoideae include, but are not limited to, those of the genera *Triticeae*, *Aveneae*, and *Poeae*.

In one embodiment, herbicide-tolerant plants of the disclosure are rice plants. Two species of rice are most frequently cultivated, *Oryza sativa* and *Oryza glaberrima*. Numerous subspecies of *Oryza sativa* are commercially important including *Oryza sativa* subsp. *indica*, *Oryza sativa* subsp. *japonica*, *Oryza sativa* subsp. *javanica*, *Oryza sativa* subsp. *glutinosa* (glutinous rice), *Oryza sativa* Aromatica group (e.g., basmati), and *Oryza sativa* (Floating rice group). The present disclosure encompasses herbicide-tolerant plants in all of the aforementioned species and subspecies.

In addition to being able to tolerate herbicides that inhibit acetyl-Coenzyme A carboxylase activity, plants of the disclosure may also be able to tolerate herbicides that work on other physiological processes. For example, plants of the disclosure may be tolerant to acetyl-Coenzyme A carboxylase inhibitors and also tolerant to other herbicides, for example, enzyme inhibitors. Examples of other enzyme inhibitors to which plants of the disclosure may be tolerant include, but are not limited to, inhibitors of 5-enolpyruvyl-shikimate-3-phosphate synthase (EPSPS) such as glyphosate, inhibitors of acetohydroxyacid synthase (AHAS) such as imidazolinones, sulfonylureas and sulfonamide herbicides, and inhibitors of glutamine synthase such as glufosinate. In addition to enzyme inhibitors, plants of the disclosure may also be tolerant of herbicides having other modes of action, for example, auxinic herbicides such as 2,4-D or dicamba, chlorophyll/carotenoid pigment inhibitors such as hydroxyphenylpyruvate dioxygenase (HPPD) inhibitors or phytoene desaturase (PDS) inhibitors, protoporphyrinogen-IX oxidase inhibitors, cell membrane destroyers, photosynthetic inhibitors such as bromoxynil or ioxynil, cell division inhibitors, root inhibitors, shoot inhibitors, and combinations thereof. Thus, plants of the disclosure tolerant to acetyl-Coenzyme A carboxylase inhibitors can be made resistant to multiple classes of herbicides.

For example, plants of the present disclosure are tolerant to acetyl-Coenzyme A carboxylase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden), in some embodiments, may be auxinic-herbicide tolerant, tolerant to EPSPS inhibitors, such as glyphosate; to PPO inhibitors, such as pyrimidinedione, such as saflufenacil, triazolinone, such as sulfentrazone, carfentrazone, flumioxazin, diphenylethers, such as acifluorfen, fomesafen, lactofen, oxyfluorfen, N-phenylphthalamides, such as flumiclorac, CGA-248757, and/or to GS inhibitors, such as glufosinate. In addition to these classes of inhibitors, plants of the disclosure tolerant to acetyl-Coenzyme A carboxylase inhibitors may also be tolerant to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof. Such tolerance traits may be expressed, e.g., as mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) proteins having an herbicide-degrading activity. Plants tolerant to acetyl-Coenzyme A carboxylase inhibitors hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, plants are also covered that, in addition to being able to tolerate herbicides that inhibit acetyl-Coenzyme A carboxylase activity, are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present disclosure these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda).

Furthermore, in one embodiment, plants are also covered that are, e.g., by the use of recombinant DNA techniques and/or by breeding and/or otherwise selected for such traits, able to synthesize one or more proteins to increase the resistance or tolerance of those plants to bacterial, viral or fungal pathogens. The methods for producing such genetically modified plants are generally known to the person skilled in the art. The plants produced as described herein can also be stacked with other traits including, but not limited to, disease resistance, enhanced mineral profile, enhanced vitamin profile, enhanced oil profile (e.g., high oleic acid content), amino acid profile (e.g., high lysine corn), and other trait types known in the art.

Furthermore, in one embodiment, plants are also covered that are, e.g., by the use of recombinant DNA techniques and/or by breeding and/or by other means of selection, able to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, in one embodiment, plants are also covered that contain, e.g., by the use of recombinant DNA techniques and/or by breeding and/or by other means of selection, a modified amount of substances of content or new substances of content, specifically to improve human or animal nutrition. Furthermore, plants are also covered that contain by the use of recombinant DNA techniques a modified amount of substances of content or new substances of content, specifically to improve raw material production.

Furthermore, in some embodiments, plants of the disclosure are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, plants of the disclosure tolerant to acetyl-Coenzyme A carboxylase inhibitors, relative to a wild-type plant, comprise an increased amount of, or an improved profile of, a compound selected from the group consisting of: glucosinolates (e.g., glucoraphanin (4-methyl sulfinylbutyl-glucosinolate), sulforaphane, 3-indolylmethyl-glucosinolate (glucobrassicin), 1-methoxy-3-indolylmethylglucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, plants of the disclosure tolerant to acetyl-Coenzyme A carboxylase inhibitors, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g., genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, plants of the disclosure tolerant to acetyl-Coenzyme A carboxylase inhibitors, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

The present disclosure also encompasses progeny of the plants of the disclosure as well as seeds derived from the herbicide-tolerant plants of the disclosure and cells derived from the herbicide-tolerant plants of the invention.

In various embodiments, plants hereof can be used to produce plant products. Thus, a method for preparing a descendant seed comprises planting a seed of a capable of producing a plant hereof, growing the resulting plant, and harvesting descendant seed thereof. In some embodiments, such a method can further comprise applying an ACCase-inhibiting herbicide composition to the resulting plant. Similarly, a method for producing a derived product from a plant hereof can comprise processing a plant part thereof to obtain a derived product. In some embodiments, such a method can be used to obtain a derived product that is any of, e.g., fodder, feed, seed meal, oil, or seed-treatment-coated seeds. Seeds, treated seeds, and other plant products obtained by such methods are useful products that can be commercialized.

In various embodiments, the present disclosure provides production of food products, consumer products, industrial products, and veterinary products from any of the plants described herein.

Acetyl-Coenzyme A carboxylase Enzymes

The present disclosure provides plants expressing acetyl-Coenzyme A carboxylase enzymes with amino acid sequences that differ from the amino acid sequence of the acetyl-Coenzyme A carboxylase enzyme found in the corresponding wild-type plant. For ease of understanding, the amino acid numbering system used herein will be the numbering system used for the acetyl-Coenzyme A carboxylase from *Alopecurus myosuroides* [Huds.] (also referred to as black grass). The mRNA sequence encoding the *A. myosuroides* acetyl-Coenzyme A carboxylase is available at GenBank accession number AJ310767 and the protein sequence is available at GenBank accession no. CAC84161 both of which are specifically incorporated herein by reference. The number of the amino acid referred to will be followed with (Am) to indicate the amino acid in the *Alopecurus myosuroides* sequence to which the amino acid corresponds. FIG. 18 provides *Alopecurus myosuroides* acetyl-Coenzyme A carboxylase amino acid sequence (GenBank accession no. CAC84161). Amino acids that may be altered in the acetyl-Coenzyme A carboxylase enzymes of the disclosure are indicated in bold double underline, and FIG. 19 depicts the amino acid sequence of wild-type *Oryza sativa* acetyl-Coenzyme A carboxylases aligned with *Alopecurus myosuroides* acetyl-Coenzyme A carboxylase with some critical residues denoted.

In one embodiment, an acetyl-Coenzyme A carboxylase of the present disclosure differs from the corresponding wild-type acetyl-Coenzyme A carboxylase at amino acid position 1,781(Am). Wild-type *A. myosuroides* acetyl-Coenzyme A carboxylase has an isoleucine at position 1,781 (Am) (I1781). The 1,781(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, leucine (I1781L), valine (I1781V), threonine (I1781T) and alanine (I1781A). In one embodiment, an acetyl-Coenzyme A carboxylase enzyme of the disclosure will have a leucine at position 1,781(Am).

In one embodiment, an acetyl-Coenzyme A carboxylase of the present disclosure differs from the corresponding wild-type acetyl-Coenzyme A carboxylase at amino acid position 1,785(Am). Wild-type *A. myosuroides* acetyl-Coenzyme A carboxylase has an alanine at position 1,785(Am) (A1785). The 1,785(Am) ACCase mutants of the disclosure will have an amino acid other than alanine at this position. Suitable examples of amino acids that may be found at this position in the acetyl-Coenzyme A carboxylase enzymes of the disclosure include, but are not limited to, glycine (A1785G). In one embodiment, an acetyl-Coenzyme A carboxylase enzyme of the disclosure will have a glycine at position 1,785(Am).

In one embodiment, an acetyl-Coenzyme A carboxylase of the present disclosure differs from the corresponding wild-type acetyl-Coenzyme A carboxylase at amino acid position 1,786(Am). Wild-type *A. myosuroides* acetyl-Coenzyme A carboxylase has an alanine at position 1,786(Am) (A1786). The 1,786(Am) ACCase mutants of the disclosure will have an amino acid other than alanine at this position. Suitable examples of amino acids that may be found at this position in the acetyl-Coenzyme A carboxylase enzymes of the disclosure include, but are not limited to, proline (A1786P). In one embodiment, an acetyl-Coenzyme A carboxylase enzyme of the disclosure will have a proline at position 1,786(Am).

In one embodiment, an acetyl-Coenzyme A carboxylase of the present disclosure differs from the corresponding wild-type acetyl-Coenzyme A carboxylase at amino acid position 1,811(Am). Wild-type *A. myosuroides* acetyl-Coenzyme A carboxylase has an isoleucine at position 1,811

(Am) (I1811). The 1,811(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (I1811N). In one embodiment, an acetyl-Coenzyme A carboxylase enzyme of the disclosure will have an asparagine at position 1,811(Am).

In one embodiment, an acetyl-Coenzyme A carboxylase of the present disclosure differs from the corresponding wild-type acetyl-Coenzyme A carboxylase at amino acid position 1,824(Am). Wild-type *A. myosuroides* acetyl-Coenzyme A carboxylase has a glutamine at position 1,824 (Am) (Q1824). The 1,824(Am) ACCase mutants of the disclosure will have an amino acid other than glutamine at this position. Suitable examples of amino acids that may be found at this position in the acetyl-Coenzyme A carboxylase enzymes of the disclosure include, but are not limited to, proline (Q1824P). In one embodiment, an acetyl-Coenzyme A carboxylase enzyme of the disclosure will have a proline at position 1,824(Am).

In one embodiment, an acetyl-Coenzyme A carboxylase of the present disclosure differs from the corresponding wild-type acetyl-Coenzyme A carboxylase at amino acid position 1,864(Am). Wild-type *A. myosuroides* acetyl-Coenzyme A carboxylase has a valine at position 1,864(Am) (V1864). The 1,864(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V1864F). In one embodiment, an acetyl-Coenzyme A carboxylase enzyme of the disclosure will have a phenylalanine at position 1,864(Am).

In one embodiment, an acetyl-Coenzyme A carboxylase of the present disclosure differs from the corresponding wild-type acetyl-Coenzyme A carboxylase at amino acid position 1,999(Am). Wild-type *A. myosuroides* acetyl-Coenzyme A carboxylase has a tryptophan at position 1,999 (Am) (W1999). The 1,999(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W1999C) and glycine (W1999G). In one embodiment, an acetyl-Coenzyme A carboxylase enzyme of the disclosure will have a glycine at position 1,999(Am).

In one embodiment, an acetyl-Coenzyme A carboxylase of the present disclosure differs from the corresponding wild-type acetyl-Coenzyme A carboxylase at amino acid position 2,027(Am). Wild-type *A. myosuroides* acetyl-Coenzyme A carboxylase has a tryptophan at position 2,027 (Am)(W2027). The 2,027(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, cysteine (W2027C) and arginine (W2027R). In one embodiment, an acetyl-Coenzyme A carboxylase enzyme of the disclosure will have a cysteine at position 2,027(Am).

In one embodiment, an acetyl-Coenzyme A carboxylase of the present disclosure differs from the corresponding wild-type acetyl-Coenzyme A carboxylase at amino acid position 2,039(Am). Wild-type *A. myosuroides* acetyl-Coenzyme A carboxylase has a glutamic acid at position 2,039(Am) (E2039). The 2,039(Am) ACCase mutants of the disclosure will have an amino acid other than glutamic acid at this position. Suitable examples of amino acids that may be found at this position in the acetyl-Coenzyme A carboxylase enzymes of the disclosure include, but are not limited to, glycine (E2039G). In one embodiment, an acetyl-Coenzyme A carboxylase enzyme of the disclosure will have an glycine at position 2,039(Am).

In one embodiment, an acetyl-Coenzyme A carboxylase of the present disclosure differs from the corresponding wild-type acetyl-Coenzyme A carboxylase at amino acid position 2,041(Am). Wild-type *A. myosuroides* acetyl-Coenzyme A carboxylase has an isoleucine at position 2,041 (Am) (I2041). The 2,041(Am) ACCase mutants of the disclosure will have an amino acid other than isoleucine at this position. Suitable examples of amino acids that may be found at this position in the acetyl-Coenzyme A carboxylase enzymes of the disclosure include, but are not limited to, asparagine (I2041N), or valine (I2041V). In one embodiment, an acetyl-Coenzyme A carboxylase enzyme of the disclosure will have an asparagine at position 2,041(Am).

In one embodiment, an acetyl-Coenzyme A carboxylase of the present disclosure differs from the corresponding wild-type acetyl-Coenzyme A carboxylase at amino acid position 2,049(Am). Wild-type *A. myosuroides* acetyl-Coenzyme A carboxylase has an valine at position 2,049(Am) (V2049). The 2,049(Am) ACCase mutants of the disclosure will have an amino acid other than valine at this position. Suitable examples of amino acids that may be found at this position in the acetyl-Coenzyme A carboxylase enzymes of the disclosure include, but are not limited to, phenylalanine (V2049F), isoleucine (V20491) and leucine (V2049L). In one embodiment, an acetyl-Coenzyme A carboxylase enzyme of the disclosure will have an phenylalanine at position 2,049(Am).

In one embodiment, an acetyl-Coenzyme A carboxylase of the present disclosure differs from the corresponding wild-type acetyl-Coenzyme A carboxylase at amino acid position 2,059(Am). Wild-type *A. myosuroides* acetyl-Coenzyme A carboxylase has an alanine at position 2,059(Am) (A2059). The 2,059(Am) ACCase mutants of the disclosure will have an amino acid other than an alanine at this position. Suitable examples of amino acids that may be found at this position in the acetyl-Coenzyme A carboxylase enzymes of the disclosure include, but are not limited to, valine (A2059V). In one embodiment, an acetyl-Coenzyme A carboxylase enzyme of the disclosure will have a valine at position 2,059(Am).

In one embodiment, an acetyl-Coenzyme A carboxylase of the present disclosure differs from the corresponding wild-type acetyl-Coenzyme A carboxylase at amino acid position 2074(Am). Wild-type *A. myosuroides* acetyl-Coenzyme A carboxylase has a tryptophan at position 2074(Am) (W2074). The 2,074(Am) ACCase mutants of the disclosure will have an amino acid other than tryptophan at this position. Suitable examples of amino acids that may be found at this position in the acetyl-Coenzyme A carboxylase enzymes of the disclosure include, but are not limited to, leucine (W2074L). In one embodiment, an acetyl-Coenzyme A carboxylase enzyme of the disclosure will have a leucine at 2074(Am).

In one embodiment, an acetyl-Coenzyme A carboxylase of the present disclosure differs from the corresponding wild-type acetyl-Coenzyme A carboxylase at amino acid position 2,075(Am). Wild-type *A. myosuroides* acetyl-Coenzyme A carboxylase has a valine at position 2,075(Am) (V2075). The 2,075(Am) ACCase mutants of the disclosure will have an amino acid other than valine at this position. Suitable examples of amino acids that may be found at this position in the acetyl-Coenzyme A carboxylase enzymes of the disclosure include, but are not limited to, methionine (V2075M), leucine (V2075L) and isoleucine (V2075I). In one embodiment, an acetyl-Coenzyme A carboxylase enzyme of the disclosure will have a leucine at position 2,075(Am). In some embodiments, an acetyl-Coenzyme A carboxylase enzyme of the disclosure will have a valine at position 2075(Am) and an additional valine immediately after position 2075(Am) and before the valine at position 2076(Am), i.e., may have three consecutive valines where the wild-type enzyme has two.

In one embodiment, an acetyl-Coenzyme A carboxylase of the present disclosure differs from the corresponding wild-type acetyl-Coenzyme A carboxylase at amino acid position 2,078(Am). Wild-type *A. myosuroides* acetyl-Coenzyme A carboxylase has an aspartate at position 2,078 (Am) (D2078). The 2,078(Am) ACCase mutants of the disclosure will have an amino acid other than aspartate at this position. Suitable examples of amino acids that may be found at this position in the acetyl-Coenzyme A carboxylase enzymes of the disclosure include, but are not limited to, lysine (D2,078K), glycine (D2078G), or threonine (D2078T). In one embodiment, an acetyl-Coenzyme A carboxylase enzyme of the disclosure will have a glycine at position 2,078(Am).

In one embodiment, an acetyl-Coenzyme A carboxylase of the present disclosure differs from the corresponding wild-type acetyl-Coenzyme A carboxylase at amino acid position 2,079(Am). Wild-type *A. myosuroides* acetyl-Coenzyme A carboxylase has a serine at position 2,079(Am) (S2079). The 2,079(Am) ACCase mutants of the disclosure will have an amino acid other than serine at this position. Suitable examples of amino acids that may be found at this position in the acetyl-Coenzyme A carboxylase enzymes of the disclosure include, but are not limited to, phenylalanine (S2079F). In one embodiment, an acetyl-Coenzyme A carboxylase enzyme of the disclosure will have a phenylalanine at position 2,079(Am).

In one embodiment, an acetyl-Coenzyme A carboxylase of the present disclosure differs from the corresponding wild-type acetyl-Coenzyme A carboxylase at amino acid position 2,080(Am). Wild-type *A. myosuroides* acetyl-Coenzyme A carboxylase has a lysine at position 2,080(Am) (K2080). The 2,080(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2080E). In one embodiment, an acetyl-Coenzyme A carboxylase enzyme of the disclosure will have a glutamic acid at position 2,080(Am). In another embodiment, acetyl-Coenzyme A carboxylase enzymes of the disclosure will typically have a deletion of this position (Δ2080).

In one embodiment, an acetyl-Coenzyme A carboxylase of the present disclosure differs from the corresponding wild-type acetyl-Coenzyme A carboxylase at amino acid position 2,081(Am). Wild-type *A. myosuroides* acetyl-Coenzyme A carboxylase has a isoleucine at position 2,081 (Am) (I2081). The 2,081(Am) ACCase mutants of the disclosure will have an amino acid other than isoleucine at this position. In one embodiment, acetyl-Coenzyme A carboxylase enzymes of the disclosure will typically have a deletion of this position (Δ2081).

In one embodiment, an acetyl-Coenzyme A carboxylase of the present disclosure differs from the corresponding wild-type acetyl-Coenzyme A carboxylase at amino acid position 2,088(Am). Wild-type *A. myosuroides* acetyl-Coenzyme A carboxylase has a cysteine at position 2,088(Am) (C2088). The 2,088(Am) ACCase mutants of the disclosure will have an amino acid other than cysteine at this position. Suitable examples of amino acids that may be found at this position in the acetyl-Coenzyme A carboxylase enzymes of the disclosure include, but are not limited to, arginine (C2088R), tryptophan (C2088W), phenylalanine (C2088F), glycine (C2088G), histidine (C2088H), lysine (C2088K), serine (C2088S), threonine (C2088T), leucine (C2088L) or valine (C2088V). In one embodiment, an acetyl-Coenzyme A carboxylase enzyme of the disclosure will have an arginine at position 2,088(Am).

In one embodiment, an acetyl-Coenzyme A carboxylase of the present disclosure differs from the corresponding wild-type acetyl-Coenzyme A carboxylase at amino acid position 2,095(Am). Wild-type *A. myosuroides* acetyl-Coenzyme A carboxylase has a lysine at position 2,095(Am) (K2095). The 2,095(Am) ACCase mutants of the disclosure will have an amino acid other than lysine at this position. Suitable examples of amino acids that may be found at this position in the acetyl-Coenzyme A carboxylase enzymes of the disclosure include, but are not limited to, glutamic acid (K2095E). In one embodiment, an acetyl-Coenzyme A carboxylase enzyme of the disclosure will have a glutamic acid at position 2,095(Am).

In one embodiment, an acetyl-Coenzyme A carboxylase of the present disclosure differs from the corresponding wild-type acetyl-Coenzyme A carboxylase at amino acid position 2,096(Am). Wild-type *A. myosuroides* acetyl-Coenzyme A carboxylase has a glycine at position 2,096(Am) (G2096). The 2,096(Am) ACCase mutants of the disclosure will have an amino acid other than glycine at this position. Suitable examples of amino acids that may be found at this position in the acetyl-Coenzyme A carboxylase enzymes of the disclosure include, but are not limited to, alanine (G2096A), or serine (G2096S). In one embodiment, an acetyl-Coenzyme A carboxylase enzyme of the disclosure will have an alanine at position 2,096(Am).

In one embodiment, an acetyl-Coenzyme A carboxylase of the present disclosure differs from the corresponding wild-type acetyl-Coenzyme A carboxylase at amino acid position 2,098(Am). Wild-type *A. myosuroides* acetyl-Coenzyme A carboxylase has a valine at position 2,098(Am) (V2098). The 2,098(Am) ACCase mutants of the disclosure will have an amino acid other than valine at this position. Suitable examples of amino acids that may be found at this position in the acetyl-Coenzyme A carboxylase enzymes of the disclosure include, but are not limited to, alanine (V2098A), glycine (V2098G), proline (V2098P), histidine (V2098H), serine (V2098S) or cysteine (V2098C). In one embodiment, an acetyl-Coenzyme A carboxylase enzyme of the disclosure will have an alanine at position 2,098(Am).

In one embodiment, the present disclosure emcompasses acetyl-Coenzyme A carboxylase of an herbicide-tolerant plant of the disclosure which differs from the acetyl-Coenzyme A carboxylase of the corresponding wild-type plant at only one of the following positions: 1,781(Am), 1,785(Am), 1,786(Am), 1,811(Am), 1,824(Am), 1,864(Am), 1,999 (Am), 2,027(Am), 2,039(Am), 2,041(Am), 2,049(Am), 2,059(Am), 2,074(Am), 2,075(Am), 2,078(Am), 2,079 (Am), 2,080(Am), 2,081(Am), 2,088(Am), 2,095(Am), 2,096(Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080(Am), or 2,095(Am). In a more preferred embodiment the acetyl-Coenzyme A carboxylase of a herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, Acetyl-Coenzyme A carboxylase enzymes of the disclosure will have only one of the following substitutions: an isoleucine at position 2,075(Am), glycine at position 2,078(Am), or arginine at position 2,088 (Am). In a preferred embodiment, Acetyl-Coenzyme A carboxylase enzymes of the disclosure will have only one of the following substitutions: a glycine at position 2,039(Am), valine at position 2,059(Am), methionine at position 2,075 (Am), duplication of position 2,075(Am) (i.e., an insertion of valine between 2,074(Am) and 2,075(Am), or an insertion of valine between position 2,075(Am) and 2,076(Am)), deletion of amino acid position 2,080(Am), glutamic acid at position 2,080(Am), deletion of position 2,081(Am), or glutamic acid at position 2,095(Am). In a more preferred embodiment, Acetyl-Coenzyme A carboxylase enzymes of the disclosure will have only one of the following substitutions: a glycine at position 1,785(Am), a proline at position 1,786(Am), an asparagine at position 1,811(Am), a leucine at position 2,075(Am), a methionine at position 2,075(Am), a threnonine at position 2,078(Am), a deletion at position 2,080(Am), a deletion at position 2,081(Am), a tryptophan, phenylalanine, glycine, histidine, lysine, leucine, serine, threonine, or valine at position 2,088(Am), a serine at position 2,096(Am), an alanine at position 2,096(Am), an alanine at position 2,098(Am), a glycine at position 2,098 (Am), an histidine at position 2,098(Am), a proline at position 2,098(Am), or a serine at position 2,098(Am). In a most preferred embodiment, Acetyl-Coenzyme A carboxylase enzymes of the disclosure will have only one of the following substitutions: a leucine at position 1,781(Am), a threonine at position 1,781(Am), a valine at position 1,781 (Am), an alanine at position 1,781(Am), a glycine at position 1,999(Am), a cysteine or arginine at position 2,027(Am), an arginine at position 2,027(Am), an asparagine at position 2,041(Am), a valine at position 2,041(Am), an alanine at position 2,096(Am), and a serine at position 2,096(Am).

In one embodiment, nucleic acids encoding Acetyl-Coenzyme A carboxylase polypeptide having only one of the following substitutions: isoleucine at position 2,075(Am), glycine at position 2,078(Am), or arginine at position 2,088 (Am) are used transgenically. In another embodiment, a monocot plant cell is transformed with an expression vector construct comprising the nucleic acid encoding Acetyl-Coenzyme A carboxylase polypeptide having only one of the following substitutions: isoleucine at position 2,075(Am), glycine at position 2,078(Am), or arginine at position 2,088 (Am).

In one embodiment, the present disclosure provides rice plants comprising nucleic acids encoding Acetyl-Coenzyme A carboxylase polypeptides having a substitution at only one amino acid position as described above.

In one embodiment, the present disclosure provides BEP clade plants comprising nucleic acids encoding Acetyl-Coenzyme A carboxylase polypeptides having a substitution at only one amino acid position as described above.

In one embodiment, the present disclosure provides BET subclade plants comprising nucleic acids encoding Acetyl-Coenzyme A carboxylase polypeptides having a substitution at only one amino acid position as described above.

In one embodiment, the present disclosure provides BET crop plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at only one amino acid position as described above.

In one embodiment, the present disclosure provides monocot plants comprising nucleic acids encoding Acetyl-Coenzyme A carboxylase polypeptides having a substitution at amino acid position 1,781(Am), wherein the amino acid at position 1,781(Am) differs from that of wild type and is not leucine.

In one embodiment, the present disclosure provides monocot plants comprising nucleic acids encoding Acetyl-Coenzyme A carboxylase polypeptides having a substitution at amino acid position 1,999(Am), wherein the amino acid at position 1,999(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,027(Am), wherein the amino acid at position 2,027(Am) differs from that of wild type and is not cysteine.

In one embodiment, the present disclosure provides monocot plants comprising nucleic acids encoding Acetyl-Coenzyme A carboxylase polypeptides having a substitution at amino acid position 2,041(Am), wherein the amino acid at position 2,041(Am) differs from that of wild type and is not valine or asparagine.

In one embodiment, the present disclosure provides monocot plants comprising nucleic acids encoding Acetyl-Coenzyme A carboxylase polypeptides having a substitution at amino acid position 2,096(Am), wherein the amino acid at position 2,096(Am) differs from that of wild type and is not alanine.

The present disclosure also provides acetyl-Coenzyme A carboxylase enzymes with an amino acid sequence that differs in more than one amino acid position from that of the acetyl-Coenzyme A carboxylase enzyme found in the corresponding wild-type plant. For example, an acetyl-Coenzyme A carboxylase of the present disclosure may differ in 2, 3, 4, 5, 6, or 7 positions from that of the acetyl-Coenzyme A carboxylase enzyme found in the corresponding wild-type plant.

In one embodiment, an acetyl-Coenzyme A carboxylase of the present disclosure differs from the corresponding wild-type acetyl-Coenzyme A carboxylase at amino acid position 1,781(Am) and at one or more additional amino acid positions. Acetyl-Coenzyme A carboxylase enzymes of the present disclosure will typically have a leucine, a threonine, a valine, or an alanine at position 1,781(Am). In addition, enzymes of this embodiment will also comprise one or more of a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074

(Am), a leucine, isoleucine, methionine, or an additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine tryptophan, phenylalanine, glycine, histidine, lysine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am) and a glycine at position 1,785(Am). In one embodiment, an acetyl-Coenzyme A carboxylase of the present disclosure will have a leucine, a threonine, a valine, or an alanine at position 1,781(Am) and a proline at position 1,786(Am). In one embodiment, an acetyl-Coenzyme A carboxylase of the present disclosure will have a leucine, a threonine, a valine, or an alanine at position 1,781(Am) and an asparagine at position 1,811(Am). In one embodiment, an acetyl-Coenzyme A carboxylase of the present disclosure will have a leucine, a threonine, a valine, or an alanine at position 1,781(Am) and a proline at position 1824(Am). In one embodiment, an acetyl-Coenzyme A carboxylase of the present disclosure will have a leucine, a threonine, a valine, or an alanine at position 1,781(Am) and a phenylalanine at position 1864(Am). In one embodiment, an acetyl-Coenzyme A carboxylase of the present disclosure will have a leucine, a threonine, a valine, or an alanine at position 1,781(Am) and a cysteine or glycine at position 1,999(Am). In one embodiment, an acetyl-Coenzyme A carboxylase of the present disclosure will have a leucine, a threonine, a valine, or an alanine at position 1,781(Am) and a cysteine or an arginine at position 2,027(Am). In one embodiment, an acetyl-Coenzyme A carboxylase of the present disclosure will have a leucine, a threonine, a valine, or an alanine at position 1,781(Am) and a glycine at position 2039(Am). In one embodiment, an acetyl-Coenzyme A carboxylase of the present disclosure will have a leucine, a threonine, a valine, or an alanine at position 1,781(Am) and an asparagine at position 2,041(Am). In one embodiment, an acetyl-Coenzyme A carboxylase of the present disclosure will have a leucine, a threonine, a valine, or an alanine at position 1,781(Am) and a phenylalanine, leucine or isoleucine at position 2,049(Am). In one embodiment, an acetyl-Coenzyme A carboxylase of the present disclosure will have a leucine, a threonine, a valine, or an alanine at position 1,781(Am) and a valine at position 2059(Am). In one embodiment, an acetyl-Coenzyme A carboxylase of the present disclosure will have a leucine, a threonine, a valine, or an alanine at position 1,781(Am) and a leucine at position 2,074(Am). In one embodiment, an acetyl-Coenzyme A carboxylase of the present disclosure will have a leucine, a threonine, a valine, or an alanine at position 1,781(Am) and a leucine, isoleucine methionine, or additional valine at position 2,075(Am). In one embodiment, an acetyl-Coenzyme A carboxylase of the present disclosure will have a leucine, a threonine, a valine, or an alanine at position 1,781(Am) and a glycine or threonine at position 2,078 (Am). In one embodiment, an acetyl-Coenzyme A carboxylase of the present disclosure will have a leucine, a threonine, a valine, or an alanine at position 1,781(Am) and a phenylalanine at position 2079(Am). In one embodiment, an acetyl-Coenzyme A carboxylase of the present disclosure will have a leucine, a threonine, a valine, or an alanine at position 1,781(Am) and a glutamic acid or a deletion at position 2080(Am). In one embodiment, an acetyl-Coenzyme A carboxylase of the present disclosure will have a leucine, a threonine, a valine, or an alanine at position 1,781(Am) and a deletion at position 2081(Am). In one embodiment, an acetyl-Coenzyme A carboxylase of the present disclosure will have a leucine, a threonine, a valine, or an alanine at position 1,781(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a leucine, a threonine, a valine, or an alanine at position 1,781(Am) and a glutamic acid at position 2,095(Am). In one embodiment, an acetyl-Coenzyme A carboxylase of the present disclosure will have a leucine, a threonine, a valine, or an alanine at position 1,781(Am) and an alanine or serine at position 2,096(Am). In one embodiment, an acetyl-Coenzyme A carboxylase of the present disclosure will have a leucine, a threonine, a valine, or an alanine at position 1,781(Am) and an alanine, glycine, proline, histidine, cysteine, or serine at position 2,098(Am). In one embodiment, an acetyl-Coenzyme A carboxylase of the present disclosure will have a leucine, a threonine, a valine, or an alanine at position 1,781(Am), a cysteine or arginine at position 2,027(Am), and an asparagine at position 2,041(Am). In one embodiment, an acetyl-Coenzyme A carboxylase of the present disclosure will have a leucine, a threonine, a valine, or an alanine at position 1,781(Am), a cysteine or arginine at position 2,027(Am), an asparagine at position 2,041(Am), and an alanine at position 2,096(Am).

In one embodiment, an acetyl-Coenzyme A carboxylase of the present disclosure differs from the corresponding wild-type acetyl-Coenzyme A carboxylase at amino acid position 1,785(Am) and at one or more additional amino acid positions. Acetyl-Coenzyme A carboxylase enzymes of the disclosure will typically have a glycine at position 1,785(Am). In addition, enzymes of this embodiment will also comprise one or more of a leucine, threonine, a valine, or alanine at position 1,781(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a glycine at position 1,785(Am) and a leucine, a threonine, a valine, or an alanine at position 1,781(Am). In one embodiment, an acetyl-Coenzyme A carboxylase of the present disclosure will have a glycine at position 1,785(Am) and a proline at position 1,786(Am). In one embodiment, an acetyl-Coenzyme A carboxylase of the present disclosure will have a glycine at position 1,785(Am) and an asparagine at position 1,811(Am). In one embodiment, an acetyl-Coenzyme A carboxylase of the present disclosure will have a glycine at position 1,785(Am) and a proline at position 1,824(Am). In one embodiment, an acetyl-Coenzyme A carboxylase of the present disclosure will have a glycine at position 1,785(Am) and a phenylalanine at position 1,864(Am). In one embodiment, an acetyl-Coenzyme A carboxylase of the present disclosure will have a glycine at position 1,785(Am) and a cysteine or glycine at position 1,999(Am). In one embodiment, an acetyl-Coenzyme A carboxylase of the present disclosure will have a glycine at position 1,785(Am) and a cysteine or an arginine at position 2,027(Am). In one embodiment, an acetyl-Coenzyme A carboxylase of the present disclosure will have a glycine at position 1,785(Am) and a glycine at position 2,039(Am). In one embodiment, an acetyl-Coenzyme A carboxylase of the present disclosure will have a glycine at position 1,785(Am) and an asparagine at position 2,041 (Am). In one embodiment, an acetyl-Coenzyme A carboxylase of the present disclosure will have a glycine at position 1,785(Am) and a phenylalanine, isoleucine or leucine at position 2,049(Am). In one embodiment, an acetyl-Coenzyme A carboxylase of the present disclosure will have a glycine at position 1,785(Am) and a valine at position 2,059(Am). In one embodiment, an acetyl-Coenzyme A carboxylase of the present disclosure will have a glycine at position 1,785(Am) and a leucine at position 2,074(Am). In one embodiment, an acetyl-Coenzyme A carboxylase of the present disclosure will have a glycine at position 1,785(Am) and a leucine, isoleucine, methionine or additional valine at position 2,075(Am). In one embodiment, an acetyl-Coenzyme A carboxylase of the present disclosure will have a glycine at position 1,785(Am) and a glycine or threonine at position 2,078(Am). In one embodiment, an acetyl-Coenzyme A carboxylase of the present disclosure will have a glycine at position 1,785(Am) and a phenylalanine at position 2,079(Am). In one embodiment, an acetyl-Coenzyme A carboxylase of the present disclosure will have a glycine at position 1,785(Am) and a glutamic acid or deletion at position 2,080(Am). In one embodiment, an acetyl-Coenzyme A carboxylase of the present disclosure will have a glycine at position 1,785(Am) and a deletion at position 2,081(Am). In one embodiment, an acetyl-Coenzyme A carboxylase of the present disclosure will have a glycine at position 1,785(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine at position 1,785(Am) and a glutamic acid at position 2,095(Am). In one embodiment, an acetyl-Coenzyme A carboxylase of the present disclosure will have a glycine at position 1,785(Am) and an alanine or serine at position 2,096(Am). In one embodiment, an acetyl-Coenzyme A carboxylase of the present disclosure will have a glycine at position 1,785(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,786(Am) and at one or more additional amino acid positions. Acetyl-Coenzyme A carboxylase enzymes of the disclosure will typically have a proline at position 1,786(Am). In addition, enzymes of this embodiment will also comprise one or more of a leucine, threonine, a valine, or alanine at position 1,781(Am), a glycine at position 1,785(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid or deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095 (Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a proline at position 1,786(Am) and a leucine, a threonine, a valine, or an alanine at position 1,781(Am). In one embodiment, an acetyl-Coenzyme A carboxylase of the present disclosure will have a proline at position 1,786(Am) and a glycine at position 1,785(Am). In one embodiment, an acetyl-Coenzyme A carboxylase of the present disclosure will have a proline at position 1,786(Am) and an asparagine at position 1,811(Am). In one embodiment, an acetyl-Coenzyme A carboxylase of the present disclosure will have a proline at position 1,786(Am) and a proline at position 1,824(Am). In one embodiment, an acetyl-Coenzyme A carboxylase of the present disclosure will have a proline at position 1,786(Am) and phenylalanine at position 1,864 (Am). In one embodiment, an acetyl-Coenzyme A carboxylase of the present disclosure will have a proline at position 1,786(Am) and a cysteine or glycine at position 1,999(Am). In one embodiment, an acetyl-Coenzyme A carboxylase of the present disclosure will have a proline at position 1,786 (Am) and a cysteine or an arginine at position 2,027(Am). In one embodiment, an acetyl-Coenzyme A carboxylase of the present disclosure will have a proline at position 1,786(Am) and a glycine at position 2,039(Am). In one embodiment, an acetyl-Coenzyme A carboxylase of the present disclosure will have a proline at position 1,786(Am) and an asparagine at position 2,041(Am). In one embodiment, an acetyl-Coenzyme A carboxylase of the present disclosure will have a proline at position 1,786(Am) and phenylalanine, isoleucine or leucine at position 2,049(Am) In one embodiment, an acetyl-Coenzyme A carboxylase of the present disclosure will have a proline at position 1,786(Am) and a valine at position 2,059(Am). In one embodiment, an acetyl-Coenzyme A carboxylase of the present disclosure will have a proline at position 1,786(Am) and a leucine at position 2,074(Am). In one embodiment, an acetyl-Coenzyme A carboxylase of the present disclosure will have a proline at position 1,786(Am) and a leucine, isoleucine, methionine or additional valine at position 2,075(Am). In one embodiment, an acetyl-Coenzyme A carboxylase of the present disclosure will have a proline at position 1,786(Am) and a glycine or threonine at position 2,078(Am). In one embodiment, an acetyl-Coenzyme A carboxylase of the present disclosure will have a proline at position 1,786(Am) and a phenylalanine at position 2,079(Am). In one embodiment, an acetyl-Coenzyme A carboxylase of the present disclosure will have a proline at position 1,786(Am) and a glutamic acid or deletion at position 2,080(Am). In one embodiment, an acetyl-Coenzyme A carboxylase of the present disclosure will have a proline at position 1,786(Am) and a deletion at position 2,081(Am). In one embodiment, an acetyl-Coenzyme A carboxylase of the present disclosure will have a proline at position 1,786(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a proline at position 1,786(Am) and a glutamic acid at position 2,095(Am). In one embodiment, an acetyl-Coenzyme A carboxylase of the present disclosure will have a proline at position 1,786(Am) and an alanine or serine at position 2,096(Am). In one embodiment, an acetyl-Coenzyme A carboxylase of the present disclosure will have a proline at position 1,786(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,811(Am) and at one or more additional amino acid positions. Acetyl-Coenzyme A carboxylase enzymes of the disclosure will typically have an asparagine at position 1,811(Am). In addition, enzymes of this embodiment will also comprise one or more of a leucine, threonine, a valine, or alanine at position 1,781(Am), a glycine at position 1,785(Am), a proline at position 1,786(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an asparagine at position 1,811(Am) and a leucine, a threonine, a valine, or an alanine at position 1,781(Am). In one embodiment, an acetyl-Coenzyme A carboxylase of the present disclosure will have an asparagine at position 1,811(Am) and a glycine at position 1,785(Am). In one embodiment, an acetyl-Coenzyme A carboxylase of the present disclosure will have an asparagine at position 1,811(Am) and a proline at position 1,786(Am). In one embodiment, an acetyl-Coenzyme A carboxylase of the present disclosure will have an asparagine at position 1,811(Am) and a proline at position 1,824(Am). In one embodiment, an acetyl-Coenzyme A carboxylase of the present disclosure will have an asparagine at position 1,811(Am) and phenylalanine at position 1,864(Am). In one embodiment, an acetyl-Coenzyme A carboxylase of the present disclosure will have an asparagine at position 1,811(Am) and a cysteine or glycine at position 1,999(Am). In one embodiment, an acetyl-Coenzyme A carboxylase of the present disclosure will have an asparagine at position 1,811(Am) and a cysteine or an arginine at position 2,027(Am). In one embodiment, an acetyl-Coenzyme A carboxylase of the present disclosure will have an asparagine at position 1,811(Am) and a glycine at position 2,039(Am). In one embodiment, an acetyl-Coenzyme A carboxylase of the present disclosure will have an asparagine at position 1,811(Am) and an asparagine at position 2,041(Am). In one embodiment, an acetyl-Coenzyme A carboxylase of the present disclosure will have an asparagine at position 1,811(Am) and phenylalanine, isoleucine or leucine at position 2,049(Am). In one embodiment, an acetyl-Coenzyme A carboxylase of the present disclosure will have an asparagine at position 1,811(Am) and a valine at position 2,059(Am). In one embodiment, an acetyl-Coenzyme A carboxylase of the present disclosure will have an asparagine at position 1,811(Am) and a leucine at position 2,074(Am). In one embodiment, an acetyl-Coenzyme A carboxylase of the present disclosure will have an asparagine at position 1,811(Am) and a leucine, isoleucine, methionine or additional valine at position 2,075(Am). In one embodiment, an acetyl-Coenzyme A carboxylase of the present disclosure will have an asparagine at position 1,811(Am) and a glycine or threonine at position 2,078(Am). In one embodiment, an acetyl-Coenzyme A carboxylase of the present disclosure will have an asparagine at position 1,811(Am) and a phenylalanine at position 2,079(Am). In one embodiment, an acetyl-Coenzyme A carboxylase of the present disclosure will have an asparagine at position 1,811(Am) and a glutamic acid or deletion at position 2,080(Am). In one embodiment, an acetyl-Coenzyme A carboxylase of the present disclosure will have an asparagine at position 1,811(Am) and a deletion at position 2,081(Am). In one embodiment, an acetyl-Coenzyme A carboxylase of the present disclosure will have an asparagine at position 1,811(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an asparagine at position 1,811(Am) and a glutamic acid at position 2,095(Am). In one embodiment, an acetyl-Coenzyme A carboxylase of the present disclosure will have an asparagine at position 1,811(Am) and an alanine or serine at position 2,096(Am). In one embodiment, an acetyl-Coenzyme A carboxylase of the present disclosure will have an asparagine at position 1,811(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,824(Am) and at one or more additional amino acid positions. Acetyl-Coenzyme A carboxylase enzymes of the disclosure will typically have a proline at position 1,824(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,864(Am) and at one or more additional amino acid positions. Acetyl-Coenzyme A carboxylase enzymes of the disclosure will typically have a phenylalanine at position 1,864(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a cysteine or glycine at position 1,999(Am), a cysteine or arginine at position 2,027(Am), a glycine at position 2,039 (Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 1,999(Am) and at one or more additional amino acid positions. Acetyl-Coenzyme A carboxylase enzymes of the disclosure will typically have a cysteine or glycine at position 1,999(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or glycine at position 1,999(Am) and a leucine, a threonine, a valine, or an alanine at position 1,781(Am). In one embodiment, an acetyl-Coenzyme A carboxylase of the present disclosure will have a cysteine or glycine at position 1,999(Am) and a glycine at position 1,785(Am). In one embodiment, an acetyl-Coenzyme A carboxylase of the present disclosure will have a cysteine or glycine at position 1,999(Am) and a proline at position 1,786(Am). In one embodiment, an acetyl-Coenzyme A carboxylase of the present disclosure will have a cysteine or glycine at position 1,999(Am) and have an asparagine at position 1,811(Am). In one embodiment, an acetyl-Coenzyme A carboxylase of the present disclosure will have a cysteine or glycine at position 1,999(Am) and a proline at position 1,824(Am). In one embodiment, an acetyl-Coenzyme A carboxylase of the present disclosure will have a cysteine or glycine at position 1,999(Am) and phenylalanine at position 1,864(Am). In one embodiment, an acetyl-Coenzyme A carboxylase of the present disclosure will have a cysteine or glycine at position 1,999(Am) and a cysteine or an arginine at position 2,027(Am). In one embodiment, an acetyl-Coenzyme A carboxylase of the present disclosure will have a cysteine or glycine at position 1,999(Am) and a glycine at position 2,039(Am). In one embodiment, an acetyl-Coenzyme A carboxylase of the present disclosure will have a cysteine or glycine at position 1,999(Am) and an asparagine at position 2,041(Am). In one embodiment, an acetyl-Coenzyme A carboxylase of the present disclosure will have a cysteine or glycine at position 1,999(Am) and a phenylalanine, isoleucine or leucine at position 2,049(Am). In one embodiment, an acetyl-Coenzyme A carboxylase of the present disclosure will have a cysteine or glycine at position 1,999(Am) and a cysteine or a valine at position 2,059(Am). In one embodiment, an acetyl-Coenzyme A carboxylase of the present disclosure will have a cysteine or glycine at position 1,999(Am) and a leucine at position 2,074(Am). In one embodiment, an acetyl-Coenzyme A carboxylase of the present disclosure will have a cysteine or glycine at position 1,999(Am) and a leucine, isoleucine, methionine or additional valine at position 2,075(Am). In one embodiment, an acetyl-Coenzyme A carboxylase of the present disclosure will have a cysteine or glycine at position 1,999(Am) and a glycine or threonine at position 2,078 (Am). In one embodiment, an acetyl-Coenzyme A carboxylase of the present disclosure will have a cysteine or glycine at position 1,999(Am) and a phenylalanine at position 2,079 (Am). In one embodiment, an acetyl-Coenzyme A carboxylase of the present disclosure will have a cysteine or glycine at position 1,999(Am) and a glutamic acid or deletion at position 2,080(Am). In one embodiment, an acetyl-Coenzyme A carboxylase of the present disclosure will have a cysteine or glycine at position 1,999(Am) and a deletion at position 2,081(Am). In one embodiment, an acetyl-Coenzyme A carboxylase of the present disclosure will have a cysteine or glycine at position 1,999(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or glycine at position 1,999(Am) and a glutamic acid at position 2,095(Am). In one embodiment, an acetyl-Coenzyme A carboxylase of the present disclosure will have a cysteine or glycine at position 1,999(Am) and an alanine or serine at position 2,096(Am). In one embodiment, an acetyl-Coenzyme A carboxylase of the present disclosure will have a cysteine or glycine at position 1,999(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,027(Am) and at one or more additional amino acid positions. Acetyl-Coenzyme A carboxylase enzymes of the disclosure will typically have a cysteine or arginine at position 2,027(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a cysteine or arginine at position 2,027(Am) and a leucine, a threonine, a valine, or an alanine at position 1,781(Am). In one embodiment, an acetyl-Coenzyme A carboxylase of the present disclosure will have a cysteine or arginine at position 2,027(Am) and a glycine at position 1,785(Am). In one embodiment, an acetyl-Coenzyme A carboxylase of the present disclosure will have a cysteine or arginine at position 2,027(Am) and a proline at position 1,786(Am). In one embodiment, an acetyl-Coenzyme A carboxylase of the present disclosure will have a cysteine or arginine at position 2,027(Am) and have an asparagine at position 1,811(Am). In one embodiment, an acetyl-Coenzyme A carboxylase of the present disclosure will have a cysteine or arginine at position 2,027(Am) and have a proline at position 1,824(Am). In one embodiment, an acetyl-Coenzyme A carboxylase of the present disclosure will have a cysteine or arginine at position 2,027(Am) and have a phenylalanine at position 1,864(Am). In one embodiment, an acetyl-Coenzyme A carboxylase of the present disclosure will have a cysteine or arginine at position 2,027(Am) and a cysteine or glycine at position 1,999(Am). In one embodiment, an acetyl-Coenzyme A carboxylase of the present disclosure will have a cysteine or arginine at position 2,027(Am) and have a glycine at position 2,039(Am). In one embodiment, an acetyl-Coenzyme A carboxylase of the present disclosure will have a cysteine or arginine at position 2,027(Am) and an asparagine at position 2,041(Am). In one embodiment, an acetyl-Coenzyme A carboxylase of the present disclosure will have a cysteine or arginine at position 2,027(Am) and a phenylalanine, isoleucine or leucine at position 2,049(Am). In one embodiment, an acetyl-Coenzyme A carboxylase of the present disclosure will have a cysteine or arginine at position 2,027(Am) and have a valine at position 2,059(Am). In one embodiment, an acetyl-Coenzyme A carboxylase of the present disclosure will have a cysteine or arginine at position 2,027(Am) and a leucine at position 2,074(Am). In one embodiment, an acetyl-Coenzyme A carboxylase of the present disclosure will have a cysteine or arginine at position 2,027(Am) and a leucine, isoleucine, methionine or additional valine at position 2,075(Am). In one embodiment, an acetyl-Coenzyme A carboxylase of the present disclosure will have a cysteine or arginine at position 2,027(Am) and a glycine or threonine at position 2,078(Am). In one embodiment, an acetyl-Coenzyme A carboxylase of the present disclosure will have a cysteine or arginine at position 2,027(Am) and a phenylalanine at position 2,079(Am). In one embodiment, an acetyl-Coenzyme A carboxylase of the present disclosure will have a cysteine or arginine at position 2,027(Am) and a glutamic acid or deletion at position 2,080(Am). In one embodiment, an acetyl-Coenzyme A carboxylase of the present disclosure will have a cysteine or arginine at position 2,027(Am) and a deletion at position 2,081(Am). In one embodiment, an acetyl-Coenzyme A carboxylase of the present disclosure will have a cysteine or arginine at position 2,027(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a cysteine or arginine at position 2,027(Am) and a glutamic acid at position 2,095(Am). In one embodiment, an acetyl-Coenzyme A carboxylase of the present disclosure will have a cysteine or arginine at position 2,027(Am) and an alanine or serine at position 2,096(Am). In one embodiment, an acetyl-Coenzyme A carboxylase of the present disclosure will have a cysteine or arginine at position 2,027(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,039(Am) and at one or more additional amino acid positions. Acetyl-Coenzyme A carboxylase enzymes of the disclosure will typically have a glycine at position 2,039(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,041(Am) and at one or more additional amino acid positions. Acetyl-Coenzyme A carboxylase enzymes of the disclosure will typically have an asparagine at position 2,041(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have an asparagine at position 2,041(Am) and a leucine, a threonine, a valine, or an alanine at position 1,781(Am). In one embodiment, an acetyl-Coenzyme A carboxylase of the present disclosure will have an asparagine at position 2,041(Am) and a glycine at position 1,785(Am). In one embodiment, an acetyl-Coenzyme A carboxylase of the present disclosure will have an asparagine at position 2,041(Am) and a proline at position 1,786(Am). In one embodiment, an acetyl-Coenzyme A carboxylase of the present disclosure will have an asparagine at position 2,041(Am) and have an asparagine at position 1,811(Am). In one embodiment, an acetyl-Coenzyme A carboxylase of the present disclosure will have an asparagine at position 2,041(Am) and a proline at position 1824(Am). In one embodiment, an acetyl-Coenzyme A carboxylase of the present disclosure will have an asparagine at position 2,041(Am) and a phenylalanine at position 1864(Am). In one embodiment, an acetyl-Coenzyme A carboxylase of the present disclosure will have an asparagine at position 2,041(Am) and a cysteine or glycine at position 1,999(Am). In one embodiment, an acetyl-Coenzyme A carboxylase of the present disclosure will have an asparagine at position 2,041(Am) and a cysteine or arginine at position 2,027(Am). In one embodiment, an acetyl-Coenzyme A carboxylase of the present disclosure will have an asparagine at position 2,041(Am) and a glycine at position 2039(Am). In one embodiment, an acetyl-Coenzyme A carboxylase of the present disclosure will have an asparagine at position 2,041(Am) and an asparagine at position 2,041(Am). In one embodiment, an acetyl-Coenzyme A carboxylase of the present disclosure will have an asparagine at position 2,041(Am) and a phenylalanine, isoleucine or leucine at position 2,049(Am) In one embodiment, an acetyl-Coenzyme A carboxylase of the present disclosure will have an asparagine at position 2,041(Am) and a valine at position 2,059(Am). In one embodiment, an acetyl-Coenzyme A carboxylase of the present disclosure will have an asparagine at position 2,041(Am) and a leucine at position 2,074(Am). In one embodiment, an acetyl-Coenzyme A carboxylase of the present disclosure will have an asparagine at position 2,041(Am) and a leucine, isoleucine, methionine or additional valine at position 2,075(Am). In one embodiment, an acetyl-Coenzyme A carboxylase of the present disclosure will have an asparagine at position 2,041 (Am) and a glycine or threonine at position 2,078(Am). In one embodiment, an acetyl-Coenzyme A carboxylase of the present disclosure will have an asparagine at position 2,041 (Am) and a phenylalanine at position 2079(Am). In one embodiment, an acetyl-Coenzyme A carboxylase of the present disclosure will have an asparagine at position 2,041 (Am) and a glutamic acid or a deletion at position 2080 (Am). In one embodiment, an acetyl-Coenzyme A carboxylase of the present disclosure will have an asparagine at position 2,041(Am) and a deletion at position 2081(Am). In one embodiment, an acetyl-Coenzyme A carboxylase of the present disclosure will have an isoleucine at position 2,041 (Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have an isoleucine at position 2,041(Am) and a glutamic acid at position 2,095(Am). In one embodiment, an acetyl-Coenzyme A carboxylase of the present disclosure will have an isoleucine at position 2,041(Am) and an alanine or serine at position 2,096(Am). In one embodiment, an acetyl-Coenzyme A carboxylase of the present disclosure will have an isoleucine at position 2,041(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,049(Am) and at one or more additional amino acid positions. Acetyl-Coenzyme A carboxylase enzymes of the disclosure will typically have a phenylalanine, isoleucine or leucine at position 2,049(Am). In addition, enzymes of this embodiment will also comprise one or more of a leucine, threonine, a valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a valine at position 2,059(Am), a leucine at position 2,074(Am), a leucine, isoleucine, methionine or additional valine at position 2,075(Am), a glycine or threonine at position 2,078 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a phenylalanine, isoleucine or leucine at position 2,049(Am) and a leucine, a threonine, a valine, or an alanine at position 1,781(Am). In one embodiment, an acetyl-Coenzyme A carboxylase of the present disclosure will have a phenylalanine, isoleucine or leucine at position 2,049(Am) and a glycine at position 1,785(Am). In one embodiment, an acetyl-Coenzyme A carboxylase of the present disclosure will have a phenylalanine, isoleucine or leucine at position 2,049(Am) and a proline at position 1,786(Am). In one embodiment, an acetyl-Coenzyme A carboxylase of the present disclosure will have a phenylalanine, isoleucine or leucine at position 2,049(Am) and have an asparagine at position 1,811(Am). In one embodiment, an acetyl-Coenzyme A carboxylase of the present disclosure will have a phenylalanine, isoleucine or leucine at position 2,049(Am) and a proline at position 1824(Am). In one embodiment, an acetyl-Coenzyme A carboxylase of the present disclosure will have a phenylalanine, isoleucine or leucine at position 2,049(Am) and a phenylalanine at position 1864(Am). In one embodiment, an acetyl-Coenzyme A carboxylase of the present disclosure will have a phenylalanine, isoleucine or leucine at position 2,049(Am) and a cysteine or glycine at position 1,999(Am). In one embodiment, an acetyl-Coenzyme A carboxylase of the present disclosure will have a phenylalanine, isoleucine or leucine at position 2,049(Am) and a cysteine or an arginine at position 2,027(Am). In one embodiment, an acetyl-Coenzyme A carboxylase of the present disclosure will have a phenylalanine, isoleucine or leucine at position 2,049(Am) and a glycine at position 2039(Am). In one embodiment, an acetyl-Coenzyme A carboxylase of the present disclosure will have a phenylalanine, isoleucine or leucine at position 2,049(Am) and an asparagine at position 2,041(Am). In one embodiment, an acetyl-Coenzyme A carboxylase of the present disclosure will have a phenylalanine, isoleucine or leucine at position 2,049(Am) and a valine at position 2059(Am). In one embodiment, an acetyl-Coenzyme A carboxylase of the present disclosure will have a phenylalanine, isoleucine or leucine at position 2,049(Am) and a leucine at position 2,074(Am). In one embodiment, an acetyl-Coenzyme A carboxylase of the present disclosure will have a phenylalanine, isoleucine or leucine at position 2,049(Am) and a leucine, isoleucine methionine, or additional valine at position 2,075(Am). In one embodiment, an acetyl-Coenzyme A carboxylase of the present disclosure will have a phenylalanine, isoleucine or leucine at position 2,049(Am) and a glycine or threonine at position 2,078 (Am). In one embodiment, an acetyl-Coenzyme A carboxylase of the present disclosure will have a phenylalanine, isoleucine or leucine at position 2,049(Am) and a phenylalanine at position 2079(Am). In one embodiment, an acetyl-Coenzyme A carboxylase of the present disclosure will have a phenylalanine, isoleucine or leucine at position 2,049(Am) and a glutamic acid or a deletion at position 2080(Am). In one embodiment, an acetyl-Coenzyme A carboxylase of the present disclosure will have a phenylalanine, isoleucine or leucine at position 2,049(Am) and a deletion at position 2081(Am). In one embodiment, an acetyl-Coenzyme A carboxylase of the present disclosure will have a phenylalanine, isoleucine or leucine at position 2,049(Am) and an arginine, tryptophan, phenylalanine, glycine, histidine, lysine, serine, threonine, or valine at position 2,088(Am). In one embodiment, an acetyl-Coenzyme A carboxylase of the present disclosure will have a phenylalanine, isoleucine or leucine at position 2,049(Am) and a glutamic acid at position 2,095(Am). In one embodiment, an acetyl-Coenzyme A carboxylase of the present disclosure will have a phenylalanine, isoleucine or leucine at position 2,049(Am) and an alanine or serine at position 2,096(Am). In one embodiment, an acetyl-Coenzyme A carboxylase of the present disclosure will have a phenylalanine, isoleucine or leucine at position 2,049(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,059(Am) and at one or more additional amino acid positions. Acetyl-Coenzyme A carboxylase enzymes of the disclosure will typically have a valine at position 2,059 (Am). In addition, enzymes of this embodiment will also comprise one or more of a leucine, threonine, a valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine or tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,074(Am) and at one or more additional amino acid positions. Acetyl-Coenzyme A carboxylase enzymes of the disclosure will typically have a leucine at position 2,074(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine at position 2,074(Am) and a leucine, a threonine, a valine, or an alanine at position 1,781(Am). In one embodiment, an acetyl-Coenzyme A carboxylase of the present disclosure will have a leucine at position 2,074(Am) and a glycine at position 1,785(Am). In one embodiment, an acetyl-Coenzyme A carboxylase of the present disclosure will have a leucine at position 2,074(Am) and a proline at position 1,786(Am). In one embodiment, an acetyl-Coenzyme A carboxylase of the present disclosure will have a leucine at position 2,074(Am) and have an asparagine at position 1,811(Am). In one embodiment, an acetyl-Coenzyme A carboxylase of the present disclosure will have a leucine at position 2,074(Am) and a proline at position 1824(Am). In one embodiment, an acetyl-Coenzyme A carboxylase of the present disclosure will have a leucine at position 2,074(Am) and a phenylalanine at position 1864(Am). In one embodiment, an acetyl-Coenzyme A carboxylase of the present disclosure will have a leucine at position 2,074(Am) and a cysteine or glycine at position 1,999(Am). In one embodiment, an acetyl-Coenzyme A carboxylase of the present disclosure will have a leucine at position 2,074(Am) and a cysteine or an arginine at position 2,027(Am). In one embodiment, an acetyl-Coenzyme A carboxylase of the present disclosure will have a leucine at position 2,074(Am) and a glycine at position 2039(Am). In one embodiment, an acetyl-Coenzyme A carboxylase of the present disclosure will have a leucine at position 2,074(Am) and an asparagine at position 2,041(Am). In one embodiment, an acetyl-Coenzyme A carboxylase of the present disclosure will have a leucine at position 2,074(Am) and a phenylalanine, leucine or isoleucine at position 2,049(Am). In one embodiment, an acetyl-Coenzyme A carboxylase of the present disclosure will have a leucine at position 2,074 (Am) and a valine at position 2059(Am). In one embodiment, an acetyl-Coenzyme A carboxylase of the present disclosure will have a leucine at position 2,074(Am) and a leucine, isoleucine methionine, or additional valine at position 2,075(Am). In one embodiment, an acetyl-Coenzyme A carboxylase of the present disclosure will have a leucine at position 2,074(Am) and a glycine or threonine at position 2,078(Am). In one embodiment, an acetyl-Coenzyme A carboxylase of the present disclosure will have a leucine at position 2,074(Am) and a phenylalanine at position 2079 (Am). In one embodiment, an acetyl-Coenzyme A carboxylase of the present disclosure will have a leucine at position 2,074(Am) and a glutamic acid or a deletion at position 2080(Am). In one embodiment, an acetyl-Coenzyme A carboxylase of the present disclosure will have a leucine at position 2,074(Am) and a deletion at position 2081(Am). In one embodiment, an acetyl-Coenzyme A carboxylase of the present disclosure will have a leucine at position 2,074(Am) and an arginine, tryptophan, phenylalanine, glycine, histidine, lysine, serine, threonine, or valine at position 2,088 (Am). In one embodiment, an acetyl-Coenzyme A carboxylase of the present disclosure will have a leucine at position 2,074(Am) and a glutamic acid at position 2,095(Am). In one embodiment, an acetyl-Coenzyme A carboxylase of the present disclosure will have a leucine at position 2,074(Am) and an alanine or serine at position 2,096(Am). In one embodiment, an acetyl-Coenzyme A carboxylase of the present disclosure will have a leucine at position 2,074(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,075(Am) and at one or more additional amino acid positions. Acetyl-Coenzyme A carboxylase enzymes of the disclosure will typically have a leucine, isoleucine, methionine or additional valine at position 2,075(Am). In addition, enzymes of this embodiment will also comprise one or more of a leucine, threonine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have a leucine, isoleucine, methionine or additional valine at position 2,075(Am) and a leucine, a threonine, a valine, or an alanine at position 1,781(Am). In one embodiment, an acetyl-Coenzyme A carboxylase of the present disclosure will have a leucine, isoleucine, methionine or additional valine at position 2,075(Am) and a glycine at position 1,785(Am). In one embodiment, an acetyl-Coenzyme A carboxylase of the present disclosure will have a leucine, isoleucine, methionine or additional valine at position 2,075(Am) and a proline at position 1,786(Am). In one embodiment, an acetyl-Coenzyme A carboxylase of the present disclosure will have a leucine, isoleucine, methionine or additional valine at position 2,075(Am) and have an asparagine at position 1,811(Am). In one embodiment, an acetyl-Coenzyme A carboxylase of the present disclosure will have a leucine, isoleucine, methionine or additional valine at position 2,075(Am) and a cysteine or glycine at position 1,999(Am). In one embodiment, an acetyl-Coenzyme A carboxylase of the present disclosure will have a leucine, isoleucine, methionine or additional valine at position 2,075(Am) and a cysteine or arginine at position 2,027 (Am). In one embodiment, an acetyl-Coenzyme A carboxylase of the present disclosure will have a leucine, isoleucine, methionine or additional valine at position 2,075(Am) and an isoleucine at position 2,041(Am). In one embodiment, an acetyl-Coenzyme A carboxylase of the present disclosure will have a leucine, isoleucine, methionine or additional valine at position 2,075(Am) and a phenylalanine, isoleucine or leucine at position 2,049(Am). In one embodiment, an acetyl-Coenzyme A carboxylase of the present disclosure will have a leucine, isoleucine, methionine or additional valine at position 2,075(Am) and a leucine at position 2,074(Am). In one embodiment, an acetyl-Coenzyme A carboxylase of the present disclosure will have a leucine, isoleucine, methionine or additional valine at position 2,075 (Am) and a glycine or threonine at position 2,078(Am). In one embodiment, an acetyl-Coenzyme A carboxylase of the present disclosure will have a leucine, isoleucine, methionine or additional valine at position 2,075(Am) and an arginine or tryptophan, phenylalanine, glycine, histidine, lysine, leucine, serine, threonine, or valine at position 2,088 (Am). In one embodiment, an acetyl-Coenzyme A carboxylase of the present disclosure will have a leucine, isoleucine, methionine or additional valine at position 2,075(Am) and an alanine or serine at position 2,096(Am). In one embodiment, an acetyl-Coenzyme A carboxylase of the present disclosure will have a leucine, isoleucine, methionine or additional valine at position 2,075(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,078(Am) and at one or more additional amino acid positions. Acetyl-Coenzyme A carboxylase enzymes of the disclosure will typically have a glycine or threonine at position 2,078(Am). In addition, enzymes of this embodiment will also comprise one or more of a leucine, threonine, a valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a phenylalanine at position 2,079(Am), a glutamic acid at position 2,080(Am), a deletion at position 2,080 (Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine or serine at position 2,098(Am). In one embodiment, an acetyl-Coenzyme A carboxylase of the present disclosure will have a glycine or threonine at position 2,078(Am) and a leucine, a threonine or an alanine at position 1,781(Am). In one embodiment, an acetyl-Coenzyme A carboxylase of the present disclosure will have a glycine or threonine at position 2,078(Am) and a glycine at position 1,785(Am). In one embodiment, an acetyl-Coenzyme A carboxylase of the present disclosure will have a glycine or threonine at position 2,078(Am) and a proline at position 1,786(Am). In one embodiment, an acetyl-Coenzyme A carboxylase of the present disclosure will have a glycine or threonine at position 2,078(Am) and an asparagine at position 1,811(Am). In one embodiment, an acetyl-Coenzyme A carboxylase of the present disclosure will have a glycine or threonine at position 2,078(Am) and a cysteine or glycine at position 1,999(Am). In one embodiment, an acetyl-Coenzyme A carboxylase of the present disclosure will have a glycine or threonine at position 2,078(Am) and a cysteine or arginine at position 2,027(Am). In one embodiment, an acetyl-Coenzyme A carboxylase of the present disclosure will have a glycine or threonine at position 2,078(Am) and an isoleucine at position 2,041(Am). In one embodiment, an acetyl-Coenzyme A carboxylase of the present disclosure will have a glycine or threonine at position 2,078(Am) and a phenylalanine, isoleucine or leucine at position 2,049(Am). In one embodiment, an acetyl-Coenzyme A carboxylase of the present disclosure will have a glycine or threonine at position 2,078(Am) and a leucine at position 2,074(Am). In one embodiment, an acetyl-Coenzyme A carboxylase of the present disclosure will have a glycine or threonine at position 2,078(Am) and a leucine, isoleucine, methionine or additional valine at position 2,075 (Am). In one embodiment, an acetyl-Coenzyme A carboxylase of the present disclosure will have a glycine or threonine at position 2,078(Am) and an arginine, tryptophan, phenylalanine, glycine, histidine, lysine, leucine, serine, threonine, or valine at position 2,088(Am). In one embodiment, an acetyl-Coenzyme A carboxylase of the present disclosure will have a glycine or threonine at position 2,078(Am) and an alanine or serine at position 2,096(Am). In one embodiment, an acetyl-Coenzyme A carboxylase of the present disclosure will have a glycine or threonine at position 2,078(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,079(Am) and at one or more additional amino acid positions. Acetyl-Coenzyme A carboxylase enzymes of the disclosure will typically have a phenylalanine at position 2,079(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,080(Am) and at one or more additional amino acid positions. Acetyl-Coenzyme A carboxylase enzymes of the disclosure will typically have a glutamic acid or a deletion at position 2,080(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075 (Am), a glycine or threonine at position 2,078(Am), a phenylalanine at position 2,079(Am), a deletion at position 2,081(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,081(Am) and at one or more additional amino acid positions. Acetyl-Coenzyme A carboxylase enzymes of the disclosure will typically have a deletion at position 2,081(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080 (Am), a deletion at position 2,080(Am), an arginine, tryptophan, phenylalanine, glycine, histidine, lysine, leucine, serine, threonine, or valine at position 2,088(Am), a glutamic acid at position 2,095(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,088(Am) and at one or more additional amino acid positions. Acetyl-Coenzyme A carboxylase enzymes of the disclosure will typically have an arginine, tryptophan, phenylalanine, glycine, histidine, lysine, leucine, serine, threonine, or valine at position 2,088(Am). In addition, enzymes of this embodiment will also comprise one or more of a leucine, threonine, valine, or alanine at position 1,781 (Am), a glycine at position 1,785(Am), a proline at position 1,786(Am), an asparagine at position 1,811(Am), a proline at position 1,824(Am), a phenylalanine at position 1,864 (Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074 (Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), a glutamic acid at position 2,095(Am), an alanine or serine at position 2,096(Am), and an alanine, glycine, proline, histidine, cysteine, or serine at position 2,098(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, a threonine, valine, or an alanine at position 1,781(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine at position 1,785(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a proline at position 1,786(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an asparagine at position 1,811(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a cysteine or glycine at position 1,999(Am). In one embodiment, an acetyl-Coenzyme A carboxylase of the present disclosure will have an arginine or tryptophan, phenylalanine, glycine, histidine, lysine, leucine, serine, threonine, or valine at position 2,088(Am) and a cysteine or arginine at position 2,027(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an isoleucine at position 2,041(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a phenylalanine, isoleucine or leucine at position 2,049(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine at position 2,074(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a leucine, isoleucine, methionine or additional valine at position 2,075(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and a glycine or threonine at position 2,078(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine or serine at position 2,096(Am). In one embodiment, an acetyl-Coenzyme A carboxylase of the present disclosure will have an arginine, tryptophan, phenylalanine, glycine, histidine, lysine, leucine, serine, threonine, or valine at position 2,088(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,095(Am) and at one or more additional amino acid positions. Acetyl-Coenzyme A carboxylase enzymes of the disclosure will typically have a glutamic acid at position 2,095(Am). In addition, enzymes of this embodiment will also comprise one or more of a leucine, threonine, valine, or alanine at position 1,781(Am), a glycine at position 1,785 (Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine or tryptophan, phenylalanine, glycine, histidine, lysine, leucine, serine, threonine, or valine at position 2,088(Am), an alanine or serine at position 2,096(Am), and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,096(Am) and at one or more additional amino acid positions. Acetyl-Coenzyme A carboxylase enzymes of the disclosure will typically have an alanine or serine at position 2,096(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081(Am), an arginine, tryptophan, phenylalanine, glycine, histidine, lysine, leucine, serine, threonine, or valine at position 2,088(Am), a glutamic acid at position 2,095(Am), and an alanine, glycine, proline, histidine, cysteine, or serine at position 2,098(Am). In one embodiment, an acetyl-Coenzyme A carboxylase of the present disclosure will have an alanine or serine at position 2,096(Am) and a leucine, a threonine or an alanine at position 1,781(Am). In one embodiment, an acetyl-Coenzyme A carboxylase of the present disclosure will have an alanine or serine at position 2,096(Am) and a glycine at position 1,785(Am). In one embodiment, an acetyl-Coenzyme A carboxylase of the present disclosure will have an alanine or serine at position 2,096(Am) and a proline at position 1,786(Am). In one embodiment, an acetyl-Coenzyme A carboxylase of the present disclosure will have an alanine or serine at position 2,096(Am) and an asparagine at position 1,811(Am). In one embodiment, an acetyl-Coenzyme A carboxylase of the present disclosure will have an alanine or serine at position 2,096(Am) and a cysteine or glycine at position 1,999(Am). In one embodiment, an acetyl-Coenzyme A carboxylase of the present disclosure will have an alanine or serine at position 2,096(Am) and a cysteine or arginine at position 2,027(Am). In one embodiment, an acetyl-Coenzyme A carboxylase of the present disclosure will have an alanine or serine at position 2,096(Am) and an isoleucine at position 2,041(Am). In one embodiment, an acetyl-Coenzyme A carboxylase of the present disclosure will have an alanine or serine at position 2,096(Am) and a phenylalanine, isoleucine or leucine at position 2,049(Am). In one embodiment, an acetyl-Coenzyme A carboxylase of the present disclosure will have an alanine or serine at position 2,096(Am) and a leucine at position 2,074(Am). In one embodiment, an acetyl-Coenzyme A carboxylase of the present disclosure will have an alanine or serine at position 2,096(Am) and a leucine, isoleucine, methionine or additional valine at position 2,075(Am). In one embodiment, an acetyl-Coenzyme A carboxylase of the present disclosure will have an alanine or serine at position 2,096(Am) and a glycine or threonine at position 2,078(Am). In one embodiment, an acetyl-Coenzyme A carboxylase of the present disclosure will have an alanine or serine at position 2,096(Am) and an an arginine, tryptophan, phenylalanine, glycine, histidine, lysine, leucine, serine, threonine, or valine at position 2,088(Am). In one embodiment, an acetyl-Coenzyme A carboxylase of the present disclosure will have an alanine or serine at position 2,096(Am) and an alanine, glycine, proline, histidine, cysteine, or serine at position 2,098(Am).

In one embodiment, an acetyl-Coenzyme A carboxylase of the present disclosure differs from the corresponding wild-type acetyl-Coenzyme A carboxylase at amino acid position 2,098(Am) and at one or more additional amino acid positions. Acetyl-Coenzyme A carboxylase enzymes of the disclosure will typically have an alanine, glycine, proline, histidine, cysteine, or serine at position 2,098(Am). In addition, enzymes of this embodiment will also comprise one or more of a leucine, threonine, valine, or alanine at position 1,781(Am), a glycine at position 1,785(Am), a proline at position 1,786(Am), an asparagine at position 1,811(Am), a proline at position 1,824(Am), a phenylalanine at position 1,864(Am), a cysteine or glycine at position 1,999(Am), a cysteine or arginine at position 2,027(Am), a glycine at position 2,039(Am), an asparagine at position 2,041(Am), a phenylalanine, isoleucine or leucine at position 2,049(Am), a valine at position 2,059(Am), a leucine at position 2,074(Am), a leucine, isoleucine, methionine or additional valine at position 2,075(Am), a glycine or threonine at position 2,078(Am), a phenylalanine at position 2,079(Am), a glutamic acid at position 2,080(Am), a deletion at position 2,080(Am), a deletion at position 2,081 (Am), an arginine, tryptophan, phenylalanine, glycine, histidine, lysine, leucine, serine, threonine, or valine at position 2,088(Am), a glutamic acid at position 2,095(Am), and an alanine or serine at position 2,096(Am). In one embodiment, an acetyl-Coenzyme A carboxylase of the present disclosure will have an alanine, glycine, proline, histidine, cysteine, or serine at position 2,098(Am) and a leucine, a threonine, valine, or an alanine at position 1,781(Am). In one embodiment, an acetyl-Coenzyme A carboxylase of the present disclosure will have an alanine, glycine, proline, histidine, cysteine, or serine at position 2,098(Am) and a glycine at position 1,785(Am). In one embodiment, an acetyl-Coenzyme A carboxylase of the present disclosure will have an alanine, glycine, proline, histidine, cysteine, or serine at position 2,098(Am) and a proline at position 1,786(Am). In one embodiment, an acetyl-Coenzyme A carboxylase of the present disclosure will have an alanine, glycine, proline, histidine, cysteine, or serine at position 2,098(Am) and an asparagine at position 1,811(Am). In one embodiment, an acetyl-Coenzyme A carboxylase of the present disclosure will have an alanine, glycine, proline, histidine, cysteine, or serine at position 2,098(Am) and a cysteine or glycine at position 1,999(Am). In one embodiment, an acetyl-Coenzyme A carboxylase of the present disclosure will have an alanine, glycine, proline, histidine, cysteine, or serine at position 2,098(Am) and a cysteine or arginine at position 2,027(Am). In one embodiment, an acetyl-Coenzyme A carboxylase of the present disclosure will have an alanine, glycine, proline, histidine, cysteine, or serine at position 2,098(Am) and an isoleucine at position 2,041(Am). In one embodiment, an acetyl-Coenzyme A carboxylase of the present disclosure will have an alanine, glycine, proline, histidine, cysteine, or serine at position 2,098(Am) and a phenylalanine, isoleucine or leucine at position 2,049(Am). In one embodiment, an acetyl-Coenzyme A carboxylase of the present disclosure will have an alanine, glycine, proline, histidine, cysteine, or serine at position 2,098(Am) and a leucine at position 2,074(Am). In one embodiment, an acetyl-Coenzyme A carboxylase of the present disclosure will have an alanine, glycine, proline, histidine, cysteine, or serine at position 2,098(Am) and a leucine, isoleucine, methionine or additional valine at position 2,075(Am). In one embodiment, an acetyl-Coenzyme A carboxylase of the present disclosure will have an alanine, glycine, proline, histidine, cysteine, or serine at position 2,098(Am) and a glycine or threonine at position 2,078(Am). In one embodiment, an acetyl-Coenzyme A carboxylase of the present disclosure will have an alanine, glycine, proline, histidine, cysteine, or serine at position 2,098(Am) and an arginine or tryptophan, phenylalanine, glycine, histidine, lysine, leucine, serine, threonine, or valine at position 2,088(Am). In one embodiment, an acetyl-Coenzyme A carboxylase of the present disclosure will have an alanine, glycine, proline, histidine, cysteine, or serine at position 2,098(Am) and an alanine or serine at position 2,096(Am).

In one embodiment, the disclosure includes acetyl-Coenzyme A carboxylases having an isoleucine at position 2,075 (Am) and a glycine at position 1,999(Am); acetyl-Coenzyme A carboxylases having a methionine at position 2,075 (Am) and a glutamic acid at position 2,080(Am); acetyl-Coenzyme A carboxylases having a methionine at position 2,075(Am) and a glutamic acid at position 2,095(Am); acetyl-Coenzyme A carboxylases having a glycine at position 2,078(Am) and a valine at position 2,041(Am); acetyl-Coenzyme A carboxylases having a glycine at position 2,078(Am) and a glycine at position 2,039(Am); acetyl-Coenzyme A carboxylases having a glycine at position 2,078(Am) and an alanine at position 2,049(Am); acetyl-Coenzyme A carboxylases having a glycine at position 2,078(Am) and a cysteine at position 2,049(Am); acetyl-Coenzyme A carboxylases having a glycine at position 2,078(Am) and a serine at position 2,049(Am); acetyl-Coenzyme A carboxylases having a glycine at position 2,078(Am) and a threonine at position 2,049(Am); acetyl-Coenzyme A carboxylases having a glycine at position 2,078(Am) and a valine at position 2,059(Am); acetyl-Coenzyme A carboxylases having a glycine at position 2,078(Am) and a phenylalanine at position 2,079(Am); acetyl-Coenzyme A carboxylases having a glycine at position 2,078(Am) and a proline at position at position 2,079 (Am); and acetyl-Coenzyme A carboxylases having a glycine at position 2,078(Am) and a glycine at position 2,088 (Am).

In a preferred embodiment, the disclosure includes acetyl-Coenzyme A carboxylases having a leucine at position 1,781(Am) and a proline at position 1,824(Am); acetyl-Coenzyme A carboxylases having a leucine at position 1,781(Am) and an arginine at position 2027(Am); and acetyl-Coenzyme A carboxylases having a glycine at position 2,078(Am) and a proline at position 1,824(Am).

In a more preferred embodiment, the disclosure includes acetyl-Coenzyme A carboxylases having a leucine at position 1,781(Am) and a phenylalanine at position 2,049(Am); acetyl-Coenzyme A carboxylases having an alanine at position 2,098(Am) and a leucine at position 2,049(Am); acetyl-Coenzyme A carboxylases having an alanine at position 2,098(Am) and a histidine at position 2088(Am); acetyl-Coenzyme A carboxylases having an alanine at position 2,098(Am) and a phenylalanine at position 2,088(Am); acetyl-Coenzyme A carboxylases having an alanine at position 2,098(Am) and a lysine at position 2,088(Am); acetyl-Coenzyme A carboxylases having an alanine at position 2,098(Am) and a leucine at position 2,088(Am); acetyl-Coenzyme A carboxylases having an alanine at position 2,098(Am) and a threonine at position 2,088(Am); acetyl-Coenzyme A carboxylases having a glycine at position 2,098(Am) and a glycine at position 2,088(Am); acetyl-Coenzyme A carboxylases having a glycine at position 2,098(Am) and a histidine at position 2,088(Am); acetyl-Coenzyme A carboxylases having a glycine at position 2,098(Am) and leucine at position 2,088(Am); acetyl-Coenzyme A carboxylases having a glycine at position 2,098 (Am) and a serine at position 2,088(Am); acetyl-Coenzyme A carboxylases having a glycine at position 2,098(Am) and threonine at position 2,088(Am); acetyl-Coenzyme A carboxylases having a glycine at position 2,098(Am) and a valine at position 2,088(Am); acetyl-Coenzyme A carboxylases having a cysteine at position 2,098(Am) and a tryptophan at position 2088(Am); acetyl-Coenzyme A carboxylases having a serine at position 2,098(Am) and a tryptophan at position 2088(Am); and acetyl-Coenzyme A carboxylases having a deletion at position 2,080(Am) and a deletion at position 2081(Am).

In a most preferred embodiment, the disclosure includes acetyl-Coenzyme A carboxylases having a leucine at position 1,781(Am) and a asparagine at position 2,041(Am); acetyl-Coenzyme A carboxylases having a leucine at position 1,781(Am) and a cysteine at position 2,027(Am); acetyl-Coenzyme A carboxylases having a leucine at position 1,781(Am) and a leucine at position 2,075(Am); acetyl-Coenzyme A carboxylases having a leucine at position 1,781(Am) and a phenylalanine at position 1,864(Am); acetyl-Coenzyme A carboxylases having a leucine at position 1,781(Am) and an alanine at position 2098(Am); acetyl-Coenzyme A carboxylases having a leucine at position 1,781(Am) and a glycine at position 2,098(Am); acetyl-Coenzyme A carboxylases having a leucine at position 1,781(Am) and a duplication 2,075(Am); acetyl-Coenzyme A carboxylases having a glycine at position 1,999(Am) and a phenylalanine at position 1,864(Am); acetyl-Coenzyme A carboxylases having a glycine at position 1,999(Am) and isoleucine at position 2,049(Am); acetyl-Coenzyme A carboxylases having a glycine at position 1,999(Am) and leucine at position 2,075(Am); and acetyl-Coenzyme A carboxylases having a glycine at position 1,999(Am) and alanine at position 2,098(Am).

Nucleic Acid Molecules

The present disclosure also encompasses nucleic acid molecules that encode all or a portion of the acetyl-Coenzyme A carboxylase enzymes described above. Nucleic acid molecules of the disclosure may comprise a nucleic acid sequence encoding an amino acid sequence comprising a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine, methionine or additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences. In some embodiments, a nucleic acid molecule of the disclosure may encode an acetyl-Coenzyme A carboxylase having multiple differences from the wild type acetyl-Coenzyme A carboxylase as described above.

In one embodiment, the present disclosure emcompasses a nucleic acid molecule encoding an acetyl-Coenzyme A carboxylase which differs from the acetyl-Coenzyme A carboxylase of the corresponding wild-type plant at only one of the following positions: 1,781(Am), 1,785(Am), 1,786 (Am), 1,811(Am), 1,824(Am), 1,864(Am), 1,999(Am), 2,027(Am), 2,039(Am), 2,041(Am), 2,049(Am), 2,059 (Am), 2,074(Am), 2,075(Am), 2,078(Am), 2,079(Am), 2,080(Am), 2,081(Am), 2,088(Am), 2,095(Am), 2,096 (Am), or 2,098(Am). In one embodiment the acetyl-Coenzyme A carboxylase of an herbicide-tolerant plant of the disclosure will differ at only one of the following positions: 2,078(Am), 2,088(Am), or 2,075(Am). In a preferred embodiment the acetyl-Coenzyme A carboxylase of an herbicide-tolerant plant of the disclosure will differ at only one of the following positions: 2,039(Am), 2,059(Am), 2,080 (Am), or 2,095(Am). In a more preferred embodiment the acetyl-Coenzyme A carboxylase of an herbicide-tolerant plant of the disclosure will differ at only one of the following positions: 1,785(Am), 1,786(Am), 1,811(Am), 1,824(Am), 1,864(Am), 2,041(Am), 2,049(Am), 2,074(Am), 2,079 (Am), 2,081(Am), 2,096(Am), or 2,098(Am). In a most preferred embodiment the acetyl-Coenzyme A carboxylase of an herbicide-tolerant plant of the disclosure will differ at only one of the following positions: 1,781(Am), 1,999(Am), 2,027(Am), 2,041(Am), or 2,096(Am).

In one embodiment, the present disclosure emcompasses a nucleic acid molecule encoding an acetyl-Coenzyme A carboxylase having only one of the following substitutions: isoleucine at position 2,075(Am), glycine at position 2,078 (Am), or arginine at position 2,088(Am). In a preferred embodiment, the present disclosure emcompasses a nucleic acid molecule encoding an acetyl-Coenzyme A carboxylase having only one of the following substitutions: glycine at position 2,039(Am), valine at position 2,059(Am), methionine at position 2,075(Am), duplication of position 2,075 (Am) (i.e., an insertion of valine between 2,074(Am) and 2,075(Am), or an insertion of valine between position 2,075 (Am) and 2,076(Am), deletion of amino acid position 2,088 (Am), glutamic acid at position 2,080(Am), deletion of position 2,088(Am), or glutamic acid at position 2,095(Am). In a more preferred embodiment, the present disclosure emcompasses a nucleic acid molecule encoding an acetyl-Coenzyme A carboxylase having only one of the following substitutions: a glycine at position 1,785(Am), a proline at position 1,786(Am), an asparagine at position 1,811(Am), a leucine at position 2,075(Am), a methionine at position 2,075(Am), a threnonine at position 2,078(Am), a deletion at position 2,080(Am), a deletion at position 2,081(Am), a tryptophan at position 2,088(Am), a serine at position 2,096 (Am), an alanine at position 2,096(Am), an alanine at position 2,098(Am), a glycine at position 2,098(Am), an histidine at position 2,098(Am), a proline at position 2,098 (Am), or a serine at position 2,098(Am). In a most preferred embodiment, the present disclosure emcompasses a nucleic acid molecule encoding an acetyl-Coenzyme A carboxylase having only one of the following substitutions: a leucine at position 1,781(Am), a threonine at position 1,781(Am), a valine at position 1,781(Am), an alanine at position 1,781 (Am), a glycine at position 1,999(Am), a cysteine at position 2,027(Am), an arginine at position 2,027(Am), an asparagine at position 2,041(Am), a valine at position 2,041(Am), an alanine at position 2,096(Am), and a serine at position 2,096(Am).

In one embodiment, a nucleic acid molecule of the disclosure may encode an acetyl-Coenzyme A carboxylase comprising a leucine, threonine, valine, or an alanine at position 1,781(Am) and a cysteine or glycine at position 1,999(Am). In one embodiment, a nucleic acid molecule of the disclosure may encode an acetyl-Coenzyme A carboxylase comprising a leucine, threonine, valine, or an alanine at position 1,781(Am) and a cysteine or arginine at position 2,027(Am). In one embodiment, a nucleic acid molecule of the disclosure may encode an acetyl-Coenzyme A carboxylase comprising a leucine, threonine, valine, or an alanine at position 1,781(Am) and an asparagine at position 2,041 (Am). In one embodiment, a nucleic acid molecule of the disclosure may encode an acetyl-Coenzyme A carboxylase comprising a leucine, threonine, valine, or an alanine at position 1,781(Am) and a phenylalanine, isoleucine or leucine at position 2,049(Am). In one embodiment, a nucleic acid molecule of the disclosure may encode an acetyl-Coenzyme A carboxylase comprising a leucine, threonine, valine, or an alanine at position 1,781(Am) and a leucine or isoleucine at position 2,075(Am). In one embodiment, a nucleic acid molecule of the disclosure may encode an acetyl-Coenzyme A carboxylase comprising a leucine, threonine, valine, or an alanine at position 1,781(Am) and a glycine at position 2,078(Am). In one embodiment, a nucleic acid molecule of the disclosure may encode an acetyl-Coenzyme A carboxylase comprising a leucine, threonine, valine, or an alanine at position 1,781(Am) and an arginine at position 2,088(Am). In one embodiment, a nucleic acid molecule of the disclosure may encode an acetyl-Coenzyme A carboxylase comprising a leucine, threonine, valine, or an alanine at position 1,781(Am) and an alanine at position 2,096(Am). In one embodiment, a nucleic acid molecule of the disclosure may encode an acetyl-Coenzyme A carboxylase comprising a leucine, threonine, valine, or an alanine at position 1,781(Am) and an alanine at position 2,098(Am). In one embodiment, a nucleic acid molecule of the disclosure may encode an acetyl-Coenzyme A carboxylase comprising a leucine, threonine, valine, or an alanine at position 1,781(Am), a cysteine at position 2,027 (Am), and an asparagine at position 2,041(Am). In one embodiment, a nucleic acid molecule of the disclosure may encode an acetyl-Coenzyme A carboxylase comprising a leucine, threonine, valine, or an alanine at position 1,781 (Am), a cysteine at position 2,027(Am), an asparagine at position 2,041(Am), and an alanine at position 2,096(Am).

In one embodiment, the disclosure includes a nucleic acid molecule encoding an acetyl-Coenzyme A carboxylase having an isoleucine at position 2,075(Am) and a glycine at position 1,999(Am); a nucleic acid molecule encoding an acetyl-Coenzyme A carboxylase having a methionine at position 2,075(Am) and a glutamic acid at position 2,080 (Am); a nucleic acid molecule encoding an acetyl-Coenzyme A carboxylase having a methionine at position 2,075 (Am) and a glutamic acid at position 2,095(Am); a nucleic acid molecule encoding an acetyl-Coenzyme A carboxylase having a glycine at position 2,078(Am) and a valine at position 2,041(Am); a nucleic acid molecule encoding an acetyl-Coenzyme A carboxylase having a glycine at position 2,078(Am) and a glycine at position 2,039(Am); a nucleic acid molecule encoding an acetyl-Coenzyme A carboxylase having a glycine at position 2,078(Am) and an alanine at position 2,049(Am); a nucleic acid molecule encoding an acetyl-Coenzyme A carboxylase having a glycine at position 2,078(Am) and a cysteine at position 2,049(Am); a nucleic acid molecule encoding an acetyl-Coenzyme A carboxylase having a glycine at position 2,078(Am) and a serine at position 2,049(Am); a nucleic acid molecule encoding an acetyl-Coenzyme A carboxylase having a glycine at position 2,078(Am) and a threonine at position 2,049(Am); a nucleic acid molecule encoding an acetyl-Coenzyme A carboxylase having a glycine at position 2,078(Am) and a valine at position 2,059(Am); a nucleic acid molecule encoding an acetyl-Coenzyme A carboxylase having a glycine at position 2,078(Am) and a phenylalanine at position 2,079(Am); a nucleic acid molecule encoding an acetyl-Coenzyme A carboxylase having a glycine at position 2,078(Am) and a proline at position at position 2,079(Am); or a nucleic acid molecule encoding an acetyl-Coenzyme A carboxylase having a glycine at position 2,078(Am) and a glycine at position 2,088(Am).

In a preferred embodiment, the disclosure includes a nucleic acid molecule encoding an acetyl-Coenzyme A carboxylase having a leucine at position 1,781(Am) and a proline at position 1,824(Am); a nucleic acid molecule encoding an acetyl-Coenzyme A carboxylase having a leucine at position 1,781(Am) and an arginine at position 2027(Am); or a nucleic acid molecule encoding an acetyl-Coenzyme A carboxylase having a glycine at position 2,078 (Am) and a proline at position 1,824(Am).

In a more preferred embodiment, the disclosure includes a nucleic acid molecule encoding an acetyl-Coenzyme A carboxylase having a leucine at position 1,781(Am) and a phenylalanine at position 2,049(Am); a nucleic acid molecule encoding an acetyl-Coenzyme A carboxylase having an alanine at position 2,098(Am) and a leucine at position 2,049(Am); a nucleic acid molecule encoding an acetyl-Coenzyme A carboxylase having an alanine at position 2,098(Am) and a histidine at position 2088(Am); a nucleic acid molecule encoding an acetyl-Coenzyme A carboxylase having an alanine at position 2,098(Am) and a phenylalanine at position 2,088(Am); a nucleic acid molecule encoding an acetyl-Coenzyme A carboxylase having an alanine at position 2,098(Am) and a lysine at position 2,088(Am); a nucleic acid molecule encoding an acetyl-Coenzyme A carboxylase having an alanine at position 2,098(Am) and a leucine at position 2,088(Am); a nucleic acid molecule encoding an acetyl-Coenzyme A carboxylase having an alanine at position 2,098(Am) and a threonine at position 2,088(Am); a nucleic acid molecule encoding an acetyl-Coenzyme A carboxylase having a glycine at position 2,098 (Am) and a glycine at position 2,088(Am); a nucleic acid molecule encoding an acetyl-Coenzyme A carboxylase having a glycine at position 2,098(Am) and a histidine at position 2,088(Am); a nucleic acid molecule encoding an acetyl-Coenzyme A carboxylase having a glycine at position 2,098(Am) and leucine at position 2,088(Am); a nucleic acid molecule encoding an acetyl-Coenzyme A carboxylase having a glycine at position 2,098(Am) and a serine at position 2,088(Am); a nucleic acid molecule encoding an acetyl-Coenzyme A carboxylase having a glycine at position 2,098

(Am) and threonine at position 2,088(Am); a nucleic acid molecule encoding an acetyl-Coenzyme A carboxylase having a glycine at position 2,098(Am) and a valine at position 2,088(Am); a nucleic acid molecule encoding an acetyl-Coenzyme A carboxylase having a cysteine at position 2,098(Am) and a tryptophan at position 2088(Am); a nucleic acid molecule encoding an acetyl-Coenzyme A carboxylase having a serine at position 2,098(Am) and a tryptophan at position 2088(Am); or a nucleic acid molecule encoding an acetyl-Coenzyme A carboxylase having a deletion at position 2,080(Am) and a deletion at position 2081(Am).

In a most preferred embodiment, the disclosure includes a nucleic acid molecule encoding an acetyl-Coenzyme A carboxylase having a leucine at position 1,781(Am) and a asparagine at position 2,041(Am); a nucleic acid molecule encoding an acetyl-Coenzyme A carboxylase having a leucine at position 1,781(Am) and a cysteine at position 2,027 (Am); a nucleic acid molecule encoding an acetyl-Coenzyme A carboxylase having a leucine at position 1,781(Am) and a leucine at position 2,075(Am); a nucleic acid molecule encoding an acetyl-Coenzyme A carboxylase having a leucine at position 1,781(Am) and a phenylalanine at position 1,864(Am); a nucleic acid molecule encoding an acetyl-Coenzyme A carboxylase having a leucine at position 1,781 (Am) and an alanine at position 2098(Am); a nucleic acid molecule encoding an acetyl-Coenzyme A carboxylase having a leucine at position 1,781(Am) and a glycine at position 2,098(Am); a nucleic acid molecule encoding an acetyl-Coenzyme A carboxylase having a leucine at position 1,781 (Am) and a duplication 2,075(Am); a nucleic acid molecule encoding an acetyl-Coenzyme A carboxylase having a glycine at position 1,999(Am) and a phenylalanine at position 1,864(Am); a nucleic acid molecule encoding an acetyl-Coenzyme A carboxylase having a glycine at position 1,999 (Am) and isoleucine at position 2,049(Am); a nucleic acid molecule encoding an acetyl-Coenzyme A carboxylase having a glycine at position 1,999(Am) and leucine at position 2,075(Am); or a nucleic acid molecule encoding an acetyl-Coenzyme A carboxylase having a glycine at position 1,999 (Am) and alanine at position 2,098(Am).

In one embodiment, the disclosure provides rice plants comprising nucleic acids encoding Acetyl-Coenzyme A carboxylase polypeptide having one or more substitutions as described above.

In one embodiment, the disclosure provides BEP clade plants comprising nucleic acids encoding Acetyl-Coenzyme A carboxylase polypeptide having one or more substitutions as described above.

In one embodiment, the disclosure provides BET subclade plant comprising nucleic acids encoding Acetyl-Coenzyme A carboxylase polypeptide having one or more substitutions as described above.

In one embodiment, the disclosure provides BET crop plants comprising nucleic acids encoding Acetyl-Coenzyme A carboxylase polypeptide having one or more substitutions as described above.

In one embodiment, the disclosure provides monocot plants comprising nucleic acids encoding Acetyl-Coenzyme A carboxylase polypeptide having one or more substitutions as described above.

A nucleic acid molecule of the disclosure may be DNA, derived from genomic DNA or cDNA, or RNA. A nucleic acid molecule of the disclosure may be naturally occurring or may be synthetic. A nucleic acid molecule of the disclosure may be isolated, recombinant and/or mutagenized.

In one embodiment, a nucleic acid molecule of the disclosure encodes an acetyl-Coenzyme A carboxylase enzyme in which the amino acid at position 1,781(Am) is leucine or alanine or is complementary to such a nucleic acid molecule. Such nucleic acid molecules include, but are not limited to, genomic DNA that serves as a template for a primary RNA transcription, a plasmid molecule encoding the acetyl-Coenzyme A carboxylase, as well as an mRNA encoding such an acetyl-Coenzyme A carboxylase.

Nucleic acid molecules of the disclosure may comprise non-coding sequences, which may or may not be transcribed. Non-coding sequences that may be included in the nucleic acid molecules of the disclosure include, but are not limited to, 5' and 3' UTRs, polyadenylation signals and regulatory sequences that control gene expression (e.g., promoters). Nucleic acid molecules of the disclosure may also comprise sequences encoding transit peptides, protease cleavage sites, covalent modification sites and the like. In one embodiment, nucleic acid molecules of the disclosure encode a chloroplast transit peptide sequence in addition to a sequence encoding an acetyl-Coenzyme A carboxylase enzyme.

In another embodiment, nucleic acid molecules of the disclosure may encode an acetyl-Coenzyme A carboxylase enzyme having at least 50%, 60%, 70%, 75%, 80%, 85%, 90%, 95% or more sequence identity to a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, leucine or isoleucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences.

As used herein, "percent (%) sequence identity" is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program BLAST available at http://blast.ncbi.nlm.nih.gov/Blast.cgi with search parameters set to default values.

The present disclosure also encompasses nucleic acid molecules that hybridize to nucleic acid molecules encoding acetyl-Coenzyme A carboxylase of the present disclosure as well as nucleic acid molecules that hybridize to the reverse complement of nucleic acid molecules encoding an acetyl- Coenzyme A carboxylase of the present disclosure. In one embodiment, nucleic acid molecules of the disclosure comprise nucleic acid molecules that hybridize to a nucleic acid molecule encoding one or more of a modified version of one or both of SEQ ID NOs: 2 and 3, wherein the sequence is modified such that the encoded protein comprises one or more of the following: the amino acid at position 1,781(Am) is leucine, threonine, valine, or alanine; the amino acid at position 1,785(Am) is glycine; the amino acid at position 1,786(Am) is proline; the amino acid at position 1,811(Am) is asparagine; the amino acid at position 1,824(Am) is proline; the amino acid at position 1,864(Am) is phenylalanine; the amino acid at position 1,999(Am) is cysteine or glycine; the amino acid at position 2,027(Am) is cysteine or arginine; the amino acid at position 2,039(Am) is glycine; the amino acid at position 2,041(Am) is asparagine; the amino acid at position 2049(Am) is phenylalanine, isoleucine or leucine; the amino acid at position 2,059(Am) is valine; the amino acid at position 2,074(Am) is leucine; the amino acid at position 2,075(Am) is leucine, isoleucine or methionine or an additional valine; the amino acid at position 2,078(Am) is glycine, or threonine; the amino acid at position 2,079(Am) is phenylalnine; the amino acid at position 2,080(Am) is glutamic acid; the amino acid at position 2,080(Am) is deleted; the amino acid at position 2,081(Am) is deleted; the amino acid at position 2,088(Am) is arginine, tryptophan, phenylalanine, glycine, histidine, lysine, leucine, serine, threonine, or valine; the amino acid at position 2,095(Am) is glutamic acid; the amino acid at position 2,096(Am) is alanine, or serine; or the amino acid at position 2,098(Am) is alanine, glycine, proline, histidine, or serine, as well as nucleic acid molecules complementary to all or a portion of the coding sequences, or the reverse complement of such nucleic acid molecules under stringent conditions. The stringency of hybridization can be controlled by temperature, ionic strength, pH, and the presence of denaturing agents such as formamide during hybridization and washing. Stringent conditions that may be used include those defined in *Current Protocols in Molecular Biology*, Vol. 1, Chap. 2.10, John Wiley & Sons, Publishers (1994) and Sambrook et al., *Molecular Cloning*, Cold Spring Harbor (1989) which are specifically incorporated herein as they relate to teaching stringent conditions.

Any of the mutants described above in a plasimd with a combination of the gene of interest can be used in transformation.

In one embodiment, the present disclosure provides expression vectors comprising nucleic acid molecules encoding any of the ACCase mutants described above.

In one embodiment, the present disclosure provides for the use of mutant ACCase nucleic acids and proteins encoded by such mutant ACCase nucleic acids as described above as selectable markers.

In one embodiment, nucleic acid molecules of the disclosure encompass oligonucleotides that may be used as hybridization probes, sequencing primers, and/or PCR primers. Such oligonucleotides may be used, for example, to determine a codon sequence at a particular position in a nucleic acid molecule encoding an acetyl-Coenzyme A carboxylase, for example, by allele specific PCR. Such oligonucleotides may be from about 15 to about 30, from about 20 to about 30, or from about 20-25 nucleotides in length.

Test for double mutant ACCase genes "DBLM Assay":

(1) In a test population (of, e.g., at least 12 and preferably at least 20) whole rice plants containing 1 or 2 copies of a transgenic ACCase gene encoding an at-least-double-mutant ACCase (i.e. 1 min. and 2 max. chromosomal insertions of the transgenic ACCase gene to be tested), wherein the rice plants are T0 ("T-zero") regenerants and in parallel with a control population of such plants to be used as untreated check plants;

(2) Application to the test population at 200 L/ha spray volume of a composition comprising Tepraloxydim (AI) and 1% Crop Oil Concentrate (COC), to provide an AI application rate equivalent to 50 g/ha of Tepraloxydim (AI);

(3) Determining a phytotoxicity score for each test and check plant, based on a traditional plant injury rating system (e.g., evaluating visual evidence of herbicide burn, leaf morphology changes, wilt, yellowing, and other morphological characteristics, preferably according to a typical, at least-5-level injury rating scale);

(4) Analyzing the collected data to determine whether at least 75% of the plants in the test population exhibit an average phytotoxicity, i.e. increase in injury relative to check plants, of less than 10%; and (5) Identifying a positive result so determined as demonstrating that the double-mutant ACCase provides an acceptable AIT.

Herbicides

The present disclosure provides plants, e.g., rice plants, that are tolerant of concentrations of herbicide that normally inhibit the growth of wild-type plants. The plants are typically resistant to herbicides that interfere with acetyl-Coenzyme A carboxylase activity. Any herbicide that inhibits acetyl-Coenzyme A carboxylase activity can be used in conjunction with the plants of the invention. Suitable examples include, but are not limited to, cyclohexanedione herbicides, aryloxyphenoxy propionate herbicides, and phenylpyrazole herbicides. In some methods of controlling weeds and/or growing herbicide-tolerant plants, at least one herbicide is selected from the group consisting of sethoxydim, cycloxydim, tepraloxydim, haloxyfop, haloxyfop-P or a derivative of any of these herbicides.

Table 1 provides a list of cyclohexanedione herbicides (DIMs, also referred to as: cyclohexene oxime cyclohexanedione oxime; and CHD) that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention. Also included in Table 1 is a list of aryloxyphenoxy propionate herbicides (also referred to as aryloxyphenoxy propanoate; aryloxyphenoxyalkanoate; oxyphenoxy; APP; AOPP; APA; APPA; FOP, note that these are sometime written with the suffix '-oic') that interfere with acetyl-Coenzyme A carboxylase activity and may be used in conjunction with the herbicide-tolerant plants of the invention. One skilled in the art will recognize that other herbicides in this class exist and may be used in conjunction with the herbicide-tolerant plants of the invention.

TABLE 1

| ACCase Inhibitor | Class | Company | Examples of Synonyms and Trade Names |
|---|---|---|---|
| alloxydim | DIM | BASF | Fervin, Kusagard, NP-48Na, BAS 9021H, Carbodimedon, Zizalon |
| butroxydim | DIM | Syngenta | Falcon, ICI-A0500, Butroxydim |
| clethodim | DIM | Valent | Select, Prism, Centurion, RE-45601, Motsa |

TABLE 1-continued

| ACCase Inhibitor | Class | Company | Examples of Synonyms and Trade Names |
|---|---|---|---|
| Clodinafop-propargyl | FOP | Syngenta | Discover, Topik, CGA 184 927 |
| clofop | FOP | | Fenofibric Acid, Alopex |
| cloproxydim | FOP | | |
| chlorazifop | FOP | | |
| cycloxydim | DIM | BASF | Focus, Laser, Stratos, BAS 517H |
| cyhalofop-butyl | FOP | Dow | Clincher, XDE 537, DEH 112, Barnstorm |
| diclofop-methyl | FOP | Bayer | Hoegrass, Hoelon, Illoxan, HOE 23408, Dichlorfop, Illoxan |
| fenoxaprop-P-ethyl | FOP | Bayer | Super Whip, Option Super, Exel Super, HOE-46360, Aclaim, Puma S, Fusion |
| fenthiaprop | FOP | | Taifun; Joker |
| fluazifop-P-butyl | FOP | Syngenta | Fusilade, Fusilade 2000, Fusilade DX, ICI-A 0009, ICI-A 0005, SL-236, IH-773B, TF-1169, Fusion |
| haloxyfop-etotyl | FOP | Dow | Gallant, DOWCO 453EE |
| haloxyfop-methyl | FOP | Dow | Verdict, DOWCO 453ME |
| haloxyfop-P-methyl | FOP | Dow | Edge, DE 535 |
| isoxapyrifop | FOP | | |
| Metamifop | FOP | Dongbu | NA |
| pinoxaden | DEN | Syngenta | Axial |
| profoxydim | DIM | BASF | Aura, Tetris, BAS 625H, Clefoxydim |
| propaquizafop | FOP | Syngenta | Agil, Shogun, Ro 17-3664, Correct |
| quizalofop-P-ethyl | FOP | DuPont | Assure, Assure II, DPX-Y6202-3, Targa Super, NC-302, Quizafop |
| quizalofop-P-tefuryl | | Uniroyal | Pantera, UBI C4874 |
| sethoxydim | DIM | BASF | Poast, Poast Plus, NABU, Fervinal, NP-55, Sertin, BAS 562H, Cyethoxydim, Rezult |
| tepraloxydim | DIM | BASF | BAS 620H, Aramo, Caloxydim |
| tralkoxydim | DIM | Syngenta | Achieve, Splendor, ICI-A0604, Tralkoxydime, Tralkoxidym |
| trifop | FOP | | |

In addition to the herbicides listed above, other ACCase-inhibitors can be used in conjunction with the herbicide-tolerant plants of the invention. For example, ACCase-inhibiting herbicides of the phenylpyrazole class, also known as DENs, can be used. An exemplary DEN is pinoxaden, which is a phenylpyrazoline-type member of this class. Herbicide compositions containing pinoxaden are sold under the brands Axial and Traxos.

The herbicidal compositions hereof comprising one or more acetyl-Coenzyme A carboxylase-inhibiting herbicides, and optionally other agronomic A.I.(s), e.g., one or more sulfonylureas (SUs) selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, or one or more imidazolinones selected from the group of imazamox, imazethapyr, imazapyr, imazapic, combinations thereof, and their agriculturally suitable salts and esters, can be used in any agronomically acceptable format. For example, these can be formulated as ready-to-spray aqueous solutions, powders, suspensions; as concentrated or highly concentrated aqueous, oily or other solutions, suspensions or dispersions; as emulsions, oil dispersions, pastes, dusts, granules, or other broadcastable formats. The herbicide compositions can be applied by any means known in the art, including, for example, spraying, atomizing, dusting, spreading, watering, seed treatment, or co-planting in admixture with the seed. The use forms depend on the intended purpose; in any case, they should ensure the finest possible distribution of the active ingredients according to the invention.

In other embodiments, where the optional A.I. includes an herbicide from a different class to which the plant(s) hereof would normally be susceptible, the plant to be used is selected from among those that further comprise a trait of tolerance to such herbicide. Such further tolerance traits can be provided to the plant by any method known in the art, e.g., including techniques of traditional breeding to obtain a tolerance trait gene by hybridization or introgression, of mutagenesis, and/or of transformation. Such plants can be described as having "stacked" traits.

In addition, any of the above acetyl-Coenzyme A carboxylase-inhibiting herbicides can be combined with one or more herbicides of another class, for example, any of the acetohydroxyacid synthase-inhibiting herbicides, EPSP synthase-inhibiting herbicides, glutamine synthase-inhibiting herbicides, lipid- or pigment-biosynthesis inhibitor herbicides, cell-membrane disruptor herbicides, photosynthesis or respiration inhibitor herbicides, or growth regulator or growth inhibitor herbicides known in the art. Non-limiting examples include those recited in Weed Science Society of America's *Herbicide Handbook*, 9th Edition edited by S. A. Senseman, copy right 2007. An herbicidal composition herein can contain one or more agricultural active ingredient(s) selected from the agriculturally-acceptable fungicides, strobilurin fungicides, insecticides (including nematicides), miticides, and molluscicides. Non-limiting examples include those recited in 2009 Crop Protection Reference (www.greenbook.net), Vance Publications.

In one embodiment of the invention, any of the above acetyl-Coenzyme A carboxylase-inhibiting herbicides are combined with herbicides which exhibit low damage to rice, whereby the rice tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, azimsulfuron, bensulfuron, chlorimuron, cyclosulfamuron, ethoxysulfuron, flucetosulfuron, halosulfuron, imazosulfuron, metsulfuron, orthosulfamuron, propyrisulfuron, pyrazosulfuron, bispyribac, pyrimisulfan or penoxsulam, the EPSP synthase-inhibiting herbicides glyphosate or sulfosate, the glutamine synthase-inhibiting herbicides glufosinate, glufosinate-P or bialaphos, the lipid biosynthesis inhibitor herbicides benfuresate, molinate or thiobencarb, the photosynthesis inhibitor herbicides bentazon, paraquat, prometryn or propanil, the bleacher herbicides benzobicyclone, clomazone or tefuryltrione, the auxin herbicides 2,4-D, fluroxypyr, MCPA, quinclorac, quinmerac or triclopyr, the microtubule inhibitor herbicide pendimethalin, the VLCFA inhibitor herbicides anilofos, butachlor, fentrazamide, ipfencarbazone, mefenacet, pretilachlor, acetochlor, metolachlor or S-metolachlor or the protoporphyrinogen-IX-oxidase inhibitor herbicides carfentrazone, oxadiazon, oxyfluorfen, pyraclonil or saflufenacil.

In one embodiment of the invention, any of the above acetyl-Coenzyme A carboxylase-inhibiting herbicides are combined with herbicides which exhibit low damage to cereals such as wheat, barley or rye, whereby the cereals tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, amidosulfuron, chlorsulfuron, flucetosulfuron, flupyrsulfuron, iodosulfuron, mesosulfuron, metsulfuron, sulfosulfuron, thifensulfuron, triasulfuron, tribenuron, tritosulfuron, florasulam, pyroxsulam, pyrimisulfan, flucarbazone, propoxycarbazone or thiencarbazone, the EPSP synthase-inhibiting herbicides glyphosate or sulfosate, the glutamine synthase-inhibiting herbicides glufosinate, glufosinate-P or bialaphos, the lipid biosynthesis inhibitor herbicides prosulfocarb, the photosynthesis inhibitor herbicides bentazon, chlorotoluron, isoproturon, ioxynil, bromoxynil, the bleacher herbicides diflufenican, flurtamone, picolinafen or pyrasulfotole, the auxin herbicides aminocyclopyrachlor, aminopyralid, 2,4-D, dicamba, fluroxypyr, MCPA, clopyralid, MCPP, or MCPP-P, the microtubule inhibitor herbicides pendimethalin or trifluralin, the VLCFA inhibitor herbicide flufenacet, or the protoporphyrinogen-IX-oxidase inhibitor herbicides bencarbazone, carfentrazone or saflufenacil, or the herbicide difenzoquat.

In one embodiment of the invention, any of the above acetyl-Coenzyme A carboxylase-inhibiting herbicides are combined with herbicides which exhibit low damage to turf, whereby the turf tolerance to such herbicides may optionally be a result of genetic modifications of the crop plants. Examples of such herbicides are the acetohydroxyacid synthase-inhibiting herbicides imazamethabenz, imazamox, imazapic, imazapyr, imazaquin, imazethapyr, flazasulfuron, foramsulfuron, halosulfuron, trifloxysulfuron, bispyribac or thiencarbazone, the EPSP synthase-inhibiting herbicides glyphosate or sulfosate, the glutamine synthase-inhibiting herbicides glufosinate, glufosinate-P or bialaphos, the photosynthesis inhibitor herbicides atrazine or bentazon, the bleacher herbicides mesotrione, picolinafen, pyrasulfotole or topramezone, the auxin herbicides aminocyclopyrachlor, aminopyralid, 2,4-D, 2,4-DB, clopyralid, dicamba, dichlorprop, dichlorprop-P, fluroxypyr, MCPA, MCPB, MCPP, MCPP-P, quinclorac, quinmerac or trichlopyr, the microtubule inhibitor herbicide pendimethalin, the VLCFA inhibitor herbicides dimethenamid, dimethenamid-P or ipfencarbazone, the protoporphyrinogen-IX-oxidase inhibitor herbicides saflufenacil or sulfentrazone, or the herbicide indaziflam.

Furthermore, any of the above acetyl-Coenzyme A carboxylase-inhibiting herbicides can be combined with safeners. Safeners are chemical compounds which prevent or reduce damage on useful plants without having a major impact on the herbicidal action of the herbicides towards unwanted plants. They can be applied either before sowings (e. g. on seed treatments, shoots or seedlings) or in the pre-emergence application or post-emergence application of the useful plant. The safeners and the aforementioned herbicides can be applied simultaneously or in succession. Suitable safeners are e. g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates. Examples of saferners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

In some embodiments, an herbicidal composition hereof can comprise, e.g., a combination of: auxinic herbicide(s), e.g., dicamba; AHAS-inhibitor(s), e.g., imidazolinone(s) and/or sulfonylurea(s); ACCase-inhibitor(s); EPSPS inhibitor(s), e.g., glyphosate; glutamine synthetase inhibitor(s), e.g., glufosinate; protoporphyrinogen-IX oxidase (PPO) inhibitor(s), e.g., saflufenacil; fungicide(s), e.g., strobilurin fungicide(s) such as pyraclostrobin; and the like. In some embodiments, an herbicidal composition hereof can comprise, e.g., a combination of auxinic herbicide(s), e.g., dicamba; a microtubule inhibitor herbicide, e.g., pendimethalin and strobilurin fungicide(s) such as pyraclostrobin(s). An herbicidal composition will be selected according to the tolerances of a plant hereof, and the plant can be selected from among those having stacked tolerance traits.

The herbicides individually and/or in combination as described in the present disclosure can be used as pre-mixes or tank mixes. Such herbicides can also be incorporated into agronomically acceptable compositions.

Those skilled in the art will recognize that some of the above mentioned herbicides and/or safeners are capable of forming geometrical isomers, for example E/Z isomers. It is possible to use both, the pure isomers and mixtures thereof, in the compositions according to the invention. Furthermore, some of the above mentioned herbicides and/or safeners have one or more centers of chirality and, as a consequence, are present as enantiomers or diastereomers. It is possible to use both, the pure enantiomers and diastereomers and their mixtures, in the compositions according to the invention. In particular, some of the aryloxyphenoxy propionate herbicides are chiral, and some of them are commonly used in enantiomerically enriched or enantiopure form, e. g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P.

Those skilled in the art will recognize that any derivative of the above mentioned herbicides and/or safeners can be used in the practice of the invention, for example agriculturally suitable salts and esters.

The herbicides and/or safeners, or the herbicidal compositions comprising them, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one of the acetyl-Coenzyme A carboxylase-inhibiting herbicides and potentially other herbicides and/or safeners and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives. The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R. T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqeuos solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types Clariant), polycarboxylates (BASF AG, Sokalan types), polyalkoxylates, polyvinyl amine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the herbicidal compositions, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

Rice-Non-Selective ACCase-Inhibitor Herbicides

Aspects of the present disclosure relate to methods for the treatment of rice comprising providing a domestic rice crop plant with at least one herbicide that is a rice-non-selective ACCase-inhibiting herbicide. The method comprises applying an effective amount (measured in g AI/Ha) of the at least one rice-non-selective ACCase-inhibiting herbicide to the domestic rice crop plant, post-emergence; thereby creating a treated rice plant; and growing the resulting treated rice plant. In some embodiments said rice-non-selective ACCase-inhibiting herbicide includes isomers, salts or esters of the rice-non-selective ACCase-inhibiting herbicide.

Some examples of rice-non-selective ACCase-inhibiting herbicides include, but are not limited to, those shown here in Table 2.

TABLE 2

| Herbicide Class (Synonyms) | Name of Active | Example Synonyms, Isomers, Salts, Esters | Example Products |
|---|---|---|---|
| Cyclohexene Oxime (Cyclohexanedione;) Cyclohexanedione oxime; CHD; DIM | alloxydim butroxydim cethoxydim clethodim cloproxydim cycloxydim | alloxydim-sodium butoxydim CGA215684 | Kusaguard; Fervin Clout Falcon; Factor; Fusion Super Select; Prism Selectone Focus 10 EC; Focus Ultra; Laser; Stratos Ultra |
|  | sethoxydim tepraloxydim tralkoxydim | cyethoxydim; sethoxydime caloxydim | Poast; Rezult; Vantage Aramo Achieve |
| Aryloxyphenoxy Propionate (Aryloxyphenoxyalkanoate; APP; AOPP; FOP) | chlorazifop clodinafop | chlorazifop-propargyl; chloroazifop-propynyl clodinafop-propargyl | Discover; Cowboy; Dynofop; Topik |
|  | clofop diclofop fenthiaprop fluazifop haloxyfop isoxapyrifop propaquizafop | clofop-isobutyl fenthiaprop-ethyl fluazifop-P haloxyfop-P | Alopex Hoelon; Hoegrass Joker Fusilade DX; Fusion Motsa; Verdict Correct; Agil 100EC; Falcon; Longhorn; Shogun; Zealot |
|  | quizalofop | quizalofop-P; quizafop; quizafop-P; quizalofop-P-ethyl; quizalofop-P-tefuryl | Assure II; Targa |
|  | trifop | trifop-methyl |  |

Field Herbicide Application

Aspects of the present disclosure relate to methods for the treatment of rice comprising providing a domestic rice crop plant in a field and at least one ACCase-inhibiting FOP herbicide. The method comprises applying an effective amount (measured in g AI/Ha) of the at least one FOP herbicide to the domestic rice crop plant, post-emergence; thereby creating a treated rice plant; and growing the resulting treated rice plant.

In other embodiments, the FOP herbicide is quizalofop or an ester thereof quizalofop or an ester thereof (e.g., the ethyl ester thereof). In some further embodiments, the effective amount of quizalofop or an ester thereof is at least 14 g AI/Ha. In other further embodiments, the effective amount of quizalofop or an ester thereof is at least 16, 18, 20, 22, 24 or 26 g AI/Ha. In still other further embodiments, the effective amount of quizalofop or an ester thereof is at least 28 g AI/Ha. In yet other further embodiments, the effective amount of quizalofop or an ester thereof is at least 32, 36 or 40 g AI/Ha.

In some embodiments, the FOP herbicide is haloxyfop. In some further embodiments, the effective amount of haloxyfop is at least 38 g AI/Ha. In other further embodiments, the effective amount of haloxyfop is at least 44, 50, 56, 62, 66 or 72 g AI/Ha. In still other further embodiments, the effective amount of haloxyfop is at least 76 g AI/Ha. In yet other further embodiments, the effective amount of haloxyfop is at least 82, 88 or 94 g AI/Ha.

In other embodiments, the FOP herbicide is fluazifop or an ester thereof (e.g., the butyl ester thereof). In some further embodiments, the effective amount of fluazifop or an ester thereof is at least 56 g AI/Ha. In other further embodiments, the effective amount of fluazifop or an ester thereof is at least 65, 74, 83, 92 or 102 g AI/Ha. In still other further embodiments, the effective amount of fluazifop or an ester thereof is at least 112 g AI/Ha. In yet other further embodiments, the effective amount of fluazifop or an ester thereof is at least 120, 130 or 140 g AI/Ha.

In some embodiments, the FOP herbicide is clodinafop or clodinafop-propargyl. In some further embodiments, the effective amount of clodinafop or clodinafop-propargyl is at least 11 g AI/Ha. In other further embodiments, the effective amount of clodinafop or clodinafop-propargyl is at least 13, 15, 17, 19 or 20 g AI/Ha. In still other further embodiments, the effective amount of clodinafop or clodinafop-propargyl is at least 22 g AI/Ha. In yet other further embodiments, the effective amount of clodinafop or clodinafop-propargyl is at least 26, 30 or 34 g AI/Ha.

In some embodiments, the FOP herbicide is diclofop or diclofop-methyl. In some further embodiments, the effective amount of diclofop or diclofop-methyl is at least 226 g AI/Ha. In other further embodiments, the effective amount of diclofop or diclofop-methyl is at least 260, 295, 330, 395 or 426 g AI/Ha. In still other further embodiments, the effective amount of diclofop or diclofop-methyl is at least 452 g AI/Ha. In yet other further embodiments, the effective amount of diclofop or diclofop-methyl is at least 480, 510 or 540 g AI/Ha.

In some embodiments, providing a domestic rice crop plant relates to planting a seed for the domestic rice crop plant and allowing the domestic rice crop plant to emerge prior to applying an effective amount of the at least one FOP herbicide.

In other embodiments, providing a domestic rice crop plant relates to transplanting the domestic rice crop plant prior to applying an effective amount of the at least one FOP herbicide.

In still other embodiments, providing a domestic rice crop plant relates to the domestic rice crop plant being previously established pre-emergence or post-emergence in a field prior to applying an effective amount of the at least one FOP herbicide post-emergence.

In some embodiments, the domestic rice crop plant was further treated pre-emergence or post-emergence with at least one additional herbicide. In some further embodiments, the at least one additional herbicide is a FOP, DIM, or DEN herbicide. In other further embodiments, the pre-emergence treatment with at least one additional herbicide is a seed coating. In still other further embodiments, the post-emergence treatment with at least one additional herbicide is prior to, concurrent with, or following the applying an effective amount of the at least one FOP herbicide to the domestic rice crop plant, post-emergence. In even other further embodiments, the DIM herbicide is selected from the group consisting of cycloxydim, sethoxydim, tepraloxydim, clethodim, and tralkoxydim.

In some embodiments, the field was previously used for the growth of a previous domestic rice crop plant that was not treated with an herbicide.

In other embodiments, the field was previously used for the growth of a previous herbicide-treated domestic rice crop plant. In some further embodiments, the previous herbicide-treated domestic rice crop plant was treated with at least one FOP, DIM, or DEN herbicide. In even other further embodiments, the DIM herbicide is selected from the group consisting of cycloxydim, sethoxydim, tepraloxydim, clethodim, and tralkoxydim.

Problem Weed Species

There are a number of weed species that present problems to the commercial cultivation of rice and that can be controlled according to the methods of the present disclosure including, but not limited to, weeds of the genera *Echinochloa* and *Leptochloa*.

Exemplary of problem *Echinochloa* species include, but are not limited to *E. colona* (common name Jungle rice), *E. crus-galli* (Barnyard grass), *E. crus-pavonis* (Gulf barnyard grass, or Gulf cockspur), *E. oryzicola* (Late Watergrass, or Late Barnyard grass; a.k.a., *E. phyllopogon* or *E. crus-galli* var. oryzicola), and *E. oryzoides* (Early Watergrass, or Early Barnyard grass).

Exemplary of problem *Leptochloa* species include, but are not limited to *L. chinensis* (Red sprangletop, Chinese sprangletop, or Asian sprangletop), *L. fascicularis* (Bearded sprangletop; a.k.a., *L. fusca* subspecies *fascicularis*), *L. panacea* (Mucronate sprangletop; a.k.a., *L. mucronata*, *L. panacea* subspecies *mucronata*, and *L. filiformis*), and *L. panicoides* (Amazon sprangletop).

Methods of Controlling Weeds

Herbicide-tolerant plants of the disclosure may be used in conjunction with an herbicide to which they are tolerant. Herbicides may be applied to the plants of the disclosure using any techniques known to those skilled in the art. Herbicides may be applied at any point in the plant cultivation process. For example, herbicides may be applied pre-planting, at planting, pre-emergence, post-emergence or combinations thereof.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides may be used to control the growth of weeds that may be found growing in the vicinity of the herbicide-tolerant plants invention. In embodiments of this type, an herbicide may be applied to a plot in which herbicide-tolerant plants of the disclosure are growing in vicinity to weeds. An herbicide to which the herbicide-tolerant plant of the disclosure is tolerant may then be applied to the plot at a concentration sufficient to kill or inhibit the growth of the weed. Concentrations of herbicide sufficient to kill or inhibit the growth of weeds are known in the art.

It will be readily apparent to one of ordinary skill in the relevant arts that other suitable modifications and adaptations to the methods and applications described herein are obvious and may be made without departing from the scope of the disclosure or any embodiment thereof. Having now described the present disclosure in detail, the same will be more clearly understood by reference to the following examples, which are included herewith for purposes of illustration only and are not intended to be limiting of the invention.

Use of Tissue Culture for Selection of Herbicide

Herbicide tolerant crops offer farmers additional options for weed management. Currently, there are genetically modified (GMO) solutions available in some crop systems. Additional, mutational techniques have been used to select for altered enzyme, activities or structures that confer herbicide resistance such as the current CLEARFIELD° solutions from BASF. In the US, CLEARFIELD Rice is the premier tool for managing red rice in infested areas (USDA-ARS, 2006); however, gene flow between red rice and CLEARFIELD Rice represents a considerable risk for the AHAS tolerance since out-crossing, has been reported at up to 170 F1 hybrids/ha (Shivrain et al, 2007). Stewardship guidelines including, amongst many other aspects, alternation non CLEARFIELD Rice can limit CLEARFIELD Rice market penetration. The generation of cultivated rice with tolerance to a different mode of action (MOA) graminicides would reduce these risks and provide more tools for weed management.

One enzyme that is already a target for many different graminaceous herbicides is acetyl CoA carboxylase (ACCase, EC 6.4.1.2), which catalyzes the first committed step in fatty acid (FA) biosynthesis. Aryloxyphenoxypropionate (APP or FOP) and cyclohexanedione (CHD or DIM) type herbicides are used post-emergence in dicot crops, with the exception of cyhalofop-butyl which is selective in rice to control grass weeds. Furthermore, most of these herbicides have relatively low persistence in soil and provide growers with flexibility for weed control and crop rotation. Mutations in this enzyme are known that confer tolerance to specific sets of FOPS and/or DIMS (Liu et al, 2007; Delye et al, 2003, 2005).

Tissue culture offers an alternative approach in that single clumps of callus represent hundreds or even thousands of cells, each of which can be selected for a novel trait such as herbicide resistance (Jain, 2001). Mutations arising spontaneously in tissue culture or upon some kind of induction can be directly selected in culture and mutated events selected.

The exploitation of somaclonal variation that is inherent to in vitro tissue culture techniques has been a successful approach to selectively generate mutations that confer DIM and FOP tolerance in corn (Somers, 1996; Somers et al., 1994; Marshal et al., 1992; Parker et al., 1990) and in seashore paspalum (Heckart et al, 2009). In the case of maize, the efficiencies of producing regenerable events can be calculated. In Somers et al, 1994, sethoxydim resistant maize plants were obtained using tissue culture selection. They utilized 100 g of callus and obtained 2 tolerant lines following stepwise selection at 0.5, 1.0, 2.0, 5.0 and 10 µM sethoxydim. A calculated mutation rate in their protocol would be 2 lines/100 g of callus or 0.02 lines/g.

In the case of seashore paspalum, Heckert directly utilized a high level of sethoxydim and recovered 3 regenerable lines in approx 10,000 callus pieces or, essentially, a 0.03% rate. While not comparable, these numbers will be later used for comparison with rice tissue culture mutagenesis. In the maize work, calli were constantly culled at each selection stage with only growing callus being transferred; however, in the case of seashore paspalum, all calli were transferred at each subculture. ACCase genes as selectable markers:

Plant transformation involves the use of selectable marker genes to identify the few transformed cells or individuals from the larger group of non-transformed cells or individuals. Selectable marker genes exist, but they are limited in number and availability. Alternative marker genes are required for stacking traits. In addition, the use of a selectable marker gene that confers an agronomic trait (i.e. herbicide resistance) is often desirable. The present disclosure discloses ACCase genes as selectable markers that can be added to the current limited suite of available selectable marker genes. Any of the mutants described herein can be introduced into a plasmid with a gene of interest and tranformed into the whole plant, plant tissue or plant cell for use as selectable markers. A detailed method is outlined in example 7 below. The selectable markers of the inventions may be utilized to produce events that confer field tolerance to a given group of herbicides and other where cross protection has been shown (i.e., FOP's).

Modern, high throughput plant transformation systems require an effective selectable marker system; however, there is a limited number available that are acceptable in the market. Therefore, selection systems which also convey a commercial trait are always valuable. The system described herein is an effective selection system in/for plant cells which also encode for an herbicide tolerance trait suitable for use in any monocotyledonous crop.

In one embodiment, the present disclosure provides a method for selecting a tranformed plant comprising introducing a nucleic acid molecule encoding a gene of interest into a plant cell, wherein the nucleic acid molecule further encodes a mutant acetyl-Coenzyme A carboxylase (ACCase) in which the amino acid sequence differs from an amino acid sequence of an ACCase of a corresponding wild-type rice plant at one amino acid position; and contacting the plant cells with an ACCase inhibitor to obtain the transformed plant, wherein said mutant ACCase confers upon the transformed plant increased herbicide tolerance as compared to the corresponding wild-type variety of the plant when expressed therein.

In one embodiment, the present disclosure provides a method of marker-assisted breeding, the method comprising breeding any plant of the disclosure with a second plant; and contacting progeny of the breeding step with an ACCase inhibitor to obtain the progeny comprising said mutant ACCase; wherein said mutant ACCase confers upon the progeny plant increased herbicide tolerance as compared to the second plant.

In one embodiment, a single ACCase gene is linked to a single gene of interest. The ACCase gene may be linked upstream or downstream of the gene of interest.

In one embodiment, the present disclosure provides for the use of ACCase nucleic acid and protein as described above in diagnostic assays. The diagnostic uses for selectable markers described herein can be employed to identify ACCase gene. Diagnostic methods can include PCR methodologies, proteins assays, labeled probes, and any other standard diagnostic methods known in the art.

EXAMPLES

Example 1: Tissue Culture Conditions

An in vitro tissue culture mutagenesis assay has been developed to isolate and characterize plant tissue (e.g., rice tissue) that is tolerant to acetyl-Coenzyme A carboxylase inhibiting herbicides, e.g., tepraloxydim, cycloxydim, and sethoxydim. The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present disclosure provides tissue culture conditions for encouraging growth of friable, embryogenic rice callus that is regenerable. Calli were initiated from 4 different rice cultivars encompassing both Japonica (Taipei 309, Nipponbare, Koshihikari) and Indica (Indica 1) varieties. Dehusked seed were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 3.

TABLE 3

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | | 30 g/L | | |
| Sucrose | VWR | | | | | 10 g/L | 30 g/L |
| NAA | Duchefa | | | | | 50 µg/L | |
| 2,4-D | Sigma | 2.0 mg/L | | | | | 1.0 mg/L |

TABLE 3-continued

| Ingredient | Supplier | R001M | R025M | R026M | R327M | R008M | MS711R |
|---|---|---|---|---|---|---|---|
| $MgCl_2 \cdot 6H_2O$ | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 2: Selection of Herbicide-Tolerant Calli

Once tissue culture conditions were determined, further establishment of selection conditions were established through the analysis of tissue survival in kill curves with cycloxydim, tepraloxydim, sethoxydim (FIG. 1) or haloxyfop (not shown). Careful consideration of accumulation of the herbicide in the tissue, as well as its persistence and stability in the cells and the culture media was performed. Through these experiments, a sub-lethal dose has been established for the initial selection of mutated material.

Figure 2:
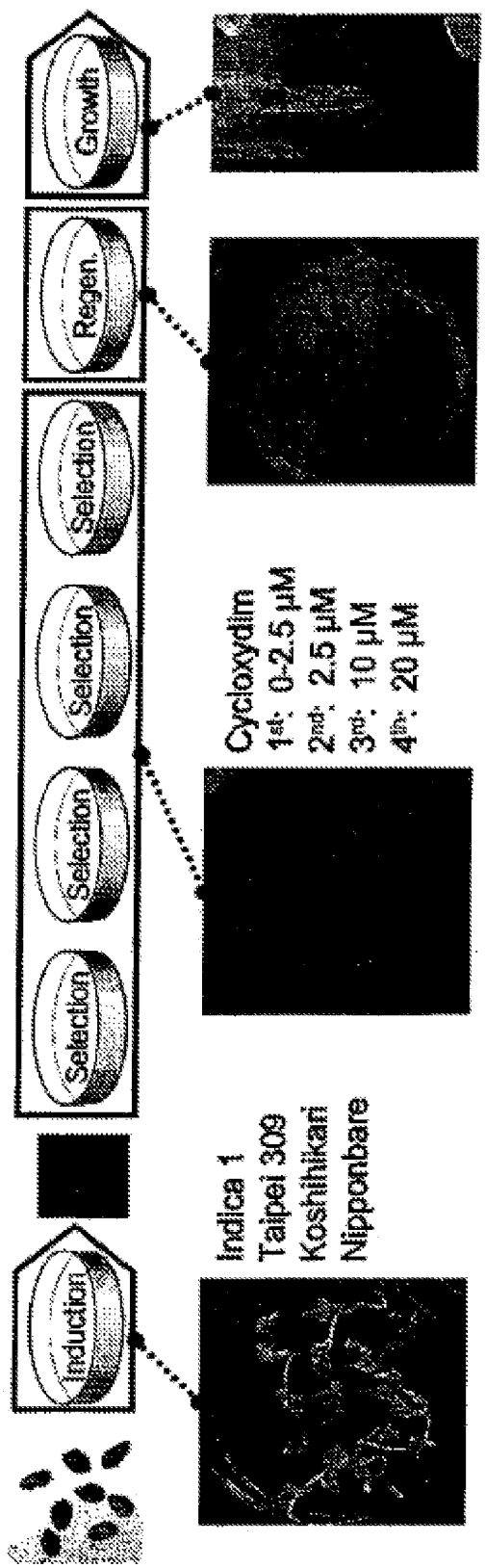
FIG. 2 is a diagram of the selection process used to produce herbicide-tolerant rice plants.

After the establishment of the starting dose of sethoxydim, cycloxydim, tepraloxydim, and haloxyfop in selection media, the tissues were selected in a step-wise fashion by increasing the concentration of the ACCase inhibitor with each transfer until cells are recovered that grew vigorously in the presence of toxic doses (see FIG. 2). The resulting calli were further subcultured every 3-4 weeks to R001M with selective agent. Over 26,000 calli were subjected to selection for 4-5 subcultures until the selective pressure was above toxic levels as determined by kill curves and observations of continued culture. Toxic levels were determined to be 50 µM sethoxydim, 20 µM cycloxydim, 2.5 µM tepraloxydim (FIG. 1) and 10 µM haloxyfop (not shown).

Alternatively, liquid cultures initiated from calli in MS711R (Table 2) with slow shaking and weekly subcultures. Once liquid cultures were established, selection agent was added directly to the flask at each subculture. Following 2-4 rounds of liquid selection, cultures were transferred to filters on solid R001M media for further growth.

Example 3: Regeneration of Plants

Tolerant tissue was regenerated and characterized molecularly for ACCase gene sequence mutations and/or biochemically for altered ACCase activity in the presence of the selective agent.

Following herbicide selection, calli were regenerated using a media regime of R025M for 10-14 days, R026M for ca. 2 weeks, R327M until well formed shoots were developed, and R0085 until shoots were well rooted for transfer to the greenhouse (Table 2). Regeneration was carried out in the light. No selection agent was included during regeneration.

Once strong roots were established, MO regenerants were transplant to the greenhouse in 4" square pots in a mixture of sand, NC Sandhills loamy soil, and Redi-earth (2:4:6) supplemented with gypsum. Transplants were maintained under a clear plastic cup until they were adapted to greenhouse conditions (ca. 1 week). The greenhouse was set to a day/night cycle of 27° C./21° C. (80° F./70° F.) with 600W high pressure sodium lights supplementing light to maintain a 14 hour day length. Plants were watered 2-3 times a day depending in the weather and fertilized daily. Rice plants selected for seed increase were transplanted into one gallon pots. As plants approached maturity and prepared to bolt, the pots were placed in small flood flats to better maintain water and nutrient delivery. Plants were monitored for insects and plant health and managed under standard Integrated Pest Management practices.

Example 4: Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using one forward and one reverse primer.

```
Forward Primers:
                                    (SEQ ID NO: 7)
OsACCpU5142:  5'-GCAAATGATATTACGTTCAGAGCTG-3'

(SEQ ID NO: 8)
OsACCpU5205:  5'-GTTACCAACCTAGCCTGTGAGAAG-3'

Reverse Primers:
                                    (SEQ ID NO: 9)
OsACCpL7100:  5'-GATTTCTTCAACAAGTTGAGCTCTTC-3'

(SEQ ID NO: 10)
OsACCpL7054:  5'-AGTAACATGGAAAGACCCTGTGGC-3'
```

PCR amplification was performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks). Chromatogram trace files (.scf) were analyzed for mutation relative to Os05g0295300 using Vector NTI Advance 10™ (Invitrogen). Based on sequence information, two mutations were identified in several individuals. I1,781(Am)L and D2,078(Am)G were present in the heterozygous state. Sequence analysis was performed on the representative chromatograms and corresponding AlignX alignment with default settings and edited to call secondary peaks.

Samples inconsistent with an ACCase mutation were spray tested for tolerance and discarded as escapes. Surprisingly, most of the recovered lines were heterozygous for the I1,781(Am)L mutation and resistant events were generated in all tested genotypes using cycloxydim or sethoxydim: Indica1 (≥18 lines), Taipei 309 (≥14 lines), Nipponbare (≥3 lines), and Koshihikare (≥6 lines). One line was heterozygous for a D2,078(Am)G mutation. The D2,078(Am)G heterozygote line appeared stunted with narrow leaves, while the I1,781(Am)L heterozygotes varied in appearance, but most looked normal relative to their parental genotype. Several escapes were recovered and confirmed by sequencing and spray testing; however, sequencing results of the herbicide sensitive region of ACCase revealed that most tolerant mutants were heterozygous for an I1,781(Am)L, A to T mutation (See Table 4). One line, OsARWI010, was heterozygous for a D2,078(Am)G, A to G mutation. To date, all recovered plants lacking an ACCase mutation have been sensitive to herbicide application in the greenhouse.

TABLE 4

Genotype of Rice Lines Recovered via Tissue Culture Selection

| Line | Parental Genotype | Rice Type | Mutation Identified | ATCC® Patent Deposit Designation |
|---|---|---|---|---|
| OsARWI1 | Indica 1 | indica | I1781(Am)L | PTA-10568 |
| OsARWI3 | Indica 1 | indica | I1781(Am)L | PTA-10569 |
| OsARWI8 | Indica 1 | indica | I1781(Am)L | PTA-10570 |
| OsARWI10 | Indica 1 | indica | D2078(Am)G | NA, sterile |
| OsARWI15 | Indica 1 | indica | I1781(Am)L | NA |
| OsHPHI2 | Indica 1 | indica | I1781(Am)L | PTA-10267 |
| OsHPHI3 | Indica 1 | indica | I1781(Am)L | NA |
| OsHPHI4 | Indica 1 | indica | I1781(Am)L | NA |
| OsHPHK1 | Koshihikari | japonica | I1781(Am)L | NA |
| OsHPHK2 | Koshihikari | japonica | I1781(Am)L | NA |
| OsHPHK3 | Koshihikari | japonica | I1781(Am)L | NA |
| OsHPHK4 | Koshihikari | japonica | I1781(Am)L | NA |
| OsHPHK6 | Koshihikari | japonica | I1781(Am)L | NA |
| OsHPHN1 | Nipponbare | japonica | I1781(Am)L | PTA-10571 |
| OsHPHT1 | Taipei 309 | japonica | I1781(Am)L | NA |
| OsHPHT4 | Taipei 309 | japonica | I1781(Am)L | NA |
| OsHPHT6 | Taipei 309 | japonica | I1781(Am)L | NA |

Example 5: Demonstration of Herbicide-Tolerance

Selected mutants and escapes were transferred to small pots. Wild-type cultivars and 3 biovars of red rice were germinated from seed to serve as controls.

Figure 3:
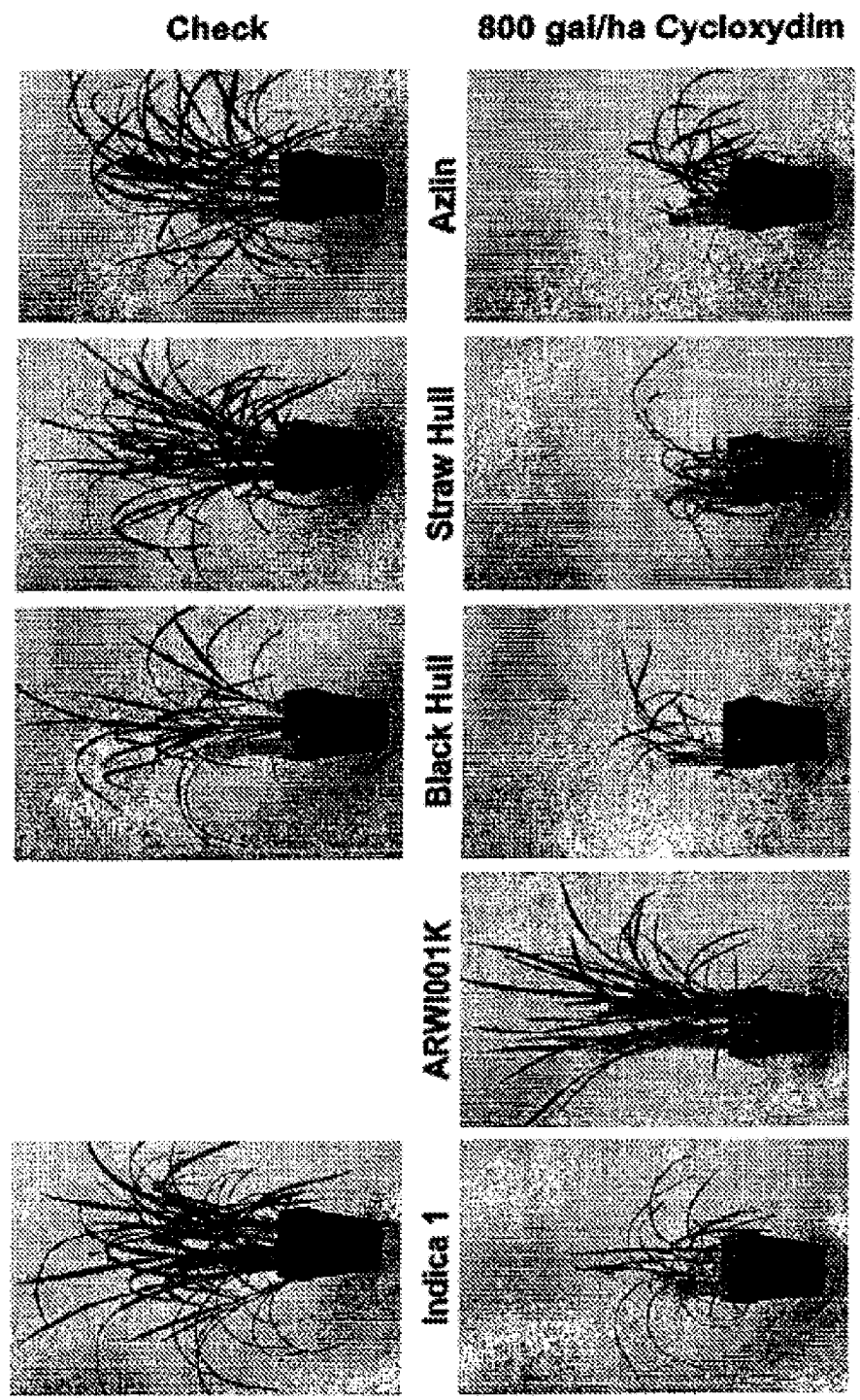
FIG. 3 shows photographs of plants taken one week after treatment with herbicide.
Figure 4:
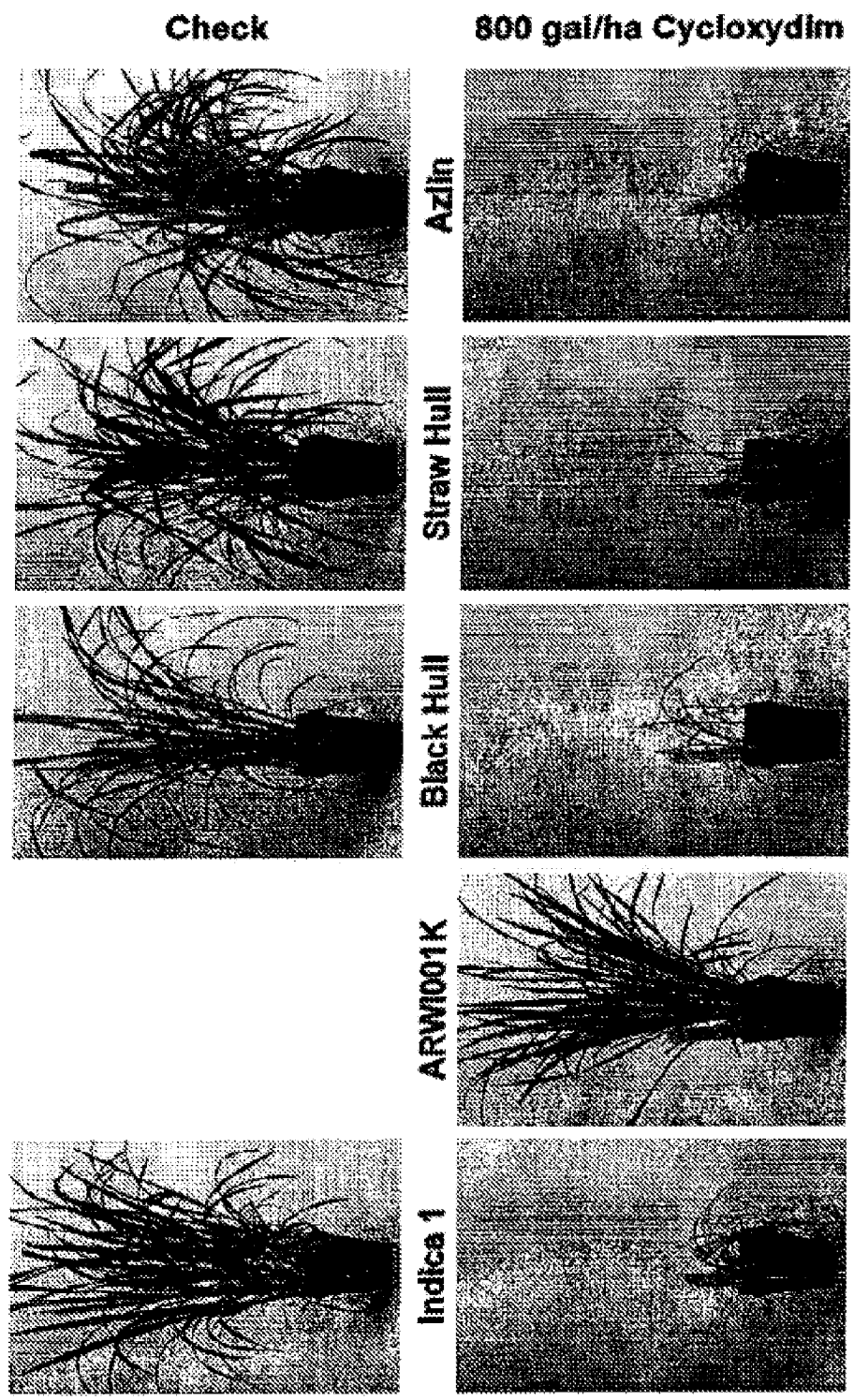
FIG. 4 shows photographs of plants taken two weeks after treatment with herbicide.
Figure 17:
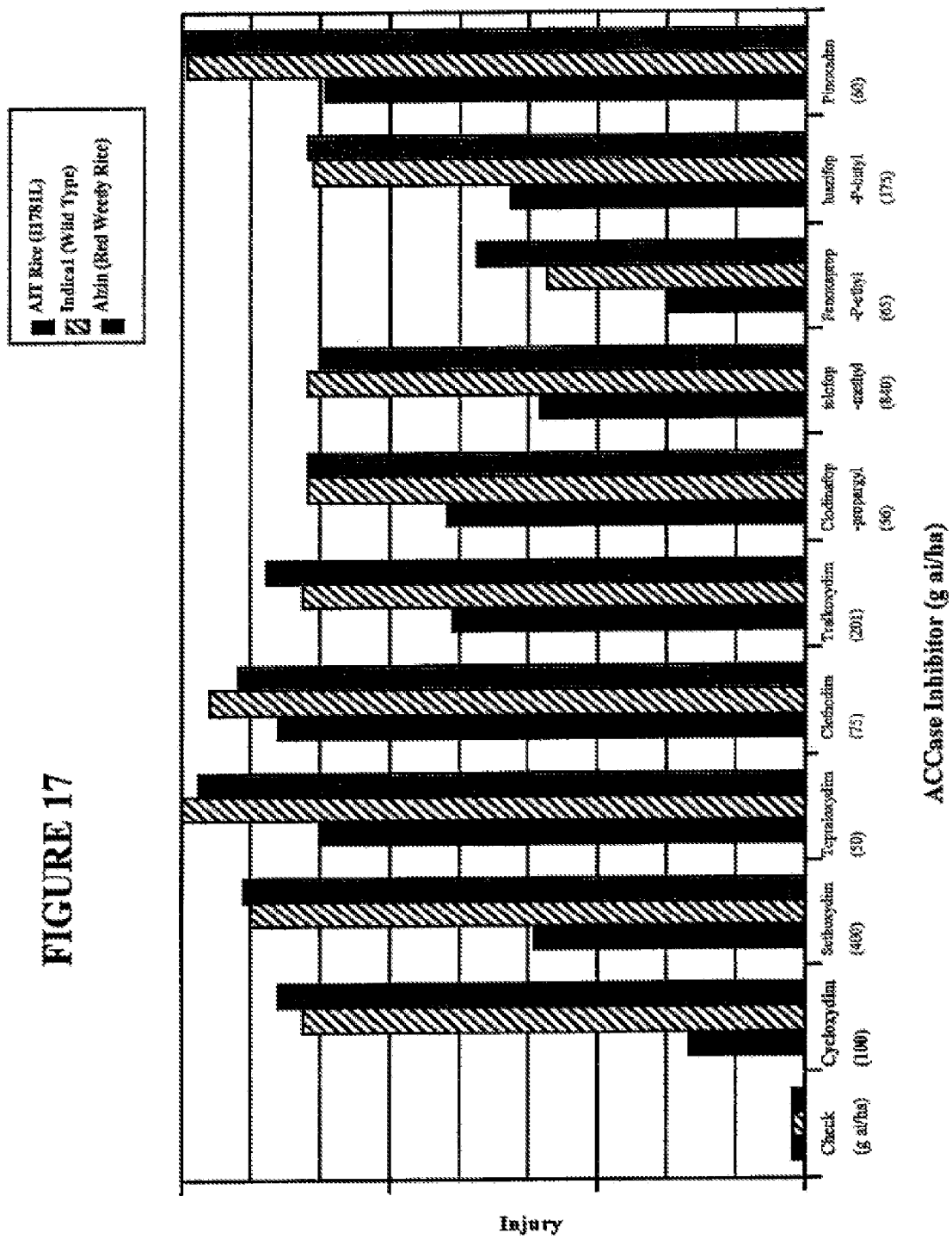
FIG. 17 provides a graph showing results for mutant rice versus various ACCase inhibitors.

After ca. 3 weeks post-transplant, MO regenerants were sprayed using a track sprayer with 400-1600 g ai/ha cycloxydim (BAS 517H) supplemented with 0.1% methylated seed oil. After the plants had adapted to greenhouse conditions, a subset were sprayed with 800 g ai/ha cycloxydim. Once sprayed, plants were kept on drought conditions for 24 hours before being watered and fertilized again. Sprayed plants were photographed and rated for herbicide injury at 1 (FIG. 3) and 2 weeks after treatment (FIG. 4). No injury was observed on plants containing the I1,781(Am)L heterozygous mutation while control plants and tissue culture escapes (regenerated plants negative for the sequenced mutations) were heavily damaged after treatment (FIGS. 3 & 4). FIGS. 5-15 provide nucleic acid and/or amino acid sequences of acetyl-Coenzyme A carboxylase enzymes from various plants. FIG. 17 provides a graph showing results for mutant rice versus various ACCase inhibitors.

Example 6: Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to: facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media.

Mutant lines were selected using cycloxydim or sethoxydim in 4 different rice genotypes. Efficiencies of obtaining mutants was high either based on a percentage of calli that gave rise to a regenerable, mutant line or the number of lines as determined by the gram of tissue utilized. Overall, the mutation frequency compared to seashore paspalum is 5 fold and compared to maize is 2 fold. In some cases, this difference is much higher (>10 fold) as shown in Table 5 below.

TABLE 5

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.04 | 0.07 |
| Indica 1 | 2640 | Sethoxydim | 3 | 0.114% | 58.08 | 0.05 |
| Koshi | 1800 | Cycloxidim | 6 | 0.333% | 39.6 | 0.15 |
| NB | 3400 | Cycloxidim | 1 | 0.029% | 74.8 | 0.01 |
| NB | 725 | Sethoxydim | 0 | 0.000% | 15.95 | 0.00 |
| T309 | 1800 | Cycloxidim | 8 | 0.444% | 36.9 | 0.20 |
| T309 | 1015 | Sethoxydim | 0 | 0.000% | 22.33 | 0.00 |
| Total | 13245 | | 21 | 0.159% | 291.39 | 0.07 |

If the data is analyzed using the criteria of selection, it is possible to see that cylcoxydim selection contributes to a higher rate of mutants isolated than sethoxydim, as shown in Table 6.

TABLE 6

| Genotype | # Calli | Selection | Mutants | Rate | Weight (g) | #/gm callus |
|---|---|---|---|---|---|---|
| Indica 1 | 1865 | Cycloxidim | 3 | 0.161% | 41.03 | 0.07 |
| Koshi | 1800 | Cycloxidim | 6 | 0.333% | 39.6 | 0.15 |
| NB | 3400 | Cycloxidim | 1 | 0.029% | 74.8 | 0.01 |
| T309 | 1800 | Cycloxidim | 8 | 0.444% | 39.6 | 0.20 |
| Total | 8865 | | 18 | 0.203% | 195.03 | 0.09 |
| Indica 1 | 2640 | Sethoxydim | 3 | 0.114% | 58.08 | 0.05 |
| NB | 725 | Sethoxydim | 0 | 0.000% | 15.95 | 0.00 |
| T309 | 1015 | Sethoxydim | 0 | 0.000% | 22.33 | 0.00 |
| Total | 4380 | | 3 | 0.068% | 96.36 | 0.03 |

Using this analysis, the rate for cycloxydim is almost 10 fold higher than either of the previous reports using sethoxydim selection, whereas rates using sethoxydim selection are similar to those previously reported. Further, 68% of the lines were confirmed as mutants when selection was on cycloxydim compared to 21% of the lines when selection was on sethoxydim. Increases seem to come from using cycloxydim instead of sethoxydim as a selection agent. Further, the use of membranes made transfer of callus significantly easier than moving each piece individually during subcultures. Over 20 mutants were obtained. Fertility appears to be high with the exception of one mutant that has a mutation known to cause a fitness penalty (D2,078(Am)G).

Example 7: Use of Mutant ACCase Genes as Selectable Markers in Plant Transformation Methods:

Indica1 and Nipponbare rice callus transformation was carried out essentially as described in Hiei and Komari (2008) with the exception of media substitutions as specified (see attached media table for details). Callus was induced on R001M media for 4-8 weeks prior to use in transformation. *Agrobacterium* utilized was LBA4404(pSB1) (Ishida et al. 1996) transformed with RLM185 (L. Mankin, unpublished: contains DsRed and a mutant AHAS for selection), ACC gene containing I1781(Am)L, ACC gene containing I1781(Am)L and W2027C, ACC gene containing I1781(Am)L and I2041(Am)N, or ACC gene containing I1781(Am)A or wild type which also contains a mutant AHAS gene for selection. *Agrobacterium* grown for 1-3 days on solid media was suspended in M-LS-002 medium and the $OD_{660}$ adjusted to approximately 0.1. Callus was immersed in the *Agrobacterium* solution for approximately 30 minutes. Liquid was removed, and then callus was moved to filter paper for co-culture on semi-solid rice cc media. Co-culture was for 3 days in the dark at 24° C. Filters containing rice callus were directly transferred to R001M media containing Timentin for 1-2 weeks for recovery and cultured in the dark at 30° C. Callus was subdivided onto fresh R001M media with Timentin and supplemented with 100 µM Imazethapyr, 10 µM Cycloxydim or 2.5 µM Tepraloxydim. After 3-4 weeks, callus was transferred to fresh selection media. Following another 3-4 weeks, growing callus was transferred to fresh media and allowed to grow prior to Taqman analysis. Taqman analysis was for the Nos terminator and was conducted to provide for a molecular confirmation of the transgenic nature of the selected calli. Growth of transgenic calli was measured with various selection agents by subculturing calli on media containing either 1004 Cycloxydim or Haloxyfop, 2.504 Tepraloxydim or 10004 Imazethapyr. Calli size was measured from scanned images following initial subculture and then after approximately 1 month of growth.

Transformation of maize immature embryos was carried out essentially as described by Lai et al (submitted). Briefly, immature embryos were co-cultured with the same *Agrobacterium* strains utilized for rice transformation suspended in M-LS-002 medium to an $OD_{660}$ of 1.0. Co-culture was on Maize CC medium for 3 days in the dark at 22° C. Embryos were removed from co-culture and transferred to M-MS-101 medium for 4-7 days at 27° C. Responding embryos were transferred to M-LS-202 medium for Imazethapyr selection or M-LS-213 media supplemented with either 1 µM Cycloxydim or 0.75 µM Tepraloxydim. Embryos were cultured for 2 weeks and growing callus was transferred to a second round of selection using the same media as previous except that Cycloxydim selection was increased to 5 µM. Selected calli were transferred to M-LS-504 or M-LS-513 media supplemented with either 5 µM Cycloxydim or 0.75 µM of Tepraloxydim for and moved to the light (16 hr/8 hr day/night) for regeneration. Shoots appeared between 2-3 weeks and were transferred to plantcon boxes containing either M-LS-618 or M-LS-613 supplemented with either 5 µM Cycloxydim or 0.7504 of Tepraloxydim for further shoot development and rooting. Leaf samples were submitted for Taqman analysis. Positive plants were transferred to soil for growth and seed generation. In the second set of experiments, conditions were identical except that Tepraloxydim selection was decreased to 0.5 µM during regeneration and shoot and root formation. In the third set of experiments, Haloxyfop was also tested as a selection agent. In these experiments, 1 µM was used throughout for selection.

Results and Discussion:

Transgenic calli were obtained from Indica1 rice transformation experiments using ACC gene containing I1781(Am)L and W2027(Am)C, and ACC gene containing I1781(Am)L and I2041(Am)N. One callus was obtained from ACC gene containing I1781(Am)L and W2027(Am)C following Tepraloxydim selection and 3 calli were obtained from ACC gene containing I1781(Am)L and I2041(Am)N. One callus was obtained from ACC gene containing I1781(Am)L and I2041(Am)N using Cycloxydim selection. Nos Taqman showed that all of these calli were transgenic. Calli were screened for growth under various selection agents including Imazethapry (Pursuit—P) for the mutant AHAS selectable marker.

As can be observed in Table 7, the double mutant constructs allowed for growth on both Cycloxydim and Tepraloxydim in addition to Haloxyfop. The levels utilized in these growth experiments are inhibitory for wild type material. Growth was measured as a % change in size following 1 month of culture on the selection media.

TABLE 7

Growth of transgenic Indica1 callus on various selection media.
Selection µM

| Construct | H10 | C10 | T2.5 | P100 |
|---|---|---|---|---|
| I1781(Am)L, W2027(Am)C | 1669% | 867% | 1416% | 739% |
| I1781(Am)L, I2041(Am)N | 1613% | 884% | 1360% | 634% |

Results from the first set of maize experiments reveal that both the single of the double mutant can be used to select for Cycloxydim resistance or both Cylcoxydim or Tepraloxydim resistance at a relatively high efficiency (FIG. 16).

Efficiencies between selection agents was relatively comparable in these experiments with maybe a slight decrease in the overall efficiency with the single mutant on Cycloxydim compared to Pursuit selection. However, the double mutant may have a slight increased efficiency. The escape rate—the percentage of non-confirmed putative events—was lower for Cycloxydim or Tepraloxydim. Further, under the conditions described, it was possible to differentiate between the single and double mutants using Tepraloxydim selection.

Similar results have been obtained in the second set of experiments (not shown). In the third set of experiments, Haloxyfop is also an efficient selectable marker for use in transformation with either the single or the double mutant (not shown).

The single mutant is useful for high efficiency transformation using Cycloxydim or Haloxyfop selection. It should also be useful for other related compounds such as Sethoxydim. The double mutant is useful for these selection agents with the addition that Tepraloxydim can be used. The single and the double mutant can be used in a two stage transformation in that the single mutant can be differentiated from the double with Tepraloxydim selection. In combination with other current BASF selection markers, these give two more options for high efficiency transformations of monocots and maize in particular.

Herbicide tolerance phenotypes as described herein have also been exhibited by ACCase-inhibitor tolerant rice plants hereof, in the field under 600 g/ha cycloxydim treatment (data not shown).

Example 8: AIT Rice Tolerance to Herbicide Versus Red Rice

The tolerance of AIT rice to a variety of FOP, DIM and DEN herbicides was evaluated and compared to the tolerance of wild-type red rice to the same herbicides.

Methods:

Untreated AIT rice and red rice seeds were sown into fields in three separate locations and allowed to emerge. At the 3-4 leaf growth stage, plots at each location were treated with single applications of varying concentrations of herbicide. All herbicides were suspended in solutions comprising 1% methylated seed oil.

Cycloxydim was applied at a rate of 300 g AI/Ha.
Sethoxydim was applied at a rate of 600 g AI/Ha.
Tepraloxydim was applied at a rate of 50 g AI/Ha.
Clethodim was applied at a rate of 100 200 g AI/Ha.
Quizalofop-P-ethyl was applied at rates of 35, 70 and 140 g AI/Ha.
Pinoxaden was applied at rates of 30, 60 and 120 g AI/Ha.
Clodinafop-propargyl was applied at rates of 35, 70 and 140 g AI/Ha.

Percent injury to treated plants was evaluated two weeks after herbicide treatment according to procedures standard in the art.

Results:

Results are shown as the average percent injury of the three plots for each plant type treated with the given application rate of herbicide.

Figure 20A:
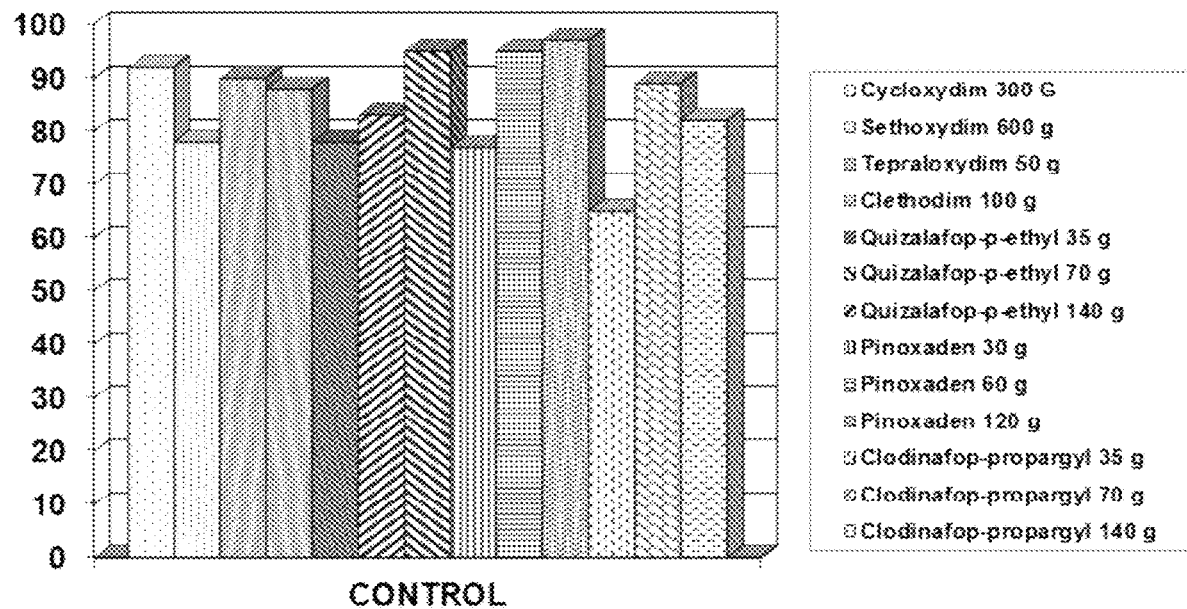
FIG. 20A shows the effect of post-emergent application of herbicides on Red rice.
Figure 20B:
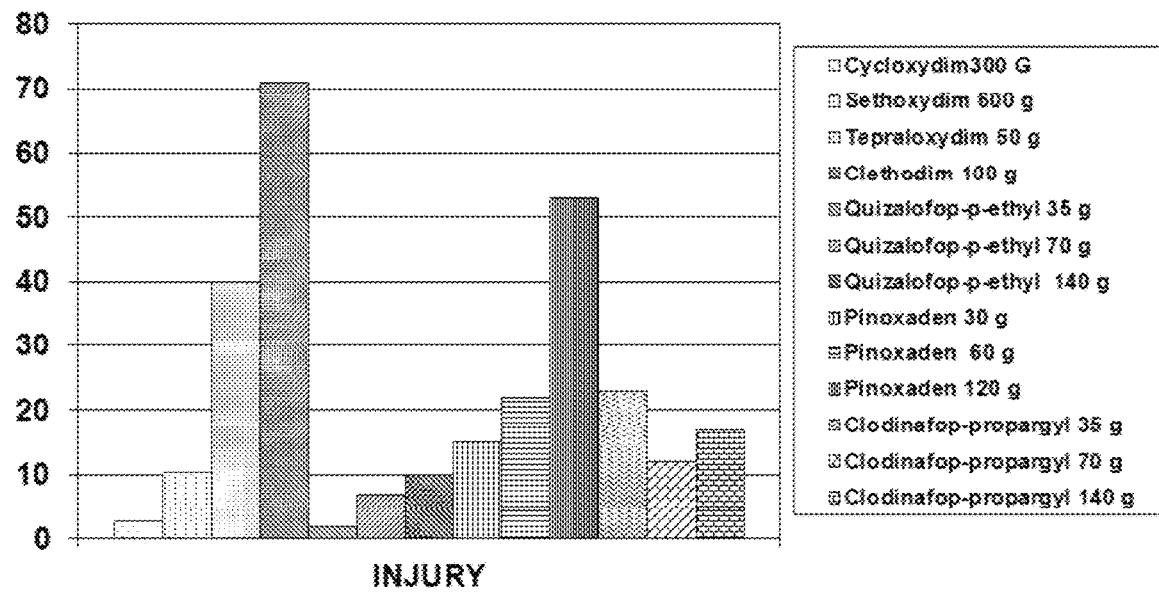
FIG. 20B shows the effect of post-emergent application of herbicides on AIT rice.

As shown in FIG. 20A, red rice suffered more injury to each herbicide at each concentration that the corresponding plots of AIT rice as shown in FIG. 20B.

The above description is for the purpose of teaching the person of ordinary skill in the art how to practice the claimed aspects of the disclosure and embodiments thereof, and it is not intended to detail all those obvious modifications and variations of it which will become apparent to the skilled worker upon reading the description. It is intended, however, that all such obvious modifications and variations be included within the scope of the present disclosure. The disclosure is intended to cover the components and steps in any sequence which is effective to meet the objectives there intended, unless the context specifically indicates the contrary. All patents and publications cited herein are entirely incorporated herein by reference.

What is claimed is:

1. A method for treating rice, comprising:
   (A) providing
   (1) a domestic rice crop plant grown from seed, the domestic rice crop plant
   (a) comprising and expressing an endogenous non-transfected mutant ACCase nucleic acid whose sequence encodes a multi-functional, plastidic ACCase containing a mutation selected from the group consisting of I1781L (Am), G2096S (Am), and W2027C (Am); and
   (b) possessing a phenotype of tolerance to quizalofop or an ester thereof, fluazifop or an ester thereof, clodinafop, clodinafop-propargyl, or diclofop or diclofop methyl, wherein said plant exhibits less than 10% herbicide injury to a field application of at least 70 g AI/ha to 140 g AI/Ha of clodinafop-propargyl, at least 11 g AI/Ha to 34 g AI/Ha of clodinafop, at least 56 g AI/Ha to 140 g AI/Ha of fluazifop or an ester thereof, at least 14 g AI/Ha to 140 g AI/Ha of quizalofop or an ester thereof, or at least 226 g AI/Ha to 540 g AI/Ha of diclofop or diclofop-methyl; and
   (2) at least one ACCase-inhibiting aryloxyphenoxypropanoate herbicide comprising quizalofop or an ester thereof, fluazifop or an ester thereof, clodinafop, clodinafop-propargyl, diclofop, or diclofop-methyl;
   (B) applying an effective amount (measured in grams of active ingredient per hectare (g AI/Ha)) of the at least one aryloxyphenoxypropanoate herbicide to the domestic rice crop plant, post-emergence, thereby creating a treated rice plant; and
   (C) growing the treated rice plant;
   wherein the effective amount of the at least one ACCase-inhibiting aryloxyphenoxy-propanoate herbicide is at least 70 g AI/Ha to 140 g AI/Ha of clodinafop-propargyl, at least 11 g AI/Ha to 34 g AI/Ha of clodinafop, at least 56 g AI/Ha to 140 g AI/Ha of fluazifop or an ester thereof, at least 14 g AI/Ha to 140 g AI/Ha of quizalofop or an ester thereof, or at least 226 g AI/Ha to 540 g AI/Ha of diclofop or diclofop-methyl.

2. The method of claim 1, further comprising harvesting seed from the treated rice plant.

3. The method of claim 1, wherein the at least one aryloxyphenoxy-propanoate herbicide comprises quizalofop or an ester thereof.

4. The method of claim 1, wherein the at least one aryloxyphenoxy-propanoate herbicide comprises fluazifop.

5. The method of claim 1, wherein the at least one aryloxyphenoxy-propanoate herbicide comprises an ester of fluazifop.

6. The method of claim 1, wherein the at least one aryloxyphenoxy-propanoate herbicide comprises clodanifop.

7. The method of claim 1, wherein the at least one aryloxyphenoxy-propanoate herbicide comprises clodinafop-propargyl.

8. The method of claim 7, wherein the effective amount of clodinafop-propargyl is-70 g AI/Ha.

9. The method of claim 1, wherein the at least one aryloxyphenoxy-propanoate herbicide comprises diclofop.

10. The method of claim 1, wherein the at least one aryloxyphenoxy-propanoate herbicide comprises diclofop-methyl.

11. The method of claim 1, wherein the effective amount is effective for killing a weed of the genus *Echinochloa*.

12. The method of claim 11, wherein the weed of the genus *Echinochloa* is selected from the group consisting of *Echinochloa colona, Echinochloa crusgalli, Echinochloa crus-pavonis, Echinochloa oryzicola*, and *Echinochloa oryzoides*.

13. The method of claim 1, wherein the effective amount is effective for killing a weed of the genus *Leptochloa*.

14. The method of claim 13, wherein the weed of the genus *Leptochloa* is selected from the group consisting of *Leptochloa chinensis, Leptochloa fascicularis, Leptochloa panacea*, and *Leptochloa panicoides*.

15. The method of claim 1, wherein the domestic rice crop plant grown from seed is provided with at least one ACCase-inhibiting aryloxyphenoxypropanoate herbicide in the absence of safeners.

* * * * *

SEQUENCE LISTING

```
<160> NUMBER OF SEQ ID NOS: 26

<210> SEQ ID NO 1
<211> LENGTH: 2320
<212> TYPE: PRT
<213> ORGANISM: Alopecurus myosuroides

<400> SEQUENCE: 1

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190
```

-continued

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro

```
                610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
                660                 665                 670

Glu Tyr Val Ser Tyr Leu Ile Lys Gly Gln Ile Pro Pro Lys His Ile
                675                 680                 685

Ser Leu Val His Ser Thr Ile Ser Leu Asn Ile Glu Glu Ser Lys Tyr
                690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
                740                 745                 750

Glu Ala Gly Gly Thr Arg Leu Leu Ile Asp Gly Lys Thr Cys Leu Leu
                755                 760                 765

Gln Asn Asp His Asp Pro Ser Arg Leu Leu Ala Glu Thr Pro Cys Lys
770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
                820                 825                 830

Gln Ala Gly Asp Leu Ile Ala Arg Leu Asp Leu Asp Asp Pro Ser Ala
                835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
                900                 905                 910

Leu Gln Trp Glu Glu Leu Met Ser Val Leu Ala Thr Arg Leu Pro Arg
                915                 920                 925

Arg Leu Lys Ser Glu Leu Glu Gly Lys Tyr Asn Glu Tyr Lys Leu Asn
930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
                980                 985                 990

Gly Gly Arg Glu Ser His Ala His Phe Ile Val Lys Ser Leu Phe Glu
                995                 1000                1005

Glu Tyr Leu Ser Val Glu Glu Leu Phe Ser Asp Gly Ile Gln Ser
        1010                1015                1020

Asp Val Ile Glu Arg Leu Arg Leu Gln Tyr Ser Lys Asp Leu Gln
        1025                1030                1035
```

-continued

```
Lys Val Val Asp Ile Val Leu Ser His Gln Gly Val Arg Asn Lys
    1040            1045                1050

Thr Lys Leu Ile Leu Ala Leu Met Glu Lys Leu Val Tyr Pro Asn
    1055            1060                1065

Pro Ala Ala Tyr Arg Asp Gln Leu Ile Arg Phe Ser Ser Leu Asn
    1070            1075                1080

His Lys Arg Tyr Tyr Lys Leu Ala Leu Lys Ala Ser Glu Leu Leu
    1085            1090                1095

Glu Gln Thr Lys Leu Ser Glu Leu Arg Thr Ser Ile Ala Arg Asn
    1100            1105                1110

Leu Ser Ala Leu Asp Met Phe Thr Glu Glu Lys Ala Asp Phe Ser
    1115            1120                1125

Leu Gln Asp Arg Lys Leu Ala Ile Asn Glu Ser Met Gly Asp Leu
    1130            1135                1140

Val Thr Ala Pro Leu Pro Val Glu Asp Ala Leu Val Ser Leu Phe
    1145            1150                1155

Asp Cys Thr Asp Gln Thr Leu Gln Gln Arg Val Ile Gln Thr Tyr
    1160            1165                1170

Ile Ser Arg Leu Tyr Gln Pro Gln Leu Val Lys Asp Ser Ile Gln
    1175            1180                1185

Leu Lys Tyr Gln Asp Ser Gly Val Ile Ala Leu Trp Glu Phe Thr
    1190            1195                1200

Glu Gly Asn His Glu Lys Arg Leu Gly Ala Met Val Ile Leu Lys
    1205            1210                1215

Ser Leu Glu Ser Val Ser Thr Ala Ile Gly Ala Ala Leu Lys Asp
    1220            1225                1230

Ala Ser His Tyr Ala Ser Ser Ala Gly Asn Thr Val His Ile Ala
    1235            1240                1245

Leu Leu Asp Ala Asp Thr Gln Leu Asn Thr Thr Glu Asp Ser Gly
    1250            1255                1260

Asp Asn Asp Gln Ala Gln Asp Lys Met Asp Lys Leu Ser Phe Val
    1265            1270                1275

Leu Lys Gln Asp Val Val Met Ala Asp Leu Arg Ala Ala Asp Val
    1280            1285                1290

Lys Val Val Ser Cys Ile Val Gln Arg Asp Gly Ala Ile Met Pro
    1295            1300                1305

Met Arg Arg Thr Phe Leu Leu Ser Glu Glu Lys Leu Cys Tyr Glu
    1310            1315                1320

Glu Glu Pro Ile Leu Arg His Val Glu Pro Pro Leu Ser Ala Leu
    1325            1330                1335

Leu Glu Leu Asp Lys Leu Lys Val Lys Gly Tyr Asn Glu Met Lys
    1340            1345                1350

Tyr Thr Pro Ser Arg Asp Arg Gln Trp His Ile Tyr Thr Leu Arg
    1355            1360                1365

Asn Thr Glu Asn Pro Lys Met Leu His Arg Val Phe Phe Arg Thr
    1370            1375                1380

Leu Val Arg Gln Pro Ser Ala Gly Asn Arg Phe Thr Ser Asp His
    1385            1390                1395

Ile Thr Asp Val Glu Val Gly His Ala Glu Pro Leu Ser Phe
    1400            1405                1410

Thr Ser Ser Ser Ile Leu Lys Ser Leu Lys Ile Ala Lys Glu Glu
    1415            1420                1425
```

```
Leu Glu Leu His Ala Ile Arg Thr Gly His Ser His Met Tyr Leu
    1430                1435                1440

Cys Ile Leu Lys Glu Gln Lys Leu Leu Asp Leu Val Pro Val Ser
    1445                1450                1455

Gly Asn Thr Val Val Asp Val Gly Gln Asp Glu Ala Thr Ala Cys
    1460                1465                1470

Ser Leu Leu Lys Glu Met Ala Leu Lys Ile His Glu Leu Val Gly
    1475                1480                1485

Ala Arg Met His His Leu Ser Val Cys Gln Trp Glu Val Lys Leu
    1490                1495                1500

Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560

Tyr Gln Pro Leu Ser Val Ile Asp Leu Lys Arg Cys Ser Ala Arg
    1565                1570                1575

Asn Asn Lys Thr Thr Tyr Cys Tyr Asp Phe Pro Leu Thr Phe Glu
    1580                1585                1590

Ala Ala Val Gln Lys Ser Trp Ser Asn Ile Ser Ser Glu Asn Asn
    1595                1600                1605

Gln Cys Tyr Val Lys Ala Thr Glu Leu Val Phe Ala Glu Lys Asn
    1610                1615                1620

Gly Ser Trp Gly Thr Pro Ile Ile Pro Met Gln Arg Ala Ala Gly
    1625                1630                1635

Leu Asn Asp Ile Gly Met Val Ala Trp Ile Leu Asp Met Ser Thr
    1640                1645                1650

Pro Glu Phe Pro Ser Gly Arg Gln Ile Ile Val Ile Ala Asn Asp
    1655                1660                1665

Ile Thr Phe Arg Ala Gly Ser Phe Gly Pro Arg Glu Asp Ala Phe
    1670                1675                1680

Phe Glu Ala Val Thr Asn Leu Ala Cys Glu Lys Lys Leu Pro Leu
    1685                1690                1695

Ile Tyr Leu Ala Ala Asn Ser Gly Ala Arg Ile Gly Ile Ala Asp
    1700                1705                1710

Glu Val Lys Ser Cys Phe Arg Val Gly Trp Thr Asp Asp Ser Ser
    1715                1720                1725

Pro Glu Arg Gly Phe Arg Tyr Ile Tyr Met Thr Asp Glu Asp His
    1730                1735                1740

Asp Arg Ile Gly Ser Ser Val Ile Ala His Lys Met Gln Leu Asp
    1745                1750                1755

Ser Gly Glu Ile Arg Trp Val Ile Asp Ser Val Val Gly Lys Glu
    1760                1765                1770

Asp Gly Leu Gly Val Glu Asn Ile His Gly Ser Ala Ala Ile Ala
    1775                1780                1785

Ser Ala Tyr Ser Arg Ala Tyr Glu Glu Thr Phe Thr Leu Thr Phe
    1790                1795                1800

Val Thr Gly Arg Thr Val Gly Ile Gly Ala Tyr Leu Ala Arg Leu
    1805                1810                1815

Gly Ile Arg Cys Ile Gln Arg Ile Asp Gln Pro Ile Ile Leu Thr
```

```
            1820                1825                1830

Gly Phe Ser Ala Leu Asn Lys Leu Leu Gly Arg Glu Val Tyr Ser
            1835                1840                1845

Ser His Met Gln Leu Gly Gly Pro Lys Ile Met Ala Thr Asn Gly
            1850                1855                1860

Val Val His Leu Thr Val Pro Asp Asp Leu Glu Gly Val Ser Asn
            1865                1870                1875

Ile Leu Arg Trp Leu Ser Tyr Val Pro Ala Asn Ile Gly Gly Pro
            1880                1885                1890

Leu Pro Ile Thr Lys Ser Leu Asp Pro Ile Asp Arg Pro Val Ala
            1895                1900                1905

Tyr Ile Pro Glu Asn Thr Cys Asp Pro Arg Ala Ala Ile Ser Gly
            1910                1915                1920

Ile Asp Asp Ser Gln Gly Lys Trp Leu Gly Gly Met Phe Asp Lys
            1925                1930                1935

Asp Ser Phe Val Glu Thr Phe Glu Gly Trp Ala Lys Thr Val Val
            1940                1945                1950

Thr Gly Arg Ala Lys Leu Gly Gly Ile Pro Val Gly Val Ile Ala
            1955                1960                1965

Val Glu Thr Gln Thr Met Met Gln Leu Val Pro Ala Asp Pro Gly
            1970                1975                1980

Gln Pro Asp Ser His Glu Arg Ser Val Pro Arg Ala Gly Gln Val
            1985                1990                1995

Trp Phe Pro Asp Ser Ala Thr Lys Thr Ala Gln Ala Met Leu Asp
            2000                2005                2010

Phe Asn Arg Glu Gly Leu Pro Leu Phe Ile Leu Ala Asn Trp Arg
            2015                2020                2025

Gly Phe Ser Gly Gly Gln Arg Asp Leu Phe Glu Gly Ile Leu Gln
            2030                2035                2040

Ala Gly Ser Thr Ile Val Glu Asn Leu Arg Thr Tyr Asn Gln Pro
            2045                2050                2055

Ala Phe Val Tyr Ile Pro Lys Ala Ala Glu Leu Arg Gly Gly Ala
            2060                2065                2070

Trp Val Val Ile Asp Ser Lys Ile Asn Pro Asp Arg Ile Glu Cys
            2075                2080                2085

Tyr Ala Glu Arg Thr Ala Lys Gly Asn Val Leu Glu Pro Gln Gly
            2090                2095                2100

Leu Ile Glu Ile Lys Phe Arg Ser Glu Glu Leu Lys Glu Cys Met
            2105                2110                2115

Gly Arg Leu Asp Pro Glu Leu Ile Asp Leu Lys Ala Arg Leu Gln
            2120                2125                2130

Gly Ala Asn Gly Ser Leu Ser Asp Gly Glu Ser Leu Gln Lys Ser
            2135                2140                2145

Ile Glu Ala Arg Lys Lys Gln Leu Leu Pro Leu Tyr Thr Gln Ile
            2150                2155                2160

Ala Val Arg Phe Ala Glu Leu His Asp Thr Ser Leu Arg Met Ala
            2165                2170                2175

Ala Lys Gly Val Ile Arg Lys Val Val Asp Trp Glu Asp Ser Arg
            2180                2185                2190

Ser Phe Phe Tyr Lys Arg Leu Arg Arg Arg Leu Ser Glu Asp Val
            2195                2200                2205

Leu Ala Lys Glu Ile Arg Gly Val Ile Gly Glu Lys Phe Pro His
            2210                2215                2220
```

```
Lys Ser Ala Ile Glu Leu Ile Lys Lys Trp Tyr Leu Ala Ser Glu
    2225                2230                2235

Ala Ala Ala Ala Gly Ser Thr Asp Trp Asp Asp Asp Asp Ala Phe
    2240                2245                2250

Val Ala Trp Arg Glu Asn Pro Glu Asn Tyr Lys Glu Tyr Ile Lys
    2255                2260                2265

Glu Leu Arg Ala Gln Arg Val Ser Arg Leu Leu Ser Asp Val Ala
    2270                2275                2280

Gly Ser Ser Ser Asp Leu Gln Ala Leu Pro Gln Gly Leu Ser Met
    2285                2290                2295

Leu Leu Asp Lys Met Asp Pro Ser Lys Arg Ala Gln Phe Ile Glu
    2300                2305                2310

Glu Val Met Lys Val Leu Lys
    2315                2320

<210> SEQ ID NO 2
<211> LENGTH: 2327
<212> TYPE: PRT
<213> ORGANISM: Oryza sativa

<400> SEQUENCE: 2

Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
                20                  25                  30

Ser Ser Arg Pro Ser Tyr Arg Lys Asn Gly Gln Arg Thr Arg Ser Leu
            35                  40                  45

Arg Glu Glu Ser Asn Gly Gly Val Ser Asp Ser Lys Lys Leu Asn His
        50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
```

```
            260                 265                 270
Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
        290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Lys Gly Ile Arg Lys Val
                325                 330                 335

His Asn Asp Asp Glu Val Arg Thr Leu Phe Lys Gln Val Gln Gly Glu
                340                 345                 350

Val Pro Gly Ser Pro Ile Phe Ile Met Arg Leu Ala Ala Gln Ser Arg
                355                 360                 365

His Leu Glu Val Gln Leu Leu Cys Asp Gln Tyr Gly Asn Val Ala Ala
                370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
                420                 425                 430

Ala Thr Val Glu Tyr Leu Tyr Ser Met Glu Thr Gly Gln Tyr Tyr Phe
                435                 440                 445

Leu Glu Leu Asn Pro Arg Leu Gln Val Glu His Pro Val Thr Glu Trp
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
                500                 505                 510

Pro Phe Asn Phe Asp Glu Val Asp Ser Lys Trp Pro Lys Gly His Cys
                515                 520                 525

Val Ala Val Arg Ile Thr Ser Glu Asp Pro Asp Asp Gly Phe Lys Pro
                530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Gly Ile His Glu Phe Ala
                565                 570                 575

Asp Ser Gln Phe Gly His Val Phe Ala Tyr Gly Thr Arg Ser Ala
                580                 585                 590

Ala Ile Thr Thr Met Ala Leu Ala Leu Lys Glu Val Gln Ile Arg Gly
                595                 600                 605

Glu Ile His Ser Asn Val Asp Tyr Thr Val Asp Leu Leu Asn Ala Ser
                610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
                660                 665                 670

Asp Tyr Val Gly Tyr Leu Thr Lys Gly Gln Ile Pro Pro Lys His Ile
                675                 680                 685
```

```
Ser Leu Val Tyr Thr Thr Val Ala Leu Asn Ile Asp Gly Lys Lys Tyr
    690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
        755                 760                 765

Gln Asn Asp His Asp Pro Ser Lys Leu Leu Ala Glu Thr Pro Cys Lys
770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ser Gly Val Ile His Val Val Met Ser Glu Gly Gln Ala Met
                820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Asp Thr Phe Pro Gln Met Gly Leu
850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
                900                 905                 910

Leu Gln Trp Glu Glu Leu Met Ser Val Leu Ala Thr Arg Leu Pro Arg
        915                 920                 925

Asn Leu Lys Ser Glu Leu Glu Gly Lys Tyr Glu Glu Tyr Lys Val Lys
930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Glu Lys Glu Lys Ala Thr
                965                 970                 975

Asn Glu Arg Leu Val Glu Pro Leu Met Ser Leu Leu Lys Ser Tyr Glu
            980                 985                 990

Gly Gly Arg Glu Ser His Ala His  Phe Val Val Lys Ser  Leu Phe Glu
        995                 1000                1005

Glu Tyr Leu Tyr Val Glu Glu  Leu Phe Ser Asp Gly  Ile Gln Ser
    1010                1015                1020

Asp Val  Ile Glu Arg Leu Arg  Leu Gln His Ser Lys  Asp Leu Gln
    1025                1030                1035

Lys Val  Val Asp Ile Val Leu  Ser His Gln Ser Val  Arg Asn Lys
    1040                1045                1050

Thr Lys  Leu Ile Leu Lys Leu  Met Glu Ser Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Ala Tyr Tyr Lys Leu  Ala Leu Lys Ala Ser  Glu Leu Leu
    1085                1090                1095
```

```
Glu Gln Thr Lys Leu Ser Glu Leu Arg Ala Arg Ile Ala Arg Ser
1100                1105                1110

Leu Ser Glu Leu Glu Met Phe Thr Glu Glu Ser Lys Gly Leu Ser
1115                1120                1125

Met His Lys Arg Glu Ile Ala Ile Lys Glu Ser Met Glu Asp Leu
1130                1135                1140

Val Thr Ala Pro Leu Pro Val Glu Asp Ala Leu Ile Ser Leu Phe
1145                1150                1155

Asp Cys Ser Asp Thr Thr Val Gln Gln Arg Val Ile Glu Thr Tyr
1160                1165                1170

Ile Ala Arg Leu Tyr Gln Pro His Leu Val Lys Asp Ser Ile Lys
1175                1180                1185

Met Lys Trp Ile Glu Ser Gly Val Ile Ala Leu Trp Glu Phe Pro
1190                1195                1200

Glu Gly His Phe Asp Ala Arg Asn Gly Gly Ala Val Leu Gly Asp
1205                1210                1215

Lys Arg Trp Gly Ala Met Val Ile Val Lys Ser Leu Glu Ser Leu
1220                1225                1230

Ser Met Ala Ile Arg Phe Ala Leu Lys Glu Thr Ser His Tyr Thr
1235                1240                1245

Ser Ser Glu Gly Asn Met Met His Ile Ala Leu Leu Gly Ala Asp
1250                1255                1260

Asn Lys Met His Ile Ile Gln Glu Ser Gly Asp Asp Ala Asp Arg
1265                1270                1275

Ile Ala Lys Leu Pro Leu Ile Leu Lys Asp Asn Val Thr Asp Leu
1280                1285                1290

His Ala Ser Gly Val Lys Thr Ile Ser Phe Ile Val Gln Arg Asp
1295                1300                1305

Glu Ala Arg Met Thr Met Arg Arg Thr Phe Leu Trp Ser Asp Glu
1310                1315                1320

Lys Leu Ser Tyr Glu Glu Pro Ile Leu Arg His Val Glu Pro
1325                1330                1335

Pro Leu Ser Ala Leu Leu Glu Leu Asp Lys Leu Lys Val Lys Gly
1340                1345                1350

Tyr Asn Glu Met Lys Tyr Thr Pro Ser Arg Asp Arg Gln Trp His
1355                1360                1365

Ile Tyr Thr Leu Arg Asn Thr Glu Asn Pro Lys Met Leu His Arg
1370                1375                1380

Val Phe Phe Arg Thr Leu Val Arg Gln Pro Ser Val Ser Asn Lys
1385                1390                1395

Phe Ser Ser Gly Gln Ile Gly Asp Met Glu Val Gly Ser Ala Glu
1400                1405                1410

Glu Pro Leu Ser Phe Thr Ser Thr Ser Ile Leu Arg Ser Leu Met
1415                1420                1425

Thr Ala Ile Glu Glu Leu Glu Leu His Ala Ile Arg Thr Gly His
1430                1435                1440

Ser His Met Tyr Leu His Val Leu Lys Glu Gln Lys Leu Leu Asp
1445                1450                1455

Leu Val Pro Val Ser Gly Asn Thr Val Leu Asp Val Gly Gln Asp
1460                1465                1470

Glu Ala Thr Ala Tyr Ser Leu Leu Lys Glu Met Ala Met Lys Ile
1475                1480                1485

His Glu Leu Val Gly Ala Arg Met His His Leu Ser Val Cys Gln
```

```
            1490                1495                1500

Trp Glu Val Lys Leu Lys Leu Asp Cys Asp Gly Pro Ala Ser Gly
    1505                1510                1515

Thr Trp Arg Ile Val Thr Thr Asn Val Thr Ser His Thr Cys Thr
    1520                1525                1530

Val Asp Ile Tyr Arg Glu Met Glu Asp Lys Glu Ser Arg Lys Leu
    1535                1540                1545

Val Tyr His Pro Ala Thr Pro Ala Ala Gly Pro Leu His Gly Val
    1550                1555                1560

Ala Leu Asn Asn Pro Tyr Gln Pro Leu Ser Val Ile Asp Leu Lys
    1565                1570                1575

Arg Cys Ser Ala Arg Asn Asn Arg Thr Thr Tyr Cys Tyr Asp Phe
    1580                1585                1590

Pro Leu Ala Phe Glu Thr Ala Val Arg Lys Ser Trp Ser Ser Ser
    1595                1600                1605

Thr Ser Gly Ala Ser Lys Gly Val Glu Asn Ala Gln Cys Tyr Val
    1610                1615                1620

Lys Ala Thr Glu Leu Val Phe Ala Asp Lys His Gly Ser Trp Gly
    1625                1630                1635

Thr Pro Leu Val Gln Met Asp Arg Pro Ala Gly Leu Asn Asp Ile
    1640                1645                1650

Gly Met Val Ala Trp Thr Leu Lys Met Ser Thr Pro Glu Phe Pro
    1655                1660                1665

Ser Gly Arg Glu Ile Ile Val Val Ala Asn Asp Ile Thr Phe Arg
    1670                1675                1680

Ala Gly Ser Phe Gly Pro Arg Glu Asp Ala Phe Phe Glu Ala Val
    1685                1690                1695

Thr Asn Leu Ala Cys Glu Lys Lys Leu Pro Leu Ile Tyr Leu Ala
    1700                1705                1710

Ala Asn Ser Gly Ala Arg Ile Gly Ile Ala Asp Glu Val Lys Ser
    1715                1720                1725

Cys Phe Arg Val Gly Trp Ser Asp Asp Gly Ser Pro Glu Arg Gly
    1730                1735                1740

Phe Gln Tyr Ile Tyr Leu Ser Glu Glu Asp Tyr Ala Arg Ile Gly
    1745                1750                1755

Thr Ser Val Ile Ala His Lys Met Gln Leu Asp Ser Gly Glu Ile
    1760                1765                1770

Arg Trp Val Ile Asp Ser Val Val Gly Lys Glu Asp Gly Leu Gly
    1775                1780                1785

Val Glu Asn Ile His Gly Ser Ala Ala Ile Ala Ser Ala Tyr Ser
    1790                1795                1800

Arg Ala Tyr Lys Glu Thr Phe Thr Leu Thr Phe Val Thr Gly Arg
    1805                1810                1815

Thr Val Gly Ile Gly Ala Tyr Leu Ala Arg Leu Gly Ile Arg Cys
    1820                1825                1830

Ile Gln Arg Leu Asp Gln Pro Ile Ile Leu Thr Gly Tyr Ser Ala
    1835                1840                1845

Leu Asn Lys Leu Leu Gly Arg Glu Val Tyr Ser Ser His Met Gln
    1850                1855                1860

Leu Gly Gly Pro Lys Ile Met Ala Thr Asn Gly Val Val His Leu
    1865                1870                1875

Thr Val Ser Asp Asp Leu Glu Gly Val Ser Asn Ile Leu Arg Trp
    1880                1885                1890
```

```
Leu Ser Tyr Val Pro Ala Tyr Ile Gly Gly Pro Leu Pro Val Thr
1895                1900                1905

Thr Pro Leu Asp Pro Pro Asp Arg Pro Val Ala Tyr Ile Pro Glu
1910                1915                1920

Asn Ser Cys Asp Pro Arg Ala Ala Ile Arg Gly Val Asp Asp Ser
1925                1930                1935

Gln Gly Lys Trp Leu Gly Gly Met Phe Asp Lys Asp Ser Phe Val
1940                1945                1950

Glu Thr Phe Glu Gly Trp Ala Lys Thr Val Val Thr Gly Arg Ala
1955                1960                1965

Lys Leu Gly Gly Ile Pro Val Gly Val Ile Ala Val Glu Thr Gln
1970                1975                1980

Thr Met Met Gln Thr Ile Pro Ala Asp Pro Gly Gln Leu Asp Ser
1985                1990                1995

Arg Glu Gln Ser Val Pro Arg Ala Gly Gln Val Trp Phe Pro Asp
2000                2005                2010

Ser Ala Thr Lys Thr Ala Gln Ala Leu Leu Asp Phe Asn Arg Glu
2015                2020                2025

Gly Leu Pro Leu Phe Ile Leu Ala Asn Trp Arg Gly Phe Ser Gly
2030                2035                2040

Gly Gln Arg Asp Leu Phe Glu Gly Ile Leu Gln Ala Gly Ser Thr
2045                2050                2055

Ile Val Glu Asn Leu Arg Thr Tyr Asn Gln Pro Ala Phe Val Tyr
2060                2065                2070

Ile Pro Met Ala Ala Glu Leu Arg Gly Gly Ala Trp Val Val Val
2075                2080                2085

Asp Ser Lys Ile Asn Pro Asp Arg Ile Glu Cys Tyr Ala Glu Arg
2090                2095                2100

Thr Ala Lys Gly Asn Val Leu Glu Pro Gln Gly Leu Ile Glu Ile
2105                2110                2115

Lys Phe Arg Ser Glu Glu Leu Gln Asp Cys Met Ser Arg Leu Asp
2120                2125                2130

Pro Thr Leu Ile Asp Leu Lys Ala Lys Leu Glu Val Ala Asn Lys
2135                2140                2145

Asn Gly Ser Ala Asp Thr Lys Ser Leu Gln Glu Asn Ile Glu Ala
2150                2155                2160

Arg Thr Lys Gln Leu Met Pro Leu Tyr Thr Gln Ile Ala Ile Arg
2165                2170                2175

Phe Ala Glu Leu His Asp Thr Ser Leu Arg Met Ala Ala Lys Gly
2180                2185                2190

Val Ile Lys Lys Val Val Asp Trp Glu Glu Ser Arg Ser Phe Phe
2195                2200                2205

Tyr Lys Arg Leu Arg Arg Arg Ile Ser Glu Asp Val Leu Ala Lys
2210                2215                2220

Glu Ile Arg Ala Val Ala Gly Glu Gln Phe Ser His Gln Pro Ala
2225                2230                2235

Ile Glu Leu Ile Lys Lys Trp Tyr Ser Ala Ser His Ala Ala Glu
2240                2245                2250

Trp Asp Asp Asp Ala Phe Val Ala Trp Met Asp Asn Pro Glu
2255                2260                2265

Asn Tyr Lys Asp Tyr Ile Gln Tyr Leu Lys Ala Gln Arg Val Ser
2270                2275                2280
```

```
Gln Ser Leu Ser Ser Leu Ser Asp Ser Ser Asp Leu Gln Ala
    2285                2290                2295

Leu Pro Gln Gly Leu Ser Met Leu Leu Asp Lys Met Asp Pro Ser
2300                2305                2310

Arg Arg Ala Gln Leu Val Glu Glu Ile Arg Lys Val Leu Gly
    2315                2320                2325

<210> SEQ ID NO 3
<211> LENGTH: 2327
<212> TYPE: PRT
<213> ORGANISM: Oryza sativa

<400> SEQUENCE: 3

Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Gly Lys Gly Ile Arg Lys Val
                325                 330                 335
```

-continued

His Asn Asp Asp Glu Val Arg Thr Leu Phe Lys Gln Val Gln Gly Glu
            340                 345                 350

Val Pro Gly Ser Pro Ile Phe Ile Met Arg Leu Ala Ala Gln Ser Arg
            355                 360                 365

His Leu Glu Val Gln Leu Leu Cys Asp Gln Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
            500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Gly Ile His Glu Phe Ala
                565                 570                 575

Asp Ser Gln Phe Gly His Val Phe Ala Tyr Gly Thr Thr Arg Ser Ala
            580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
    610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
            660                 665                 670

Asp Tyr Val Gly Tyr Leu Thr Lys Gly Gln Ile Pro Pro Lys His Ile
        675                 680                 685

Ser Leu Val Tyr Thr Thr Val Ala Leu Asn Ile Asp Gly Lys Lys Tyr
    690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

```
Glu Ala Ser Gly Thr Arg Leu Leu Ile Asp Gly Lys Thr Cys Met Leu
            755                 760                 765
Gln Asn Asp His Asp Pro Ser Lys Leu Leu Ala Glu Thr Pro Cys Lys
770                 775                 780
Leu Leu Arg Phe Leu Val Ala Asp Gly Ala His Val Asp Ala Asp Val
785                 790                 795                 800
Pro Tyr Ala Glu Val Glu Val Met Lys Met Cys Met Pro Leu Leu Ser
                805                 810                 815
Pro Ala Ser Gly Val Ile His Val Val Met Ser Glu Gly Gln Ala Met
                820                 825                 830
Gln Ala Gly Asp Leu Ile Ala Arg Leu Asp Leu Asp Asp Pro Ser Ala
            835                 840                 845
Val Lys Arg Ala Glu Pro Phe Glu Asp Thr Phe Pro Gln Met Gly Leu
850                 855                 860
Pro Ile Ala Ala Ser Gly Gln Val His Lys Leu Cys Ala Ala Ser Leu
865                 870                 875                 880
Asn Ala Cys Arg Met Ile Leu Ala Gly Tyr Glu His Asp Ile Asp Lys
                885                 890                 895
Val Val Pro Glu Leu Val Tyr Cys Leu Asp Thr Pro Glu Leu Pro Phe
                900                 905                 910
Leu Gln Trp Glu Glu Leu Met Ser Val Leu Ala Thr Arg Leu Pro Arg
            915                 920                 925
Asn Leu Lys Ser Glu Leu Glu Gly Lys Tyr Glu Glu Tyr Lys Val Lys
            930                 935                 940
Phe Asp Ser Gly Ile Ile Asn Asp Phe Pro Ala Asn Met Leu Arg Val
945                 950                 955                 960
Ile Ile Glu Glu Asn Leu Ala Cys Gly Ser Glu Lys Glu Lys Ala Thr
                965                 970                 975
Asn Glu Arg Leu Val Glu Pro Leu Met Ser Leu Leu Lys Ser Tyr Glu
            980                 985                 990
Gly Gly Arg Glu Ser His Ala His Phe Val Val Lys Ser Leu Phe Glu
            995                 1000                1005
Glu Tyr Leu Tyr Val Glu Glu Leu Phe Ser Asp Gly Ile Gln Ser
    1010                1015                1020
Asp Val Ile Glu Arg Leu Arg Leu Gln His Ser Lys Asp Leu Gln
    1025                1030                1035
Lys Val Val Asp Ile Val Leu Ser His Gln Ser Val Arg Asn Lys
    1040                1045                1050
Thr Lys Leu Ile Leu Lys Leu Met Glu Ser Leu Val Tyr Pro Asn
    1055                1060                1065
Pro Ala Ala Tyr Arg Asp Gln Leu Ile Arg Phe Ser Ser Leu Asn
    1070                1075                1080
His Lys Ala Tyr Tyr Lys Leu Ala Leu Lys Ala Ser Glu Leu Leu
    1085                1090                1095
Glu Gln Thr Lys Leu Ser Glu Leu Arg Ala Arg Ile Ala Arg Ser
    1100                1105                1110
Leu Ser Glu Leu Glu Met Phe Thr Glu Glu Ser Lys Gly Leu Ser
    1115                1120                1125
Met His Lys Arg Glu Ile Ala Ile Lys Glu Ser Met Glu Asp Leu
    1130                1135                1140
Val Thr Ala Pro Leu Pro Val Glu Asp Ala Leu Ile Ser Leu Phe
    1145                1150                1155
Asp Cys Ser Asp Thr Thr Val Gln Gln Arg Val Ile Glu Thr Tyr
```

```
              1160                1165                1170
Ile Ala Arg Leu Tyr Gln Pro His Leu Val Lys Asp Ser Ile Lys
    1175                1180                1185

Met Lys Trp Ile Glu Ser Gly Val Ile Ala Leu Trp Glu Phe Pro
    1190                1195                1200

Glu Gly His Phe Asp Ala Arg Asn Gly Gly Ala Val Leu Gly Asp
    1205                1210                1215

Lys Arg Trp Gly Ala Met Val Ile Val Lys Ser Leu Glu Ser Leu
    1220                1225                1230

Ser Met Ala Ile Arg Phe Ala Leu Lys Glu Thr Ser His Tyr Thr
    1235                1240                1245

Ser Ser Glu Gly Asn Met Met His Ile Ala Leu Leu Gly Ala Asp
    1250                1255                1260

Asn Lys Met His Ile Ile Gln Glu Ser Gly Asp Asp Ala Asp Arg
    1265                1270                1275

Ile Ala Lys Leu Pro Leu Ile Leu Lys Asp Asn Val Thr Asp Leu
    1280                1285                1290

His Ala Ser Gly Val Lys Thr Ile Ser Phe Ile Val Gln Arg Asp
    1295                1300                1305

Glu Ala Arg Met Thr Met Arg Arg Thr Phe Leu Trp Ser Asp Glu
    1310                1315                1320

Lys Leu Ser Tyr Glu Glu Glu Pro Ile Leu Arg His Val Glu Pro
    1325                1330                1335

Pro Leu Ser Ala Leu Leu Glu Leu Asp Lys Leu Lys Val Lys Gly
    1340                1345                1350

Tyr Asn Glu Met Lys Tyr Thr Pro Ser Arg Asp Arg Gln Trp His
    1355                1360                1365

Ile Tyr Thr Leu Arg Asn Thr Glu Asn Pro Lys Met Leu His Arg
    1370                1375                1380

Val Phe Phe Arg Thr Leu Val Arg Gln Pro Ser Val Ser Asn Lys
    1385                1390                1395

Phe Ser Ser Gly Gln Ile Gly Asp Met Glu Val Gly Ser Ala Glu
    1400                1405                1410

Glu Pro Leu Ser Phe Thr Ser Thr Ser Ile Leu Arg Ser Leu Met
    1415                1420                1425

Thr Ala Ile Glu Glu Leu Glu Leu His Ala Ile Arg Thr Gly His
    1430                1435                1440

Ser His Met Tyr Leu His Val Leu Lys Glu Gln Lys Leu Leu Asp
    1445                1450                1455

Leu Val Pro Val Ser Gly Asn Thr Val Leu Asp Val Gly Gln Asp
    1460                1465                1470

Glu Ala Thr Ala Tyr Ser Leu Leu Lys Glu Met Ala Met Lys Ile
    1475                1480                1485

His Glu Leu Val Gly Ala Arg Met His His Leu Ser Val Cys Gln
    1490                1495                1500

Trp Glu Val Lys Leu Lys Leu Asp Cys Asp Gly Pro Ala Ser Gly
    1505                1510                1515

Thr Trp Arg Ile Val Thr Thr Asn Val Thr Ser His Thr Cys Thr
    1520                1525                1530

Val Asp Ile Tyr Arg Glu Met Glu Asp Lys Glu Ser Arg Lys Leu
    1535                1540                1545

Val Tyr His Pro Ala Thr Pro Ala Ala Gly Pro Leu His Gly Val
    1550                1555                1560
```

```
Ala Leu Asn Asn Pro Tyr Gln Pro Leu Ser Val Ile Asp Leu Lys
1565                1570                1575

Arg Cys Ser Ala Arg Asn Asn Arg Thr Thr Tyr Cys Tyr Asp Phe
1580                1585                1590

Pro Leu Ala Phe Glu Thr Ala Val Arg Lys Ser Trp Ser Ser Ser
1595                1600                1605

Thr Ser Gly Ala Ser Lys Gly Val Glu Asn Ala Gln Cys Tyr Val
1610                1615                1620

Lys Ala Thr Glu Leu Val Phe Ala Asp Lys His Gly Ser Trp Gly
1625                1630                1635

Thr Pro Leu Val Gln Met Asp Arg Pro Ala Gly Leu Asn Asp Ile
1640                1645                1650

Gly Met Val Ala Trp Thr Leu Lys Met Ser Thr Pro Glu Phe Pro
1655                1660                1665

Ser Gly Arg Glu Ile Ile Val Ala Asn Asp Ile Thr Phe Arg
1670                1675                1680

Ala Gly Ser Phe Gly Pro Arg Glu Asp Ala Phe Phe Glu Ala Val
1685                1690                1695

Thr Asn Leu Ala Cys Glu Lys Lys Leu Pro Leu Ile Tyr Leu Ala
1700                1705                1710

Ala Asn Ser Gly Ala Arg Ile Gly Ile Ala Asp Glu Val Lys Ser
1715                1720                1725

Cys Phe Arg Val Gly Trp Ser Asp Asp Gly Ser Pro Glu Arg Gly
1730                1735                1740

Phe Gln Tyr Ile Tyr Leu Ser Glu Glu Asp Tyr Ala Arg Ile Gly
1745                1750                1755

Thr Ser Val Ile Ala His Lys Met Gln Leu Asp Ser Gly Glu Ile
1760                1765                1770

Arg Trp Val Ile Asp Ser Val Val Gly Lys Glu Asp Gly Leu Gly
1775                1780                1785

Val Glu Asn Ile His Gly Ser Ala Ala Ile Ala Ser Ala Tyr Ser
1790                1795                1800

Arg Ala Tyr Lys Glu Thr Phe Thr Leu Thr Phe Val Thr Gly Arg
1805                1810                1815

Thr Val Gly Ile Gly Ala Tyr Leu Ala Arg Leu Gly Ile Arg Cys
1820                1825                1830

Ile Gln Arg Leu Asp Gln Pro Ile Ile Leu Thr Gly Tyr Ser Ala
1835                1840                1845

Leu Asn Lys Leu Leu Gly Arg Glu Val Tyr Ser Ser His Met Gln
1850                1855                1860

Leu Gly Gly Pro Lys Ile Met Ala Thr Asn Gly Val Val His Leu
1865                1870                1875

Thr Val Ser Asp Asp Leu Glu Gly Val Ser Asn Ile Leu Arg Trp
1880                1885                1890

Leu Ser Tyr Val Pro Ala Tyr Ile Gly Gly Pro Leu Pro Val Thr
1895                1900                1905

Thr Pro Leu Asp Pro Pro Asp Arg Pro Val Ala Tyr Ile Pro Glu
1910                1915                1920

Asn Ser Cys Asp Pro Arg Ala Ala Ile Arg Gly Val Asp Asp Ser
1925                1930                1935

Gln Gly Lys Trp Leu Gly Gly Met Phe Asp Lys Asp Ser Phe Val
1940                1945                1950
```

-continued

Glu Thr Phe Glu Gly Trp Ala Lys Thr Val Val Thr Gly Arg Ala
1955                1960                1965

Lys Leu Gly Gly Ile Pro Val Gly Val Ile Ala Val Glu Thr Gln
1970                1975                1980

Thr Met Met Gln Thr Ile Pro Ala Asp Pro Gly Gln Leu Asp Ser
1985                1990                1995

Arg Glu Gln Ser Val Pro Arg Ala Gly Gln Val Trp Phe Pro Asp
2000                2005                2010

Ser Ala Thr Lys Thr Ala Gln Ala Leu Leu Asp Phe Asn Arg Glu
2015                2020                2025

Gly Leu Pro Leu Phe Ile Leu Ala Asn Trp Arg Gly Phe Ser Gly
2030                2035                2040

Gly Gln Arg Asp Leu Phe Glu Gly Ile Leu Gln Ala Gly Ser Thr
2045                2050                2055

Ile Val Glu Asn Leu Arg Thr Tyr Asn Gln Pro Ala Phe Val Tyr
2060                2065                2070

Ile Pro Met Ala Ala Glu Leu Arg Gly Gly Ala Trp Val Val Val
2075                2080                2085

Asp Ser Lys Ile Asn Pro Asp Arg Ile Glu Cys Tyr Ala Glu Arg
2090                2095                2100

Thr Ala Lys Gly Asn Val Leu Glu Pro Gln Gly Leu Ile Glu Ile
2105                2110                2115

Lys Phe Arg Ser Glu Glu Leu Gln Asp Cys Met Ser Arg Leu Asp
2120                2125                2130

Pro Thr Leu Ile Asp Leu Lys Ala Lys Leu Glu Val Ala Asn Lys
2135                2140                2145

Asn Gly Ser Ala Asp Thr Lys Ser Leu Gln Glu Asn Ile Glu Ala
2150                2155                2160

Arg Thr Lys Gln Leu Met Pro Leu Tyr Thr Gln Ile Ala Ile Arg
2165                2170                2175

Phe Ala Glu Leu His Asp Thr Ser Leu Arg Met Ala Ala Lys Gly
2180                2185                2190

Val Ile Lys Lys Val Val Asp Trp Glu Glu Ser Arg Ser Phe Phe
2195                2200                2205

Tyr Lys Arg Leu Arg Arg Arg Ile Ser Glu Asp Val Leu Ala Lys
2210                2215                2220

Glu Ile Arg Ala Val Ala Gly Glu Gln Phe Ser His Gln Pro Ala
2225                2230                2235

Ile Glu Leu Ile Lys Lys Trp Tyr Ser Ala Ser His Ala Ala Glu
2240                2245                2250

Trp Asp Asp Asp Asp Ala Phe Val Ala Trp Met Asp Asn Pro Glu
2255                2260                2265

Asn Tyr Lys Asp Tyr Ile Gln Tyr Leu Lys Ala Gln Arg Val Ser
2270                2275                2280

Gln Ser Leu Ser Ser Leu Ser Asp Ser Ser Ser Asp Leu Gln Ala
2285                2290                2295

Leu Pro Gln Gly Leu Ser Met Leu Leu Asp Lys Met Asp Pro Ser
2300                2305                2310

Arg Arg Ala Gln Leu Val Glu Glu Ile Arg Lys Val Leu Gly
2315                2320                2325

<210> SEQ ID NO 4
<211> LENGTH: 6963
<212> TYPE: DNA

<213> ORGANISM: Alopecurus myosuroides

<400> SEQUENCE: 4

```
atgggatcca cacatctgcc cattgtcggg tttaatgcat ccacaacacc atcgctatcc    60
actcttcgcc agataaactc agctgctgct gcattccaat cttcgtcccc ttcaaggtca   120
tccaagaaga aaagccgacg tgttaagtca ataagggatg atggcgatgg aagcgtgcca   180
gaccctgcag gccatggcca gtctattcgc caaggtctcg ctggcatcat cgacctccca   240
aaggagggcg catcagctcc agatgtggac atttcacatg gtctgaaga ccacaaggcc    300
tcctaccaaa tgaatgggat actgaatgaa tcacataacg ggaggcacgc ctctctgtct   360
aaagtttatg aattttgcac ggaattgggt ggaaaaacac caattcacag tgtattagtc   420
gccaacaatg gaatggcagc agctaagttc atgcggagtg tccggacatg ggctaatgat   480
acatttgggt cagagaaggc gattcagttg atagctatgg caactccgga agacatgaga   540
ataaatgcag agcacattag aattgctgat cagtttgttg aagtacctgg tggaacaaac   600
aataacaact atgcaaatgt ccaactcata gtggagatag cagagagaac tggtgtctcc   660
gccgtttggc ctggttgggg ccatgcatct gagaatcctg aacttccaga tgcactaact   720
gcaaaaggaa ttgttttct tgggccacca gcatcatcaa tgaacgcact aggcgacaag   780
gttggttcag ctctcattgc tcaagcagca ggggttccca ctcttgcttg gagtggatca   840
catgtgaaa ttccattaga actttgtttg gactcgatac ctgaggagat gtataggaaa   900
gcctgtgtta caaccgctga tgaagcagtt gcaagttgtc agatgattgg ttaccctgcc   960
atgatcaagg catcctgggg tggtggtggt aaagggatta gaaaggttaa taatgatgac  1020
gaggtgaaag cactgttta gcaagtacag ggtgaagttc ctggctcccc gatatttatc  1080
atgagacttg catctcagag tcgtcatctt gaagtccagc tgctttgtga tgaatatggc  1140
aatgtagcag cacttcacag tcgtgattgc agtgtgcaac gacgacacca aaagattatc  1200
gaggaaggac cagttactgt tgctcctcgt gaaacagtga agagctaga gcaagcagca  1260
aggaggcttg ctaaggccgt gggttacgtc ggtgctgcta ctgttgaata tctctacagc  1320
atggagactg tgaatactta ttttctggag cttaatccac ggttgcaggt tgagcaccca  1380
gtcaccgagt cgatagctga agtaaatttg cctgcagccc aagttgcagt tgggatgggt  1440
ataccccttt ggcagattcc agagatcaga cgtttctacg aatggacaa tggaggaggc  1500
tatgatattt ggaggaaaac agcagctctc gctactccat tcaactttga tgaagtagat  1560
tctcaatggc cgaagggtca ttgtgtggca gttaggataa ccagtgagaa tccagatgat  1620
ggattcaagc ctactggtgg aaaagtaaag gagataagtt ttaaaagtaa gccaaatgtc  1680
tggggatatt tctcagttaa gtctggtgga ggcattcatg aatttgcgga ttctcagttt  1740
ggacacgttt ttgcctatgg agagactaga tcagcagcaa taaccagcat gtctcttgca  1800
ctaaaagaga ttcaaattcg tggagaaatt catacaaacg ttgattacac ggttgatctc  1860
ttgaatgccc cagacttcag agaaaacacg atccataccg gttggctgga taccagaata  1920
gctatgcgtg ttcaagctga gaggcctccc tggtatattt cagtggttgg aggagctcta  1980
tataaaacaa taaccaccaa tgcggagacc gtttctgaat atgttagcta tctcatcaag  2040
ggtcagattc caccaaagca catatccctt gtccattcaa ctatttcttt gaatatagag  2100
gaaagcaaat ataccattga gattgtgagg agtggacagg gtagctacag attgagactg  2160
aatgatcac ttattgaagc caatgtacaa acattatgtg atggaggcct tttaatgcag  2220
ctggatggaa atagccatgt tatttatgct gaagaagaag cgggtggtac acggcttctt  2280
```

```
attgatggaa aaacatgctt gctacagaat gaccatgatc cgtcaaggtt attagctgag    2340
acaccctgca aacttcttcg tttcttgatt gccgatggtg ctcatgttga tgctgatgta    2400
ccatacgcgg aagttgaggt tatgaagatg tgcatgcccc tcttgtcgcc tgctgctggt    2460
gtcattaatg ttttgttgtc tgagggccag gcgatgcagg ctggtgatct tatagcgaga    2520
cttgatctcg atgacccttc tgctgtgaag agagccgagc catttgaagg atcttttcca    2580
gaaatgagcc ttcctattgc tgcttctggc caagttcaca aaagatgtgc tgcaagtttg    2640
aacgctgctc gaatggtcct tgcaggatat gaccatgcgg ccaacaaagt tgtgcaagat    2700
ttggtatggt gccttgatac acctgctctt cctttcctac aatgggaaga gcttatgtct    2760
gttttagcaa ctagacttcc aagacgtctt aagagcgagt tggagggcaa atacaatgaa    2820
tacaagttaa atgttgacca tgtgaagatc aaggatttcc ctaccgagat gcttagagag    2880
acaatcgagg aaaatcttgc atgtgtttcc gagaaggaaa tggtgacaat tgagaggctt    2940
gttgaccctc tgatgagcct gctgaagtca tacgagggtg ggagagaaag ccatgcccac    3000
tttattgtca agtcccttt tgaggagtat ctctcggttg aggaactatt cagtgatggc    3060
attcagtctg acgtgattga acgcctgcgc ctacaatata gtaaagacct ccagaaggtt    3120
gtagacattg ttttgtctca ccagggtgtg agaaacaaaa caaagctgat actcgcgctc    3180
atggagaaac tggtctatcc aaaccctgct gcctacagag atcagttgat tcgcttttct    3240
tccctcaacc ataaaagata ttataagttg gctcttaaag ctagtgaact tcttgaacaa    3300
accaagctca gcgaactccg cacaagcatt gcaggaacc tttcagcgct ggatatgttc    3360
accgaggaaa aggcagattt ctccttgcaa gacagaaaat tggccattaa tgagagcatg    3420
ggagatttag tcactgcccc actgccagtt gaagatgcac ttgtttcttt gtttgattgt    3480
actgatcaaa ctcttcagca gagagtgatt cagacataca tatctcgatt ataccagcct    3540
caacttgtga aggatagcat ccagctgaaa tatcaggatt ctggtgttat tgctttatgg    3600
gaattcactg aaggaaatca tgagaagaga ttgggtgcta tggttatcct gaagtcacta    3660
gaatctgtgt caacagccat tggagctgct ctaaaggatg catcacatta tgcaagctct    3720
gcgggcaaca cggtgcatat tgctttgttg gatgctgata cccaactgaa tacaactgaa    3780
gatagtggtg ataatgacca agctcaagac aagatggata aactttcttt tgtactgaaa    3840
caagatgttg tcatggctga tctacgtgct gctgatgtca aggttgttag ttgcattgtt    3900
caaagagatg gagcaatcat gcctatgcgc cgtaccttcc tcttgtcaga ggaaaaactt    3960
tgttacgagg aagagccgat tcttcggcat gtggagcctc cactttctgc acttcttgag    4020
ttggataaat tgaaagtgaa aggatacaat gagatgaagt atacaccgtc acgtgatcgt    4080
cagtggcata tatacacact tagaaatact gaaaatccaa aaatgctgca cagggtattt    4140
ttccgaacac ttgtcagaca acccagtgca ggcaacaggt ttacatcaga ccatatcact    4200
gatgttgaag taggacacgc agaggaacct ctttcattta cttcaagcag catattaaaa    4260
tcgttgaaga ttgctaaaga agaattggag cttcacgcga tcaggactgg ccattctcat    4320
atgtacttgt gcatattgaa agagcaaaag cttcttgacc ttgttcctgt ttcagggaac    4380
actgttgtgg atgttggtca agatgaagct actgcatgct ctcttttgaa agaaatggct    4440
ttaaagatac atgaacttgt tggtgcaaga atgcatcatc tttctgtatg ccagtgggaa    4500
gtgaaactta agttggtgag cgatgggcct gccagtggta gctggagagt tgtaacaacc    4560
aatgttactg gtcacacctg cactgtggat atctaccggg aggtcgaaga tacagaatca    4620
```

```
cagaaactag tataccactc caccgcattg tcatctggtc ctttgcatgg tgttgcactg    4680
aatacttcgt atcagccttt gagtgttatt gatttaaaac gttgctctgc caggaacaac    4740
aaaactacat actgctatga ttttccattg acatttgaag ctgcagtgca gaagtcgtgg    4800
tctaacattt ccagtgaaaa caaccaatgt tatgttaaag cgacagagct tgtgtttgct    4860
gaaaagaatg ggtcgtgggg cactcctata attcctatgc agcgtgctgc tgggctgaat    4920
gacattggta tggtagcctg gatcttggac atgtccactc ctgaatttcc cagcggcaga    4980
cagatcattg ttatcgcaaa tgatattaca tttagagctg atcatttgg cccaagggaa     5040 gatgcatttt tcgaagctgt aaccaacctg gcttgtgaga agaagcttcc acttatctac    5100
ttggctgcaa actctggtgc tcggattggc attgctgatg aagtaaaatc ttgcttccgt    5160
gttggatgga ctgatgatag cagccctgaa cgtggattta ggtacattta tatgactgac    5220
gaagaccatg atcgtattgg ctcttcagtt atagcacaca agatgcagct agatagtggc    5280
gagatcaggt gggttattga ttctgttgtg ggaaaagagg atggactagg tgtggagaac    5340
atacatggaa gtgctgctat tgccagtgcc tattctaggg cgtacgagga gacatttaca    5400
cttacattcg ttactggacg aactgttgga atcggagcct atcttgctcg acttggcata    5460
cggtgcatac agcgtattga ccagcccatt attttgaccg ggttttctgc cctgaacaag    5520
cttcttgggc gggaggtgta cagctcccac atgcagttgg gtggtcccaa aatcatggcg    5580
acgaatggtg ttgtccatct gactgttcca gatgaccttg aaggtgtttc taatatattg    5640
aggtggctca gctatgttcc tgcaaacatt ggtggacctc ttcctattac aaaatctttg    5700
gacccaatag acagacccgt tgcatacatc cctgagaata catgtgatcc tcgtgcagcc    5760
atcagtggca ttgatgacag ccaagggaaa tggttgggtg gcatgtttga caaagacagt    5820
tttgtggaga catttgaagg atgggcgaag acagtagtta ctggcagagc aaaacttgga    5880
gggattcctg ttggtgttat agctgtggag acacagacca tgatgcagct cgtccccgct    5940
gatccaggcc agcctgattc ccacgagcgg tctgttcctc gtgctgggca gtttggtttt    6000
ccagattctg ctaccaagac agcgcaggcg atgttggact caaccgtga aggattacct     6060 ctgttcatac ttgctaactg gagaggcttc tctggagggc aaagagatct ttttgaagga    6120
attctgcagg ctgggtcaac aattgttgag aaccttagga catacaatca gcctgccttt    6180
gtatatatcc ccaaggctgc agagctacgt ggaggagcct gggtcgtgat tgatagcaag    6240
ataaacccag atcgcatcga gtgctatgct gagaggactg caagggtaa tgttctcgaa     6300 cctcaagggt tgattgagat caagttcagg tcagaggaac tcaaagaatg catgggtagg    6360
cttgatccag aattgataga tctgaaagca agactccagg gagcaaatgg aagcctatct    6420
gatggagaat cccttcagaa gagcatgaa gctcggaaga aacagttgct gcctctgtac     6480
acccaaatcg cggtacgttt tgcggaattg cacgacactt cccttagaat ggctgctaaa    6540
ggtgtgatca ggaaagttgt agactgggaa gactctcggt cttcttcta caagagatta     6600 cggaggaggc tatccgagga cgttctggca aaggagatta gaggtgtaat tggtgagaag    6660
tttcctcaca aatcagcgat cgagctgatc aagaaatggt acttggcttc tgaggcagct    6720
gcagcaggaa gcaccgactg ggatgacgac gatgcttttg tcgcctggag ggagaaccct    6780
gaaaactata aggagtatat caaagagctt agggctcaaa gggtatctcg gttgctctca    6840
gatgttgcag gctccagttc ggatttacaa gccttgccgc agggtctttc catgctacta    6900
gataagatga tccctctaa gagagcacag tttatcgagg aggtcatgaa ggtcctgaaa    6960
tga                                                                 6963
```

<210> SEQ ID NO 5
<211> LENGTH: 11927
<212> TYPE: DNA
<213> ORGANISM: Oryza sativa

<400> SEQUENCE: 5

| | | | | | |
|---|---|---|---|---|---|
| atgacatcca | cacatgtggc | gacattggga | gttggtgccc | aggcacctcc | tcgtcaccag | 60 |
| aaaaagtcag | ctggcactgc | atttgtatca | tctgggtcat | caagaccctc | ataccgaaag | 120 |
| aatggtcagc | gtactcggtc | acttagggaa | gaaagcaatg | gaggagtgtc | tgattccaaa | 180 |
| aagcttaacc | actctattcg | ccaaggtgac | cactagctac | tttacatatg | ctataatttg | 240 |
| tgccaaacat | aaacatgcaa | tggctgctat | tatttaaacg | ttaatgttga | aatagctgct | 300 |
| ataggataca | gcaaaaatat | ataattgact | gggcaagatg | caacaattgt | ttttcactaa | 360 |
| agttagttat | cttttgctgt | aaaagacaac | tgtttttttac | ataaaatggt | attaataacc | 420 |
| ttgtaatatt | caatgcaaca | tgttctcaag | taaaaaaaaa | cattgcctgg | ttgtataagc | 480 |
| aaatgtgtcg | ttgtagacat | cttattaaac | cttttttgtga | tatctattac | cgtagggaac | 540 |
| aggggagctg | tttaaatctg | ttatcataga | gtaatatgag | aaaagtggat | tgtgcgactt | 600 |
| tggcatgtat | acctgctcaa | tttcaaatat | atgtctatgt | gcaggtcttg | ctggcatcat | 660 |
| tgacctccca | aatgacgcag | cttcagaagt | tgatatttca | cagtaaggac | tttatatttt | 720 |
| ataataatta | ttatataatt | ttctgacatg | ttttgagaac | ctcaaaacat | gtgattgcac | 780 |
| cttccttttt | tatgtctggt | tcagaaactg | ataagtttttg | acagtgttta | ggatggatct | 840 |
| ttgatgcgca | cagtgctttc | taatgttttc | attttttgaaa | gtaatgtttt | aggaagaaat | 900 |
| atctgattaa | atttatactt | tatctttaca | aaagtcaaat | gcgttctgta | tcaattgcgg | 960 |
| tttgtaatat | ggcaagaaca | tgcttttcaga | atttgttcat | acaatgcttt | ctttctatta | 1020 |
| ttatgtagaa | caaataccta | atactttgtt | caccttttat | agtggacacc | tctcacagct | 1080 |
| ttttcagtaa | gtgatgcaat | tttgtacatt | tgtaagatgt | gttccagaaa | ccttttctcc | 1140 |
| tgcaattcta | atgtacccac | tcaaactggt | atcaccaaag | atctccatct | gattgaaaaa | 1200 |
| aagctgcgtg | aagtatgctt | atttatgcta | accatacatg | atttatactg | ttttatagta | 1260 |
| caatgcttat | ttatgctaac | catacataat | tttattctgt | tttctagtac | attatttgtg | 1320 |
| cccctgacca | taaatgatcc | tttcttttac | agtggttccg | aagatcccag | ggggcctacg | 1380 |
| gtcccaggtt | cctaccaaat | gaatgggatt | atcaatgaaa | cacataatgg | gaggcatgct | 1440 |
| tcagtctcca | aggttgttga | gttttgtacg | gcacttggtg | gcaaaacacc | aattcacagt | 1500 |
| gtattagtgg | ccaacaatgg | aatggcagca | gctaagttca | tgcggagtgt | ccgaacatgg | 1560 |
| gctaatgata | ctttttggatc | agagaaggca | attcagctga | tagctatggc | aactccggag | 1620 |
| gatctgagga | taaatgcaga | gcacatcaga | attgccgatc | aatttgtaga | ggtacctggt | 1680 |
| ggaacaaaca | acaacaacta | tgcaaatgtc | caactcatag | tggaggttag | ttcagctcat | 1740 |
| ccctcaacac | aacattttcg | tttctatttta | agttagggaa | aaatctctac | gaccctccaa | 1800 |
| tttctgaaca | tccaattttc | accatcaact | gcaatcacag | atagcagaga | gaacaggtgt | 1860 |
| ttctgctgtt | tggcctggtt | ggggtcatgc | atctgagaat | cctgaacttc | cagatgcgct | 1920 |
| gactgcaaaa | ggaattgttt | ttcttgggcc | accagcatca | tcaatgcatg | cattaggaga | 1980 |
| caaggttggc | tcagctctca | ttgctcaagc | agctggagtt | ccaacacttg | cttggagtgg | 2040 |
| atcacatgtg | agccttgtct | tctctttttt | agcttatcat | cttatctttt | cggtgatgca | 2100 |

```
ttatcccaat gacactaaac cataggtgga agttcctctg gagtgttgct tggactcaat    2160
acctgatgag atgtatagaa aagcttgtgt tactaccaca gaggaagcag ttgcaagttg    2220
tcaggtggtt ggttatcctg ccatgattaa ggcatcttgg ggtggtggtg gtaaaggaat    2280
aaggaaggtt tgttcttctt gtagttatca agagattgtt tggattgcaa gtgtttagtg    2340
cccatagtta actctggtct ttctaacatg agtaactcaa ctttcttgca ggttcataat    2400
gatgatgagg ttaggacatt atttaagcaa gttcaaggcg aagtacctgg ttccccaata    2460
tttatcatga ggctagctgc tcaggtgggg cctttatgg aagttacacc ttttccctta     2520
atgttgagtt attccggagt tattatggtt atgttctgta tgtttgatct gtaaattatt    2580
gaaattcacc tccattggtt ctccagatta gcagacctac aattctacat atggtttata    2640
ctttataaat actaggattt agggatcttc atatagttta tacatggtat ttagatttca    2700
tttgtaaccc tattgaagac atcctgattg ttgtcttatg tagagtcgac atcttgaagt    2760
tcagttgctt tgtgatcaat atggcaacgt agcagcactt cacagtcgag attgcagtgt    2820
acaacggcga caccaaaagg tctgctgtct cagttaaatc acccctctga atgatctact    2880
tcttgcctgc tgcgttggtc agaggaataa tggttgtatt ctactgaaca gataatcgag    2940
gaaggaccag ttactgttgc tcctcgtgag actgtgaaag agcttgagca ggcagcacgg    3000
aggcttgcta aagctgtggg ttatgttggt gctgctactg ttgaataccct ttacagcatg   3060 gaaactggtg aatattattt tctggaactt aatccacggc tacaggtcgg ctcctttgac    3120
attcttcagg aattaatttc tgttgaccac atgatttaca ttgtcaaatg gtctcacagg    3180
ttgagcatcc tgtcactgag tggatagctg aagtaaattt gcctgcggct caagttgctg    3240
ttggaatggg tataccccctt tggcagattc caggtaatgc ttcttcattt agttcctgct   3300
ctttgttaat tgaatgagct cttatacaga ccatgagaca cattctactg ttaattcata    3360
gtatcccctg acttgttagt gttagagata cagagatgta tcacaaattc attgtatctc    3420
ctcaaggact gtaaaaatcc tataattaaa tttctgaaaa tttgttcttt taagcagaaa    3480
aaaaatctct aaattatctc cctgtataca gagatcaggc gcttctacgg aatgaaccat    3540
ggaggaggct atgaccttg gaggaaaaca gcagctctag cgactccatt taactttgat     3600
gaagtagatt ctaaatggcc aaaaggccac tgcgtagctg ttagaataac tagcgaggat    3660
ccagatgatg ggtttaagcc tactggtgga aaagtaaagg tgcggtttcc tgatgttagg    3720
tgtatgaatt gaacacattg ctatattgca gctagtgaaa tgactggatc atggttctct    3780
tattttcagg agataagttt caagagtaaa ccaaatgttt gggcctattt ctcagtaaag    3840
gtagtcctca atattgttgc actgccacat tatttgagtt gtcctaacaa ttgtgctgca    3900
attgttagtt ttcaactatt tgttgttctg tttggttgac tggtaccctc tctttgcagt    3960
ctggtggagg catccatgaa ttcgctgatt ctcagttcgg tatgtaaagt taaaagagta    4020
atattgtctt tgctatttat gtttgtcctc acttttaaaa gatattgcct tccattacag    4080
gacatgtttt tgcgtatgga actactagat cggcagcaat aactaccatg gctcttgcac    4140
taaaagaggt tcaaattcgt ggagaaattc attcaaacgt agactacaca gttgacctat    4200
taaatgtaag gactaaatat ctgcttattg aaccttgctt tttggttccc taatgccatt    4260
ttagtctggc tactgaagaa cttatccatc atgccatttc tgttatctta aattcaggcc    4320
tcagatttta gagaaaataa gattcatact ggttggctgg ataccaggat agccatgcgt    4380
gttcaagcta gagggcctcc atggtatatt tcagtcgttg gaggggcttt atatgtaaga    4440
caaactatgc cactcattag catttatgtg aagcaaatgc ggaaaacatg atcaatatgt    4500
```

```
cgtcttattt aaatttattt atttttgtgc tgcagaaaac agtaactgcc aacacggcca    4560
ctgtttctga ttatgttggt tatcttacca agggccagat tccaccaaag gtactattct    4620
gttttttcag gatatgaatg ctgtttgaat gtgaaaacca ttgaccataa atccttgttt    4680
gcagcatata tcccttgtct atacgactgt tgctttgaat atagatggga aaaaatatac    4740
agtaagtgtg acattcttaa tggggaaact taatttgttg taaataatca atatcatatt    4800
gactcgtgta tgctgcatca tagatcgata ctgtgaggag tggacatggt agctacagat    4860
tgcgaatgaa tggatcaacg gttgacgcaa atgtacaaat attatgtgat ggtgggcttt    4920
taatgcaggt aatatcttct tcctagttaa agaagatata tcttgttcaa agaattctga    4980
ttattgatct tttaatgttt tcagctggat ggaaacagcc atgtaattta tgctgaagaa    5040
gaggccagtg gtacacgact tcttattgat ggaaagacat gcatgttaca ggtaatgata    5100
gccttgttct ttttagttct agtcacggtg tttgcttgct atttgttgta tctatttaat    5160
gcattcacta attactatat tagttttgcat catcaagtta aaatggaact tctttcttgc    5220
agaatgacca tgacccatca aagttattag ctgagacacc atgcaaactt cttcgtttct    5280
tggttgctga tggtgctcat gttgatgctg atgtaccata tgcggaagtt gaggttatga    5340
agatgtgcat gccctctta tcacccgctt ctggtgtcat acatgttgta atgtctgagg    5400
gccaagcaat gcaggtacat tcctacattc cattcattgt gctgtgctga catgaacatt    5460
tcaagtaaat acctgtaact tgtttattat tctaggctgg tgatcttata gctaggctgg    5520
atcttgatga cccttctgct gttaagagag ctgagccgtt cgaagatact tttccacaaa    5580
tgggtctccc tattgctgct tctggccaag ttcacaaatt atgtgctgca agtctgaatg    5640
cttgtcgaat gatccttgcg gggtatgagc atgatattga caaggtaaac atcatgtcct    5700
cttgtttttt cttttgttta tcatgcattc ttatgttcat catgtcctct ggcaaatcta    5760
gattccgctg tcgtttcaca cagattttc tcattctcat aatggtgcca acataaata    5820
tgctgctata ttcatcaatg ttttcactcg atttctaatt ttgcttttga gttttaaact    5880
ttagtacaat ccatatctaa tctcctttgg caacagtgaa tccattatat atatttttat    5940
taaactgctt tctttttcag gttgtgccag agttggtata ctgcctagac actccggagc    6000
ttccttcct gcagtgggag gagcttatgt ctgttttagc aactagactt ccaagaaatc    6060
ttaaaagtga ggtatattat ggttgacaag atagctagtc tcatgctcta aggacttgta    6120
catttcgcca cataggttaa ttttccatat caagttctaa tgtacgatat aaaagtagta    6180
ctggcctaaa acagtattgg tggttgacta tctttgttgt gtaagatcaa gtatttcttt    6240
ttcatgctta gtttgtcaat acttcacatt tatcactgac ttgtcgagct aaatgagatt    6300
ttatttgatt tctgtgctcc attattttg tatatatata tatatattta actatgacta    6360
tatgttatgc ctcaaacgtt tcaaactctt tcagttggag ggcaaatatg aggaatacaa    6420
agtaaaattt gactctggga taatcaatga tttccctgcc aatatgctac gagtgataat    6480
tgaggtcagt tattcaattt gttgtgataa tcactgcctt aactgttcgt tcttttaaca    6540
agcggtttta taggaaaatc ttgcatgtgg ttctgagaag gagaaggcta caaatgagag    6600
gcttgttgag cctcttatga gcctactgaa gtcatatgag ggtgggagag aaagtcatgc    6660
tcactttgtt gtcaagtccc tttttgagga gtatctctat gttgaagaat tgttcagtga    6720
tggaattcag gttaacttac ctattcgcat taaacaaatc atcagttgtt ttatgataaa    6780
gtcaaaatgt ttatatttcc cattcttctg tggatcaaat atatcacgga catgatatag    6840
```

```
tttccttagg ctatataatg gttcttcatc aaataatatt gcaggaaaca gtatagcaaa      6900
ctatttgtat atactcgaga tggaaattgt tagaaacatc attgactaaa tctgtccttt      6960
gttacgctgt ttttgtagtc tgatgtgatt gagcgtctgc gccttcaaca tagtaaagac      7020
ctacagaagg tcgtagacat tgtgttgtcc caccaggtaa atttcttcat ggtctgatga      7080
cttcactgcg aatggttact gaactgtctt cttgttctga caatgtgact tttctttgta      7140
gagtgttaga aataaaacta agctgatact aaaactcatg gagagtctgg tctatccaaa      7200
tcctgctgcc tacagggatc aattgattcg cttttcttcc cttaatcaca aagcgtatta      7260
caaggtgacc aggataaaca taaataaacg tgaattttc aatgacctt tcttctgaca       7320 tctgaatctg atgaatttct tgcatattaa tacagttggc acttaaagct agtgaacttc      7380
ttgaacaaac aaaacttagt gagctccgtg caagaatagc aaggagcctt tcagagctgg      7440
agatgtttac tgaggaaagc aagggtctct ccatgcataa gcgagaaatt gccattaagg      7500
agagcatgga agatttagtc actgctccac tgccagttga agatgcgctc atttctttat      7560
ttgattgtag tgatacaact gttcaacaga gagtgattga gacttatata gctcgattat      7620
accaggtatg agaagaaaga ccttttgaaa ttatttatat taacatatcc tagtaaaaca      7680
gcatgctcat catttcttaa aaaaagttta cagcacctga tgtttggtta ctgaccgcat      7740
cattaaaata aagttacttg ttgtggagag atgtattttg gaacttgtgg cacatgcagt      7800
aacatgctac tgctcgatat gtttgctaac ttgacaacaa tattttcag cctcatcttg       7860 taaaggacag tatcaaaatg aaatggatag aatcgggtgt tattgcttta tgggaatttc      7920
ctgaagggca ttttgatgca agaaatggag gagcggttct tggtgacaaa agatggggtg      7980
ccatggtcat tgtcaagtct cttgaatcac tttcaatggc cattagattt gcactaaagg      8040
agacatcaca ctacactagc tctgagggca atatgatgca tattgctttg ttgggtgctg      8100
ataataagat gcatataatt caagaaaggt atgttcatat gctatgttgg tgctgaaata      8160
gttatatatg tagttagctg gtggagttct ggtaattaac ctatcccatt gttcagtggt      8220
gatgatgctg acagaatagc caaacttccc ttgatactaa aggataatgt aaccgatctg      8280
catgcctctg tgtgaaaac aataagtttc attgttcaaa gagatgaagc acggatgaca       8340
atgcgtcgta ccttcctttg gtctgatgaa aagctttctt atgaggaaga gccaattctc      8400
cggcatgtgg aacctcctct ttctgcactt cttgagttgg tacgtgatat catcaaaatg      8460
ataatgtttt ggtatggcat tgattatctt ctatgctctt tgtatttatt cagcctattg      8520
tggatacaga acaagttgaa agtgaaagga tacaatgaaa tgaagtatac cccatcacgg      8580
gatcgtcaat ggcatatcta cacacttaga aatactgaaa accccaaaat gttgcaccgg      8640 gtattttcc gaaccttgt caggcaaccc agtgtatcca acaagttttc ttcgggccag        8700
attggtgaca tggaagttgg gagtgctgaa gaacctctgt catttacatc aaccagcata      8760
ttaagatctt tgatgactgc tatagaggaa ttggagcttc acgcaattag aactggccat      8820
tcacacatgt atttgcatgt attgaaagaa caaaagcttc ttgatcttgt tccagtttca      8880
gggtaagtgc gcatatttct ttttgggaac atatgcttgc ttatgaggtt ggtcttctca      8940
atgatcttct tatcttactc aggaatacag ttttggatgt tggtcaagat gaagctactg      9000
catattcact tttaaaagaa atggctatga agatacatga acttgttggt gcaagaatgc      9060
accatctttc tgtatgccaa tgggaagtga aacttaagtt ggactgcgat ggtcctgcca      9120
gtggtacctg gaggattgta acaaccaatg ttactagtca cacttgcact gtggatgtaa      9180
gtttaatcct ctagcatttt gttttctttg gaaaagcatg tgatttaag ccggctggtc       9240
```

```
ctcataccca gacctagtga tctttatata gtgtagacat ttttctaact gcttttaatt    9300
gttttagatc taccgtgaga tggaagataa agaatcacgg aagttagtat accatcccgc    9360
cactccggcg gctggtcctc tgcatggtgt ggcactgaat aatccatatc agcctttgag    9420
tgtcattgat ctcaaacgct gttctgctag gaataataga actacatact gctatgattt    9480
tccactggtg agttgactgc tcccttatat tcaatgcatt accatagcaa attcatattc    9540
gttcatgttg tcaaaataag ccgatgaaaa ttcaaaactg taggcatttg aaactgcagt    9600
gaggaagtca tggtcctcta gtacctctgg tgcttctaaa ggtgttgaaa atgcccaatg    9660
ttatgttaaa gctacagagt tggtatttgc ggacaaacat gggtcatggg gcactccttt    9720
agttcaaatg gaccggcctg ctgggctcaa tgacattggt atggtagctt ggaccttgaa    9780
gatgtccact cctgaatttc ctagtggtag ggagattatt gttgttgcaa atgatattac    9840
gttcagagct ggatcatttg gcccaaggga agatgcattt tttgaagctg ttaccaacct    9900
agcctgtgag aagaaacttc ctcttattta tttggcagca aattctggtg ctcgaattgg    9960
catagcagat gaagtgaaat cttgcttccg tgttgggtgg tctgatgatg gcagccctga   10020
acgtgggttt cagtacattt atctaagcga agaagactat gctcgtattg cacttctgt    10080 catagcacat aagatgcagc tagacagtgg tgaaattagg tgggttattg attctgttgt   10140
gggcaaggaa gatggacttg gtgtggagaa tatacatgga agtgctgcta ttgccagtgc   10200
ttattctagg gcatataagg agacatttac acttacattt gtgactggaa gaactgttgg   10260
aataggagct tatcttgctc gacttggcat ccggtgcata cagcgtcttg accagcctat   10320
tattcttaca ggctattctg cactgaacaa gcttcttggg cgggaagtgt acagctccca   10380
catgcagttg ggtggtccca aaatcatggc aactaatggt gttgtccatc ttactgtttc   10440
agatgacctt gaaggcgttt ctaatatatt gaggtggctc agttatgttc ctgcctacat   10500
tggtggacca cttccagtaa caacaccgtt ggacccaccg gacagacctg ttgcatacat   10560
tcctgagaac tcgtgtgatc ctcgagcggc tatccgtggt gttgatgaca gccaagggaa   10620
atggttaggt ggtatgtttg ataaagacag ctttgtggaa acatttgaag gttgggctaa   10680
gacagtggtt actggcagag caaagcttgg tggaattcca gtgggtgtga tagctgtgga   10740
gactcagacc atgatgcaaa ctatccctgc tgaccctggt cagcttgatt cccgtgagca   10800
atctgttcct cgtgctggac aagtgtggtt tccagattct gcaaccaaga ctgcgcaggc   10860
attgctggac ttcaaccgtg aaggattacc tctgttcatc ctcgctaact ggagaggctt   10920
ctctggtgga caaagagatc tttttgaagg aattcttcag gctggctcga ctattgttga   10980
gaaccttagg acatacaatc agcctgcctt tgtctacatt cccatggctg cagagctacg   11040
aggaggggct tgggttgtgg ttgatagcaa gataaaccca gaccgcattg agtgctatgc   11100
tgagaggact gcaaaaggca atgttctgga accgcaaggg ttaattgaga tcaagttcag   11160
gtcagaggaa ctccaggatt gcatgagtcg gcttgaccca acattaattg atctgaaagc   11220
aaaactcgaa gtagcaaata aaaatggaag tgctgacaca aaatcgcttc aagaaaatat   11280
agaagctcga acaaaacagt tgatgcctct atatactcag attgcgatac ggtttgctga   11340
attgcatgat acatccctca gaatggctgc gaaaggtgtg attaagaaag ttgtggactg   11400
ggaagaatca cgatctttct tctataagag attacggagg aggatctctg aggatgttct   11460
tgcaaaagaa attagagctg tagcaggtga gcagttttcc caccaaccag caatcgagct   11520
gatcaagaaa tggtattcag cttcacatgc agctgaatgg gatgatgacg atgctttgt   11580
```

```
tgcttggatg gataaccctg aaaactacaa ggattatatt caatatctta aggctcaaag    11640
agtatcccaa tccctctcaa gtctttcaga ttccagctca gatttgcaag ccctgccaca    11700
gggtctttcc atgttactag ataaggtaat tagcttactg atgcttatat aaattctttt    11760
tcattacata tggctggaga actatctaat caaataatga ttataattcc aatcgttctt    11820
tttatgccat tatgatcttc tgaaatttcc ttctttggac acttattcag atggatccct    11880
ctagaagagc tcaacttgtt gaagaaatca ggaaggtcct tggttga                 11927

<210> SEQ ID NO 6
<211> LENGTH: 6984
<212> TYPE: DNA
<213> ORGANISM: Oryza sativa

<400> SEQUENCE: 6
atgacatcca cacatgtggc gacattggga gttggtgccc aggcacctcc tcgtcaccag      60
aaaaagtcag ctggcactgc atttgtatca tctgggtcat caagaccctc ataccgaaag     120
aatggtcagc gtactcggtc acttaggcaa gaaagcaatg gaggagtgtc tgattccaaa     180
aagcttaacc actctattcg ccaaggtctt gctggcatca ttgacctccc aaatgacgca     240
gcttcagaag ttgatatttc acatggttcc gaagatccca gggggcctac ggtcccaggt     300
tcctaccaaa tgaatgggat tatcaatgaa acacataatg ggaggcatgc ttcagtctcc     360
aaggttgttg agttttgtac ggcacttggt ggcaaaacac caattcacag tgtattagtg     420
gccaacaatg gaatggcagc agctaagttc atgcggagtg tccgaacatg gctaatgat      480 acttttggat cagagaaggc aattcagctg atagctatgg caactccgga ggatctgagg     540
ataaatgcag agcacatcag aattgccgat caatttgtag aggtacctgg tggaacaaac     600
aacaacaact atgcaaatgt ccaactcata gtggagatag cagagagaac aggtgtttct     660
gctgtttggc ctggttgggg tcatgcatct gagaatcctg aacttccaga tgcgctgact     720
gcaaaaggaa ttgtttttct tgggccacca gcatcatcaa tgcatgcatt aggagacaag     780
gttggctcag ctctcattgc tcaagcagct ggagttccaa cacttgcttg agtggatca     840 catgtgaag ttcctctgga gtgttgcttg gactcaatac ctgatgagat gtatagaaaa     900
gcttgtgtta ctaccacaga ggaagcagtt gcaagttgtc aggtggttgg ttatcctgcc     960
atgattaagg catcttgggg tggtggtggt aaaggaataa ggaaggttca taatgatgat    1020
gaggttagga cattatttaa gcaagttcaa ggcgaagtac ctggttcccc aatatttatc    1080
atgaggctag ctgctcagag tcgacatctt gaagttcagt tgctttgtga tcaatatggc    1140
aacgtagcag cacttcacag tcgagattgc agtgtacaac ggcgacacca aagataatc    1200 gaggaaggac cagttactgt tgctcctcgt gagactgtga agagcttga gcaggcagca    1260 cggaggcttg ctaaagctgt gggttatgtt ggtgctgcta ctgttgaata cctttacagc    1320
atggaaactg gtgaatatta ttttctggaa cttaatccac ggctacaggt tgagcatcct    1380
gtcactgagt ggatagctga agtaaatttg cctgcggctc aagttgctgt tggaatgggt    1440 atacccettt ggcagattcc agagatcagg cgcttctacg gaatgaacca tggaggaggc    1500
tatgaccttt ggaggaaaac agcagctcta gcgactccat ttaactttga tgaagtagat    1560
tctaaatggc caaaaggcca ctgcgtagct gttagaataa ctagcgagga tccagatgat    1620
gggtttaagc ctactggtgg aaaagtaaag gagataagtt tcaagagtaa accaaatgtt    1680
tgggcctatt tctcagtaaa gtctggtgga ggcatccatg aattcgctga ttctcagttc    1740
ggacatgttt ttgcgtatgg aactactaga tcggcagcaa taactaccat ggctcttgca    1800
```

```
ctaaaagagg ttcaaattcg tggagaaatt cattcaaacg tagactacac agttgaccta      1860
ttaaatgcct cagattttag agaaaataag attcatactg gttggctgga taccaggata      1920
gccatgcgtg ttcaagctga gaggcctcca tggtatattt cagtcgttgg aggggcttta      1980
tataaaacag taactgccaa cacgccact gtttctgatt atgttggtta tcttaccaag       2040
ggccagattc caccaaagca tatatccctt gtctatacga ctgttgcttt gaatatagat      2100
gggaaaaaat atacaatcga tactgtgagg agtggacatg gtagctacag attgcgaatg      2160
aatggatcaa cggttgacgc aaatgtacaa atattatgtg atggtgggct tttaatgcag      2220
ctggatggaa acagccatgt aatttatgct gaagaagagg ccagtggtac acgacttctt      2280
attgatggaa agacatgcat gttacagaat gaccatgacc catcaaagtt attagctgag      2340
acaccatgca aacttcttcg tttcttggtt gctgatggtg tcatgttga tgctgatgta       2400 ccatatgcgg aagttgaggt tatgaagatg tgcatgcccc tcttatcacc cgcttctggt      2460
gtcatacatg ttgtaatgtc tgagggccaa gcaatgcagg ctggtgatct tatagctagg      2520
ctggatcttg atgacccttc tgctgttaag agagctgagc cgttcgaaga tacttttcca      2580
caaatgggtc tccctattgc tgcttctggc caagttcaca aattatgtgc tgcaagtctg      2640
aatgcttgtc gaatgatcct tgcggggtat gagcatgata ttgacaaggt tgtgccagag      2700
ttggtatact gcctagacac tccggagctt ccttttcctgc agtgggagga gcttatgtct      2760
gttttagcaa ctagacttcc aagaaatctt aaaagtgagt tggagggcaa atatgaggaa      2820
tacaaagtaa aatttgactc tgggataatc aatgatttcc ctgccaatat gctacgagtg      2880
ataattgagg aaaatcttgc atgtggttct gagaaggaga aggctacaaa tgagaggctt      2940
gttgagcctc ttatgagcct actgaagtca tatgagggtg ggagagaaag tcatgctcac      3000
tttgttgtca agtcccttt tgaggagtat ctctatgttg aagaattgtt cagtgatgga      3060
attcagtctg atgtgattga gcgtctgcgc cttcaacata gtaaagacct acagaaggtc      3120
gtagacattg tgttgtccca ccagagtgtt agaaataaaa ctaagctgat actaaaactc      3180
atggagagtc tggtctatcc aaatcctgct gcctacaggg atcaattgat tcgcttttct      3240
tcccttaatc acaaagcgta ttacaagttg gcacttaaag ctagtgaact tcttgaacaa      3300
acaaaactta gtgagctccg tgcaagaata gcaggagcc tttcagagct ggagatgttt       3360
actgaggaaa gcaagggtct ctccatgcat aagcgagaaa ttgccattaa ggagagcatg      3420
gaagatttag tcactgctcc actgccagtt gaagatgcgc tcatttcttt atttgattgt      3480
agtgatacaa ctgttcaaca gagagtgatt gagacttata tagctcgatt ataccagcct      3540
catcttgtaa aggacagtat caaaatgaaa tggatagaat cgggtgttat tgctttatgg      3600
gaatttcctg aagggcattt tgatgcaaga aatggaggag cggttcttgg tgacaaaaga      3660
tggggtgcca tggtcattgt caagtctctt gaatcacttt caatggccat tagatttgca      3720
ctaaaggaga catcacacta cactagctct gagggcaata tgatgcatat tgctttgttg      3780
ggtgctgata ataagatgca tataattcaa gaaagtggtg atgatgctga cagaatagcc      3840
aaacttccct tgatactaaa ggataatgta accgatctgc atgcctctgg tgtgaaaaca      3900
ataagtttca ttgttcaaag agatgaagca cggatgacaa tgcgtcgtac cttcctttgg      3960
tctgatgaaa agcttttctta tgaggaagag ccaattctcc ggcatgtgga acctcctctt      4020
tctgcacttc ttgagttgga caagttgaaa gtgaaaggat acaatgaaat gaagtatacc      4080
ccatcacggg atcgtcaatg gcatatctac acacttagaa atactgaaaa ccccaaaatg      4140
```

```
ttgcaccggg tattttccg aacccttgtc aggcaaccca gtgtatccaa caagttttct    4200
tcgggccaga ttggtgacat ggaagttggg agtgctgaag aacctctgtc atttacatca    4260
accagcatat taagatcttt gatgactgct atagaggaat tggagcttca cgcaattaga    4320
actggccatt cacacatgta tttgcatgta ttgaaagaac aaaagcttct tgatcttgtt    4380
ccagtttcag ggaatacagt tttggatgtt ggtcaagatg aagctactgc atattcactt    4440
ttaaaagaaa tggctatgaa gatacatgaa cttgttggtg caagaatgca ccatcttttct   4500 gtatgccaat gggaagtgaa acttaagttg gactgcgatg gtcctgccag tggtacctgg    4560
aggattgtaa caaccaatgt tactagtcac acttgcactg tggatatcta ccgtgagatg    4620
gaagataaag aatcacggaa gttagtatac catcccgcca ctccggcggc tggtcctctg    4680
catggtgtgg cactgaataa tccatatcag cctttgagtg tcattgatct caaacgctgt    4740
tctgctagga ataatagaac tacatactgc tatgattttc cactggcatt tgaaactgca    4800
gtgaggaagt catggtcctc tagtacctct ggtgcttcta aggtgttga aaatgcccaa    4860 tgttatgtta aagctacaga gttggtattt gcggacaaac atgggtcatg ggcactcct    4920 ttagttcaaa tggaccggcc tgctgggctc aatgacattg gtatggtagc ttggaccttg    4980
aagatgtcca ctcctgaatt tcctagtggt agggagatta ttgttgttgc aaatgatatt    5040
acgttcagag ctggatcatt tggcccaagg gaagatgcat tttttgaagc tgttaccaac    5100
ctagcctgtg agaagaaact tcctcttatt tatttggcag caaattctgg tgctcgaatt    5160
ggcatagcag atgaagtgaa atcttgcttc cgtgttgggt ggtctgatga tggcagccct    5220
gaacgtgggt tcagtacat ttatctaagc gaagaagact atgctcgtat tggcacttct    5280
gtcatagcac ataagatgca gctagacagt ggtgaaatta ggtgggttat tgattctgtt    5340
gtgggcaagg aagatggact tggtgtggag aatatacatg gaagtgctgc tattgccagt    5400
gcttattcta gggcatataa ggagacattt acacttacat ttgtgactgg aagaactgtt    5460
ggaataggag cttatcttgc tcgacttggc atccggtgca tacagcgtct tgaccagcct    5520
attattctta caggctattc tgcactgaac aagcttcttg ggcgggaagt gtacagctcc    5580
cacatgcagt tgggtggtcc caaaatcatg gcaactaatg tgttgtcca tcttactgtt    5640 tcagatgacc ttgaaggcgt ttctaatata ttgaggtggc tcagttatgt tcctgcctac    5700
attggtggac cacttccagt aacaacaccg ttggacccac cggacagacc tgttgcatac    5760
attcctgaga actcgtgtga tcctcgagcg gctatccgtg gtgttgatga cagccaaggg    5820
aaatggttag gtggtatgtt tgataaagac agctttgtgg aaacatttga aggttgggct    5880
aagacagtgg ttactggcag agcaaagctt ggtggaattc cagtgggtgt gatagctgtg    5940
gagactcaga ccatgatgca aactatccct gctgaccctg gtcagcttga ttcccgtgag    6000
caatctgttc ctcgtgctgg acaagtgtgg tttccagatt ctgcaaccaa gactgcgcag    6060
gcattgctgg acttcaaccg tgaaggatta cctctgttca tcctcgctaa ctggagaggc    6120
ttctctggtg gacaaagaga tcttttttgaa ggaattcttc aggctggctc gactattgtt    6180
gagaacctta ggacatacaa tcagcctgcc tttgtctaca ttcccatggc tgcagagcta    6240
cgaggagggg cttgggttgt ggttgatagc aagataaacc cagaccgcat tgagtgctat    6300
gctgagagga ctgcaaaagg caatgttctg gaaccgcaag ggttaattga gatcaagttc    6360
aggtcagagg aactccagga ttgcatgagt cggcttgacc aacattaat tgatctgaaa    6420 gcaaaactcg aagtagcaaa taaaatgga agtgctgaca caaaatcgct tcaagaaaat    6480
atagaagctc gaacaaaaca gttgatgcct ctatatactc agattgcgat acggtttgct    6540
```

```
gaattgcatg atacatccct cagaatggct gcgaaaggtg tgattaagaa agttgtggac    6600
tgggaagaat cacgatcttt cttctataag agattacgga ggaggatctc tgaggatgtt    6660
cttgcaaaag aaattagagc tgtagcaggt gagcagtttt cccaccaacc agcaatcgag    6720
ctgatcaaga aatggtattc agcttcacat gcagctgaat gggatgatga cgatgctttt    6780
gttgcttgga tggataaccc tgaaaactac aaggattata ttcaatatct taaggctcaa    6840
agagtatccc aatccctctc aagtctttca gattccagct cagatttgca agccctgcca    6900
cagggtcttt ccatgttact agataagatg gatccctcta aagagctca acttgttgaa    6960 gaaatcagga aggtccttgg ttga                                          6984

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcaaatgata ttacgttcag agctg                                         25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttaccaacc tagcctgtga gaag                                          24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatttcttca acaagttgag ctcttc                                        26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtaacatgg aaagaccctg tggc                                          24

<210> SEQ ID NO 11
<211> LENGTH: 6978
<212> TYPE: DNA
<213> ORGANISM: Zea mays

<400> SEQUENCE: 11
atgtcacagc ttggattagc cgcagctgcc tcaaaggcct tgccactact ccctaatcgc    60
```

| | |
|---|---|
| cagagaagtt cagctgggac tacattctca tcatcttcat tatcgaggcc cttaaacaga | 120 |
| aggaaaagcc gtactcgttc actccgtgat ggcggagatg gggtatcaga tgccaaaaag | 180 |
| cacagccagt ctgttcgtca aggtcttgct ggcattatcg acctcccaag tgaggcacct | 240 |
| tccgaagtgg atatttcaca tggatctgag gatcctaggg ggccaacaga ttcttatcaa | 300 |
| atgaatggga ttatcaatga aacacataat ggaagacatg cctcagtgtc caaggttgtt | 360 |
| gaattttgtg cggcactagg tggcaaaaca ccaattcaca gtatattagt ggccaacaat | 420 |
| ggaatggcag cagcaaaatt tatgaggagt gtccggacat gggctaatga tacttttgga | 480 |
| tctgagaagg caattcaact catagctatg caactccgg aagacatgag gataaatgca | 540 |
| gaacacatta gaattgctga ccaattcgta gaggtgcctg gtggaacaaa caataataac | 600 |
| tacgccaatg ttcaactcat agtggagatg gcacaaaaac taggtgtttc tgctgtttgg | 660 |
| cctggttggg gtcatgcttc tgagaatcct gaactgccag atgcattgac cgcaaaaggg | 720 |
| atcgttttc ttggcccacc tgcatcatca atgaatgctt tgggagataa ggtcggctca | 780 |
| gctctcattg ctcaagcagc cggggtccca actcttgctc ggagtggatc acatgttgaa | 840 |
| gttccattag agtgctgctt agacgcgata cctgaggaga tgtatagaaa agcttgcgtt | 900 |
| actaccacag aggaagcagt tgcaagttgt caagtggttg gttatcctgc catgattaag | 960 |
| gcatcctggg gaggtggtgg taaaggaata agaaaggttc ataatgatga tgaggttaga | 1020 |
| gcgctgttta agcaagtaca aggtgaagtc cctggctccc caatatttgt catgaggctt | 1080 |
| gcatcccaga gtcggcatct tgaagttcag ttgctttgtg atcaatatgg taatgtagca | 1140 |
| gcacttcaca gtcgtgattg cagtgtgcaa cggcgacacc agaagattat tgaagaaggt | 1200 |
| ccagttactg ttgctcctcg tgagacagtt aaagcacttg agcaggcagc aaggaggctt | 1260 |
| gctaaggctg tgggttatgt tggtgctgct actgttgagt atctttacag catggaaact | 1320 |
| ggagactact attttctgga acttaatccc cgactacagg ttgagcatcc agtcaccgag | 1380 |
| tggatagctg aagtaaatct gcctgcagct caagttgctg ttggaatggg catacctctt | 1440 |
| tggcagattc cagaaatcag acgtttctat ggaatggact atggaggagg gtatgacatt | 1500 |
| tggaggaaaa cagcagctct tgctacacca tttaattttg atgaagtaga ttctcaatgg | 1560 |
| ccaaagggcc attgtgtagc agttagaatt actagtgagg acccagatga tggtttcaaa | 1620 |
| cctactggtg ggaaagtgaa ggagataagt tttaaaagca agcctaatgt ttgggcctac | 1680 |
| ttctcagtaa agtctggtgg aggcattcat gaatttgctg attctcagtt cggacatgtt | 1740 |
| tttgcatatg ggctctctag atcagcagca ataacaaaca tgactcttgc attaaaagag | 1800 |
| attcaaattc gtgagaaat tcattcaaat gttgattaca cagttgacct cttaaatgct | 1860 |
| tcagactta gagaaaacaa gattcatact ggttggctcg acaccagaat agctatgcgt | 1920 |
| gttcaagctg agaggccccc atggtatatt tcagtggttg gaggtgcttt atataaaaca | 1980 |
| gtaaccacca atgcagccac tgtttctgaa tatgttagtt atctcaccaa gggccagatt | 2040 |
| ccaccaaagc atatatccct tgtcaattct acagttaatt tgaatataga agggagcaaa | 2100 |
| tacacaattg aaactgtaag gactggacat ggtagctaca ggttgagaat gaatgattca | 2160 |
| acagttgaag cgaatgtaca atctttatgt gatggtggcc tcttaatgca gttggatgga | 2220 |
| aacagccatg taatttatgc agaagaagaa gctggtggta cacggcttca gattgatgga | 2280 |
| aagacatgtt tattgcagaa tgaccatgat ccatcaaagt tattagctga cacccctgc | 2340 |
| aaacttcttc gtttcttggt tgctgatggt gctcatgttg atgcggatgt accatacgcg | 2400 |
| gaagttgagg ttatgaagat gtgcatgcct ctcttgtcac ctgcttctgg tgtcattcat | 2460 |

```
tgtatgatgt ctgagggcca ggcattgcag gctggtgatc ttatagcaag gttggatctt    2520
gatgacccct ctgctgtgaa aagagctgag ccatttgatg gaatatttcc acaaatggag    2580
ctccctgttg ctgtctctag tcaagtacac aaaagatatg ctgcaagttt gaatgctgct    2640
cgaatggtcc ttgcaggata tgagcacaat attaatgaag tcgttcaaga tttggtatgc    2700
tgcctggaca accctgagct tccttcccta cagtgggatg aacttatgtc tgttctagca    2760
acgaggcttc caagaaatct caagagtgag ttagaggata aatacaagga atacaagttg    2820 aattttttacc atggaaaaaa cgaggacttt ccatccaagt tgctaagaga catcattgag    2880
gaaaatcttt cttatggttc agagaaggaa aaggctacaa atgagaggct tgttgagcct    2940
cttatgaacc tactgaagtc atatgagggt gggagagaga gccatgcaca ttttgttgtc    3000
aagtctcttt tcgaggagta tcttacagtg aagaactttt ttagtgatgg cattcagtct    3060
gacgtgattg aaacattgcg gcatcagcac agtaaagacc tgcagaaggt tgtagacatt    3120
gtgttgtctc accagggtgt gaggaacaaa gctaagcttg taacggcact tatggaaaag    3180
ctggtttatc caaatcctgg tggttacagg gatctgttag ttcgcttttc ttccctcaat    3240
cataaaagat attataagtt ggcccttaaa gcaagtgaac ttcttgaaca aaccaaacta    3300
agtgaactcc gtgcaagcgt tgcaagaagc ctttcggatc tggggatgca taagggagaa    3360
atgagtatta aggataacat ggaagattta gtctctgccc cattacctgt tgaagatgct    3420
ctgatttctt tgtttgatta cagtgatcga actgttcagc agaaagtgat tgagacatac    3480
atatcacgat tgtaccagcc tcatcttgta aaggatagca tccaaatgaa attcaaggaa    3540
tctggtgcta ttactttttg ggaattttat gaagggcatg ttgatactag aaatggacat    3600
ggggctatta ttggtgggaa gcgatggggt gccatggtcg ttctcaaatc acttgaatct    3660
gcgtcaacag ccattgtggc tgcattaaag gattcggcac agttcaacag ctctgagggc    3720
aacatgatgc acattgcatt attgagtgct gaaaatgaaa gtaatataag tggaataagc    3780
agtgatgatc aagctcaaca taagatggaa aagcttagca agatactgaa ggatactagc    3840
gttgcaagtg atctccaagc tgctggtttg aaggttataa gttgcattgt tcaaagagat    3900
gaagctcgca tgccaatgcg ccacacattc ctctggttgg atgacaagag ttgttatgaa    3960
gaagagcaga ttctccggca tgtggagcct cccctctcta cacttcttga attggataag    4020
ttgaaggtga aggatacaa tgaaatgaag tatactcctt cgcgtgaccg ccaatggcat    4080
atctacacac taagaaatac tgaaaacccc aaaatgttgc atagggtgtt tttccgaact    4140
attgtcaggc aacccaatgc aggcaacaag tttacatcgg ctcagatcag cgacgctgaa    4200
gtaggatgtc ccgaagaatc tctttcattt acatcaaata gcatcttaag atcattgatg    4260
actgctattg aagaattaga gcttcatgca attaggacag tcattctca catgtatttg    4320 tgcatactga aagagcaaaa gcttcttgac ctcattccat tttcagggag tacaattgtt    4380
gatgttggcc aagatgaagc taccgcttgt tcactttttaa aatcaatggc tttgaagata    4440
catgagcttg ttggtgcaag gatgcatcat ctgtctgtat gccagtggga ggtgaaactc    4500
aagttggact gtgatggccc tgcaagtggt acctggagag ttgtaactac aaatgttact    4560
ggtcacacct gcaccattga tatataccga gaagtggagg aaatagaatc gcagaagtta    4620
gtgtaccatt cagccacttc gtcagctgga ccattgcatg tgttgcact gaataatcca    4680 tatcaacctt tgagtgtgat tgatctaaag cgctgctctg ctaggaacaa cagaacaaca    4740
tattgctatg attttccgct ggcctttgaa actgcactgc agaagtcatg gcagtccaat    4800
```

```
ggctctactg tttctgaagg caatgaaaat agtaaatcct acgtgaaggc aactgagcta    4860
gtgtttgctg aaaaacatgg gtcctggggc actcctataa ttccgatgga acgccctgct    4920
gggctcaacg acattggtat ggtcgcttgg atcatggaga tgtcaacacc tgaatttccc    4980
aatggcaggc agattattgt tgtagcaaat gatatcactt tcagagctgg atcatttggc    5040
ccaagggaag atgcattttt tgaaactgtc actaacctgg cttgcgaaag gaaacttcct    5100
cttatatact tggcagcaaa ctctggtgct aggattggca tagctgatga agtaaaatct    5160
tgcttccgtg ttggatggtc tgacgaaggc agtcctgaac gagggtttca gtacatctat    5220
ctgactgaag aagactatgc tcgcattagc tcttctgtta tagcacataa gctggagcta    5280
gatagtggtg aaattaggtg gattattgac tctgttgtgg gcaaggagga tgggcttggt    5340
gtcgagaaca tacatggaag tgctgctatt gccagtgctt attctagggc atatgaggag    5400
acatttacac ttacatttgt gactgggcgg actgtaggaa taggagctta tcttgctcga    5460
cttggtatac ggtgcataca gcgtcttgac cagcctatta ttttaacagg gttttctgcc    5520
ctgaacaagc tccttgggcg ggaagtgtac agctcccaca tgcagcttgg tggtcctaag    5580
atcatggcga ctaatggtgt tgtccacctc actgttccag atgaccttga aggtgtttcc    5640
aatatattga ggtggctcag ctatgttcct gcaaacattg gtggacctct tcctattacc    5700
aaacctctgg accctccaga cagacctgtt gcttacatcc tgagaacac atgcgatcca    5760
cgtgcagcta tctgtggtgt agatgacagc caagggaaat ggttgggtgg tatgtttgac    5820
aaagacagct tgtggagac atttgaagga tgggcaaaaa cagtggttac tggcagagca    5880
aagcttggag gaattcctgt gggcgtcata gctgtggaga cacagaccat gatgcagatc    5940
atccctgctg atccaggtca gcttgattcc catgagcgat ctgtccctcg tgctggacaa    6000
gtgtggttcc cagattctgc aaccaagacc gctcaggcat tattagactt caaccgtgaa    6060
ggattgcctc tgttcatcct ggctaattgg agaggcttct ctggtggaca aagagatctc    6120
tttgaaggaa ttcttcaggc tgggtcaaca attgtcgaga accttaggac atctaatcag    6180
cctgcttttg tgtacattcc tatggctgga gagcttcgtg gaggagcttg ggttgtggtc    6240
gatagcaaaa taaatccaga ccgcattgag tgttatgctg aaaggactgc caaaggtaat    6300
gttctcgaac ctcaagggtt aattgaaatc aagttcaggt cagaggaact ccaagactgt    6360
atgggtaggc ttgacccaga gttgataaat ctgaaagcaa aactccaaga tgtaaatcat    6420
ggaaatggaa gtctaccaga catagaaggg attcggaaga gtatagaagc acgtacgaaa    6480
cagttgctgc ctttatatac ccagattgca atacggtttg ctgaattgca tgatacttcc    6540
ctaagaatgg cagctaaagg tgtgattaag aaagttgtag actgggaaga atcacgctcg    6600
ttcttctata aaaggctacg gaggaggatc gcagaagatg ttcttgcaaa agaaataagg    6660
cagatagtcg gtgataaatt tacgcaccaa ttagcaatgg agctcatcaa ggaatggtac    6720
cttgcttctc aggccacaac aggaagcact ggatgggatg acgatgatgc ttttgttgcc    6780
tggaaggaca gtcctgaaaa ctacaagggg catatccaaa agcttagggc tcaaaaagtg    6840
tctcattcgc tctctgatct tgctgactcc agttcagatc tgcaagcatt ctcgcagggt    6900
cttttctacgc tattagataa gatggatccc tctcagagag cgaagtttgt tcaggaagtc    6960
aagaaggtcc ttgattga                                                 6978
```

<210> SEQ ID NO 12
<211> LENGTH: 2325
<212> TYPE: PRT
<213> ORGANISM: Zea mays

<400> SEQUENCE: 12

```
Met Ser Gln Leu Gly Leu Ala Ala Ala Ser Lys Ala Leu Pro Leu
1               5                   10                  15

Leu Pro Asn Arg Gln Arg Ser Ser Ala Gly Thr Thr Phe Ser Ser
            20                  25                  30

Ser Leu Ser Arg Pro Leu Asn Arg Arg Lys Ser Arg Thr Arg Ser Leu
        35                  40                  45

Arg Asp Gly Gly Asp Gly Val Ser Asp Ala Lys Lys His Ser Gln Ser
    50                  55                  60

Val Arg Gln Gly Leu Ala Gly Ile Ile Asp Leu Pro Ser Glu Ala Pro
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Ile Asn Glu Thr His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Met Ala Gln Lys Leu Gly Val Ser Ala Val Trp Pro Gly Trp Gly
210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Ala Arg Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Val Met Arg Leu Ala Ser Gln Ser Arg His Leu Glu
        355                 360                 365

Val Gln Leu Leu Cys Asp Gln Tyr Gly Asn Val Ala Ala Leu His Ser
370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
```

```
                    405                 410                 415
Ala Arg Arg Leu Ala Lys Ala Val Gly Tyr Val Gly Ala Ala Thr Val
                420                 425                 430
Glu Tyr Leu Tyr Ser Met Glu Thr Gly Asp Tyr Tyr Phe Leu Glu Leu
                435                 440                 445
Asn Pro Arg Leu Gln Val Glu His Pro Val Thr Glu Trp Ile Ala Glu
            450                 455                 460
Val Asn Leu Pro Ala Ala Gln Val Ala Val Gly Met Gly Ile Pro Leu
465                 470                 475                 480
Trp Gln Ile Pro Glu Ile Arg Arg Phe Tyr Gly Met Asp Tyr Gly Gly
                485                 490                 495
Gly Tyr Asp Ile Trp Arg Lys Thr Ala Ala Leu Ala Thr Pro Phe Asn
            500                 505                 510
Phe Asp Glu Val Asp Ser Gln Trp Pro Lys Gly His Cys Val Ala Val
        515                 520                 525
Arg Ile Thr Ser Glu Asp Pro Asp Gly Phe Lys Pro Thr Gly Gly
    530                 535                 540
Lys Val Lys Glu Ile Ser Phe Lys Ser Lys Pro Asn Val Trp Ala Tyr
545                 550                 555                 560
Phe Ser Val Lys Ser Gly Gly Ile His Glu Phe Ala Asp Ser Gln
                565                 570                 575
Phe Gly His Val Phe Ala Tyr Gly Leu Ser Arg Ser Ala Ala Ile Thr
            580                 585                 590
Asn Met Thr Leu Ala Leu Lys Glu Ile Gln Ile Arg Gly Glu Ile His
        595                 600                 605
Ser Asn Val Asp Tyr Thr Val Asp Leu Leu Asn Ala Ser Asp Phe Arg
    610                 615                 620
Glu Asn Lys Ile His Thr Gly Trp Leu Asp Thr Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Val Thr Thr Asn Ala Ala Thr Val Ser Glu Tyr Val
            660                 665                 670
Ser Tyr Leu Thr Lys Gly Gln Ile Pro Pro Lys His Ile Ser Leu Val
        675                 680                 685
Asn Ser Thr Val Asn Leu Asn Ile Glu Gly Ser Lys Tyr Thr Ile Glu
    690                 695                 700
Thr Val Arg Thr Gly His Gly Ser Tyr Arg Leu Arg Met Asn Asp Ser
705                 710                 715                 720
Thr Val Glu Ala Asn Val Gln Ser Leu Cys Asp Gly Gly Leu Leu Met
                725                 730                 735
Gln Leu Asp Gly Asn Ser His Val Ile Tyr Ala Glu Glu Ala Gly
            740                 745                 750
Gly Thr Arg Leu Gln Ile Asp Gly Lys Thr Cys Leu Leu Gln Asn Asp
        755                 760                 765
His Asp Pro Ser Lys Leu Leu Ala Glu Thr Pro Cys Lys Leu Leu Arg
    770                 775                 780
Phe Leu Val Ala Asp Gly Ala His Val Asp Ala Asp Val Pro Tyr Ala
785                 790                 795                 800
Glu Val Glu Val Met Lys Met Cys Met Pro Leu Leu Ser Pro Ala Ser
                805                 810                 815
Gly Val Ile His Cys Met Met Ser Glu Gly Gln Ala Leu Gln Ala Gly
            820                 825                 830
```

-continued

Asp Leu Ile Ala Arg Leu Asp Leu Asp Asp Pro Ser Ala Val Lys Arg
            835                 840                 845

Ala Glu Pro Phe Asp Gly Ile Phe Pro Gln Met Glu Leu Pro Val Ala
        850                 855                 860

Val Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asn Pro Glu Leu Pro Phe Leu Gln Trp
                900                 905                 910

Asp Glu Leu Met Ser Val Leu Ala Thr Arg Leu Pro Arg Asn Leu Lys
            915                 920                 925

Ser Glu Leu Glu Asp Lys Tyr Lys Glu Tyr Lys Leu Asn Phe Tyr His
        930                 935                 940

Gly Lys Asn Glu Asp Phe Pro Ser Lys Leu Leu Arg Asp Ile Ile Glu
945                 950                 955                 960

Glu Asn Leu Ser Tyr Gly Ser Glu Lys Glu Lys Ala Thr Asn Glu Arg
                965                 970                 975

Leu Val Glu Pro Leu Met Asn Leu Leu Lys Ser Tyr Glu Gly Gly Arg
            980                 985                 990

Glu Ser His Ala His Phe Val Val Lys Ser Leu Phe Glu Glu Tyr Leu
        995                 1000                1005

Thr Val Glu Glu Leu Phe Ser Asp Gly Ile Gln Ser Asp Val Ile
    1010                1015                1020

Glu Thr Leu Arg His Gln His Ser Lys Asp Leu Gln Lys Val Val
    1025                1030                1035

Asp Ile Val Leu Ser His Gln Gly Val Arg Asn Lys Ala Lys Leu
    1040                1045                1050

Val Thr Ala Leu Met Glu Lys Leu Val Tyr Pro Asn Pro Gly Gly
    1055                1060                1065

Tyr Arg Asp Leu Leu Val Arg Phe Ser Ser Leu Asn His Lys Arg
    1070                1075                1080

Tyr Tyr Lys Leu Ala Leu Lys Ala Ser Glu Leu Leu Glu Gln Thr
    1085                1090                1095

Lys Leu Ser Glu Leu Arg Ala Ser Val Ala Arg Ser Leu Ser Asp
    1100                1105                1110

Leu Gly Met His Lys Gly Glu Met Ser Ile Lys Asp Asn Met Glu
    1115                1120                1125

Asp Leu Val Ser Ala Pro Leu Pro Val Glu Asp Ala Leu Ile Ser
    1130                1135                1140

Leu Phe Asp Tyr Ser Asp Arg Thr Val Gln Gln Lys Val Ile Glu
    1145                1150                1155

Thr Tyr Ile Ser Arg Leu Tyr Gln Pro His Leu Val Lys Asp Ser
    1160                1165                1170

Ile Gln Met Lys Phe Lys Glu Ser Gly Ala Ile Thr Phe Trp Glu
    1175                1180                1185

Phe Tyr Glu Gly His Val Asp Thr Arg Asn Gly His Gly Ala Ile
    1190                1195                1200

Ile Gly Gly Lys Arg Trp Gly Ala Met Val Val Leu Lys Ser Leu
    1205                1210                1215

Glu Ser Ala Ser Thr Ala Ile Val Ala Ala Leu Lys Asp Ser Ala
    1220                1225                1230

```
Gln Phe Asn Ser Ser Glu Gly Asn Met Met His Ile Ala Leu Leu
1235                1240                1245

Ser Ala Glu Asn Glu Ser Asn Ile Ser Gly Ile Ser Ser Asp Asp
1250                1255                1260

Gln Ala Gln His Lys Met Glu Lys Leu Ser Lys Ile Leu Lys Asp
1265                1270                1275

Thr Ser Val Ala Ser Asp Leu Gln Ala Ala Gly Leu Lys Val Ile
1280                1285                1290

Ser Cys Ile Val Gln Arg Asp Glu Ala Arg Met Pro Met Arg His
1295                1300                1305

Thr Phe Leu Trp Leu Asp Asp Lys Ser Cys Tyr Glu Glu Glu Gln
1310                1315                1320

Ile Leu Arg His Val Glu Pro Pro Leu Ser Thr Leu Leu Glu Leu
1325                1330                1335

Asp Lys Leu Lys Val Lys Gly Tyr Asn Glu Met Lys Tyr Thr Pro
1340                1345                1350

Ser Arg Asp Arg Gln Trp His Ile Tyr Thr Leu Arg Asn Thr Glu
1355                1360                1365

Asn Pro Lys Met Leu His Arg Val Phe Phe Arg Thr Ile Val Arg
1370                1375                1380

Gln Pro Asn Ala Gly Asn Lys Phe Thr Ser Ala Gln Ile Ser Asp
1385                1390                1395

Ala Glu Val Gly Cys Pro Glu Glu Ser Leu Ser Phe Thr Ser Asn
1400                1405                1410

Ser Ile Leu Arg Ser Leu Met Thr Ala Ile Glu Glu Leu Glu Leu
1415                1420                1425

His Ala Ile Arg Thr Gly His Ser His Met Tyr Leu Cys Ile Leu
1430                1435                1440

Lys Glu Gln Lys Leu Leu Asp Leu Ile Pro Phe Ser Gly Ser Thr
1445                1450                1455

Ile Val Asp Val Gly Gln Asp Glu Ala Thr Ala Cys Ser Leu Leu
1460                1465                1470

Lys Ser Met Ala Leu Lys Ile His Glu Leu Val Gly Ala Arg Met
1475                1480                1485

His His Leu Ser Val Cys Gln Trp Glu Val Lys Leu Lys Leu Asp
1490                1495                1500

Cys Asp Gly Pro Ala Ser Gly Thr Trp Arg Val Thr Thr Asn
1505                1510                1515

Val Thr Gly His Thr Cys Thr Ile Asp Ile Tyr Arg Glu Val Glu
1520                1525                1530

Glu Ile Glu Ser Gln Lys Leu Val Tyr His Ser Ala Thr Ser Ser
1535                1540                1545

Ala Gly Pro Leu His Gly Val Ala Leu Asn Asn Pro Tyr Gln Pro
1550                1555                1560

Leu Ser Val Ile Asp Leu Lys Arg Cys Ser Ala Arg Asn Asn Arg
1565                1570                1575

Thr Thr Tyr Cys Tyr Asp Phe Pro Leu Ala Phe Glu Thr Ala Leu
1580                1585                1590

Gln Lys Ser Trp Gln Ser Asn Gly Ser Thr Val Ser Glu Gly Asn
1595                1600                1605

Glu Asn Ser Lys Ser Tyr Val Lys Ala Thr Glu Leu Val Phe Ala
1610                1615                1620

Glu Lys His Gly Ser Trp Gly Thr Pro Ile Ile Pro Met Glu Arg
```

```
            1625                1630                1635

Pro Ala Gly Leu Asn Asp Ile Gly Met Val Ala Trp Ile Met Glu
            1640                1645                1650

Met Ser Thr Pro Glu Phe Pro Asn Gly Arg Gln Ile Ile Val Val
            1655                1660                1665

Ala Asn Asp Ile Thr Phe Arg Ala Gly Ser Phe Gly Pro Arg Glu
            1670                1675                1680

Asp Ala Phe Phe Glu Thr Val Thr Asn Leu Ala Cys Glu Arg Lys
            1685                1690                1695

Leu Pro Leu Ile Tyr Leu Ala Ala Asn Ser Gly Ala Arg Ile Gly
            1700                1705                1710

Ile Ala Asp Glu Val Lys Ser Cys Phe Arg Val Gly Trp Ser Asp
            1715                1720                1725

Glu Gly Ser Pro Glu Arg Gly Phe Gln Tyr Ile Tyr Leu Thr Glu
            1730                1735                1740

Glu Asp Tyr Ala Arg Ile Ser Ser Ser Val Ile Ala His Lys Leu
            1745                1750                1755

Glu Leu Asp Ser Gly Glu Ile Arg Trp Ile Ile Asp Ser Val Val
            1760                1765                1770

Gly Lys Glu Asp Gly Leu Gly Val Glu Asn Ile His Gly Ser Ala
            1775                1780                1785

Ala Ile Ala Ser Ala Tyr Ser Arg Ala Tyr Glu Glu Thr Phe Thr
            1790                1795                1800

Leu Thr Phe Val Thr Gly Arg Thr Val Gly Ile Gly Ala Tyr Leu
            1805                1810                1815

Ala Arg Leu Gly Ile Arg Cys Ile Gln Arg Leu Asp Gln Pro Ile
            1820                1825                1830

Ile Leu Thr Gly Phe Ser Ala Leu Asn Lys Leu Leu Gly Arg Glu
            1835                1840                1845

Val Tyr Ser Ser His Met Gln Leu Gly Gly Pro Lys Ile Met Ala
            1850                1855                1860

Thr Asn Gly Val Val His Leu Thr Val Pro Asp Asp Leu Glu Gly
            1865                1870                1875

Val Ser Asn Ile Leu Arg Trp Leu Ser Tyr Val Pro Ala Asn Ile
            1880                1885                1890

Gly Gly Pro Leu Pro Ile Thr Lys Pro Leu Asp Pro Pro Asp Arg
            1895                1900                1905

Pro Val Ala Tyr Ile Pro Glu Asn Thr Cys Asp Pro Arg Ala Ala
            1910                1915                1920

Ile Cys Gly Val Asp Asp Ser Gln Gly Lys Trp Leu Gly Gly Met
            1925                1930                1935

Phe Asp Lys Asp Ser Phe Val Glu Thr Phe Glu Gly Trp Ala Lys
            1940                1945                1950

Thr Val Val Thr Gly Arg Ala Lys Leu Gly Gly Ile Pro Val Gly
            1955                1960                1965

Val Ile Ala Val Glu Thr Gln Thr Met Met Gln Ile Ile Pro Ala
            1970                1975                1980

Asp Pro Gly Gln Leu Asp Ser His Glu Arg Ser Val Pro Arg Ala
            1985                1990                1995

Gly Gln Val Trp Phe Pro Asp Ser Ala Thr Lys Thr Ala Gln Ala
            2000                2005                2010

Leu Leu Asp Phe Asn Arg Glu Gly Leu Pro Leu Phe Ile Leu Ala
            2015                2020                2025
```

Asn Trp Arg Gly Phe Ser Gly Gly Gln Arg Asp Leu Phe Glu Gly
         2030                2035                2040

Ile Leu Gln Ala Gly Ser Thr Ile Val Glu Asn Leu Arg Thr Ser
         2045                2050                2055

Asn Gln Pro Ala Phe Val Tyr Ile Pro Met Ala Gly Glu Leu Arg
         2060                2065                2070

Gly Gly Ala Trp Val Val Val Asp Ser Lys Ile Asn Pro Asp Arg
         2075                2080                2085

Ile Glu Cys Tyr Ala Glu Arg Thr Ala Lys Gly Asn Val Leu Glu
         2090                2095                2100

Pro Gln Gly Leu Ile Glu Ile Lys Phe Arg Ser Glu Glu Leu Gln
         2105                2110                2115

Asp Cys Met Gly Arg Leu Asp Pro Glu Leu Ile Asn Leu Lys Ala
         2120                2125                2130

Lys Leu Gln Asp Val Asn His Gly Asn Gly Ser Leu Pro Asp Ile
         2135                2140                2145

Glu Gly Ile Arg Lys Ser Ile Glu Ala Arg Thr Lys Gln Leu Leu
         2150                2155                2160

Pro Leu Tyr Thr Gln Ile Ala Ile Arg Phe Ala Glu Leu His Asp
         2165                2170                2175

Thr Ser Leu Arg Met Ala Ala Lys Gly Val Ile Lys Lys Val Val
         2180                2185                2190

Asp Trp Glu Glu Ser Arg Ser Phe Phe Tyr Lys Arg Leu Arg Arg
         2195                2200                2205

Arg Ile Ala Glu Asp Val Leu Ala Lys Glu Ile Arg Gln Ile Val
         2210                2215                2220

Gly Asp Lys Phe Thr His Gln Leu Ala Met Glu Leu Ile Lys Glu
         2225                2230                2235

Trp Tyr Leu Ala Ser Gln Ala Thr Thr Gly Ser Thr Gly Trp Asp
         2240                2245                2250

Asp Asp Asp Ala Phe Val Ala Trp Lys Asp Ser Pro Glu Asn Tyr
         2255                2260                2265

Lys Gly His Ile Gln Lys Leu Arg Ala Gln Lys Val Ser His Ser
         2270                2275                2280

Leu Ser Asp Leu Ala Asp Ser Ser Ser Asp Leu Gln Ala Phe Ser
         2285                2290                2295

Gln Gly Leu Ser Thr Leu Leu Asp Lys Met Asp Pro Ser Gln Arg
         2300                2305                2310

Ala Lys Phe Val Gln Glu Val Lys Lys Val Leu Asp
         2315                2320                2325

<210> SEQ ID NO 13
<211> LENGTH: 6975
<212> TYPE: DNA
<213> ORGANISM: Zea mays

<400> SEQUENCE: 13
atgtcacagc ttggattagc cgcagctgcc tcaaaggcct tgccactact ccctaatcgc     60
cagagaagtt cagctgggac tacattctca tcatcttcat tatcgaggcc cttaaacaga    120
aggaaaagcc gtactcgttc actccgtgat ggcggagatg gggtatcaga tgccaaaaag    180
cacagccagt ctgttcgtca aggtcttgct ggcattatcg acctcccaag tgaggcacct    240
tccgaagtgg atatttcaca tggatctgag gatcctaggg ggccaacaga ttcttatcaa    300

```
atgaatggga ttatcaatga acacataat ggaagacatg cctcagtgtc caaggttgtt    360
gaattttgtg cggcactagg tggcaaaaca ccaattcaca gtatattagt ggccaacaat    420
ggaatggcag cagcaaaatt tatgaggagt gtccggacat gggctaatga cttttggga    480 tctgagaagg caattcaact catagctatg caactccgg aagacatgag ataaatgca     540 gaacacatta gaattgctga ccaattcgta gaggtgcctg gtggaacaaa caataataac   600
tacgccaatg ttcaactcat agtggagatg cacaaaaac taggtgtttc tgctgtttgg    660
cctggttggg gtcatgcttc tgagaatcct gaactgccag atgcattgac cgcaaaaggg   720 atcgttttc ttggcccacc tgcatcatca atgaatgctt tgggagataa ggtcggctca    780
gctctcattg ctcaagcagc cggggtccca actcttgctt ggagtggatc acatgttgaa   840
gttccattag agtgctgctt agacgcgata cctgaggaga tgtatagaaa agcttgcgtt   900
actaccacag aggaagcagt tgcaagttgt caagtggttg ttatcctgc catgattaag    960 gcatcctggg gaggtggtgg taaaggaata agaaaggttc ataatgatga tgaggttaga   1020
gcgctgttta agcaagtaca aggtgaagtc cctggctccc caatatttgt catgaggctt   1080
gcatcccaga gtcggcatct tgaagttcag ttgctttgtg atcaatatgg taatgtagca   1140
gcacttcaca gtcgtgattg cagtgtgcaa cggcgacacc agaagattat tgaagaaggt   1200
ccagttactg ttgctcctcg tgagacagtt aaagcacttg agcaggcagc aaggaggctt   1260
gctaaggctg tgggttatgt tggtgctgct actgttgagt atctttacag catggaaact   1320
ggagactact attttctgga acttaatccc cgactacagg ttgagcatcc agtcaccgag   1380
tggatagctg aagtaaatct gcctgcagct caagttgctg ttggaatggg catacctctt   1440
tggcagattc cagaaatcag acgtttctat ggaatggact atggaggagg gtatgacatt   1500
tggaggaaaa cagcagctct tgctacacca tttaattttg atgaagtaga ttctcaatgg   1560
ccaaagggcc attgtgtagc agttagaatt actagtgagg acccagatga tggtttcaaa   1620
cctactggtg ggaaagtgaa ggagataagt tttaaaagca agcctaatgt ttgggcctac   1680
ttctcagtaa agtctggtgg aggcattcat gaatttgctg attctcagtt cggacatgtt   1740
tttgcatatg ggctctctag atcagcagca ataacaaaca tgactcttgc attaaaagag   1800
attcaaattc gtggagaaat tcattcaaat gttgattaca cagttgacct cttaaatgct   1860
tcagacttta gagaaaacaa gattcatact ggttggctcg acaccagaat agctatgcgt   1920
gttcaagctg agaggccccc atggtatatt tcagtggttg ggggtgcttt atataaaaca   1980
gtaaccacca atgcagccac tgtttctgaa tatgttagtt atctcaccaa gggccagatt   2040
ccaccaaagc atatatccct tgtcaattct acagttaatt tgaatataga agggagcaaa   2100
tacacaattg aaactgtaag gactggacat ggtagctaca ggttgagaat gaatgattca   2160
acagttgaag cgaatgtaca atctttatgt gatggtggcc tcttaatgca gttggatgga   2220
aacagccatg taatttatgc agaagaagaa gctggtggta cacggcttca gattgatgga   2280
aagacatgtt tattgcagaa tgaccatgat ccatcaaagt tattagctga gacaccctgc   2340
aaacttcttc gttccttggt tgctgatggt gctcatgttg atgcggatgt accatacgcg   2400
gaagttgagg ttatgaagat gtgcatgcct ctcttgtcgc ctgcttctgg tgtcattcat   2460
tgtatgatgt ctgagggcca ggcattgcag gctggtgatc ttatagcaag gttggatctt   2520
gatgacccct tctgctgtgaa aagagctgag ccatttgatg gaatatttcc acaaatggag   2580
ctccctgttg ctgtctctag tcaagtacac aaaagatatg ctgcaagttt gaatgctgct   2640
cgaatggtcc ttgcaggata tgagcacaat attaatgaag tcgttcaaga tttggtatgc   2700
```

```
tgcctggaca accctgagct tcctttccta cagtgggatg aacttatgtc tgttctagca   2760
acgaggcttc aagaaatct caagagtgag ttagaggata aatacaagga atacaagttg    2820 aattttacc atggaaaaaa cgaggacttt ccatccaagt tgctaagaga catcattgag    2880
gaaaatcttt cttatggttc agagaaggaa aaggctacaa atgagaggct tgttgagcct   2940
cttatgaacc tactgaagtc atatgagggt gggagagaga gccatgcaca ttttgttgtc   3000
aagtctcttt tcgaggagta tcttacagtg gaagaacttt ttagtgatgg cattcagtct   3060
gacgtgattg aaacattgcg gcatcagcac agtaaagacc tgcagaaggt tgtagacatt   3120
gtgttgtctc accagggtgt gaggaacaaa gctaagcttg taacggcact tatgaaaaag   3180
ctggtttatc caaatcctgg tggttacagg gatctgttag ttcgcttttc ttccctcaat   3240
cataaaagat attataagtt ggcccttaaa gcaagtgaac ttcttgaaca aaccaaacta   3300
agtgaactcc gtgcaagcgt tgcaagaagc ctttcggatc tggggatgca taagggagaa   3360
atgagtatta aggataacat ggaagattta gtctctgccc cattacctgt tgaagatgct   3420
ctgatttctt tgtttgatta cagtgatcga actgttcagc agaaagtgat tgagacatac   3480
atatcacgat tgtaccagcc tcatcttgta aaggatagca tccaaatgaa attcaaggaa   3540
tctggtgcta ttacttttttg ggaattttat gaagggcatg ttgatactag aaatggacat   3600
ggggctatta ttggtgggaa gcgatggggt gccatggtcg ttctcaaatc acttgaatct   3660
gcgtcaacag ccattgtggc tgcattaaag gattcggcac agttcaacag ctctgagggc   3720
aacatgatgc acattgcatt attgagtgct gaaaatgaaa gtaatataag tggaataagt   3780
gatgatcaag ctcaacataa gatggaaaag cttagcaaga tactgaagga tactagcgtt   3840
gcaagtgatc tccaagctgc tggtttgaag gttataagtt gcattgttca aagagatgaa   3900
gctcgcatgc caatgcgcca cacattcctc tggttggatg acaagagttg ttatgaagaa   3960
gagcagattc tccggcatgt ggagcctccc ctctctacac ttcttgaatt ggataagttg   4020
aaggtgaaag gatacaatga aatgaagtat actccttcgc gtgaccgcca atggcatatc   4080
tacacactaa gaaatactga aaacccccaaa atgttgcata gggtgttttt ccgaactatt   4140
gtcaggcaac ccaatgcagg caacaagttt acatcggctc agatcagcga cgctgaagta   4200
ggatgtcccg aagaatctct ttcatttaca tcaaatagca tcttaagatc attgatgact   4260
gctattgaag aattagagct tcatgcaatt aggacaggtc attctcacat gtatttgtgc   4320
atactgaaag agcaaaagct tcttgacctc attccatttt cagggagtac aattgttgat   4380
gttggccaag atgaagctac cgcttgttca ctttttaaaat caatggcttt gaagatacat   4440
gagcttgttg gtgcaaggat gcatcatctg tctgtatgcc agtgggaggt gaaactcaag   4500
ttggactgtg atggccctgc aagtggtacc tggagagttg taactacaaa tgttactggt   4560
cacacctgca ccattgatat ataccgagaa gtggaggaaa tagaatcgca gaagttagtg   4620
taccattcag ccacttcgtc agctggacca ttgcatggtg ttgcactgaa taatccatat   4680
caacctttga gtgtgattga tctaaagcgc tgctctgcta ggaacaacag aacaacatat   4740
tgctatgatt ttccgctggc ctttgaaact gcactgcaga agtcatggca gaccaatggc   4800
tctactgttt ctgaaggcaa tgaaaatagt aaatcctacg tgaaggcaac tgagctagtg   4860
tttgctgaaa acatgggtc ctggggcact cctataattc cgatggaacg ccctgctggg   4920
ctcaacgaca ttggtatggt cgcttggatc atggagatgt caacacctga atttcccaat   4980
ggcaggcaga ttattgttgt agcaaatgat atcacttttca gagctggatc atttggccca   5040
```

```
aggggaagatg catttttttga aactgtcact aacctggctt gcgaaaggaa acttcctctt    5100
atatacttgg cagcaaactc tggtgctagg attggcatag ctgatgaagt aaaatcttgc    5160
ttccgtgttg gatggtctga cgaaggcagt cctgaacgag ggtttcagta catctatctg    5220
actgaagaag actatgctcg cattagctct tctgttatag cacataagct ggagctagat    5280
agtggtgaaa ttaggtggat tattgactct gttgtgggca aggaggatgg gcttggtgtc    5340
gagaacatac atggaagtgc tgctattgcc agtgcttatt ctagggcata tgaggagaca    5400
tttacactta catttgtgac tgggcggact gtaggaatag gagcttatct tgctcgactt    5460
ggtatacggt gcatacagcg tcttgaccag cctattattt taacagggtt ttctgccctg    5520
aacaagctcc ttgggcggga agtgtacagc tcccacatgc agcttggtgg tcctaagatc    5580
atggcgacta atggtgttgt ccacctcact gttccagatg accttgaagg tgtttccaat    5640
atattgaggt ggctcagcta tgttcctgca acattggtg gacctcttcc tattaccaaa    5700
cctctggacc ctccagacag acctgttgct tacatccctg agaacacatg cgatccacgt    5760
gcagctatct gtggtgtaga tgacagccaa gggaaatggt tgggtggtat gtttgacaaa    5820
gacagctttg tggagacatt tgaaggatgg gcaaaaacag tggttactgg cagagcaaag    5880
cttggaggaa ttcctgtggg cgtcatagct gtggagacac agaccatgat gcagatcatc    5940
cctgctgatc caggtcagct tgattcccat gagcgatctg tccctcgtgc tggacaagtg    6000
tggttcccag attctgcaac caagaccgct caggcattat tagacttcaa ccgtgaagga    6060
ttgcctctgt tcatcctggc taattggaga ggcttctctg gtggacaaag agatctcttt    6120
gaaggaattc ttcaggctgg gtcaacaatt gtcgagaacc ttaggacata taatcagcct    6180
gcttttgtgt acattcctat ggctggagag cttcgtggag gagcttgggt tgtggtcgat    6240
agcaaaataa atccagaccg cattgagtgt tatgctgaaa ggactgccaa aggtaatgtt    6300
ctcgaacctc aagggttaat tgaaatcaag ttcaggtcag aggaactcca agactgtatg    6360
ggtaggcttg acccagagtt gataaatctg aaagcaaaac tccaagatgt aaatcatgga    6420
aatggaagtc taccagacat agaagggatt cggaagagta tagaagcacg tacgaaacag    6480
ttgctgcctt tatatacccca gattgcaata cggtttgctg aattgcatga tacttccctta    6540 agaatggcag ctaaaggtgt gattaagaaa gttgtagact gggaagaatc acgctcgttc    6600
ttctataaaa ggctacggag gaggatcgca gaagatgttc ttgcaaaaga ataaggcag    6660 atagtcggtg ataaatttac gcaccaatta gcaatggagc tcatcaagga atggtacctt    6720
gcttctcagg ccacaacagg aagcactgga tgggatgacg atgatgcttt tgttgcctgg    6780
aaggacagtc ctgaaaacta caaggggcat atccaaaagc ttagggctca aaaagtgtct    6840
cattcgctct ctgatcttgc tgactccagt tcagatctgc aagcattctc gcagggtctt    6900
tctacgctat tagataagat ggatccctct cagagagcga agtttgttca ggaagtcaag    6960
aaggtccttg attga                                                      6975
```

<210> SEQ ID NO 14  
<211> LENGTH: 2324  
<212> TYPE: PRT  
<213> ORGANISM: Zea mays

<400> SEQUENCE: 14

Met Ser Gln Leu Gly Leu Ala Ala Ala Ala Ser Lys Ala Leu Pro Leu  
1               5                   10                  15

Leu Pro Asn Arg Gln Arg Ser Ser Ala Gly Thr Thr Phe Ser Ser Ser  
            20                  25                  30

```
Ser Leu Ser Arg Pro Leu Asn Arg Arg Lys Ser Arg Thr Arg Ser Leu
        35                  40                  45

Arg Asp Gly Gly Asp Gly Val Ser Asp Ala Lys Lys His Ser Gln Ser
50                  55                  60

Val Arg Gln Gly Leu Ala Gly Ile Ile Asp Leu Pro Ser Glu Ala Pro
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Ile Asn Glu Thr His Asn Gly Arg
                100                 105                 110

His Ala Ser Val Ser Lys Val Val Glu Phe Cys Ala Ala Leu Gly Gly
            115                 120                 125

Lys Thr Pro Ile His Ser Ile Leu Val Ala Asn Asn Gly Met Ala Ala
        130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Met Ala Gln Lys Leu Gly Val Ser Ala Val Trp Pro Gly Trp Gly
210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Ala Trp Ser Gly Ser His Val Glu Val Pro Leu Glu Cys Cys Leu Asp
        275                 280                 285

Ala Ile Pro Glu Glu Met Tyr Arg Lys Ala Cys Val Thr Thr Thr Glu
290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Val Met Arg Leu Ala Ser Gln Ser Arg His Leu Glu
        355                 360                 365

Val Gln Leu Leu Cys Asp Gln Tyr Gly Asn Val Ala Ala Leu His Ser
370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Asp Tyr Phe Leu Glu Leu
        435                 440                 445
```

Asn Pro Arg Leu Gln Val Glu His Pro Val Thr Glu Trp Ile Ala Glu
450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
            485                 490                 495

Gly Tyr Asp Ile Trp Arg Lys Thr Ala Ala Leu Ala Thr Pro Phe Asn
                500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Thr Leu Ala Leu Lys Glu Ile Gln Ile Arg Gly Glu Ile His
                595                 600                 605

Ser Asn Val Asp Tyr Thr Val Asp Leu Leu Asn Ala Ser Asp Phe Arg
610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
            645                 650                 655

Leu Tyr Lys Thr Val Thr Thr Asn Ala Ala Thr Val Ser Glu Tyr Val
                660                 665                 670

Ser Tyr Leu Thr Lys Gly Gln Ile Pro Pro Lys His Ile Ser Leu Val
        675                 680                 685

Asn Ser Thr Val Asn Leu Asn Ile Glu Gly Ser Lys Tyr Thr Ile Glu
690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
            725                 730                 735

Gln Leu Asp Gly Asn Ser His Val Ile Tyr Ala Glu Glu Ala Gly
                740                 745                 750

Gly Thr Arg Leu Gln Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
            805                 810                 815

Gly Val Ile His Cys Met Met Ser Glu Gly Gln Ala Leu Gln Ala Gly
                820                 825                 830

Asp Leu Ile Ala Arg Leu Asp Leu Asp Asp Pro Ser Ala Val Lys Arg
        835                 840                 845

Ala Glu Pro Phe Asp Gly Ile Phe Pro Gln Met Glu Leu Pro Val Ala
850                 855                 860

Val Ser Ser Gln Val His Lys Arg Tyr Ala Ala Ser Leu Asn Ala Ala

-continued

```
865                 870                 875                 880
Arg Met Val Leu Ala Gly Tyr Glu His Asn Ile Asn Glu Val Val Gln
                885                 890                 895
Asp Leu Val Cys Cys Leu Asp Asn Pro Glu Leu Pro Phe Leu Gln Trp
                900                 905                 910
Asp Glu Leu Met Ser Val Leu Ala Thr Arg Leu Pro Arg Asn Leu Lys
                915                 920                 925
Ser Glu Leu Glu Asp Lys Tyr Lys Glu Tyr Lys Leu Asn Phe Tyr His
    930                 935                 940
Gly Lys Asn Glu Asp Phe Pro Ser Lys Leu Leu Arg Asp Ile Ile Glu
945                 950                 955                 960
Glu Asn Leu Ser Tyr Gly Ser Glu Lys Glu Lys Ala Thr Asn Glu Arg
                965                 970                 975
Leu Val Glu Pro Leu Met Asn Leu Leu Lys Ser Tyr Glu Gly Gly Arg
                980                 985                 990
Glu Ser His Ala His Phe Val Val Lys Ser Leu Phe Glu Glu Tyr Leu
                995                1000                1005
Thr Val Glu Glu Leu Phe Ser Asp Gly Ile Gln Ser Asp Val Ile
    1010                1015                1020
Glu Thr Leu Arg His Gln His Ser Lys Asp Leu Gln Lys Val Val
    1025                1030                1035
Asp Ile Val Leu Ser His Gln Gly Val Arg Asn Lys Ala Lys Leu
    1040                1045                1050
Val Thr Ala Leu Met Glu Lys Leu Val Tyr Pro Asn Pro Gly Gly
    1055                1060                1065
Tyr Arg Asp Leu Leu Val Arg Phe Ser Ser Leu Asn His Lys Arg
    1070                1075                1080
Tyr Tyr Lys Leu Ala Leu Lys Ala Ser Glu Leu Leu Glu Gln Thr
    1085                1090                1095
Lys Leu Ser Glu Leu Arg Ala Ser Val Ala Arg Ser Leu Ser Asp
    1100                1105                1110
Leu Gly Met His Lys Gly Glu Met Ser Ile Lys Asp Asn Met Glu
    1115                1120                1125
Asp Leu Val Ser Ala Pro Leu Pro Val Glu Asp Ala Leu Ile Ser
    1130                1135                1140
Leu Phe Asp Tyr Ser Asp Arg Thr Val Gln Gln Lys Val Ile Glu
    1145                1150                1155
Thr Tyr Ile Ser Arg Leu Tyr Gln Pro His Leu Val Lys Asp Ser
    1160                1165                1170
Ile Gln Met Lys Phe Lys Glu Ser Gly Ala Ile Thr Phe Trp Glu
    1175                1180                1185
Phe Tyr Glu Gly His Val Asp Thr Arg Asn Gly His Gly Ala Ile
    1190                1195                1200
Ile Gly Gly Lys Arg Trp Gly Ala Met Val Val Leu Lys Ser Leu
    1205                1210                1215
Glu Ser Ala Ser Thr Ala Ile Val Ala Ala Leu Lys Asp Ser Ala
    1220                1225                1230
Gln Phe Asn Ser Ser Glu Gly Asn Met Met His Ile Ala Leu Leu
    1235                1240                1245
Ser Ala Glu Asn Glu Ser Asn Ile Ser Gly Ile Ser Asp Asp Gln
    1250                1255                1260
Ala Gln His Lys Met Glu Lys Leu Ser Lys Ile Leu Lys Asp Thr
    1265                1270                1275
```

```
Ser Val Ala Ser Asp Leu Gln Ala Ala Gly Leu Lys Val Ile Ser
    1280            1285            1290

Cys Ile Val Gln Arg Asp Glu Ala Arg Met Pro Met Arg His Thr
    1295            1300            1305

Phe Leu Trp Leu Asp Asp Lys Ser Cys Tyr Glu Glu Gln Ile
    1310            1315            1320

Leu Arg His Val Glu Pro Pro Leu Ser Thr Leu Glu Leu Asp
    1325            1330            1335

Lys Leu Lys Val Lys Gly Tyr Asn Glu Met Lys Tyr Thr Pro Ser
    1340            1345            1350

Arg Asp Arg Gln Trp His Ile Tyr Thr Leu Arg Asn Thr Glu Asn
    1355            1360            1365

Pro Lys Met Leu His Arg Val Phe Phe Arg Thr Ile Val Arg Gln
    1370            1375            1380

Pro Asn Ala Gly Asn Lys Phe Thr Ser Ala Gln Ile Ser Asp Ala
    1385            1390            1395

Glu Val Gly Cys Pro Glu Glu Ser Leu Ser Phe Thr Ser Asn Ser
    1400            1405            1410

Ile Leu Arg Ser Leu Met Thr Ala Ile Glu Glu Leu Glu Leu His
    1415            1420            1425

Ala Ile Arg Thr Gly His Ser His Met Tyr Leu Cys Ile Leu Lys
    1430            1435            1440

Glu Gln Lys Leu Leu Asp Leu Ile Pro Phe Ser Gly Ser Thr Ile
    1445            1450            1455

Val Asp Val Gly Gln Asp Glu Ala Thr Ala Cys Ser Leu Leu Lys
    1460            1465            1470

Ser Met Ala Leu Lys Ile His Glu Leu Val Gly Ala Arg Met His
    1475            1480            1485

His Leu Ser Val Cys Gln Trp Glu Val Lys Leu Lys Leu Asp Cys
    1490            1495            1500

Asp Gly Pro Ala Ser Gly Thr Trp Arg Val Val Thr Thr Asn Val
    1505            1510            1515

Thr Gly His Thr Cys Thr Ile Asp Ile Tyr Arg Glu Val Glu Glu
    1520            1525            1530

Ile Glu Ser Gln Lys Leu Val Tyr His Ser Ala Thr Ser Ser Ala
    1535            1540            1545

Gly Pro Leu His Gly Val Ala Leu Asn Asn Pro Tyr Gln Pro Leu
    1550            1555            1560

Ser Val Ile Asp Leu Lys Arg Cys Ser Ala Arg Asn Asn Arg Thr
    1565            1570            1575

Thr Tyr Cys Tyr Asp Phe Pro Leu Ala Phe Glu Thr Ala Leu Gln
    1580            1585            1590

Lys Ser Trp Gln Thr Asn Gly Ser Thr Val Ser Glu Gly Asn Glu
    1595            1600            1605

Asn Ser Lys Ser Tyr Val Lys Ala Thr Glu Leu Val Phe Ala Glu
    1610            1615            1620

Lys His Gly Ser Trp Gly Thr Pro Ile Ile Pro Met Glu Arg Pro
    1625            1630            1635

Ala Gly Leu Asn Asp Ile Gly Met Val Ala Trp Ile Met Glu Met
    1640            1645            1650

Ser Thr Pro Glu Phe Pro Asn Gly Arg Gln Ile Ile Val Val Ala
    1655            1660            1665
```

-continued

```
Asn Asp Ile Thr Phe Arg Ala Gly Ser Phe Gly Pro Arg Glu Asp
    1670                1675                1680

Ala Phe Phe Glu Thr Val Thr Asn Leu Ala Cys Glu Arg Lys Leu
    1685                1690                1695

Pro Leu Ile Tyr Leu Ala Ala Asn Ser Gly Ala Arg Ile Gly Ile
    1700                1705                1710

Ala Asp Glu Val Lys Ser Cys Phe Arg Val Gly Trp Ser Asp Glu
    1715                1720                1725

Gly Ser Pro Glu Arg Gly Phe Gln Tyr Ile Tyr Leu Thr Glu Glu
    1730                1735                1740

Asp Tyr Ala Arg Ile Ser Ser Ser Val Ile Ala His Lys Leu Glu
    1745                1750                1755

Leu Asp Ser Gly Glu Ile Arg Trp Ile Ile Asp Ser Val Val Gly
    1760                1765                1770

Lys Glu Asp Gly Leu Gly Val Glu Asn Ile His Gly Ser Ala Ala
    1775                1780                1785

Ile Ala Ser Ala Tyr Ser Arg Ala Tyr Glu Glu Thr Phe Thr Leu
    1790                1795                1800

Thr Phe Val Thr Gly Arg Thr Val Gly Ile Gly Ala Tyr Leu Ala
    1805                1810                1815

Arg Leu Gly Ile Arg Cys Ile Gln Arg Leu Asp Gln Pro Ile Ile
    1820                1825                1830

Leu Thr Gly Phe Ser Ala Leu Asn Lys Leu Leu Gly Arg Glu Val
    1835                1840                1845

Tyr Ser Ser His Met Gln Leu Gly Gly Pro Lys Ile Met Ala Thr
    1850                1855                1860

Asn Gly Val Val His Leu Thr Val Pro Asp Asp Leu Glu Gly Val
    1865                1870                1875

Ser Asn Ile Leu Arg Trp Leu Ser Tyr Val Pro Ala Asn Ile Gly
    1880                1885                1890

Gly Pro Leu Pro Ile Thr Lys Pro Leu Asp Pro Pro Asp Arg Pro
    1895                1900                1905

Val Ala Tyr Ile Pro Glu Asn Thr Cys Asp Pro Arg Ala Ala Ile
    1910                1915                1920

Cys Gly Val Asp Asp Ser Gln Gly Lys Trp Leu Gly Gly Met Phe
    1925                1930                1935

Asp Lys Asp Ser Phe Val Glu Thr Phe Glu Gly Trp Ala Lys Thr
    1940                1945                1950

Val Val Thr Gly Arg Ala Lys Leu Gly Gly Ile Pro Val Gly Val
    1955                1960                1965

Ile Ala Val Glu Thr Gln Thr Met Met Gln Ile Ile Pro Ala Asp
    1970                1975                1980

Pro Gly Gln Leu Asp Ser His Glu Arg Ser Val Pro Arg Ala Gly
    1985                1990                1995

Gln Val Trp Phe Pro Asp Ser Ala Thr Lys Thr Ala Gln Ala Leu
    2000                2005                2010

Leu Asp Phe Asn Arg Glu Gly Leu Pro Leu Phe Ile Leu Ala Asn
    2015                2020                2025

Trp Arg Gly Phe Ser Gly Gly Gln Arg Asp Leu Phe Glu Gly Ile
    2030                2035                2040

Leu Gln Ala Gly Ser Thr Ile Val Glu Asn Leu Arg Thr Tyr Asn
    2045                2050                2055

Gln Pro Ala Phe Val Tyr Ile Pro Met Ala Gly Glu Leu Arg Gly
```

```
                2060                2065                2070
Gly Ala Trp Val Val Val Asp Ser Lys Ile Asn Pro Asp Arg Ile
    2075                2080                2085

Glu Cys Tyr Ala Glu Arg Thr Ala Lys Gly Asn Val Leu Glu Pro
    2090                2095                2100

Gln Gly Leu Ile Glu Ile Lys Phe Arg Ser Glu Glu Leu Gln Asp
    2105                2110                2115

Cys Met Gly Arg Leu Asp Pro Glu Leu Ile Asn Leu Lys Ala Lys
    2120                2125                2130

Leu Gln Asp Val Asn His Gly Asn Gly Ser Leu Pro Asp Ile Glu
    2135                2140                2145

Gly Ile Arg Lys Ser Ile Glu Ala Arg Thr Lys Gln Leu Leu Pro
    2150                2155                2160

Leu Tyr Thr Gln Ile Ala Ile Arg Phe Ala Glu Leu His Asp Thr
    2165                2170                2175

Ser Leu Arg Met Ala Ala Lys Gly Val Ile Lys Lys Val Val Asp
    2180                2185                2190

Trp Glu Glu Ser Arg Ser Phe Phe Tyr Lys Arg Leu Arg Arg Arg
    2195                2200                2205

Ile Ala Glu Asp Val Leu Ala Lys Glu Ile Arg Gln Ile Val Gly
    2210                2215                2220

Asp Lys Phe Thr His Gln Leu Ala Met Glu Leu Ile Lys Glu Trp
    2225                2230                2235

Tyr Leu Ala Ser Gln Ala Thr Thr Gly Ser Thr Gly Trp Asp Asp
    2240                2245                2250

Asp Asp Ala Phe Val Ala Trp Lys Asp Ser Pro Glu Asn Tyr Lys
    2255                2260                2265

Gly His Ile Gln Lys Leu Arg Ala Gln Lys Val Ser His Ser Leu
    2270                2275                2280

Ser Asp Leu Ala Asp Ser Ser Ser Asp Leu Gln Ala Phe Ser Gln
    2285                2290                2295

Gly Leu Ser Thr Leu Leu Asp Lys Met Asp Pro Ser Gln Arg Ala
    2300                2305                2310

Lys Phe Val Gln Glu Val Lys Lys Val Leu Asp
    2315                2320

<210> SEQ ID NO 15
<211> LENGTH: 6936
<212> TYPE: DNA
<213> ORGANISM: Triticum aestivum

<400> SEQUENCE: 15
atgggatcca cacatttgcc cattgtcggc cttaatgcct cgacaacacc atcgctatcc      60
actattcgcc cggtaaattc agccggtgct gcattccaac catctgcccc ttctagaacc     120
tccaagaaga aaagtcgtcg tgttcagtca ttaaggatg gaggcgatgg aggcgtgtca     180
gaccctaacc agtctattcg ccaaggtctt gccggcatca ttgacctccc aaaggagggc     240
acatcagctc cggaagtgga tatttcacat gggtccgaag aacccagggg ctcctaccaa     300
atgaatggga tactgaatga agcacataat ggaggcatg cttcgctgtc taaggttgtc     360
gaattttgta tggcattggg cggcaaaaca ccaattcaca gtgtattagt tgcgaacaat     420
ggaatggcag cagctaagtt catgcggagt gtccgaacat gggctaatga aacatttggg     480
tcagagaagg caattcagtt gatagctatg gctactccag aagacatgag gataaatgca     540
```

```
gagcacatta gaattgctga tcaatttgtt gaagtacccg gtggaacaaa caataacaac      600
tatgcaaatg tccaactcat agtggagata gcagtgagaa ccggtgtttc tgctgtttgg      660
cctggttggg gccatgcatc tgagaatcct gaacttccag atgcactaaa tgcaaacgga      720 attgttttc ttgggccacc atcatcatca atgaacgcac taggtgacaa ggttggttca       780
gctctcattg ctcaagcagc aggggttccg actcttcctt ggagtggatc acaggtggaa      840
attccattag aagtttgttt ggactcgata cccgcggaga tgtataggaa agcttgtgtt      900
agtactacgg aggaagcact tgcgagttgt cagatgattg ggtatcccgc catgattaaa      960
gcatcatggg gtggtggtgg taaagggatc cgaaaggtta ataatgacga tgatgtcaga     1020
gcactgttta agcaagtgca aggtgaagtt cctggctccc caatatttat catgagactt     1080
gcatctcaga gtcgacatct tgaagttcag ttgctttgtg atcaatatgg caatgtagct     1140
gcgcttcaca gtcgtgactg cagtgtgcaa cggcgacacc aaaagattat tgaggaagga     1200
ccagttactg ttgctcctcg cgagacagtg aaagagctag agcaagcagc aaggaggctt     1260
gctaaggctg tgggttatgt tggtgctgct actgttgaat atctctacag catggagact     1320
ggtgaatact attttctgga acttaatcca cggttgcagg ttgagcatcc agtcaccgag     1380
tggatagctg aagtaaactt gcctgcagct caagttgcag ttggaatggg tatacccctt     1440
tggcaggttc cagagatcag acgtttctat ggaatggaca atggaggagg ctatgacatt     1500
tggaggaaaa cagcagctct tgctactcca tttaacttcg atgaagtgga ttctcaatgg     1560
ccaaagggtc attgtgtagc agttaggata accagtgagg atccagatga cggattcaag     1620
cctaccggtg gaaaagtaaa ggagatcagt tttaaaagca agccaaatgt ttgggcctat     1680
ttctctgtta agtccggtgg aggcattcat gaatttgctg attctcagtt tggacatgtt     1740
tttgcatatg gagtgtctag agcagcagca ataaccaaca tgtctcttgc gctaaaagag     1800
attcaaattc gtggagaaat tcattcaaat gttgattaca cagttgatct cttgaatgcc     1860
tcagacttca agaaaacag gattcatact ggctggctgg ataacagaat agcaatgcga     1920
gtccaagctg agagacctcc gtggtatatt tcagtggttg gaggagctct atataaaaca     1980
ataacgagca cacagacac tgtttctgaa tatgttagct atctcgtcaa gggtcagatt     2040
ccaccgaagc atatatccct tgtccattca actgtttctt tgaatataga ggaaagcaaa     2100
tatacaattg aaactataag gagcggacag ggtagctaca gattgcgaat gaatggatca     2160
gttattgaag caaatgtcca aacattatgt gatggtggac ttttaatgca gttggatgga     2220
aacagccatg taattatgc tgaagaagag gccgtggta cacggcttct aattgatgga      2280
aagacatgct tgttacagaa tgatcacgat ccttcaaggt tattagctga gacaccctgc     2340
aaacttcttc gtttcttggt tgccgatggt gctcatgttg aagctgatgt accatatgcg     2400
gaagttgagg ttatgaagat gtgcatgccc ctcttgtcac ctgctgctgg tgtcattaat     2460
gttttgttgt ctgagggcca gcctatgcag gctggtgatc ttatagcaag acttgatctt     2520 gatgacccctt ctgctgtgaa gagagctgag ccatttaacg atctttccc agaaatgagc     2580 cttcctattg ctgcttctgg ccaagttcac aaaagatgtg ccacaagctt gaatgctgct     2640
cggatggtcc ttgcaggata tgatcacccg atcaacaaag ttgtacaaga tctggtatcc     2700
tgtctagatg ctcctgagct tccttttccta caatgggaag agcttatgtc tgttttagca     2760
actagacttc caaggcttct taagagcgag ttggagggta aatacagtga atataagtta     2820
aatgttggcc atgggaagag caaggatttc ccttccaaga tgctaagaga gataatcgag     2880
gaaaatcttg cacatggttc tgagaaggaa attgctacaa atgagaggct tgttgagcct     2940
```

```
cttatgagcc tactgaagtc atatgagggt ggcagagaaa gccatgcaca ctttattgtg    3000
aagtcccttt tcgaggacta tctctcggtt gaggaactat tcagtgatgg cattcagtct    3060
gatgtgattg aacgcctgcg ccaacaacat agtaaagatc tccagaaggt tgtagacatt    3120
gtgttgtctc accagggtgt gagaaacaaa actaagctga tactaacact catggagaaa    3180
ctggtctatc caaaccctgc tgtctacaag gatcagttga ctcgcttttc ctccctcaat    3240
cacaaaagat attataagtt ggcccttaaa gctagcgagc ttcttgaaca aaccaagctt    3300
agtgagctcc gcacaagcat tgcaaggagc ctttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattatacca gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat gcgccatacc    3900
ttcctcttgt cggatgaaaa gctttgttat gaggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatataca cacttagaaa tacagagaac    4080
cccaaaatgt tgcacagggt gtttttccga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
gcgattagga caggtcactc tcatatgttt ttgtgcatat tgaaagagca aaagcttctt    4320
gatcttgttc ccgtttcagg gaacaaagtt gtggatattg gccaagatga agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggtcg aagatacaga atcacagaaa ctagtgtacc actctgctcc atcgtcatct    4620
ggtcctttgc atggcgttgc actgaatact ccatatcagc ctttgagtgt tattgatctg    4680
aaacgttgct ccgctagaaa taacagaact acatactgct atgattttcc gttggcattt    4740
gaaactgcag tgcagaagtc atggtctaac atttctagtg cactaaccg atgttatgtt    4800
aaagcgacgg agctggtgtt tgctcacaag aacgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tacttttaga    4980
gctggatcgt ttggtccaag ggaagatgca ttttttgaaa ctgttaccaa cctagcttgt    5040
gagaggaagc ttcctctcat ctacttggca gcaaactctg gtgctcggat cggcatagca    5100
gatgaagtaa atcttgctt ccgtgttgga tggtctgatg atggcagccc tgaacgtggg    5160
tttcaatata tttatctgac tgaagaagac catgctcgta ttagcgcttc tgttatagcg    5220
cacaagatgc agcttgataa tggtgaaatt aggtgggtta ttgattctgt tgtagggaag    5280
```

```
gaggatgggc taggtgtgga aacatacat ggaagtgctg ctattgccag tgcctattct    5340
agggcctatg aggagacatt tacgcttaca tttgtgactg aaggactgt tggaatagga    5400
gcatatcttg ctcgacttgg catacggtgc atacagcgta ctgaccagcc cattatccta    5460
actgggttct ctgccttgaa caagcttctt ggccgggaag tttacagctc ccacatgcag    5520
ttgggtggcc ccaaaattat ggcgacaaac ggtgttgtcc atctgacagt ttcagatgac    5580
cttgaaggtg tatctaatat attgaggtgg ctcagctatg ttcctgccaa cattggtgga    5640
cctcttccta ttacaaaatc tttggaccca cctgacagac ccgttgctta catccctgag    5700
aatacatgcg atcctcgtgc tgccatcagt ggcattgatg atagccaagg gaaatggttg    5760
gggggcatgt tcgacaaaga cagttttgtg agacatttg aaggatgggc gaagtcagtt    5820
gttactggca gagcgaaact cggagggatt ccggtgggtg ttatagctgt ggagacacag    5880
actatgatgc agctcatccc tgctgatcca ggccagcttg attcccatga gcgatctgtt    5940
cctcgtgctg ggcaagtctg gtttccagat tcagctacta agacagcgca ggcaatgctg    6000
gacttcaacc gtgaaggatt acctctgttc atccttgcta actggagagg cttctctggt    6060
ggacaaagag atcttttttga aggaatcctt caggctgggt caacaattgt tgagaaccctt   6120
aggacataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct cgaacctcaa gggttgatcg agatcaagtt caggtcagag    6300
gaactccaag agtgcatggg taggcttgat ccagaattga taaatctgaa ggcaaagctc    6360
cagggagtaa agcatgaaaa tggaagtcta cctgagtcag aatcccttca gaagagcata    6420
gaagcccgga gaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcgttctt ctacaagaga ttacggagga ggatatccga ggatgttctt    6600
gcgaaggaaa ttagaggtgt aagtggcaag cagtttttctc accaatcggc aatcgagctg    6660
atccagaaat ggtacttggc ctctaaggga gctgaaacag gaagcactga atgggatgat    6720
gacgatgctt tgttgcctg gagggaaaac cctgaaaact accaggagta tatcaaagaa    6780
ctcagggctc aaagggtatc tcagttgctc tcagatgttg cagactccag tccagatcta    6840
gaagccttgc cacagggtct ttctatgcta ttagagaaga tggatccctc aaggagagca    6900
cagtttgttg aggaagtcaa gaaagtccct aaatga                              6936
```

<210> SEQ ID NO 16
<211> LENGTH: 2311
<212> TYPE: PRT
<213> ORGANISM: Triticum aestivum

<400> SEQUENCE: 16

Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

```
Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
            115                 120                 125

Lys Thr Pro Ile His Ser Val Leu Val Ala Asn Asn Gly Met Ala Ala
130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
            195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
                260                 265                 270

Pro Trp Ser Gly Ser Gln Val Glu Ile Pro Leu Glu Val Cys Leu Asp
            275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
    355                 360                 365

Val Gln Leu Leu Cys Asp Gln Tyr Gly Asn Val Ala Ala Leu His Ser
    370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
            435                 440                 445

Asn Pro Arg Leu Gln Val Glu His Pro Val Thr Glu Trp Ile Ala Glu
        450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Lys Thr Ala Ala Leu Ala Thr Pro Phe Asn
```

-continued

```
                500             505             510
Phe Asp Glu Val Asp Ser Gln Trp Pro Lys Gly His Cys Val Ala Val
            515             520             525
Arg Ile Thr Ser Glu Asp Pro Asp Gly Phe Lys Pro Thr Gly Gly
        530             535             540
Lys Val Lys Glu Ile Ser Phe Lys Ser Lys Pro Asn Val Trp Ala Tyr
545             550             555             560
Phe Ser Val Lys Ser Gly Gly Ile His Glu Phe Ala Asp Ser Gln
                565             570             575
Phe Gly His Val Phe Ala Tyr Gly Val Ser Arg Ala Ala Ala Ile Thr
            580             585             590
Asn Met Ser Leu Ala Leu Lys Glu Ile Gln Ile Arg Gly Glu Ile His
        595             600             605
Ser Asn Val Asp Tyr Thr Val Asp Leu Leu Asn Ala Ser Asp Phe Lys
        610             615             620
Glu Asn Arg Ile His Thr Gly Trp Leu Asp Asn Arg Ile Ala Met Arg
625             630             635             640
Val Gln Ala Glu Arg Pro Pro Trp Tyr Ile Ser Val Val Gly Gly Ala
            645             650             655
Leu Tyr Lys Thr Ile Thr Ser Asn Thr Asp Thr Val Ser Glu Tyr Val
            660             665             670
Ser Tyr Leu Val Lys Gly Gln Ile Pro Pro Lys His Ile Ser Leu Val
        675             680             685
His Ser Thr Val Ser Leu Asn Ile Glu Glu Ser Lys Tyr Thr Ile Glu
        690             695             700
Thr Ile Arg Ser Gly Gln Gly Ser Tyr Arg Leu Arg Met Asn Gly Ser
705             710             715             720
Val Ile Glu Ala Asn Val Gln Thr Leu Cys Asp Gly Gly Leu Leu Met
            725             730             735
Gln Leu Asp Gly Asn Ser His Val Ile Tyr Ala Glu Glu Ala Gly
            740             745             750
Gly Thr Arg Leu Leu Ile Asp Gly Lys Thr Cys Leu Leu Gln Asn Asp
        755             760             765
His Asp Pro Ser Arg Leu Leu Ala Glu Thr Pro Cys Lys Leu Leu Arg
        770             775             780
Phe Leu Val Ala Asp Gly Ala His Val Glu Ala Asp Val Pro Tyr Ala
785             790             795             800
Glu Val Glu Val Met Lys Met Cys Met Pro Leu Leu Ser Pro Ala Ala
                805             810             815
Gly Val Ile Asn Val Leu Leu Ser Glu Gly Gln Pro Met Gln Ala Gly
            820             825             830
Asp Leu Ile Ala Arg Leu Asp Leu Asp Pro Ser Ala Val Lys Arg
            835             840             845
Ala Glu Pro Phe Asn Gly Ser Phe Pro Glu Met Ser Leu Pro Ile Ala
850             855             860
Ala Ser Gly Gln Val His Lys Arg Cys Ala Thr Ser Leu Asn Ala Ala
865             870             875             880
Arg Met Val Leu Ala Gly Tyr Asp His Pro Ile Asn Lys Val Val Gln
            885             890             895
Asp Leu Val Ser Cys Leu Asp Ala Pro Glu Leu Pro Phe Leu Gln Trp
            900             905             910
Glu Glu Leu Met Ser Val Leu Ala Thr Arg Leu Pro Arg Leu Leu Lys
        915             920             925
```

```
Ser Glu Leu Glu Gly Lys Tyr Ser Glu Tyr Lys Leu Asn Val Gly His
    930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Leu Lys Ser Tyr Glu Gly Gly Arg
            980                 985                 990

Glu Ser His Ala His Phe Ile Val  Lys Ser Leu Phe Glu  Asp Tyr Leu
        995                 1000                1005

Ser Val  Glu Glu Leu Phe Ser  Asp Gly Ile Gln Ser   Asp Val Ile
    1010                 1015                1020

Glu Arg  Leu Arg Gln Gln His  Ser Lys Asp Leu Gln  Lys Val Val
    1025                 1030                1035

Asp Ile  Val Leu Ser His Gln  Gly Val Arg Asn Lys   Thr Lys Leu
    1040                 1045                1050

Ile Leu  Thr Leu Met Glu Lys  Leu Val Tyr Pro Asn   Pro Ala Val
    1055                 1060                1065

Tyr Lys  Asp Gln Leu Thr Arg  Phe Ser Ser Leu Asn   His Lys Arg
    1070                 1075                1080

Tyr Tyr  Lys Leu Ala Leu Lys  Ala Ser Glu Leu Leu   Glu Gln Thr
    1085                 1090                1095

Lys Leu  Ser Glu Leu Arg Thr  Ser Ile Ala Arg Ser   Leu Ser Glu
    1100                 1105                1110

Leu Glu  Met Phe Thr Glu Glu  Arg Thr Ala Ile Ser   Glu Ile Met
    1115                 1120                1125

Gly Asp  Leu Val Thr Ala Pro  Leu Pro Val Glu Asp   Ala Leu Val
    1130                 1135                1140

Ser Leu  Phe Asp Cys Ser Asp  Gln Thr Leu Gln Gln   Arg Val Ile
    1145                 1150                1155

Glu Thr  Tyr Ile Ser Arg Leu  Tyr Gln Pro His Leu   Val Lys Asp
    1160                 1165                1170

Ser Ile  Gln Leu Lys Tyr Gln  Glu Ser Gly Val Ile   Ala Leu Trp
    1175                 1180                1185

Glu Phe  Ala Glu Ala His Ser  Glu Lys Arg Leu Gly   Ala Met Val
    1190                 1195                1200

Ile Val  Lys Ser Leu Glu Ser  Val Ser Ala Ala Ile   Gly Ala Ala
    1205                 1210                1215

Leu Lys  Gly Thr Ser Arg Tyr  Ala Ser Ser Glu Gly   Asn Ile Met
    1220                 1225                1230

His Ile  Ala Leu Leu Gly Ala  Asp Asn Gln Met His   Gly Thr Glu
    1235                 1240                1245

Asp Ser  Gly Asp Asn Asp Gln  Ala Gln Val Arg Ile   Asp Lys Leu
    1250                 1255                1260

Ser Ala  Thr Leu Glu Gln Asn  Thr Val Thr Ala Asp   Leu Arg Ala
    1265                 1270                1275

Ala Gly  Val Lys Val Ile Ser  Cys Ile Val Gln Arg   Asp Gly Ala
    1280                 1285                1290

Leu Met  Pro Met Arg His Thr  Phe Leu Leu Ser Asp   Glu Lys Leu
    1295                 1300                1305

Cys Tyr  Glu Glu Glu Pro Val  Leu Arg His Val Glu   Pro Pro Leu
    1310                 1315                1320
```

-continued

```
Ser Ala Leu Leu Glu Leu Gly Lys Leu Lys Val Lys Gly Tyr Asn
1325                1330                1335

Glu Val Lys Tyr Thr Pro Ser Arg Asp Arg Gln Trp Asn Ile Tyr
1340                1345                1350

Thr Leu Arg Asn Thr Glu Asn Pro Lys Met Leu His Arg Val Phe
1355                1360                1365

Phe Arg Thr Leu Val Arg Gln Pro Gly Ala Ser Asn Lys Phe Thr
1370                1375                1380

Ser Gly Asn Ile Ser Asp Val Glu Val Gly Gly Ala Glu Glu Ser
1385                1390                1395

Leu Ser Phe Thr Ser Ser Ser Ile Leu Arg Ser Leu Met Thr Ala
1400                1405                1410

Ile Glu Glu Leu Glu Leu His Ala Ile Arg Thr Gly His Ser His
1415                1420                1425

Met Phe Leu Cys Ile Leu Lys Glu Gln Lys Leu Leu Asp Leu Val
1430                1435                1440

Pro Val Ser Gly Asn Lys Val Val Asp Ile Gly Gln Asp Glu Ala
1445                1450                1455

Thr Ala Cys Leu Leu Leu Lys Glu Met Ala Leu Gln Ile His Glu
1460                1465                1470

Leu Val Gly Ala Arg Met His His Leu Ser Val Cys Gln Trp Glu
1475                1480                1485

Val Lys Leu Lys Leu Asp Ser Asp Gly Pro Ala Ser Gly Thr Trp
1490                1495                1500

Arg Val Val Thr Thr Asn Val Thr Ser His Thr Cys Thr Val Asp
1505                1510                1515

Ile Tyr Arg Glu Val Glu Asp Thr Glu Ser Gln Lys Leu Val Tyr
1520                1525                1530

His Ser Ala Pro Ser Ser Ser Gly Pro Leu His Gly Val Ala Leu
1535                1540                1545

Asn Thr Pro Tyr Gln Pro Leu Ser Val Ile Asp Leu Lys Arg Cys
1550                1555                1560

Ser Ala Arg Asn Asn Arg Thr Thr Tyr Cys Tyr Asp Phe Pro Leu
1565                1570                1575

Ala Phe Glu Thr Ala Val Gln Lys Ser Trp Ser Asn Ile Ser Ser
1580                1585                1590

Asp Thr Asn Arg Cys Tyr Val Lys Ala Thr Glu Leu Val Phe Ala
1595                1600                1605

His Lys Asn Gly Ser Trp Gly Thr Pro Val Ile Pro Met Glu Arg
1610                1615                1620

Pro Ala Gly Leu Asn Asp Ile Gly Met Val Ala Trp Ile Leu Asp
1625                1630                1635

Met Ser Thr Pro Glu Tyr Pro Asn Gly Arg Gln Ile Val Val Ile
1640                1645                1650

Ala Asn Asp Ile Thr Phe Arg Ala Gly Ser Phe Gly Pro Arg Glu
1655                1660                1665

Asp Ala Phe Phe Glu Thr Val Thr Asn Leu Ala Cys Glu Arg Lys
1670                1675                1680

Leu Pro Leu Ile Tyr Leu Ala Ala Asn Ser Gly Ala Arg Ile Gly
1685                1690                1695

Ile Ala Asp Glu Val Lys Ser Cys Phe Arg Val Gly Trp Ser Asp
1700                1705                1710

Asp Gly Ser Pro Glu Arg Gly Phe Gln Tyr Ile Tyr Leu Thr Glu
```

```
                1715                1720                1725

Glu Asp His Ala Arg Ile Ser Ala Ser Val Ile Ala His Lys Met
    1730                1735                1740

Gln Leu Asp Asn Gly Glu Ile Arg Trp Val Ile Asp Ser Val Val
    1745                1750                1755

Gly Lys Glu Asp Gly Leu Gly Val Glu Asn Ile His Gly Ser Ala
    1760                1765                1770

Ala Ile Ala Ser Ala Tyr Ser Arg Ala Tyr Glu Glu Thr Phe Thr
    1775                1780                1785

Leu Thr Phe Val Thr Gly Arg Thr Val Gly Ile Gly Ala Tyr Leu
    1790                1795                1800

Ala Arg Leu Gly Ile Arg Cys Ile Gln Arg Thr Asp Gln Pro Ile
    1805                1810                1815

Ile Leu Thr Gly Phe Ser Ala Leu Asn Lys Leu Leu Gly Arg Glu
    1820                1825                1830

Val Tyr Ser Ser His Met Gln Leu Gly Gly Pro Lys Ile Met Ala
    1835                1840                1845

Thr Asn Gly Val Val His Leu Thr Val Ser Asp Asp Leu Glu Gly
    1850                1855                1860

Val Ser Asn Ile Leu Arg Trp Leu Ser Tyr Val Pro Ala Asn Ile
    1865                1870                1875

Gly Gly Pro Leu Pro Ile Thr Lys Ser Leu Asp Pro Pro Asp Arg
    1880                1885                1890

Pro Val Ala Tyr Ile Pro Glu Asn Thr Cys Asp Pro Arg Ala Ala
    1895                1900                1905

Ile Ser Gly Ile Asp Asp Ser Gln Gly Lys Trp Leu Gly Gly Met
    1910                1915                1920

Phe Asp Lys Asp Ser Phe Val Glu Thr Phe Glu Gly Trp Ala Lys
    1925                1930                1935

Ser Val Val Thr Gly Arg Ala Lys Leu Gly Gly Ile Pro Val Gly
    1940                1945                1950

Val Ile Ala Val Glu Thr Gln Thr Met Met Gln Leu Ile Pro Ala
    1955                1960                1965

Asp Pro Gly Gln Leu Asp Ser His Glu Arg Ser Val Pro Arg Ala
    1970                1975                1980

Gly Gln Val Trp Phe Pro Asp Ser Ala Thr Lys Thr Ala Gln Ala
    1985                1990                1995

Met Leu Asp Phe Asn Arg Glu Gly Leu Pro Leu Phe Ile Leu Ala
    2000                2005                2010

Asn Trp Arg Gly Phe Ser Gly Gly Gln Arg Asp Leu Phe Glu Gly
    2015                2020                2025

Ile Leu Gln Ala Gly Ser Thr Ile Val Glu Asn Leu Arg Thr Tyr
    2030                2035                2040

Asn Gln Pro Ala Phe Val Tyr Ile Pro Lys Ala Ala Glu Leu Arg
    2045                2050                2055

Gly Gly Ala Trp Val Val Ile Asp Ser Lys Ile Asn Pro Asp Arg
    2060                2065                2070

Ile Glu Phe Tyr Ala Glu Arg Thr Ala Lys Gly Asn Val Leu Glu
    2075                2080                2085

Pro Gln Gly Leu Ile Glu Ile Lys Phe Arg Ser Glu Glu Leu Gln
    2090                2095                2100

Glu Cys Met Gly Arg Leu Asp Pro Glu Leu Ile Asn Leu Lys Ala
    2105                2110                2115
```

| | | | | | | | | | |
|---|---|---|---|---|---|---|---|---|---|
|Lys|Leu|Gln|Gly|Val|Lys|His|Glu|Asn|Gly|Ser|Leu|Pro|Glu|Ser|
| |2120| | | |2125| | | |2130| | | | | |

Lys Leu Gln Gly Val Lys His Glu Asn Gly Ser Leu Pro Glu Ser
    2120                2125                2130

Glu Ser Leu Gln Lys Ser Ile Glu Ala Arg Lys Lys Gln Leu Leu
    2135                2140                2145

Pro Leu Tyr Thr Gln Ile Ala Val Arg Phe Ala Glu Leu His Asp
    2150                2155                2160

Thr Ser Leu Arg Met Ala Ala Lys Gly Val Ile Lys Lys Val Val
    2165                2170                2175

Asp Trp Glu Asp Ser Arg Ser Phe Phe Tyr Lys Arg Leu Arg Arg
    2180                2185                2190

Arg Ile Ser Glu Asp Val Leu Ala Lys Glu Ile Arg Gly Val Ser
    2195                2200                2205

Gly Lys Gln Phe Ser His Gln Ser Ala Ile Glu Leu Ile Gln Lys
    2210                2215                2220

Trp Tyr Leu Ala Ser Lys Gly Ala Glu Thr Gly Ser Thr Glu Trp
    2225                2230                2235

Asp Asp Asp Ala Phe Val Ala Trp Arg Glu Asn Pro Glu Asn
    2240                2245                2250

Tyr Gln Glu Tyr Ile Lys Glu Leu Arg Ala Gln Arg Val Ser Gln
    2255                2260                2265

Leu Leu Ser Asp Val Ala Asp Ser Ser Pro Asp Leu Glu Ala Leu
    2270                2275                2280

Pro Gln Gly Leu Ser Met Leu Leu Glu Lys Met Asp Pro Ser Arg
    2285                2290                2295

Arg Ala Gln Phe Val Glu Glu Val Lys Lys Val Leu Lys
    2300                2305                2310

<210> SEQ ID NO 17
<211> LENGTH: 6966
<212> TYPE: DNA
<213> ORGANISM: Setaria italica

<400> SEQUENCE: 17

```
atgtcgcaac ttggattagc tgcagctgcc tcaaaggcgc tgccactact tcctaatcgc      60
catagaactt cagctggaac tacattccca tcacctgtat catcgcggcc ctcaaaccga     120
aggaaaagcc gcactcgttc acttcgtgat ggaggagatg gggtatcaga tgccaaaaag     180
cacaaccagt ctgtccgtca aggtcttgct ggcatcatcg acctcccaaa tgaggcaaca     240
tcggaagtgg atatttctca tggatccgag gatcccaggg ggccaaccga ttcatatcaa     300
atgaatggga ttgtaagtga agcacataat ggcagacatg cctcagtgtc caaggttgtt     360
gaattttgtg cggcgctagg tggcaaaaca ccaattcaca gtatactagt ggccaacaat     420
ggaatggcag cagcaaagtt catgaggagt gtccggacat gggctaatga tacttttgga     480
tcggagaagg cgattcagct catagctatg caactccag aagacatgag ataaatgca     540
gaacacatta gaattgctga tcaatttgtg gaggtgcctg gtggaacaaa caataacaac     600
tatgcaaatg ttcaactcat agtggaggta gcagaaagaa taggtgtttc tgctgtttgg     660
cctggttggg gtcatgcttc tgagaatcct gaacttccag atgcattgac cgcaaaagga     720
gttgttttcc ttgggccacc tcggcatca atgaatgcat gggagataa ggtcggttca     780
gctctcattg ctcaagcagc tggggtcccg acccctttcgt ggagtggatc acatgttgaa     840
gttccattag agtgctgctt agatgcgata cctgaggaaa tgtatagaaa agcttgtgtt     900
actaccacag aagaagctgt tgcgagttgt caggtggttg gttatcctgc catgattaag     960
```

```
gcatcctggg gaggtggtgg taaaggaata agaaaggttc ataatgacga tgaggttaga    1020
gcactgttta agcaagtaca aggtgaagtc cctggctccc caatatttat catgaggctt    1080
gcatcccaga gtcgtcatct tgaagttcag ttgctttgtg atcaatatgg caatgtggca    1140
gcacttcaca gtcgtgattg cagtgtgcaa cggcgacacc aaaagattat tgaggaaggc    1200
ccagttactg ttgctcctcg tgagacagtt aaagcgcttg agcaggcagc aaggaggctt    1260
gctaaggctg tgggttatgt tggtgctgct actgttgaat acctttacag catggagact    1320
ggggaatact attttctgga gcttaatccc agattacagg tcgagcatcc agtcactgag    1380
tggattgctg aagtaaatct tcctgcagct caagttgcag ttggaatggg catacctctt    1440
tggcagattc cagaaatcag acgtttcgat ggaatggact atggaggagg atatgacatt    1500
tggaggaaaa cagcagctct tgccacacca tttaattttg atgaagtaga ttctcaatgg    1560
ccaaagggcc attgtgtagc agttagaatt actagcgagg atccagatga tggtttcaaa    1620
cctactggtg ggaaagtgaa ggagataagt tttaaaagca agcctaatgt ttgggcctac    1680
ttctcagtaa agtctggtgg aggcattcat gaatttgttg attctcagtt tgggcatgtt    1740
tttgcatatg ggctctctag atcagcagca ataacgaaca tggctcttgc attaaaagag    1800
attcaaattc gtggagaaat tcattcaaat gttgattaca cagttgatct cttaaatgct    1860
tcagacttca gagaaaataa gattcatact ggctggcttg ataccagaat agctatgcgt    1920
gttcaagctg agaggccccc atggtatatt tcagtggttg gaggagctct atataaaaca    1980
gtaactgcca atgcagccac tgtttctgat tatgtcagtt atctcaccaa gggccagatt    2040
ccaccaaagc atatatccct tgtcagttca acagttaatc tgaatatcga agggagcaaa    2100
tacacagttg aaactgtaag gactggacat ggtagctaca gattacgaat gaatgattca    2160
gcaattgaag cgaatgtaca atccttatgt gatggaggcc tcttaatgca gttggatgga    2220
aatagccatg taatttacgc ggaagaagaa gctggtggta cacgacttct gattgatgga    2280
aagacatgct tgttacagaa tgatcatgat ccatcaaagt tattagctga gacaccctgc    2340
aaacttcttc ggttcttggt tgctgatggt gcccatgttg atgctgatgt accatatgcg    2400
gaagttgagg ttatgaaaat gtgcatgcct ctcttgtcgc ctgcttctgg tgtcattcat    2460
gttatgatgt ctgagggcca ggcattgcag gctggtgatc ttatagcaag gctggatctt    2520
gatgacccct ctgctgtgaa aagagctgaa ccatttcatg gaatatttcc acaaatggac    2580
cttcctgttg ctgcctctag ccaagtacac aaaagatatg ctgcaagttg gaatgctgct    2640
cgaatggtcc ttgcaggata cgagcataat atcaatgaag ttgtacaaga tttggtatgc    2700
tgcctggatg atcccgagct tcccttccta cagtgggatg aacttatgtc agttctagca    2760
actaggcttc caagaaatct taagagtgag ttagaggata aatacatgga atacaagttg    2820
aacttttacc atgggaaaaa caaggacttc ccgtccaagc tgctgagaga catcattgag    2880
gcaaatcttg catatggttc agagaaggaa aaagctacga atgagaggct tattgagcct    2940
cttatgagcc tacttaagtc atatgagggt gggagagaaa gccatgctca ttttgttgtc    3000
aagtcccttt tcaaggagta ccttgctgtg aagaactttt cagtgatgg gattcagtct    3060 gatgtgattg aaaccctgcg tcatcagcac agtaaagact gcagaaggt tgtagacatt    3120 gtgttgtctc accagggtgt gaggaacaaa gctaagcttg taacagcact tatggaaaag    3180
ctggtttatc caaatcctgc tgcttacagg gatctgttgg ttcgcttttc ttcactcaat    3240
cataaaagat attataagtt ggcccttaaa gcaagcgaac ttcttgaaca aactaaacta    3300
```

```
agtgaactcc gtgcaagcat cgcaagaagc ctttctgatc tggggatgca taagggagaa   3360
atgactattg aagatagcat ggaagattta gtctctgccc cattacctgt cgaagatgca   3420
cttatttctt tgtttgatta cagtgatcca actgttcagc agaaagtgat cgagacatac   3480
atatctcgat tgtatcagcc tcttcttgtg aaagatagca tccaagtgaa atttaaggaa   3540
tctggtgcct ttgctttatg ggaattttct gaagggcatg ttgatactaa aaatggacaa   3600
gggaccgttc ttggtcgaac aagatggggt gccatggtag ctgtcaaatc agttgaatct   3660
gcacgaacag ccattgtagc tgcattaaag gattcggcac agcatgccag ctctgagggc   3720
aacatgatgc acattgcctt attgagtgct gaaaatgaaa ataatatcag tgatgatcaa   3780
gctcaacata ggatggaaaa acttaacaag atactcaagg atactagtgt cgcaaatgat   3840
cttcgagctg ctggtttgaa ggttataagt tgcattgttc aaagagatga agcacgcatg   3900
ccaatgcgcc acacattact ctggtcagat gaaaagagtt gttatgagga agagcagatt   3960
cttcggcatg tggagcctcc cctctccatg cttcttgaaa tggataagtt gaaagtgaaa   4020
ggatacaatg aaatgaagta tactccatca cgtgatcgtc aatggcatat ctacacacta   4080
agaaatactg aaaaccccaa aatgttgcat agggtatttt tccgaactat tgtcaggcaa   4140
cccaatgcag gcaacaagtt tatatcagcc caaattggcg acactgaagt aggaggtcct   4200
gaggaatctt tgtcatttac atctaatagc attttaagag ccttgatgac tgctattgaa   4260
gaattagagc ttcatgcaat taggactgat cattctcaca tgtatttgtg catattgaaa   4320
gaacaaaagc ttcttgatct cattccgttt tcagggagca caatcgtcga tgttgtccaa   4380
gacgaagcta ctgcttgttc acttttaaaa tcaatggctt tgaagataca cgaacttgtt   4440
ggtgcacaga tgcatcatct ttctgtatgc cagtgggagg tgaaactcaa gttgtactgc   4500
gatgggcctg ccagtggcac ctggagagtt gtaactacaa atgttactag tcacacttgc   4560
accgttgata tctaccggga agtggaagat actgaatcgc agaagttagt ataccattca   4620
gcttctccgt cagctagtcc tttgcatggt gtggccctgg ataatccgta tcaacctttg   4680
agtgtcattg atctaaaaca ctgctctgct aggaacaaca gaactacata ttgctatgat   4740
tttccactgg catttgaaac tgccctgcag aagtcatggc agtccaatgg ctccagtgtt   4800
tctgaaggca gtgaaaatag taggtcttat gtgaaagcaa cagagctggt gtttgctgaa   4860
aaacatgggt cctggggcac tcctataatt tccatggagc gtcccgctgg gctcaatgac   4920
attggcatgg tagcttggat cttagagatg tccactcctg aatttcccaa tggcaggcag   4980
attattgtca tagcaaatga tattacttc agagctggat catttggccc aagggaagat   5040
gcgttttttg aagctgtcac gaacctggcc tgcgagagga gcttcctct tatatacttg   5100 gcagcaaact ccggtgctag gattggcata gccgatgaag tgaaatcttg cttccgtgtt   5160
gggtggtccg atgaaggcag ccctgaacgg ggttttcagt acatttatct gactgacgaa   5220
gactatgccc gtattagctt gtctgttata gcacacaagc tgcagctgga taatggtgaa   5280
attaggtgga ttattgactc tgttgtgggc aaggaggatg gcttggtgt tgagaatata   5340 catggaagtg ctgctattgc cagtgcttat tctagggcat atgaggagac atttacactt   5400
acatttgtga ctgggcggac tgttggaata ggagcatatc ttgctcggct cggtatacgg   5460
tgcatacagc gtcttgacca gcctattatt ttaactgggt tttctgccct gaacaagctt   5520
cttgggcggg aagtgtacag ctcccacatg cagttgggtg gtcctaagat catggcgacc   5580
aatggtgttg tccacttgac tgtttcagat gaccttgaag tgtttccaa tatattgagg   5640 tggctcagct atgttcctgc caacattggt ggacctcttc ctattacaaa acctttggac   5700
```

```
ccaccagaca gacctgttgc atacatccct gagaacacat gtgatccgcg cgcagccatt   5760
cgtggtgtag atgacagcca agggaaatgg ttgggtggta tgtttgacaa agacagcttt   5820
gtcgagacat ttgaaggatg ggcgaaaaca gtggttacgg gcagagcaaa gcttggagga   5880
attcctgttg gcgtcatagc tgtgagacac aaaccatga tgcagcttat ccctgctgat    5940
ccaggccagc ttgattccca tgagcgatct gttcctcggg ctggacaagt gtggttccca   6000
gattctgcaa ccaagacagc tcaggcattg ttggacttca accgtgaagg attgccgctg   6060
ttcatccttg ctaactggag aggattctct ggtggacaaa gagatctgtt tgaaggaatt   6120
cttcaggctg gtcaacaat tgttgagaac ttaggacac aatcagcc tgcttttgtc       6180
tacattccta tggctggaga gctgcgtgga ggagcttggg ttgtggttga tagcaaaata   6240
aatccagacc gaattgagtg ttatgctgag aggactgcta aaggcaatgt tctggaacct   6300
caagggttaa ttgaaatcaa attcagatca gaggagctcc aagactgtat gggtaggctt   6360
gacccagggt tgataaatct gaaagcaaaa ctccaaggtg caaagcttgg aaatggaagc   6420
ctaacagatg tagaatccct tcagaagagt atagatgctc gtacgaaaca gttgttgcct   6480
ttatacaccc agattgcaat acggtttgct gaattgcatg atacttccct cagaatggca   6540
gctaaaggtg tgattaagaa agttgtagat tgggaagaat cacgttcttt cttctacaga   6600
aggctacgga ggaggatctc tgaagatgtt cttgcaaaag aaataagagg aatagctggt   6660
gaccacttca ctcaccaatc agcagttgag ctgatcaagg aatggtactt ggcttctcaa   6720
gccacaacag gaagcactga atgggatgat gatgatgctt ttgttgcctg gaaggagaat   6780
cctgaaaact ataagggata tatccaagag ttaagggctc aaaaggtgtc tcagtcgctc   6840
tccgatcttg cagactccag ttcagatcta gaagcattct cacagggtct ttccacatta   6900
ttagataaga tggatcctc tcagagagcc aagttcattc aggaagtcaa gaaggtcctg   6960
ggttga                                                              6966

<210> SEQ ID NO 18
<211> LENGTH: 2321
<212> TYPE: PRT
<213> ORGANISM: Setaria italica

<400> SEQUENCE: 18

Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Ser Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140
```

```
Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
            195                 200                 205

Glu Val Ala Glu Arg Ile Gly Val Ser Ala Val Trp Pro Gly Trp Gly
210                 215                 220

His Ala Ser Glu Asn Pro Glu Leu Pro Asp Ala Leu Thr Ala Lys Gly
225                 230                 235                 240

Val Val Phe Leu Gly Pro Pro Ala Ala Ser Met Asn Ala Leu Gly Asp
                245                 250                 255

Lys Val Gly Ser Ala Leu Ile Ala Gln Ala Ala Gly Val Pro Thr Leu
            260                 265                 270

Ser Trp Ser Gly Ser His Val Glu Val Pro Leu Glu Cys Cys Leu Asp
            275                 280                 285

Ala Ile Pro Glu Glu Met Tyr Arg Lys Ala Cys Val Thr Thr Thr Glu
290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
            355                 360                 365

Val Gln Leu Leu Cys Asp Gln Tyr Gly Asn Val Ala Ala Leu His Ser
370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
            435                 440                 445

Asn Pro Arg Leu Gln Val Glu His Pro Val Thr Glu Trp Ile Ala Glu
450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Asp Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
            515                 520                 525

Arg Ile Thr Ser Glu Asp Pro Asp Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560
```

```
Phe Ser Val Lys Ser Gly Gly Gly Ile His Glu Phe Val Asp Ser Gln
                565                 570                 575
Phe Gly His Val Phe Ala Tyr Gly Leu Ser Arg Ser Ala Ala Ile Thr
            580                 585                 590
Asn Met Ala Leu Ala Leu Lys Glu Ile Gln Ile Arg Gly Glu Ile His
        595                 600                 605
Ser Asn Val Asp Tyr Thr Val Asp Leu Leu Asn Ala Ser Asp Phe Arg
    610                 615                 620
Glu Asn Lys Ile His Thr Gly Trp Leu Asp Thr Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Val Thr Ala Asn Ala Ala Thr Val Ser Asp Tyr Val
            660                 665                 670
Ser Tyr Leu Thr Lys Gly Gln Ile Pro Pro Lys His Ile Ser Leu Val
        675                 680                 685
Ser Ser Thr Val Asn Leu Asn Ile Glu Gly Ser Lys Tyr Thr Val Glu
    690                 695                 700
Thr Val Arg Thr Gly His Gly Ser Tyr Arg Leu Arg Met Asn Asp Ser
705                 710                 715                 720
Ala Ile Glu Ala Asn Val Gln Ser Leu Cys Asp Gly Gly Leu Leu Met
                725                 730                 735
Gln Leu Asp Gly Asn Ser His Val Ile Tyr Ala Glu Glu Ala Gly
            740                 745                 750
Gly Thr Arg Leu Leu Ile Asp Gly Lys Thr Cys Leu Leu Gln Asn Asp
        755                 760                 765
His Asp Pro Ser Lys Leu Leu Ala Glu Thr Pro Cys Lys Leu Leu Arg
    770                 775                 780
Phe Leu Val Ala Asp Gly Ala His Val Asp Ala Asp Val Pro Tyr Ala
785                 790                 795                 800
Glu Val Glu Val Met Lys Met Cys Met Pro Leu Leu Ser Pro Ala Ser
                805                 810                 815
Gly Val Ile His Val Met Met Ser Glu Gly Gln Ala Leu Gln Ala Gly
            820                 825                 830
Asp Leu Ile Ala Arg Leu Asp Leu Asp Asp Pro Ser Ala Val Lys Arg
        835                 840                 845
Ala Glu Pro Phe His Gly Ile Phe Pro Gln Met Asp Leu Pro Val Ala
    850                 855                 860
Ala Ser Ser Gln Val His Lys Arg Tyr Ala Ala Ser Trp Asn Ala Ala
865                 870                 875                 880
Arg Met Val Leu Ala Gly Tyr Glu His Asn Ile Asn Glu Val Val Gln
                885                 890                 895
Asp Leu Val Cys Cys Leu Asp Asp Pro Glu Leu Pro Phe Leu Gln Trp
            900                 905                 910
Asp Glu Leu Met Ser Val Leu Ala Thr Arg Leu Pro Arg Asn Leu Lys
        915                 920                 925
Ser Glu Leu Glu Asp Lys Tyr Met Glu Tyr Lys Leu Asn Phe Tyr His
    930                 935                 940
Gly Lys Asn Lys Asp Phe Pro Ser Lys Leu Leu Arg Asp Ile Ile Glu
945                 950                 955                 960
Ala Asn Leu Ala Tyr Gly Ser Glu Lys Glu Lys Ala Thr Asn Glu Arg
                965                 970                 975
Leu Ile Glu Pro Leu Met Ser Leu Leu Lys Ser Tyr Glu Gly Gly Arg
```

-continued

```
                980             985             990
Glu Ser His Ala His Phe Val Val Lys Ser Leu Phe Lys Glu Tyr Leu
                995                 1000                1005
Ala Val Glu Glu Leu Phe Ser Asp Gly Ile Gln Ser Asp Val Ile
        1010                1015                1020
Glu Thr Leu Arg His Gln His Ser Lys Asp Leu Gln Lys Val Val
        1025                1030                1035
Asp Ile Val Leu Ser His Gln Gly Val Arg Asn Lys Ala Lys Leu
        1040                1045                1050
Val Thr Ala Leu Met Glu Lys Leu Val Tyr Pro Asn Pro Ala Ala
        1055                1060                1065
Tyr Arg Asp Leu Leu Val Arg Phe Ser Ser Leu Asn His Lys Arg
        1070                1075                1080
Tyr Tyr Lys Leu Ala Leu Lys Ala Ser Glu Leu Leu Glu Gln Thr
        1085                1090                1095
Lys Leu Ser Glu Leu Arg Ala Ser Ile Ala Arg Ser Leu Ser Asp
        1100                1105                1110
Leu Gly Met His Lys Gly Glu Met Thr Ile Glu Asp Ser Met Glu
        1115                1120                1125
Asp Leu Val Ser Ala Pro Leu Pro Val Glu Asp Ala Leu Ile Ser
        1130                1135                1140
Leu Phe Asp Tyr Ser Asp Pro Thr Val Gln Gln Lys Val Ile Glu
        1145                1150                1155
Thr Tyr Ile Ser Arg Leu Tyr Gln Pro Leu Leu Val Lys Asp Ser
        1160                1165                1170
Ile Gln Val Lys Phe Lys Glu Ser Gly Ala Phe Ala Leu Trp Glu
        1175                1180                1185
Phe Ser Glu Gly His Val Asp Thr Lys Asn Gly Gln Gly Thr Val
        1190                1195                1200
Leu Gly Arg Thr Arg Trp Gly Ala Met Val Ala Val Lys Ser Val
        1205                1210                1215
Glu Ser Ala Arg Thr Ala Ile Val Ala Ala Leu Lys Asp Ser Ala
        1220                1225                1230
Gln His Ala Ser Ser Glu Gly Asn Met Met His Ile Ala Leu Leu
        1235                1240                1245
Ser Ala Glu Asn Glu Asn Asn Ile Ser Asp Asp Gln Ala Gln His
        1250                1255                1260
Arg Met Glu Lys Leu Asn Lys Ile Leu Lys Asp Thr Ser Val Ala
        1265                1270                1275
Asn Asp Leu Arg Ala Ala Gly Leu Lys Val Ile Ser Cys Ile Val
        1280                1285                1290
Gln Arg Asp Glu Ala Arg Met Pro Met Arg His Thr Leu Leu Trp
        1295                1300                1305
Ser Asp Glu Lys Ser Cys Tyr Glu Glu Glu Gln Ile Leu Arg His
        1310                1315                1320
Val Glu Pro Pro Leu Ser Met Leu Leu Glu Met Asp Lys Leu Lys
        1325                1330                1335
Val Lys Gly Tyr Asn Glu Met Lys Tyr Thr Pro Ser Arg Asp Arg
        1340                1345                1350
Gln Trp His Ile Tyr Thr Leu Arg Asn Thr Glu Asn Pro Lys Met
        1355                1360                1365
Leu His Arg Val Phe Phe Arg Thr Ile Val Arg Gln Pro Asn Ala
        1370                1375                1380
```

```
Gly Asn Lys Phe Ile Ser Ala Gln Ile Gly Asp Thr Glu Val Gly
    1385                1390                1395

Gly Pro Glu Glu Ser Leu Ser Phe Thr Ser Asn Ser Ile Leu Arg
    1400                1405                1410

Ala Leu Met Thr Ala Ile Glu Glu Leu Glu Leu His Ala Ile Arg
    1415                1420                1425

Thr Asp His Ser His Met Tyr Leu Cys Ile Leu Lys Glu Gln Lys
    1430                1435                1440

Leu Leu Asp Leu Ile Pro Phe Ser Gly Ser Thr Ile Val Asp Val
    1445                1450                1455

Val Gln Asp Glu Ala Thr Ala Cys Ser Leu Leu Lys Ser Met Ala
    1460                1465                1470

Leu Lys Ile His Glu Leu Val Gly Ala Gln Met His His Leu Ser
    1475                1480                1485

Val Cys Gln Trp Glu Val Lys Leu Lys Leu Tyr Cys Asp Gly Pro
    1490                1495                1500

Ala Ser Gly Thr Trp Arg Val Val Thr Thr Asn Val Thr Ser His
    1505                1510                1515

Thr Cys Thr Val Asp Ile Tyr Arg Glu Val Glu Asp Thr Glu Ser
    1520                1525                1530

Gln Lys Leu Val Tyr His Ser Ala Ser Pro Ser Ala Ser Pro Leu
    1535                1540                1545

His Gly Val Ala Leu Asp Asn Pro Tyr Gln Pro Leu Ser Val Ile
    1550                1555                1560

Asp Leu Lys His Cys Ser Ala Arg Asn Asn Arg Thr Thr Tyr Cys
    1565                1570                1575

Tyr Asp Phe Pro Leu Ala Phe Glu Thr Ala Leu Gln Lys Ser Trp
    1580                1585                1590

Gln Ser Asn Gly Ser Ser Val Ser Glu Gly Ser Glu Asn Ser Arg
    1595                1600                1605

Ser Tyr Val Lys Ala Thr Glu Leu Val Phe Ala Glu Lys His Gly
    1610                1615                1620

Ser Trp Gly Thr Pro Ile Ile Ser Met Glu Arg Pro Ala Gly Leu
    1625                1630                1635

Asn Asp Ile Gly Met Val Ala Trp Ile Leu Glu Met Ser Thr Pro
    1640                1645                1650

Glu Phe Pro Asn Gly Arg Gln Ile Ile Val Ile Ala Asn Asp Ile
    1655                1660                1665

Thr Phe Arg Ala Gly Ser Phe Gly Pro Arg Glu Asp Ala Phe Phe
    1670                1675                1680

Glu Ala Val Thr Asn Leu Ala Cys Glu Arg Lys Leu Pro Leu Ile
    1685                1690                1695

Tyr Leu Ala Ala Asn Ser Gly Ala Arg Ile Gly Ile Ala Asp Glu
    1700                1705                1710

Val Lys Ser Cys Phe Arg Val Gly Trp Ser Asp Glu Gly Ser Pro
    1715                1720                1725

Glu Arg Gly Phe Gln Tyr Ile Tyr Leu Thr Asp Glu Asp Tyr Ala
    1730                1735                1740

Arg Ile Ser Leu Ser Val Ile Ala His Lys Leu Gln Leu Asp Asn
    1745                1750                1755

Gly Glu Ile Arg Trp Ile Ile Asp Ser Val Val Gly Lys Glu Asp
    1760                1765                1770
```

| | | | | | | | | | | | |
|---|---|---|---|---|---|---|---|---|---|---|---|
|Gly|Leu|Gly|Val|Glu|Asn|Ile|His|Gly|Ser|Ala|Ala|Ile|Ala|Ser|
| |1775| | | |1780| | | |1785| | | | | |
|Ala|Tyr|Ser|Arg|Ala|Tyr|Glu|Glu|Thr|Phe|Thr|Leu|Thr|Phe|Val|
| |1790| | | |1795| | | |1800| | | | | |
|Thr|Gly|Arg|Thr|Val|Gly|Ile|Gly|Ala|Tyr|Leu|Ala|Arg|Leu|Gly|
| |1805| | | |1810| | | |1815| | | | | |
|Ile|Arg|Cys|Ile|Gln|Arg|Leu|Asp|Gln|Pro|Ile|Ile|Leu|Thr|Gly|
| |1820| | | |1825| | | |1830| | | | | |
|Phe|Ser|Ala|Leu|Asn|Lys|Leu|Leu|Gly|Arg|Glu|Val|Tyr|Ser|Ser|
| |1835| | | |1840| | | |1845| | | | | |
|His|Met|Gln|Leu|Gly|Gly|Pro|Lys|Ile|Met|Ala|Thr|Asn|Gly|Val|
| |1850| | | |1855| | | |1860| | | | | |
|Val|His|Leu|Thr|Val|Ser|Asp|Asp|Leu|Glu|Gly|Val|Ser|Asn|Ile|
| |1865| | | |1870| | | |1875| | | | | |
|Leu|Arg|Trp|Leu|Ser|Tyr|Val|Pro|Ala|Asn|Ile|Gly|Gly|Pro|Leu|
| |1880| | | |1885| | | |1890| | | | | |
|Pro|Ile|Thr|Lys|Pro|Leu|Asp|Pro|Pro|Asp|Arg|Pro|Val|Ala|Tyr|
| |1895| | | |1900| | | |1905| | | | | |
|Ile|Pro|Glu|Asn|Thr|Cys|Asp|Pro|Arg|Ala|Ala|Ile|Arg|Gly|Val|
| |1910| | | |1915| | | |1920| | | | | |
|Asp|Asp|Ser|Gln|Gly|Lys|Trp|Leu|Gly|Gly|Met|Phe|Asp|Lys|Asp|
| |1925| | | |1930| | | |1935| | | | | |
|Ser|Phe|Val|Glu|Thr|Phe|Glu|Gly|Trp|Ala|Lys|Thr|Val|Val|Thr|
| |1940| | | |1945| | | |1950| | | | | |
|Gly|Arg|Ala|Lys|Leu|Gly|Gly|Ile|Pro|Val|Gly|Val|Ile|Ala|Val|
| |1955| | | |1960| | | |1965| | | | | |
|Glu|Thr|Gln|Thr|Met|Met|Gln|Leu|Ile|Pro|Ala|Asp|Pro|Gly|Gln|
| |1970| | | |1975| | | |1980| | | | | |
|Leu|Asp|Ser|His|Glu|Arg|Ser|Val|Pro|Arg|Ala|Gly|Gln|Val|Trp|
| |1985| | | |1990| | | |1995| | | | | |
|Phe|Pro|Asp|Ser|Ala|Thr|Lys|Thr|Ala|Gln|Ala|Leu|Leu|Asp|Phe|
| |2000| | | |2005| | | |2010| | | | | |
|Asn|Arg|Glu|Gly|Leu|Pro|Leu|Phe|Ile|Leu|Ala|Asn|Trp|Arg|Gly|
| |2015| | | |2020| | | |2025| | | | | |
|Phe|Ser|Gly|Gly|Gln|Arg|Asp|Leu|Phe|Glu|Gly|Ile|Leu|Gln|Ala|
| |2030| | | |2035| | | |2040| | | | | |
|Gly|Ser|Thr|Ile|Val|Glu|Asn|Leu|Arg|Thr|Tyr|Asn|Gln|Pro|Ala|
| |2045| | | |2050| | | |2055| | | | | |
|Phe|Val|Tyr|Ile|Pro|Met|Ala|Gly|Glu|Leu|Arg|Gly|Gly|Ala|Trp|
| |2060| | | |2065| | | |2070| | | | | |
|Val|Val|Val|Asp|Ser|Lys|Ile|Asn|Pro|Asp|Arg|Ile|Glu|Cys|Tyr|
| |2075| | | |2080| | | |2085| | | | | |
|Ala|Glu|Arg|Thr|Ala|Lys|Gly|Asn|Val|Leu|Glu|Pro|Gln|Gly|Leu|
| |2090| | | |2095| | | |2100| | | | | |
|Ile|Glu|Ile|Lys|Phe|Arg|Ser|Glu|Glu|Leu|Gln|Asp|Cys|Met|Gly|
| |2105| | | |2110| | | |2115| | | | | |
|Arg|Leu|Asp|Pro|Gly|Leu|Ile|Asn|Leu|Lys|Ala|Lys|Leu|Gln|Gly|
| |2120| | | |2125| | | |2130| | | | | |
|Ala|Lys|Leu|Gly|Asn|Gly|Ser|Leu|Thr|Asp|Val|Glu|Ser|Leu|Gln|
| |2135| | | |2140| | | |2145| | | | | |
|Lys|Ser|Ile|Asp|Ala|Arg|Thr|Lys|Gln|Leu|Leu|Pro|Leu|Tyr|Thr|
| |2150| | | |2155| | | |2160| | | | | |
|Gln|Ile|Ala|Ile|Arg|Phe|Ala|Glu|Leu|His|Asp|Thr|Ser|Leu|Arg|

```
                    2165                2170                2175
Met Ala Ala Lys Gly Val Ile Lys Lys Val Val Asp Trp Glu Glu
            2180                2185                2190

Ser Arg Ser Phe Phe Tyr Arg Arg Leu Arg Arg Ile Ser Glu
    2195                2200                2205

Asp Val Leu Ala Lys Glu Ile Arg Gly Ile Ala Gly Asp His Phe
    2210                2215                2220

Thr His Gln Ser Ala Val Glu Leu Ile Lys Glu Trp Tyr Leu Ala
    2225                2230                2235

Ser Gln Ala Thr Thr Gly Ser Thr Glu Trp Asp Asp Asp Ala
    2240                2245                2250

Phe Val Ala Trp Lys Glu Asn Pro Glu Asn Tyr Lys Gly Tyr Ile
    2255                2260                2265

Gln Glu Leu Arg Ala Gln Lys Val Ser Gln Ser Leu Ser Asp Leu
    2270                2275                2280

Ala Asp Ser Ser Ser Asp Leu Glu Ala Phe Ser Gln Gly Leu Ser
    2285                2290                2295

Thr Leu Leu Asp Lys Met Asp Pro Ser Gln Arg Ala Lys Phe Ile
    2300                2305                2310

Gln Glu Val Lys Lys Val Leu Gly
    2315                2320

<210> SEQ ID NO 19
<211> LENGTH: 6966
<212> TYPE: DNA
<213> ORGANISM: Setaria italica

<400> SEQUENCE: 19
atgtcgcaac ttggattagc tgcagctgcc tcaaaggcgc tgccactact tcctaatcgc      60
catagaactt cagctggaac tacattccca tcacctgtat catcgcggcc ctcaaaccga     120
aggaaaagcc gcactcgttc acttcgtgat ggagagatg gggtatcaga tgccaaaaag      180
cacaaccagt ctgtccgtca aggtcttgct ggcatcatcg acctcccaaa tgaggcaaca     240
tcggaagtgg atatttctca tggatccgag gatcccaggg ggccaaccga ttcatatcaa     300
atgaatggga ttgtaaatga agcacataat ggcagacatg cctcagtgtc caaggttgtt     360
gaattttgtg cggcgctagg tggcaaaaca ccaattcaca gtatactagt ggccaacaat     420
ggaatggcag cagcaaagtt catgaggagt gtccggacat gggctaatga ctttttgga    480 tcggagaagg cgattcagct catagctatg caactccag aagacatgag gataaatgca     540
gaacacatta gaattgctga tcaatttgta gaggtgcctg gtggaacaaa caataacaac     600
tatgcaaatg ttcaactcat agtggaggta gcagaaagaa taggtgtttc tgctgtttgg     660
cctggttggg gtcatgcttc tgagaatcct gaacttccag atgcattgac cgcaaaagga     720
attgttttcc ttgggccacc tgcggcatca atgaatgcat gggagataa ggtcggttca      780 gctctcattg ctcaagcagc tggggtcccg acccttcgt ggagtggatc acatgttgaa     840
gttccattag agtgctgctt agatgcgata cctgaggaaa tgtatagaaa agcttgtgtt     900
actaccacag aagaagctgt tgcgagttgt caggtggttg ttatcctgc catgattaag     960 gcatcctggg gaggtggtgg taaaggaata agaaaggttc ataatgacga tgaggttaga    1020
gcactgttta gcaagtaca aggtgaagtc cctggctccc caatatttat catgaggctt    1080
gcatcccaga gtcgtcatct tgaagttcag ttgctttgtg atcaatatgg caatgtggca    1140
gcacttcaca gtcgtgattg cagtgtgcaa cggcgacacc aaaagattat tgaggaaggc    1200
```

-continued

```
ccagttactg ttgctcctcg tgagacagtt aaagcgcttg agcaggcagc aaggaggctt    1260
gctaaggctg tgggttatgt tggtgctgct actgttgaat acctttacag catgagact     1320 ggggaatact attttctgga gcttaatccc agattacagg tcgagcatcc agtcactgag    1380
tggattgctg aagtaaatct tcctgcagct caagttgcag ttggaatggg catacctctt    1440
tggcagattc cagaaatcag acgtttctat ggaatggact atggaggagg atatgacatt    1500
tggaggaaaa cagcagctct tgccacacca tttaattttg atgaagtaga ttctcaatgg    1560
ccaaagggcc attgtgtagc agttagaatt actagcgagg atccagatga tggtttcaaa    1620
cctactggtg ggaaagtgaa ggagataagt tttaaaagca agcctaatgt ttgggcctac    1680
ttctcagtaa agtctggtgg aggcattcat gaatttgctg attctcagtt tgggcatgtt    1740
tttgcatatg ggctctctag atcagcagca ataacgaaca tggctcttgc attaaaagag    1800
attcaaattc gtggagaaat tcattcaaat gttgattaca cagttgatct cttaaatgct    1860
tcagacttca gagaaaataa gattcatact ggctggcttg ataccagaat agctatgcgt    1920
gttcaagctg agaggccccc atggtatatt tcagtggttg gaggagctct atataaaaca    1980
gtaactgcca atgcagccac tgtttctgat tatgtcagtt atctcaccaa gggccagatt    2040
ccaccaaagc atatatccct tgtcagttca acagttaatc tgaatatcga agggagcaaa    2100
tacacagttg aaactgtaag gactggacat ggtagctaca gattacgaat gaatgattca    2160
gcaattgaag cgaatgtaca atctttatgt gatggaggcc tcttaatgca gttggatgga    2220
aatagccatg taatttacgc ggaagaagaa gctggtggta cacgacttct gattgatgga    2280
aagacatgct tgttacagaa tgatcatgat ccatcaaagt tattagctga gacaccctgc    2340
aaacttcttc ggttcttggt tgctgatggt gctcatgttg atgctgatgt accatatgcg    2400
gaagttgagg ttatgaaaat gtgcatgcct ctcttgtcgc ctgcttctgg tgtcattcat    2460
gttatgatgt ctgagggcca ggcattgcag gctggtgatc ttatagcaag gctggatctt    2520
gatgacccct ctgctgtgaa aagagctgaa ccatttcatg gaatatttcc acaaatggac    2580
cttcctgttg ctgcctctag ccaagtacac aaaagatatg ctgcaagttt gaatgctgct    2640
cgaatggtcc ttgcaggata cgagcataat atcaatgaag ttgtacaaga tttggtatgc    2700
tgcctggatg atcccgagct tcccttccta cagtgggatg aacttatgtc agttctagca    2760
actaggcttc aagaaatctt aagagtgag ttagaggata aatacatgga atacaagttg    2820
aacttttacc atgggaaaaa caaggacttc ccgtccaagc tgctgagaga catcattgag    2880
gcaaatcttg catatggttc agagaaggaa aaagctacga atgagaggct tattgagcct    2940
cttatgagcc tacttaagtc atatgagggt gggagagaaa gccatgctca ttttgttgtc    3000
aagtcccttt tcaaggagta ccttgctgtg aagaactttt cagtgatgg gattcagtct    3060 gatgtgattg aaaccctgcg tcatcagcac agtaaagact tgcagaaggt tgtagacatt    3120
gtgttgtctc accagggtgt gaggaacaaa gctaagcttg taacagcact tatggaaaag    3180
ctggtttatc caaatcctgc tgcttacagg gatctgttgg ttcgcttttc ttcactcaat    3240
cataaaagat attataagtt ggcccttaaa gcaagcgaac ttcttgaaca aactaaacta    3300
agtgaactcc gtgcaagcat cgcaagaagc ctttctgatc tggggatgca taagggagaa    3360
atgactattg aagatagcat ggaagattta gtctctgccc cattacctgt cgaagatgca    3420
cttatttctt tgtttgatta cagtgatcca actgttcagc agaaagtgat cgagacatac    3480
atatctcgat tgtatcagcc tcttcttgtg aaagatagca tccaagtgaa atttaaggaa    3540
```

-continued

```
tctggtgcct ttgctttatg ggaattttct gaagggcatg ttgatactaa aaatggacaa    3600
gggaccgttc ttggtcgaac aagatggggt gccatggtag ctgtcaaatc agttgaatct    3660
gcacgaacag ccattgtagc tgcattaaag gattcggcac agcatgccag ctctgagggc    3720
aacatgatgc acattgcctt attgagtgct gaaaatgaaa ataatatcag tgatgatcaa    3780
gctcaacata ggatggaaaa acttaacaag atactcaagg atactagtgt cgcaaatgat    3840
cttgagctg ctggtttgaa ggttataagt tgcattgttc aaagagatga agcacgcatg    3900
ccaatgcgcc acacattact ctggtcagat gaaaagagtt gttatgagga agagcagatt    3960
cttcggcatg tggagcctcc cctctccatg cttcttgaaa tggataagtt gaaagtgaaa    4020
ggatacaatg aaatgaagta tactccatca cgtgatcgtc aatggcatat ctacacacta    4080
agaaatactg aaaccccaa aatgttgcat agggtatttt ccgaactat tgtcaggcaa     4140
cccaatgcag gcaacaagtt tatatcagcc caaattggcg acactgaagt aggaggtcct    4200
gaggaatctt tgtcatttac atctaatagc attttaagag ccttgatgac tgctattgaa    4260
gaattagagc ttcatgcaat taggactggt cattctcaca tgtatttgtg catattgaaa    4320
gaacaaaagc ttcttgatct cattccgttt tcagggagca caatcgtcga tgttggccaa    4380
gacgaagcta ctgcttgttc acttttaaaa tcaatggctt tgaagataca cgaacttgtt    4440
ggtgcacaga tgcatcatct ttctgtatgc cagtgggagg tgaaactcaa gttgtactgc    4500
gatgggcctg ccagtggcac ctggagagtt gtaactacaa atgttactag tcacacttgc    4560
accattgata tctaccggga agtggaagat actgaatcgc agaagttagt ataccattca    4620
gcttctccgt cagctagtcc tttgcatggt gtggccctgg ataatccgta tcaacctttg    4680
agtgtcattg atctaaaacg ctgctctgct aggaacaaca gaactacata ttgctatgat    4740
tttccactgg catttgaaac tgccctgcag aagtcatggc agtccaatgg ctccagtgtt    4800
tctgaaggca gtgaaaatag taggtcttat gtgaaagcaa cagagctggt gtttgctgaa    4860
aaacatgggt cctggggcac tcctataatt tccatggagc gtcccgctgg gctcaatgac    4920
attggcatgg tagcttggat cttagagatg tccactcctg aatttcccaa tggcaggcag    4980
attattgtca tagcaaatga tattactttc agagctggat catttggccc aagggaagat    5040
gcgttttttg aagctgtcac gaacctggcc tgcgagagga agcttcctct tatatacttg    5100
gcagcaaact ccggtgctag gattggcata gccgatgaag tgaaatcttg cttccgtgtt    5160
gggtggtccg atgaaggcag ccctgaacgg ggttttcagt acatttatct gactgacgaa    5220
gactatgccc gtattagctt gtctgttata gcacacaagc tgcagctgga taatggtgaa    5280
attaggtgga ttattgactc tgttgtgggc aaggaggatg ggcttggtgt tgagaatcta    5340
catgaagtg ctgctattgc cagtgcttat tctagggcat atgaggagac atttacactt    5400
acatttgtga ctgggcggac tgttggaata ggagcatatc tcgctcggct cggtatacgg    5460
tgcatacagc gtcttgacca gcctattatt ttaactgggt tttctgccct gaacaagctt    5520
cttgggcggg aagtgtacag ctcccacatg cagttgggtg gtcctaagat catggcgacc    5580
aatggtgttg tccacttgac tgtttcagat gaccttgaag gtgtttccaa tatattgagg    5640
tggctcagct atgttcctgc caacattggt ggacctcttc ctattacaaa acctttggac    5700
ccaccagaca gacctgttgc atacatccct gagaacacat gtgatccgcg cgcagccatt    5760
cgtggtgtag atgacagcca agggaaatgg ttgggtggta tgtttgacaa agacagcttt    5820
gtcgagacat ttgaaggatg ggcgaaaaca gtggttacgg gcagagcaaa gcttggagga    5880
attcctgttg gtgtcatagc tgtggagaca caaaccatga tgcagcttat ccctgctgat    5940
```

-continued

```
ccaggccagc ttgattccca tgagcgatct gttcctcggg ctggacaagt gtggttccca      6000
gattctgcaa ccaagacagc tcaggcattg ttggacttca accgtgaagg attgccgctg      6060
ttcatccttg ctaactggag aggattctct ggtggacaaa gagatctgtt tgaaggaatt      6120
cttcaggctg ggtcaacaat tgttgagaac cttaggacat acaatcagcc tgcttttgtc      6180
tacattccta tggctggaga gctgcgtgga ggagcttggg ttgtggttga tagcaaaata      6240
aatccagacc gaattgagtg ttatgctgag aggactgcta aaggcaatgt tcttgaacct      6300
caagggttaa ttgaaatcaa attcagatca gaggagctcc aagactgtat gggtaggctt      6360
gacccagagt tgataaatct gaaagcaaaa ctccaaggtg caaagcttgg aaatggaagc      6420
ctaacagatg tagaatccct tcagaagagt atagatgctc gtacgaaaca gttgttgcct      6480
ttatacaccc agattgcaat acggtttgct gaattgcatg atacttccct cagaatggca      6540
gctaaaggtg tgattaagaa agttgtagat tgggaagaat cacgttcttt cttctacaga      6600
aggctacgga ggaggatctc tgaagatgtt cttgcaaaag aaataagagg aatagctggt      6660
gaccacttca ctcaccaatc agcagttgag ctgatcaagg aatggtactt ggcttctcaa      6720
gccacaacag gaagcactga atgggatgat gatgatgctt tgttgcctg aaggagaat       6780 cctgaaaact ataagggata tatccaagag ttaagggctc aaaaggtgtc tcagtcgctc      6840
tccgatcttg cagactccag ttcagatcta gaagcattct cacagggtct ttccacatta      6900
ttagataaga tggatccctc tcagagagcc aagttcattc aggaagtcaa gaaggtcctg      6960
ggttga                                                                6966

<210> SEQ ID NO 20
<211> LENGTH: 2321
<212> TYPE: PRT
<213> ORGANISM: Setaria italica

<400> SEQUENCE: 20

Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
            20                  25                  30

Val Ser Ser Arg Pro Ser Asn Arg Arg Lys Ser Arg Thr Arg Ser Leu
        35                  40                  45

Arg Asp Gly Gly Asp Gly Val Ser Asp Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
```

```
            180                 185                 190
Pro Gly Gly Thr Asn Asn Asn Tyr Ala Asn Val Gln Leu Ile Val
            195                 200                 205
Glu Val Ala Glu Arg Ile Gly Val Ser Ala Val Trp Pro Gly Trp
            210                 215                 220
His Ala Ser Glu Asn Pro Glu Leu Pro Asp Ala Leu Thr Ala Lys Gly
225                 230                 235                 240
Ile Val Phe Leu Gly Pro Pro Ala Ala Ser Met Asn Ala Leu Gly Asp
            245                 250                 255
Lys Val Gly Ser Ala Leu Ile Ala Gln Ala Ala Gly Val Pro Thr Leu
            260                 265                 270
Ser Trp Ser Gly Ser His Val Glu Val Pro Leu Glu Cys Cys Leu Asp
            275                 280                 285
Ala Ile Pro Glu Glu Met Tyr Arg Lys Ala Cys Val Thr Thr Thr Glu
            290                 295                 300
Glu Ala Val Ala Ser Cys Gln Val Val Gly Tyr Pro Ala Met Ile Lys
305                 310                 315                 320
Ala Ser Trp Gly Gly Gly Gly Lys Gly Ile Arg Lys Val His Asn Asp
            325                 330                 335
Asp Glu Val Arg Ala Leu Phe Lys Gln Val Gln Gly Glu Val Pro Gly
            340                 345                 350
Ser Pro Ile Phe Ile Met Arg Leu Ala Ser Gln Ser Arg His Leu Glu
            355                 360                 365
Val Gln Leu Leu Cys Asp Gln Tyr Gly Asn Val Ala Ala Leu His Ser
            370                 375                 380
Arg Asp Cys Ser Val Gln Arg Arg His Gln Lys Ile Ile Glu Glu Gly
385                 390                 395                 400
Pro Val Thr Val Ala Pro Arg Glu Thr Val Lys Ala Leu Glu Gln Ala
            405                 410                 415
Ala Arg Arg Leu Ala Lys Ala Val Gly Tyr Val Gly Ala Ala Thr Val
            420                 425                 430
Glu Tyr Leu Tyr Ser Met Glu Thr Gly Glu Tyr Tyr Phe Leu Glu Leu
            435                 440                 445
Asn Pro Arg Leu Gln Val Glu His Pro Val Thr Glu Trp Ile Ala Glu
            450                 455                 460
Val Asn Leu Pro Ala Ala Gln Val Ala Val Gly Met Gly Ile Pro Leu
465                 470                 475                 480
Trp Gln Ile Pro Glu Ile Arg Arg Phe Tyr Gly Met Asp Tyr Gly Gly
            485                 490                 495
Gly Tyr Asp Ile Trp Arg Lys Thr Ala Ala Leu Ala Thr Pro Phe Asn
            500                 505                 510
Phe Asp Glu Val Asp Ser Gln Trp Pro Lys Gly His Cys Val Ala Val
            515                 520                 525
Arg Ile Thr Ser Glu Asp Pro Asp Asp Gly Phe Lys Pro Thr Gly Gly
            530                 535                 540
Lys Val Lys Glu Ile Ser Phe Lys Ser Lys Pro Asn Val Trp Ala Tyr
545                 550                 555                 560
Phe Ser Val Lys Ser Gly Gly Ile His Glu Phe Ala Asp Ser Gln
            565                 570                 575
Phe Gly His Val Phe Ala Tyr Gly Leu Ser Arg Ser Ala Ala Ile Thr
            580                 585                 590
Asn Met Ala Leu Ala Leu Lys Glu Ile Gln Ile Arg Gly Glu Ile His
            595                 600                 605
```

Ser Asn Val Asp Tyr Thr Val Asp Leu Leu Asn Ala Ser Asp Phe Arg
610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Ala Asn Ala Ala Thr Val Ser Asp Tyr Val
                660                 665                 670

Ser Tyr Leu Thr Lys Gly Gln Ile Pro Pro Lys His Ile Ser Leu Val
                675                 680                 685

Ser Ser Thr Val Asn Leu Asn Ile Glu Gly Ser Lys Tyr Thr Val Glu
690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Gly Leu Leu Met
                725                 730                 735

Gln Leu Asp Gly Asn Ser His Val Ile Tyr Ala Glu Glu Ala Gly
                740                 745                 750

Gly Thr Arg Leu Leu Ile Asp Gly Lys Thr Cys Leu Leu Gln Asn Asp
                755                 760                 765

His Asp Pro Ser Lys Leu Leu Ala Glu Thr Pro Cys Lys Leu Leu Arg
770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Val Met Met Ser Glu Gly Gln Ala Leu Gln Ala Gly
                820                 825                 830

Asp Leu Ile Ala Arg Leu Asp Leu Asp Asp Pro Ser Ala Val Lys Arg
                835                 840                 845

Ala Glu Pro Phe His Gly Ile Phe Pro Gln Met Asp Leu Pro Val Ala
850                 855                 860

Ala Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asp Pro Glu Leu Pro Phe Leu Gln Trp
                900                 905                 910

Asp Glu Leu Met Ser Val Leu Ala Thr Arg Leu Pro Arg Asn Leu Lys
                915                 920                 925

Ser Glu Leu Glu Asp Lys Tyr Met Glu Tyr Lys Leu Asn Phe Tyr His
930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
                980                 985                 990

Glu Ser His Ala His Phe Val Val Lys Ser Leu Phe Lys Glu Tyr Leu
                995                 1000                1005

Ala Val Glu Glu Leu Phe Ser Asp Gly Ile Gln Ser Asp Val Ile
    1010                1015                1020

```
Glu Thr Leu Arg His Gln His  Ser Lys Asp Leu Gln  Lys Val Val
    1025                1030                1035

Asp Ile Val Leu Ser His Gln  Gly Val Arg Asn Lys  Ala Lys Leu
    1040                1045                1050

Val Thr Ala Leu Met Glu Lys  Leu Val Tyr Pro Asn  Pro Ala Ala
    1055                1060                1065

Tyr Arg Asp Leu Leu Val Arg  Phe Ser Ser Leu Asn  His Lys Arg
    1070                1075                1080

Tyr Tyr Lys Leu Ala Leu Lys  Ala Ser Glu Leu Leu  Glu Gln Thr
    1085                1090                1095

Lys Leu Ser Glu Leu Arg Ala  Ser Ile Ala Arg Ser  Leu Ser Asp
    1100                1105                1110

Leu Gly Met His Lys Gly Glu  Met Thr Ile Glu Asp  Ser Met Glu
    1115                1120                1125

Asp Leu Val Ser Ala Pro Leu  Pro Val Glu Asp Ala  Leu Ile Ser
    1130                1135                1140

Leu Phe Asp Tyr Ser Asp Pro  Thr Val Gln Gln Lys  Val Ile Glu
    1145                1150                1155

Thr Tyr Ile Ser Arg Leu Tyr  Gln Pro Leu Leu Val  Lys Asp Ser
    1160                1165                1170

Ile Gln Val Lys Phe Lys Glu  Ser Gly Ala Phe Ala  Leu Trp Glu
    1175                1180                1185

Phe Ser Glu Gly His Val Asp  Thr Lys Asn Gly Gln  Gly Thr Val
    1190                1195                1200

Leu Gly Arg Thr Arg Trp Gly  Ala Met Val Ala Val  Lys Ser Val
    1205                1210                1215

Glu Ser Ala Arg Thr Ala Ile  Val Ala Ala Leu Lys  Asp Ser Ala
    1220                1225                1230

Gln His Ala Ser Ser Glu Gly  Asn Met Met His Ile  Ala Leu Leu
    1235                1240                1245

Ser Ala Glu Asn Glu Asn Asn  Ile Ser Asp Asp Gln  Ala Gln His
    1250                1255                1260

Arg Met Glu Lys Leu Asn Lys  Ile Leu Lys Asp Thr  Ser Val Ala
    1265                1270                1275

Asn Asp Leu Arg Ala Ala Gly  Leu Lys Val Ile Ser  Cys Ile Val
    1280                1285                1290

Gln Arg Asp Glu Ala Arg Met  Pro Met Arg His Thr  Leu Leu Trp
    1295                1300                1305

Ser Asp Glu Lys Ser Cys Tyr  Glu Glu Glu Gln Ile  Leu Arg His
    1310                1315                1320

Val Glu Pro Pro Leu Ser Met  Leu Leu Glu Met Asp  Lys Leu Lys
    1325                1330                1335

Val Lys Gly Tyr Asn Glu Met  Lys Tyr Thr Pro Ser  Arg Asp Arg
    1340                1345                1350

Gln Trp His Ile Tyr Thr Leu  Arg Asn Thr Glu Asn  Pro Lys Met
    1355                1360                1365

Leu His Arg Val Phe Phe Arg  Thr Ile Val Arg Gln  Pro Asn Ala
    1370                1375                1380

Gly Asn Lys Phe Ile Ser Ala  Gln Ile Gly Asp Thr  Glu Val Gly
    1385                1390                1395

Gly Pro Glu Glu Ser Leu Ser  Phe Thr Ser Asn Ser  Ile Leu Arg
    1400                1405                1410

Ala Leu Met Thr Ala Ile Glu  Glu Leu Glu Leu His  Ala Ile Arg
```

```
                1415                1420                1425
Thr Gly His Ser His Met Tyr Leu Cys Ile Leu Lys Glu Gln Lys
    1430                1435                1440

Leu Leu Asp Leu Ile Pro Phe Ser Gly Ser Thr Ile Val Asp Val
    1445                1450                1455

Gly Gln Asp Glu Ala Thr Ala Cys Ser Leu Leu Lys Ser Met Ala
    1460                1465                1470

Leu Lys Ile His Glu Leu Val Gly Ala Gln Met His His Leu Ser
    1475                1480                1485

Val Cys Gln Trp Glu Val Lys Leu Lys Leu Tyr Cys Asp Gly Pro
    1490                1495                1500

Ala Ser Gly Thr Trp Arg Val Val Thr Thr Asn Val Thr Ser His
    1505                1510                1515

Thr Cys Thr Ile Asp Ile Tyr Arg Glu Val Glu Asp Thr Glu Ser
    1520                1525                1530

Gln Lys Leu Val Tyr His Ser Ala Ser Pro Ser Ala Ser Pro Leu
    1535                1540                1545

His Gly Val Ala Leu Asp Asn Pro Tyr Gln Pro Leu Ser Val Ile
    1550                1555                1560

Asp Leu Lys Arg Cys Ser Ala Arg Asn Asn Arg Thr Thr Tyr Cys
    1565                1570                1575

Tyr Asp Phe Pro Leu Ala Phe Glu Thr Ala Leu Gln Lys Ser Trp
    1580                1585                1590

Gln Ser Asn Gly Ser Ser Val Ser Glu Gly Ser Glu Asn Ser Arg
    1595                1600                1605

Ser Tyr Val Lys Ala Thr Glu Leu Val Phe Ala Glu Lys His Gly
    1610                1615                1620

Ser Trp Gly Thr Pro Ile Ile Ser Met Glu Arg Pro Ala Gly Leu
    1625                1630                1635

Asn Asp Ile Gly Met Val Ala Trp Ile Leu Glu Met Ser Thr Pro
    1640                1645                1650

Glu Phe Pro Asn Gly Arg Gln Ile Ile Val Ile Ala Asn Asp Ile
    1655                1660                1665

Thr Phe Arg Ala Gly Ser Phe Gly Pro Arg Glu Asp Ala Phe Phe
    1670                1675                1680

Glu Ala Val Thr Asn Leu Ala Cys Glu Arg Lys Leu Pro Leu Ile
    1685                1690                1695

Tyr Leu Ala Ala Asn Ser Gly Ala Arg Ile Gly Ile Ala Asp Glu
    1700                1705                1710

Val Lys Ser Cys Phe Arg Val Gly Trp Ser Asp Glu Gly Ser Pro
    1715                1720                1725

Glu Arg Gly Phe Gln Tyr Ile Tyr Leu Thr Asp Glu Asp Tyr Ala
    1730                1735                1740

Arg Ile Ser Leu Ser Val Ile Ala His Lys Leu Gln Leu Asp Asn
    1745                1750                1755

Gly Glu Ile Arg Trp Ile Ile Asp Ser Val Val Gly Lys Glu Asp
    1760                1765                1770

Gly Leu Gly Val Glu Asn Leu His Gly Ser Ala Ala Ile Ala Ser
    1775                1780                1785

Ala Tyr Ser Arg Ala Tyr Glu Glu Thr Phe Thr Leu Thr Phe Val
    1790                1795                1800

Thr Gly Arg Thr Val Gly Ile Gly Ala Tyr Leu Ala Arg Leu Gly
    1805                1810                1815
```

```
Ile Arg Cys Ile Gln Arg Leu Asp Gln Pro Ile Ile Leu Thr Gly
1820            1825                1830

Phe Ser Ala Leu Asn Lys Leu Leu Gly Arg Glu Val Tyr Ser Ser
1835            1840                1845

His Met Gln Leu Gly Gly Pro Lys Ile Met Ala Thr Asn Gly Val
1850            1855                1860

Val His Leu Thr Val Ser Asp Asp Leu Glu Gly Val Ser Asn Ile
1865            1870                1875

Leu Arg Trp Leu Ser Tyr Val Pro Ala Asn Ile Gly Gly Pro Leu
1880            1885                1890

Pro Ile Thr Lys Pro Leu Asp Pro Pro Asp Arg Pro Val Ala Tyr
1895            1900                1905

Ile Pro Glu Asn Thr Cys Asp Pro Arg Ala Ala Ile Arg Gly Val
1910            1915                1920

Asp Asp Ser Gln Gly Lys Trp Leu Gly Gly Met Phe Asp Lys Asp
1925            1930                1935

Ser Phe Val Glu Thr Phe Glu Gly Trp Ala Lys Thr Val Val Thr
1940            1945                1950

Gly Arg Ala Lys Leu Gly Gly Ile Pro Val Gly Val Ile Ala Val
1955            1960                1965

Glu Thr Gln Thr Met Met Gln Leu Ile Pro Ala Asp Pro Gly Gln
1970            1975                1980

Leu Asp Ser His Glu Arg Ser Val Pro Arg Ala Gly Gln Val Trp
1985            1990                1995

Phe Pro Asp Ser Ala Thr Lys Thr Ala Gln Ala Leu Leu Asp Phe
2000            2005                2010

Asn Arg Glu Gly Leu Pro Leu Phe Ile Leu Ala Asn Trp Arg Gly
2015            2020                2025

Phe Ser Gly Gly Gln Arg Asp Leu Phe Glu Gly Ile Leu Gln Ala
2030            2035                2040

Gly Ser Thr Ile Val Glu Asn Leu Arg Thr Tyr Asn Gln Pro Ala
2045            2050                2055

Phe Val Tyr Ile Pro Met Ala Gly Glu Leu Arg Gly Gly Ala Trp
2060            2065                2070

Val Val Val Asp Ser Lys Ile Asn Pro Asp Arg Ile Glu Cys Tyr
2075            2080                2085

Ala Glu Arg Thr Ala Lys Gly Asn Val Leu Glu Pro Gln Gly Leu
2090            2095                2100

Ile Glu Ile Lys Phe Arg Ser Glu Glu Leu Gln Asp Cys Met Gly
2105            2110                2115

Arg Leu Asp Pro Glu Leu Ile Asn Leu Lys Ala Lys Leu Gln Gly
2120            2125                2130

Ala Lys Leu Gly Asn Gly Ser Leu Thr Asp Val Glu Ser Leu Gln
2135            2140                2145

Lys Ser Ile Asp Ala Arg Thr Lys Gln Leu Leu Pro Leu Tyr Thr
2150            2155                2160

Gln Ile Ala Ile Arg Phe Ala Glu Leu His Asp Thr Ser Leu Arg
2165            2170                2175

Met Ala Ala Lys Gly Val Ile Lys Lys Val Val Asp Trp Glu Glu
2180            2185                2190

Ser Arg Ser Phe Phe Tyr Arg Arg Leu Arg Arg Ile Ser Glu
2195            2200                2205
```

| | | | | | | | | | | | |
|---|---|---|---|---|---|---|---|---|---|---|---|
| Asp | Val | Leu | Ala | Lys | Glu | Ile | Arg | Gly | Ile | Ala | Gly | Asp | His | Phe |
| 2210 | | | | | 2215 | | | | | 2220 | | | | |
| Thr | His | Gln | Ser | Ala | Val | Glu | Leu | Ile | Lys | Glu | Trp | Tyr | Leu | Ala |
| 2225 | | | | | 2230 | | | | | 2235 | | | | |
| Ser | Gln | Ala | Thr | Thr | Gly | Ser | Thr | Glu | Trp | Asp | Asp | Asp | Ala |
| 2240 | | | | | 2245 | | | | | 2250 | | | | |
| Phe | Val | Ala | Trp | Lys | Glu | Asn | Pro | Glu | Asn | Tyr | Lys | Gly | Tyr | Ile |
| 2255 | | | | | 2260 | | | | | 2265 | | | | |
| Gln | Glu | Leu | Arg | Ala | Gln | Lys | Val | Ser | Gln | Ser | Leu | Ser | Asp | Leu |
| 2270 | | | | | 2275 | | | | | 2280 | | | | |
| Ala | Asp | Ser | Ser | Ser | Asp | Leu | Glu | Ala | Phe | Ser | Gln | Gly | Leu | Ser |
| 2285 | | | | | 2290 | | | | | 2295 | | | | |
| Thr | Leu | Leu | Asp | Lys | Met | Asp | Pro | Ser | Gln | Arg | Ala | Lys | Phe | Ile |
| 2300 | | | | | 2305 | | | | | 2310 | | | | |
| Gln | Glu | Val | Lys | Lys | Val | Leu | Gly |
| 2315 | | | | | 2320 | | |

<210> SEQ ID NO 21
<211> LENGTH: 6966
<212> TYPE: DNA
<213> ORGANISM: Setaria italica

<400> SEQUENCE: 21

```
atgtcgcaac ttggattagc tgcagctgcc tcaaaggcgc tgccactact tcctaatcgc    60
catagaactt cagctggaac tacattccca tcacctgtat catcgcggcc ctcaaaccga   120
aggaaaagcc gcactcgttc acttcgtgat ggaggagatg gggtatcaga tgccaaaaag   180
cacaaccagt ctgtccgtca aggtcttgct ggcatcatcg acctcccaaa tgaggcaaca   240
tcggaagtgg atatttctca tggatccgag atcccagggg gccaaccga ttcatatcaa    300
atgaatggga ttgtaaatga agcacataat ggcagacatg cctcagtgtc caaggttgtt   360
gaattttgtg cggcgctagg tggcaaaaca ccaattcaca gtatactagt ggccaacaat   420
ggaatggcag cagcaaagtt catgaggagt gtccggacat gggctaatga cttttggga    480
tcggagaagg cgattcagct catagctatg caactccag aagacatgag ataaatgca     540
gaacacatta gaattgctga tcaatttgta gaggtgcctg gtgaacaaa caataacaac    600
tatgcaaatg ttcaactcat agtggaggta gcagaaagaa taggtgtttc tgctgtttgg   660
cctggttggg gtcatgcttc tgagaatcct gaacttccag atgcattgac cgcaaaagga   720
attgttttcc ttgggccacc tcggcatca atgaatgcat ggagataa ggtcggttca      780
gctctcattg ctcaagcagc tgggtcccg accctttcgt ggagtggatc acatgttgaa   840
gttccattag agtgctgctt agatgcgata cctgaggaaa tgtatagaaa agcttgtgtt   900
actaccacag aagaagctgt tgcgagttgt caggtggttg gttatcctgc catgattaag   960
gcatcctggg gaggtggtgg taaaggaata agaaaggttc ataatgacga tgaggttaga  1020
gcactgttta gcaagtaca aggtgaagtc cctggctccc caatatttat catgaggctt  1080
gcatcccaga gtcgtcatct tgaagttcag ttgctttgtg atcaatatgg caatgtggca  1140
gcacttcaca gtcgtgattg cagtgtgcaa cggcgacacc aaaagattat tgaggaaggc  1200
ccagttactg ttgctcctcg tgagacagtt aaagcgcttg agcaggcagc aaggaggctt  1260
gctaaggctg tgggttatgt tggtgctgct actgttgaat accttacag catggagact  1320
ggggaatact attttctgga gcttaatccc agattacagg tcgagcatcc agtcactgag  1380
tggattgctg aagtaaatct tcctgcagct caagttgcag ttggaatggg catacctctt  1440
```

```
tggcagattc cagaaatcag acgtttctat ggaatggact atggaggagg atatgacatt    1500
tggaggaaaa cagcagctct tgccacacca tttaattttg atgaagtaga ttctcaatgg    1560
ccaaagggcc attgtgtagc agttagaatt actagcgagg atccagatga tggtttcaaa    1620
cctactggtg ggaaagtgaa ggagataagt tttaaaagca agcctaatgt ttgggcctac    1680
ttctcagtaa agtctggtgg aggcattcat gaatttgctg attctcagtt tgggcatgtt    1740
tttgcatatg ggctctctag atcagcagca ataacgaaca tggctcttgc attaaaagag    1800
attcaaattc gtggagaaat tcattcaaat gttgattaca cagttgatct cttaaatgct    1860
tcagacttca gagaaaataa gattcatact ggctggcttg ataccagaat agctatgcgt    1920
gttcaagctg agaggccccc atggtatatt tcagtggttg gaggagctct atataaaaca    1980
gtaactgcca atgcagccac tgtttctgat tatgtcagtt atctcaccaa gggccagatt    2040
ccaccaaagc atatatccct tgtcagttca acagttaatc tgaatatcga agggagcaaa    2100
tacacagttg aaactgtaag gactggacat ggtagctaca gattacgaat gaatgattca    2160
gcaattgaag cgaatgtaca atctttatgt gatggaggcc tcttaatgca gttggatgga    2220
aatagccatg taatttacgc ggaagaagaa gctggtggta cacgacttct gattgatgga    2280
aagacatgct tgttacagaa tgatcatgat ccatcaaagt tattagctga cacaccctgc    2340
aaacttcttc ggttcttggt tgctgatggt gctcatgttg atgctgatgt accatatgcg    2400
gaagttgagg ttatgaaaat gtgcatgcct ctcttgtcgc ctgcttctgg tgtcattcat    2460
gttatgatgt ctgagggcca ggcattgcag gctggtgatc ttatagcaag gctggatctt    2520
gatgacccct ctgctgtgaa aagagctgaa ccatttcatg gaatatttcc acaaatggac    2580
cttcctgttg ctgcctctag ccaagtacac aaaagatatg ctgcaagttt gaatgctgct    2640
cgaatggtcc ttgcaggata cgagcataat atcaatgaag ttgtacaaga tttggtatgc    2700
tgcctggatg atcccgagct tcccttccta cagtgggatg aacttatgtc agttctagca    2760
actaggcttc caagaaatct taagagtgag ttagaggata aatacatgga atacaagttg    2820
aacttttacc atgggaaaaa caaggacttc ccgtccaagc tgctgagaga catcattgag    2880
gcaaatcttg catatggttc agagaaggaa aaagctacga atgagaggct tattgagcct    2940
cttatgagcc tacttaagtc atatgagggt gggagagaaa gccatgctca ttttgttgtc    3000
aagtcccttt tcaaggagta ccttgctgtg aagaactttt cagtgatgg gattcagtct    3060 gatgtgattg aaaccctgcg tcatcagcac agtaaagact gcagaaggt tgtagacatt    3120 gtgttgtctc accagggtgt gaggaacaaa gctaagcttg taacagcact tatggaaaag    3180
ctggtttatc caaatcctgc tgcttacagg atctgttgg ttcgcttttc ttcactcaat    3240
cataaaagat attataagtt ggcccttaaa gcaagcgaac ttcttgaaca aactaaacta    3300
agtgaactcc gtgcaagcat cgcaagaagc ctttctgatc tggggatgca taagggagaa    3360
atgactattg aagatagcat ggaagattta gtctctgccc cattacctgt cgaagatgca    3420
cttatttctt tgtttgatta cagtgatcca actgttcagc agaaagtgat cgagacatac    3480
atatctcgat tgtatcagcc tcttcttgtg aaagatagca tccaagtgaa atttaaggaa    3540
tctggtgcct ttgctttatg ggaattttct gaagggcatg ttgatactaa aaatggacaa    3600
gggaccgttc ttggtcgaac aagatggggt gccatggtag ctgtcaaatc agttgaatct    3660
gcacgaacag ccattgtagc tgcattaaag gattcggcac agcatgccag ctctgagggc    3720
aacatgatgc acattgcctt attgagtgct gaaaatgaaa ataatatcag tgatgatcaa    3780
```

```
gctcaacata ggatggaaaa acttaacaag atactcaagg atactagtgt cgcaaatgat    3840
cttcgagctg ctggtttgaa ggttataagt tgcattgttc aaagagatga agcacgcatg    3900
ccaatgcgcc acacattact ctggtcagat gaaaagagtt gttatgagga agagcagatt    3960
cttcggcatg tggagcctcc cctctccatg cttcttgaaa tggataagtt gaaagtgaaa    4020
ggatacaatg aaatgaagta tactccatca cgtgatcgtc aatggcatat ctacacacta    4080
agaaatactg aaaaccccaa aatgttgcat agggtatttt tccgaactat tgtcaggcaa    4140
cccaatgcag gcaacaagtt tatatcagcc caaattggcg acactgaagt aggaggtcct    4200
gaggaatctt tgtcatttac atctaatagc attttaagag ccttgatgac tgctattgaa    4260
gaattagagc ttcatgcaat taggactggt cattctcaca tgtatttgtg catattgaaa    4320
gaacaaaagc ttcttgatct cattccgttt tcagggagca caatcgtcga tgttggccaa    4380
gacgaagcta ctgcttgttc acttttaaaa tcaatggctt tgaagataca cgaacttgtt    4440
ggtgcacaga tgcatcatct ttctgtatgc cagtgggagg tgaaactcaa gttgtactgc    4500
gatgggcctg ccagtggcac ctggagagtt gtaactacaa atgttactag tcacacttgc    4560
accgttgata tctaccggga agtggaagat actgaatcgc agaagttagt ataccattca    4620
gcttctccgt cagctagtcc tttgcatggt gtggccctgg ataatccgta tcaacctttg    4680
agtgtcattg atctaaaacg ctgctctgct aggaacaaca gaactacata ttgctatgat    4740
tttccactgg catttgaaac tgccctgcag aagtcatggc agtccaatgg ctccagtgtt    4800
tctgaaggca gtgaaaatag taggtcttat gtgaaagcaa cagagctggt gtttgctgaa    4860
aaacatgggt cctggggcac tcctataatt tccatggagc gtcccgctgg gctcaatgac    4920
attggcatgg tagcttggat cttagagatg tccactcctg aatttcccaa tggcaggcag    4980
attattgtca tagcaaatga tattactttc agagctggat catttggccc aagggaagat    5040
gcgttttttg aagctgtcac gaacctggcc tgcgagagga agcttcctct tatatacttg    5100
gcagcaaact ccggtgctag gattggcata gccgatgaag tgaaatcttg cttccgtgtt    5160
gggtggtccg atgaaggcag ccctgaacgg ggttttcagt acatttatct gactgacgaa    5220
gactatgccc gtattagctt gtctgttata gcacacaagc tgcagctgga taatggtgaa    5280
attaggtgga ttattgactc tgttgtgggc aaggaggatg ggcttggtgt tgagaatata    5340
catgaaagtg ctgctattgc cagtgcttat tctagggcat atgaggagac atttacactt    5400
acatttgtga ctgggcggac tgttggaata ggagcatatc ttgctcggct cggtatacgg    5460
tgcatacagc gtcttgacca gcctattatt ttaactgggt tttctgccct gaacaagctt    5520
cttgggcggg aagtgtacag ctcccacatg cagttgggtg gtcctaagat catggcgacc    5580
aatggtgttg tccacttgac tgtttcagat gaccttgaag tgtttccaa tatattgagg    5640 tggctcagct atgttcctgc caacattggt ggacctcttc ctattacaaa acctttggac    5700
ccaccagaca gacctgttgc atacatccct gagaacacat gtgatccgcg cgcagccatt    5760
cgtggtgtag atgacagcca agggaaatgg ttggtggta tgtttgacaa agacagcttt    5820
gtcgagacat ttgaaggatg ggcgaaaaca gtggttacgg gcagagcaaa gcttggagga    5880
attcctgttg gtgtcatagc tgtggagaca caaaccatga tgcagcttat ccctgctgat    5940
ccaggccagc ttgattccca tgagcgatct gttcctcggg ctggacaagt gtggttccca    6000
gattctgcaa ccaagacagc tcaggcattg ttggacttca accgtgaagg attgccgctg    6060
ttcatccttg ctaactggag aggattctct ggtggacaaa gagatctgtt tgaaggaatt    6120
cttcaggctg ggtcaacaat tgttgagaac cttaggacat acaatcagcc tgcttttgtc    6180
```

```
tacattccta tggctggaga gctgcgtgga ggagcttggg ttgtggttga tagcaaaata    6240
aatccagacc gaattgagtg ttatgctgag aggactgcta aaggcaatgt tctggaacct    6300
caagggttaa ttgaaatcaa attcagatca gaggagctcc aagactgtat gggtaggctt    6360
gacccagagt tgataaatct gaaagcaaaa ctccaaggtg caaagcttgg aaatggaagc    6420
ctaacagatg tagaatccct tcagaagagt atagatgctc gtacgaaaca gttgttgcct    6480
ttatacaccc agattgcaat acggtttgct gaattgcatg atacttccct cagaatggca    6540
gctaaaggtg tgattaagaa agttgtagat tgggaagaat tacgttcttt cttctacaga    6600
aggctacgga ggaggatctc tgaagatgtt cttgcaaaag aaataagagg aatagctggt    6660
gaccacttca ctcaccaatc agcagttgag ctgatcaagg aatggtactt ggcttctcaa    6720
gccacaacag gaagcactga atgggatgat gatgatgctt tgttgcctg gaaggagaat    6780 cctgaaaact ataagggata tatccaagag ttaagggctc aaaaggtgtc tcagtcgctc    6840
tccgatcttg cagactccag ttcagatcta gaagcattct cacagggtct ttccacatta    6900
ttagataaga tggatccctc tcagagagcc aagttcattc aggaagtcaa gaaggtcctg    6960
ggttga                                                               6966

<210> SEQ ID NO 22
<211> LENGTH: 2321
<212> TYPE: PRT
<213> ORGANISM: Setaria italica

<400> SEQUENCE: 22

Met Ser Gln Leu Gly Leu Ala Ala Ala Ser Lys Ala Leu Pro Leu
1               5                   10                  15

Leu Pro Asn Arg His Arg Thr Ser Ala Gly Thr Thr Phe Pro Ser Pro
                20                  25                  30

Val Ser Ser Arg Pro Ser Asn Arg Arg Lys Ser Arg Thr Arg Ser Leu
            35                  40                  45

Arg Asp Gly Gly Asp Gly Val Ser Ala Lys Lys His Asn Gln Ser
    50                  55                  60

Val Arg Gln Gly Leu Ala Gly Ile Ile Asp Leu Pro Asn Glu Ala Thr
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Val Asn Glu Ala His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
    130                 135                 140

Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Val Ala Glu Arg Ile Gly Val Ser Ala Val Trp Pro Gly Trp Gly
    210                 215                 220
```

```
His Ala Ser Glu Asn Pro Glu Leu Pro Asp Ala Leu Thr Ala Lys Gly
225                 230                 235                 240

Ile Val Phe Leu Gly Pro Pro Ala Ala Ser Met Asn Ala Leu Gly Asp
            245                 250                 255

Lys Val Gly Ser Ala Leu Ile Ala Gln Ala Ala Gly Val Pro Thr Leu
        260                 265                 270

Ser Trp Ser Gly Ser His Val Glu Val Pro Leu Glu Cys Cys Leu Asp
    275                 280                 285

Ala Ile Pro Glu Glu Met Tyr Arg Lys Ala Cys Val Thr Thr Thr Glu
290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
                340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
                420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
        450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Val Phe Ala Tyr Gly Leu Ser Arg Ser Ala Ala Ile Thr
            580                 585                 590

Asn Met Ala Leu Ala Leu Lys Glu Ile Gln Ile Arg Gly Glu Ile His
            595                 600                 605

Ser Asn Val Asp Tyr Thr Val Asp Leu Leu Asn Ala Ser Asp Phe Arg
            610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
```

```
                    645                 650                 655
Leu Tyr Lys Thr Val Thr Ala Asn Ala Ala Thr Val Ser Asp Tyr Val
                660                 665                 670

Ser Tyr Leu Thr Lys Gly Gln Ile Pro Pro Lys His Ile Ser Leu Val
                675                 680                 685

Ser Ser Thr Val Asn Leu Asn Ile Glu Gly Ser Lys Tyr Thr Val Glu
                690                 695                 700

Thr Val Arg Thr Gly His Gly Ser Tyr Arg Leu Arg Met Asn Asp Ser
705                 710                 715                 720

Ala Ile Glu Ala Asn Val Gln Ser Leu Cys Asp Gly Leu Leu Met
                    725                 730                 735

Gln Leu Asp Gly Asn Ser His Val Ile Tyr Ala Glu Glu Ala Gly
                740                 745                 750

Gly Thr Arg Leu Leu Ile Asp Gly Lys Thr Cys Leu Leu Gln Asn Asp
                755                 760                 765

His Asp Pro Ser Lys Leu Leu Ala Glu Thr Pro Cys Lys Leu Leu Arg
                770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                    805                 810                 815

Gly Val Ile His Val Met Met Ser Glu Gly Gln Ala Leu Gln Ala Gly
                820                 825                 830

Asp Leu Ile Ala Arg Leu Asp Leu Asp Asp Pro Ser Ala Val Lys Arg
                835                 840                 845

Ala Glu Pro Phe His Gly Ile Phe Pro Gln Met Asp Leu Pro Val Ala
850                 855                 860

Ala Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
                    885                 890                 895

Asp Leu Val Cys Cys Leu Asp Asp Pro Glu Leu Pro Phe Leu Gln Trp
                900                 905                 910

Asp Glu Leu Met Ser Val Leu Ala Thr Arg Leu Pro Arg Asn Leu Lys
                915                 920                 925

Ser Glu Leu Glu Asp Lys Tyr Met Glu Tyr Lys Leu Asn Phe Tyr His
                930                 935                 940

Gly Lys Asn Lys Asp Phe Pro Ser Lys Leu Leu Arg Asp Ile Ile Glu
945                 950                 955                 960

Ala Asn Leu Ala Tyr Gly Ser Glu Lys Glu Lys Ala Thr Asn Glu Arg
                965                 970                 975

Leu Ile Glu Pro Leu Met Ser Leu Leu Lys Ser Tyr Glu Gly Gly Arg
                980                 985                 990

Glu Ser His Ala His Phe Val Val Lys Ser Leu Phe Lys Glu Tyr Leu
                995                 1000                1005

Ala Val Glu Glu Leu Phe Ser Asp Gly Ile Gln Ser Asp Val Ile
    1010                1015                1020

Glu Thr Leu Arg His Gln His Ser Lys Asp Leu Gln Lys Val Val
    1025                1030                1035

Asp Ile Val Leu Ser His Gln Gly Val Arg Asn Lys Ala Lys Leu
    1040                1045                1050

Val Thr Ala Leu Met Glu Lys Leu Val Tyr Pro Asn Pro Ala Ala
    1055                1060                1065
```

```
Tyr Arg Asp Leu Leu Val Arg Phe Ser Ser Leu Asn His Lys Arg
    1070            1075            1080

Tyr Tyr Lys Leu Ala Leu Lys Ala Ser Glu Leu Leu Glu Gln Thr
    1085            1090            1095

Lys Leu Ser Glu Leu Arg Ala Ser Ile Ala Arg Ser Leu Ser Asp
    1100            1105            1110

Leu Gly Met His Lys Gly Glu Met Thr Ile Glu Asp Ser Met Glu
    1115            1120            1125

Asp Leu Val Ser Ala Pro Leu Pro Val Glu Asp Ala Leu Ile Ser
    1130            1135            1140

Leu Phe Asp Tyr Ser Asp Pro Thr Val Gln Gln Lys Val Ile Glu
    1145            1150            1155

Thr Tyr Ile Ser Arg Leu Tyr Gln Pro Leu Leu Val Lys Asp Ser
    1160            1165            1170

Ile Gln Val Lys Phe Lys Glu Ser Gly Ala Phe Ala Leu Trp Glu
    1175            1180            1185

Phe Ser Glu Gly His Val Asp Thr Lys Asn Gly Gln Gly Thr Val
    1190            1195            1200

Leu Gly Arg Thr Arg Trp Gly Ala Met Val Ala Val Lys Ser Val
    1205            1210            1215

Glu Ser Ala Arg Thr Ala Ile Val Ala Ala Leu Lys Asp Ser Ala
    1220            1225            1230

Gln His Ala Ser Ser Glu Gly Asn Met Met His Ile Ala Leu Leu
    1235            1240            1245

Ser Ala Glu Asn Glu Asn Asn Ile Ser Asp Asp Gln Ala Gln His
    1250            1255            1260

Arg Met Glu Lys Leu Asn Lys Ile Leu Lys Asp Thr Ser Val Ala
    1265            1270            1275

Asn Asp Leu Arg Ala Ala Gly Leu Lys Val Ile Ser Cys Ile Val
    1280            1285            1290

Gln Arg Asp Glu Ala Arg Met Pro Met Arg His Thr Leu Leu Trp
    1295            1300            1305

Ser Asp Glu Lys Ser Cys Tyr Glu Glu Glu Gln Ile Leu Arg His
    1310            1315            1320

Val Glu Pro Pro Leu Ser Met Leu Leu Glu Met Asp Lys Leu Lys
    1325            1330            1335

Val Lys Gly Tyr Asn Glu Met Lys Tyr Thr Pro Ser Arg Asp Arg
    1340            1345            1350

Gln Trp His Ile Tyr Thr Leu Arg Asn Thr Glu Asn Pro Lys Met
    1355            1360            1365

Leu His Arg Val Phe Phe Arg Thr Ile Val Arg Gln Pro Asn Ala
    1370            1375            1380

Gly Asn Lys Phe Ile Ser Ala Gln Ile Gly Asp Thr Glu Val Gly
    1385            1390            1395

Gly Pro Glu Glu Ser Leu Ser Phe Thr Ser Asn Ser Ile Leu Arg
    1400            1405            1410

Ala Leu Met Thr Ala Ile Glu Glu Leu Glu Leu His Ala Ile Arg
    1415            1420            1425

Thr Gly His Ser His Met Tyr Leu Cys Ile Leu Lys Glu Gln Lys
    1430            1435            1440

Leu Leu Asp Leu Ile Pro Phe Ser Gly Ser Thr Ile Val Asp Val
    1445            1450            1455
```

```
Gly Gln Asp Glu Ala Thr Ala Cys Ser Leu Leu Lys Ser Met Ala
    1460                1465                1470

Leu Lys Ile His Glu Leu Val Gly Ala Gln Met His His Leu Ser
    1475                1480                1485

Val Cys Gln Trp Glu Val Lys Leu Lys Leu Tyr Cys Asp Gly Pro
    1490                1495                1500

Ala Ser Gly Thr Trp Arg Val Val Thr Thr Asn Val Thr Ser His
    1505                1510                1515

Thr Cys Thr Val Asp Ile Tyr Arg Glu Val Glu Asp Thr Glu Ser
    1520                1525                1530

Gln Lys Leu Val Tyr His Ser Ala Ser Pro Ser Ala Ser Pro Leu
    1535                1540                1545

His Gly Val Ala Leu Asp Asn Pro Tyr Gln Pro Leu Ser Val Ile
    1550                1555                1560

Asp Leu Lys Arg Cys Ser Ala Arg Asn Asn Arg Thr Thr Tyr Cys
    1565                1570                1575

Tyr Asp Phe Pro Leu Ala Phe Glu Thr Ala Leu Gln Lys Ser Trp
    1580                1585                1590

Gln Ser Asn Gly Ser Ser Val Ser Glu Gly Ser Glu Asn Ser Arg
    1595                1600                1605

Ser Tyr Val Lys Ala Thr Glu Leu Val Phe Ala Glu Lys His Gly
    1610                1615                1620

Ser Trp Gly Thr Pro Ile Ile Ser Met Glu Arg Pro Ala Gly Leu
    1625                1630                1635

Asn Asp Ile Gly Met Val Ala Trp Ile Leu Glu Met Ser Thr Pro
    1640                1645                1650

Glu Phe Pro Asn Gly Arg Gln Ile Ile Val Ile Ala Asn Asp Ile
    1655                1660                1665

Thr Phe Arg Ala Gly Ser Phe Gly Pro Arg Glu Asp Ala Phe Phe
    1670                1675                1680

Glu Ala Val Thr Asn Leu Ala Cys Glu Arg Lys Leu Pro Leu Ile
    1685                1690                1695

Tyr Leu Ala Ala Asn Ser Gly Ala Arg Ile Gly Ile Ala Asp Glu
    1700                1705                1710

Val Lys Ser Cys Phe Arg Val Gly Trp Ser Asp Glu Gly Ser Pro
    1715                1720                1725

Glu Arg Gly Phe Gln Tyr Ile Tyr Leu Thr Asp Glu Asp Tyr Ala
    1730                1735                1740

Arg Ile Ser Leu Ser Val Ile Ala His Lys Leu Gln Leu Asp Asn
    1745                1750                1755

Gly Glu Ile Arg Trp Ile Ile Asp Ser Val Val Gly Lys Glu Asp
    1760                1765                1770

Gly Leu Gly Val Glu Asn Ile His Gly Ser Ala Ala Ile Ala Ser
    1775                1780                1785

Ala Tyr Ser Arg Ala Tyr Glu Glu Thr Phe Thr Leu Thr Phe Val
    1790                1795                1800

Thr Gly Arg Thr Val Gly Ile Gly Ala Tyr Leu Ala Arg Leu Gly
    1805                1810                1815

Ile Arg Cys Ile Gln Arg Leu Asp Gln Pro Ile Ile Leu Thr Gly
    1820                1825                1830

Phe Ser Ala Leu Asn Lys Leu Leu Gly Arg Glu Val Tyr Ser Ser
    1835                1840                1845

His Met Gln Leu Gly Gly Pro Lys Ile Met Ala Thr Asn Gly Val
```

-continued

```
                1850                1855                1860
Val His Leu Thr Val Ser Asp Asp Leu Glu Gly Val Ser Asn Ile
    1865                1870                1875
Leu Arg Trp Leu Ser Tyr Val Pro Ala Asn Ile Gly Gly Pro Leu
    1880                1885                1890
Pro Ile Thr Lys Pro Leu Asp Pro Pro Asp Arg Pro Val Ala Tyr
    1895                1900                1905
Ile Pro Glu Asn Thr Cys Asp Pro Arg Ala Ala Ile Arg Gly Val
    1910                1915                1920
Asp Asp Ser Gln Gly Lys Trp Leu Gly Gly Met Phe Asp Lys Asp
    1925                1930                1935
Ser Phe Val Glu Thr Phe Glu Gly Trp Ala Lys Thr Val Val Thr
    1940                1945                1950
Gly Arg Ala Lys Leu Gly Gly Ile Pro Val Gly Val Ile Ala Val
    1955                1960                1965
Glu Thr Gln Thr Met Met Gln Leu Ile Pro Ala Asp Pro Gly Gln
    1970                1975                1980
Leu Asp Ser His Glu Arg Ser Val Pro Arg Ala Gly Gln Val Trp
    1985                1990                1995
Phe Pro Asp Ser Ala Thr Lys Thr Ala Gln Ala Leu Leu Asp Phe
    2000                2005                2010
Asn Arg Glu Gly Leu Pro Leu Phe Ile Leu Ala Asn Trp Arg Gly
    2015                2020                2025
Phe Ser Gly Gly Gln Arg Asp Leu Phe Glu Gly Ile Leu Gln Ala
    2030                2035                2040
Gly Ser Thr Ile Val Glu Asn Leu Arg Thr Tyr Asn Gln Pro Ala
    2045                2050                2055
Phe Val Tyr Ile Pro Met Ala Gly Glu Leu Arg Gly Gly Ala Trp
    2060                2065                2070
Val Val Val Asp Ser Lys Ile Asn Pro Asp Arg Ile Glu Cys Tyr
    2075                2080                2085
Ala Glu Arg Thr Ala Lys Gly Asn Val Leu Glu Pro Gln Gly Leu
    2090                2095                2100
Ile Glu Ile Lys Phe Arg Ser Glu Glu Leu Gln Asp Cys Met Gly
    2105                2110                2115
Arg Leu Asp Pro Glu Leu Ile Asn Leu Lys Ala Lys Leu Gln Gly
    2120                2125                2130
Ala Lys Leu Gly Asn Gly Ser Leu Thr Asp Val Glu Ser Leu Gln
    2135                2140                2145
Lys Ser Ile Asp Ala Arg Thr Lys Gln Leu Leu Pro Leu Tyr Thr
    2150                2155                2160
Gln Ile Ala Ile Arg Phe Ala Glu Leu His Asp Thr Ser Leu Arg
    2165                2170                2175
Met Ala Ala Lys Gly Val Ile Lys Lys Val Val Asp Trp Glu Glu
    2180                2185                2190
Leu Arg Ser Phe Phe Tyr Arg Arg Leu Arg Arg Arg Ile Ser Glu
    2195                2200                2205
Asp Val Leu Ala Lys Glu Ile Arg Gly Ile Ala Gly Asp His Phe
    2210                2215                2220
Thr His Gln Ser Ala Val Glu Leu Ile Lys Glu Trp Tyr Leu Ala
    2225                2230                2235
Ser Gln Ala Thr Thr Gly Ser Thr Glu Trp Asp Asp Asp Asp Ala
    2240                2245                2250
```

```
Phe Val Ala Trp Lys Glu Asn Pro Glu Asn Tyr Lys Gly Tyr Ile
    2255                2260                2265

Gln Glu Leu Arg Ala Gln Lys Val Ser Gln Ser Leu Ser Asp Leu
    2270                2275                2280

Ala Asp Ser Ser Ser Asp Leu Glu Ala Phe Ser Gln Gly Leu Ser
    2285                2290                2295

Thr Leu Leu Asp Lys Met Asp Pro Ser Gln Arg Ala Lys Phe Ile
    2300                2305                2310

Gln Glu Val Lys Lys Val Leu Gly
    2315                2320

<210> SEQ ID NO 23
<211> LENGTH: 6963
<212> TYPE: DNA
<213> ORGANISM: Alopecurus myosuroides

<400> SEQUENCE: 23
atgggatcca cacatctgcc cattgtcggg tttaatgcat ccacaacacc atcgctatcc      60
actcttcgcc agataaactc agctgctgct gcattccaat cttcgtcccc ttcaaggtca     120
tccaagaaga aagccgacg  tgttaagtca ataagggatg atggcgatgg aagcgtgcca     180
gaccctgcag ccatggcca  gtctattcgc caaggtctcg ctggcatcat cgacctccca     240
aaggagggcg catcagctcc agatgtggac atttcacatg ggtctgaaga ccacaaggcc     300
tcctaccaaa tgaatgggat actgaatgaa tcacataacg ggaggcacgc ctctctgtct     360
aaagtttatg aattttgcac ggaattgggt ggaaaaacac caattcacag tgtattagtc     420
gccaacaatg gaatggcagc agctaagttc atgcggagtg tccggacatg gctaatgat      480 acatttgggt cagagaaggc gattcagttg atagctatgg caactccgga agacatgaga     540
ataaatgcag agcacattag aattgctgat cagtttgttg aagtacctgg tggaacaaac     600
aataacaact atgcaaatgt ccaactcata gtggagatag cagagagaac tggtgtctcc     660
gccgtttggc ctggttgggg ccatgcatct gagaatcctg aacttccaga tgcactaact     720
gcaaaaggaa ttgttttct  tgggccacca gcatcatcaa tgaacgcact aggcgacaag     780
gttggttcag ctctcattgc tcaagcagca ggggttccca ctcttgcttg gagtggatca     840
catgtggaaa ttccattaga actttgtttg gactcgatac ctgaggagat gtataggaaa     900
gcctgtgtta caaccgctga tgaagcagtt gcaagttgtc agatgattgg ttaccctgcc     960
atgatcaagg catcctgggg tggtggtggt aaagggatta gaaaggttaa taatgatgac    1020
gaggtgaaag cactgttaa  gcaagtacag ggtgaagttc ctggctcccc gatatttatc    1080
atgagacttg catctcagag tcgtcatctt gaagtccagc tgctttgtga tgaatatggc    1140
aatgtagcag cacttcacag tcgtgattgc agtgtgcaac gacgacacca aaagattatc    1200
gaggaaggac cagttactgt tgctcctcgt gaaacagtga agagctaga  gcaagcagca    1260 aggaggcttg ctaaggccgt gggttacgtc ggtgctgcta ctgttgaata tctctacagc    1320
atggagactg gtgaatacta ttttctggag cttaatccac ggttgcaggt tgagcaccca    1380
gtcaccgagt cgatagctga agtaaatttg cctgcagccc aagttgcagt tgggatgggt    1440
ataccccttt ggcagattcc agagatcaga cgtttctacg gaatggacaa tggaggaggc    1500
tatgatattt ggaggaaaac agcagctctc gctactccat caactttga  tgaagtagat    1560 tctcaatggc cgaagggtca ttgtgtggca gttaggataa ccagtgagaa tccagatgat    1620
ggattcaagc ctactggtgg aaaagtaaag gagataagtt ttaaaagtaa gccaaatgtc    1680
```

```
tggggatatt tctcagttaa gtctggtgga ggcattcatg aatttgcgga ttctcagttt    1740
ggacacgttt ttgcctatgg agagactaga tcagcagcaa taaccagcat gtctcttgca    1800
ctaaaagaga ttcaaattcg tggagaaatt catacaaacg ttgattacac ggttgatctc    1860
ttgaatgccc cagacttcag agaaaacacg atccataccg gttggctgga taccagaata    1920
gctatgcgtg ttcaagctga gaggcctccc tggtatattt cagtggttgg aggagctcta    1980
tataaaacaa taaccaccaa tgcggagacc gtttctgaat atgttagcta tctcatcaag    2040
ggtcagattc caccaaagca catatccctt gtccattcaa ctatttcttt gaatatagag    2100
gaaagcaaat atacaattga gattgtgagg agtggacagg gtagctacag attgagactg    2160
aatggatcac ttattgaagc caatgtacaa acattatgtg atggaggcct tttaatgcag    2220
ctggatggaa atagccatgt tatttatgct gaagaagaag cgggtggtac acggcttctt    2280
attgatggaa aaacatgctt gctacagaat gaccatgatc cgtcaaggtt attagctgag    2340
acaccctgca aacttcttcg tttcttgatt gccgatggtg ctcatgttga tgctgatgta    2400
ccatacgcgg aagttgaggt tatgaagatg tgcatgcccc tcttgtcgcc tgctgctggt    2460
gtcattaatg ttttgttgtc tgagggccag gcgatgcagg ctggtgatct tatagcgaga    2520
cttgatctcg atgacccttc tgctgtgaag agagccgagc catttgaagg atcttttcca    2580
gaaatgagcc ttcctattgc tgcttctggc caagttcaca aaagatgtgc tgcaagtttg    2640
aacgctgctc gaatggtcct tgcaggatat gaccatgcgg ccaacaaagt tgtgcaagat    2700
ttggtatggt gccttgatac acctgctctt cctttcctac aatgggaaga gcttatgtct    2760
gttttagcaa ctagacttcc aagacgtctt aagagcgagt tggagggcaa atacaatgaa    2820
tacaagttaa atgttgacca tgtgaagatc aaggatttcc ctaccgagat gcttagagag    2880
acaatcgagg aaaatcttgc atgtgtttcc gagaaggaaa tggtgacaat tgagaggctt    2940
gttgaccctc tgatgagcct gctgaagtca tacgagggtg ggagagaaag ccatgcccac    3000
tttattgtca agtccctttt tgaggagtat ctctcggttg aggaactatt cagtgatggc    3060
attcagtctg acgtgattga acgcctgcgc ctacaatata gtaaagacct ccagaaggtt    3120
gtagacattg ttttgtctca ccagggtgtg agaaacaaaa caaagctgat actcgcgctc    3180
atggagaaac tggtctatcc aaaccctgct gcctacagag atcagttgat tcgcttttct    3240
tccctcaacc ataaaagata ttataagttg gctcttaaag ctagtgaact tcttgaacaa    3300
accaagctca gcgaactccg cacaagcatt gcaaggaacc tttcagcgct ggatatgttc    3360
accgaggaaa aggcagattt ctccttgcaa gacagaaaat tggccattaa tgagagcatg    3420
ggagatttag tcactgcccc actgccagtt gaagatgcac ttgtttcttt gtttgattgt    3480
actgatcaaa ctcttcagca gagagtgatt cagacataca tatctcgatt ataccagcct    3540
caacttgtga aggatagcat ccagctgaaa tatcaggatt ctggtgttat tgctttatgg    3600
gaattcactg aaggaaatca tgagaagaga ttgggtgcta tggttatcct gaagtcacta    3660
gaatctgtgt caacagccat tggagctgct ctaaaggatg catcacatta tgcaagctct    3720
gcgggcaaca cggtgcatat tgctttgttg gatgctgata cccaactgaa tacaactgaa    3780
gatagtggtg ataatgacca agctcaagac aagatggata aactttcttt tgtactgaaa    3840
caagatgttg tcatggctga tctacgtgct gctgatgtca aggttgttag ttgcattgtt    3900
caaagagatg gagcaatcat gcctatgcgc cgtaccttcc tcttgtcaga ggaaaaactt    3960
tgttacgagg aagagccgat tcttcggcat gtggagcctc cactttctgc acttcttgag    4020
```

| | |
|---|---|
| ttggataaat tgaaagtgaa aggatacaat gagatgaagt atacaccgtc acgtgatcgt | 4080 |
| cagtggcata tatacacact tagaaatact gaaaatccaa aaatgctgca cagggtattt | 4140 |
| ttccgaacac ttgtcagaca acccagtgca ggcaacaggt ttacatcaga ccatatcact | 4200 |
| gatgttgaag taggacacgc agaggaacct ctttcattta cttcaagcag catattaaaa | 4260 |
| tcgttgaaga ttgctaaaga agaattggag cttcacgcga tcaggactgg ccattctcat | 4320 |
| atgtacttgt gcatattgaa agagcaaaag cttcttgacc ttgttcctgt ttcagggaac | 4380 |
| actgttgtgg atgttggtca agatgaagct actgcatgct ctcttttgaa agaaatggct | 4440 |
| ttaaagatac atgaacttgt tggtgcaaga atgcatcatc tttctgtatg ccagtgggaa | 4500 |
| gtgaaactta agttggtgag cgatgggcct gccagtggta gctggagagt tgtaacaacc | 4560 |
| aatgttactg gtcacacctg cactgtggat atctaccggg aggtcgaaga tacagaatca | 4620 |
| cagaaactag tataccactc caccgcattg tcatctggtc ctttgcatgg tgttgcactg | 4680 |
| aatacttcgt atcagccttt gagtgttatt gatttaaaac gttgctctgc caggaacaac | 4740 |
| aaaactacat actgctatga ttttccattg acatttgaag ctgcagtgca gaagtcgtgg | 4800 |
| tctaacattt ccagtgaaaa caaccaatgt tatgttaaag cgacagagct tgtgtttgct | 4860 |
| gaaaagaatg ggtcgtgggg cactcctata attcctatgc agcgtgctgc tgggctgaat | 4920 |
| gacattggta tggtagcctg atcttggac atgtccactc ctgaatttcc cagcggcaga | 4980 |
| cagatcattg ttatcgcaaa tgatattaca tttagagctg gatcatttgg cccaagggaa | 5040 |
| gatgcatttt tcgaagctgt aaccaacctg gcttgtgaga agaagcttcc acttatctac | 5100 |
| ttggctgcaa actctggtgc tcggattggc attgctgatg aagtaaaatc ttgcttccgt | 5160 |
| gttggatgga ctgatgatag cagccctgaa cgtggattta ggtacattta tatgactgac | 5220 |
| gaagaccatg atcgtattgg ctcttcagtt atagcacaca agatgcagct agatagtggc | 5280 |
| gagatcaggt gggttattga ttctgttgtg ggaaagagg atggactagg tgtggagaac | 5340 |
| atacatggaa gtgctgctat tgccagtgcc tattctaggg cgtacgagga gacatttaca | 5400 |
| cttacattcg ttactggacg aactgttgga atcggagcct atcttgctcg acttggcata | 5460 |
| cggtgcatac agcgtattga ccagcccatt attttgaccg ggttttctgc cctgaacaag | 5520 |
| cttcttgggc gggaggtgta cagctcccac atgcagttgg gtggtcccaa aatcatggcg | 5580 |
| acgaatggtg ttgtccatct gactgttcca gatgaccttg aaggtgtttc taatatattg | 5640 |
| aggtggctca gctatgttcc tgcaaacatt ggtggacctc ttcctattac aaaatctttg | 5700 |
| gacccaatag acagacccgt tgcatacatc cctgagaata catgtgatcc tcgtgcagcc | 5760 |
| atcagtggca ttgatgacag ccaagggaaa tggttgggtg gcatgtttga caaagacagt | 5820 |
| tttgtggaga catttgaagg atgggcgaag acagtagtta ctggcagagc aaaacttgga | 5880 |
| gggattcctg ttggtgttat agctgtggag acacagacca tgatgcagct cgtccccgct | 5940 |
| gatccaggcc agcctgattc ccacgagcgg tctgttcctc gtgctgggca agtttggttt | 6000 |
| ccagattctg ctaccaagac agcgcaggcg atgttggact caaccgtga aggattacct | 6060 |
| ctgttcatac ttgctaactg gagaggcttc tctggagggc aaagagatct ttttgaagga | 6120 |
| attctgcagg ctgggtcaac aattgttgag aaccttagga catacaatca gcctgccttt | 6180 |
| gtatatatcc ccaaggctgc agagctacgt ggaggagcct gggtcgtgat tgatagcaag | 6240 |
| ataaacccag atcgcatcga gtgctatgct gagaggactg caaagggtaa tgttctcgaa | 6300 |
| cctcaagggt tgattgagat caagttcagg tcagaggaac tcaaagaatg catgggtagg | 6360 |
| cttgatccag aattgataga tctgaaagca agactccagg gagcaaatgg aagcctatct | 6420 |

-continued

```
gatggagaat cccttcagaa gagcatagaa gctcggaaga aacagttgct gcctctgtac    6480
acccaaatcg cggtacgttt tgcggaattg cacgacactt cccttagaat ggctgctaaa    6540
ggtgtgatca ggaaagttgt agactgggaa gactctcggt ctttcttcta caagagatta    6600
cggaggaggc tatccgagga cgttctggca aaggagatta gaggtgtaat tggtgagaag    6660
tttcctcaca aatcagcgat cgagctgatc aagaaatggt acttggcttc tgaggcagct    6720
gcagcaggaa gcaccgactg ggatgacgac gatgcttttg tcgcctggag ggagaaccct    6780
gaaaactata aggagtatat caaagagctt agggctcaaa gggtatctcg gttgctctca    6840
gatgttgcag gctccagttc ggatttacaa gccttgccgc agggtctttc catgctacta    6900
gataagatgg atccctctaa gagagcacag tttatcgagg aggtcatgaa ggtcctgaaa    6960
tga                                                                  6963
```

<210> SEQ ID NO 24
<211> LENGTH: 2320
<212> TYPE: PRT
<213> ORGANISM: Alopecurus myosuroides

<400> SEQUENCE: 24

```
Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270
```

```
Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Lys Gly Ile Arg Lys Val
                325                 330                 335

Asn Asn Asp Asp Glu Val Lys Ala Leu Phe Lys Gln Val Gln Gly Glu
                340                 345                 350

Val Pro Gly Ser Pro Ile Phe Ile Met Arg Leu Ala Ser Gln Ser Arg
            355                 360                 365

His Leu Glu Val Gln Leu Leu Cys Asp Glu Tyr Gly Asn Val Ala Ala
        370                 375                 380

Leu His Ser Arg Asp Cys Ser Val Gln Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
                500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
        610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685
```

```
Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His Phe Ile Val Lys Ser Leu Phe Glu
        995                 1000                1005

Glu Tyr Leu Ser Val Glu Glu Leu Phe Ser Asp Gly Ile Gln Ser
    1010                1015                1020

Asp Val Ile Glu Arg Leu Arg Leu Gln Tyr Ser Lys Asp Leu Gln
    1025                1030                1035

Lys Val Val Asp Ile Val Leu Ser His Gln Gly Val Arg Asn Lys
    1040                1045                1050

Thr Lys Leu Ile Leu Ala Leu Met Glu Lys Leu Val Tyr Pro Asn
    1055                1060                1065

Pro Ala Ala Tyr Arg Asp Gln Leu Ile Arg Phe Ser Ser Leu Asn
    1070                1075                1080

His Lys Arg Tyr Tyr Lys Leu Ala Leu Lys Ala Ser Glu Leu Leu
    1085                1090                1095

Glu Gln Thr Lys Leu Ser Glu Leu Arg Thr Ser Ile Ala Arg Asn
```

```
                   1100                1105                1110

Leu Ser Ala Leu Asp Met Phe Thr Glu Lys Ala Asp Phe Ser
                   1115                1120                1125

Leu Gln Asp Arg Lys Leu Ala Ile Asn Glu Ser Met Gly Asp Leu
                   1130                1135                1140

Val Thr Ala Pro Leu Pro Val Glu Asp Ala Leu Val Ser Leu Phe
                   1145                1150                1155

Asp Cys Thr Asp Gln Thr Leu Gln Gln Arg Val Ile Gln Thr Tyr
                   1160                1165                1170

Ile Ser Arg Leu Tyr Gln Pro Gln Leu Val Lys Asp Ser Ile Gln
                   1175                1180                1185

Leu Lys Tyr Gln Asp Ser Gly Val Ile Ala Leu Trp Glu Phe Thr
                   1190                1195                1200

Glu Gly Asn His Glu Lys Arg Leu Gly Ala Met Val Ile Leu Lys
                   1205                1210                1215

Ser Leu Glu Ser Val Ser Thr Ala Ile Gly Ala Ala Leu Lys Asp
                   1220                1225                1230

Ala Ser His Tyr Ala Ser Ser Ala Gly Asn Thr Val His Ile Ala
                   1235                1240                1245

Leu Leu Asp Ala Asp Thr Gln Leu Asn Thr Thr Glu Asp Ser Gly
                   1250                1255                1260

Asp Asn Asp Gln Ala Gln Asp Lys Met Asp Lys Leu Ser Phe Val
                   1265                1270                1275

Leu Lys Gln Asp Val Val Met Ala Asp Leu Arg Ala Ala Asp Val
                   1280                1285                1290

Lys Val Val Ser Cys Ile Val Gln Arg Asp Gly Ala Ile Met Pro
                   1295                1300                1305

Met Arg Arg Thr Phe Leu Leu Ser Glu Glu Lys Leu Cys Tyr Glu
                   1310                1315                1320

Glu Glu Pro Ile Leu Arg His Val Glu Pro Leu Ser Ala Leu
                   1325                1330                1335

Leu Glu Leu Asp Lys Leu Lys Val Lys Gly Tyr Asn Glu Met Lys
                   1340                1345                1350

Tyr Thr Pro Ser Arg Asp Arg Gln Trp His Ile Tyr Thr Leu Arg
                   1355                1360                1365

Asn Thr Glu Asn Pro Lys Met Leu His Arg Val Phe Phe Arg Thr
                   1370                1375                1380

Leu Val Arg Gln Pro Ser Ala Gly Asn Arg Phe Thr Ser Asp His
                   1385                1390                1395

Ile Thr Asp Val Glu Val Gly His Ala Glu Pro Leu Ser Phe
                   1400                1405                1410

Thr Ser Ser Ser Ile Leu Lys Ser Leu Lys Ile Ala Lys Glu Glu
                   1415                1420                1425

Leu Glu Leu His Ala Ile Arg Thr Gly His Ser His Met Tyr Leu
                   1430                1435                1440

Cys Ile Leu Lys Glu Gln Lys Leu Leu Asp Leu Val Pro Val Ser
                   1445                1450                1455

Gly Asn Thr Val Val Asp Val Gly Gln Asp Glu Ala Thr Ala Cys
                   1460                1465                1470

Ser Leu Leu Lys Glu Met Ala Leu Lys Ile His Glu Leu Val Gly
                   1475                1480                1485

Ala Arg Met His His Leu Ser Val Cys Gln Trp Glu Val Lys Leu
                   1490                1495                1500
```

```
Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560

Tyr Gln Pro Leu Ser Val Ile Asp Leu Lys Arg Cys Ser Ala Arg
    1565                1570                1575

Asn Asn Lys Thr Thr Tyr Cys Tyr Asp Phe Pro Leu Thr Phe Glu
    1580                1585                1590

Ala Ala Val Gln Lys Ser Trp Ser Asn Ile Ser Ser Glu Asn Asn
    1595                1600                1605

Gln Cys Tyr Val Lys Ala Thr Glu Leu Val Phe Ala Glu Lys Asn
    1610                1615                1620

Gly Ser Trp Gly Thr Pro Ile Ile Pro Met Gln Arg Ala Ala Gly
    1625                1630                1635

Leu Asn Asp Ile Gly Met Val Ala Trp Ile Leu Asp Met Ser Thr
    1640                1645                1650

Pro Glu Phe Pro Ser Gly Arg Gln Ile Ile Val Ile Ala Asn Asp
    1655                1660                1665

Ile Thr Phe Arg Ala Gly Ser Phe Gly Pro Arg Glu Asp Ala Phe
    1670                1675                1680

Phe Glu Ala Val Thr Asn Leu Ala Cys Glu Lys Lys Leu Pro Leu
    1685                1690                1695

Ile Tyr Leu Ala Ala Asn Ser Gly Ala Arg Ile Gly Ile Ala Asp
    1700                1705                1710

Glu Val Lys Ser Cys Phe Arg Val Gly Trp Thr Asp Asp Ser Ser
    1715                1720                1725

Pro Glu Arg Gly Phe Arg Tyr Ile Tyr Met Thr Asp Glu Asp His
    1730                1735                1740

Asp Arg Ile Gly Ser Ser Val Ile Ala His Lys Met Gln Leu Asp
    1745                1750                1755

Ser Gly Glu Ile Arg Trp Val Ile Asp Ser Val Val Gly Lys Glu
    1760                1765                1770

Asp Gly Leu Gly Val Glu Asn Ile His Gly Ser Ala Ala Ile Ala
    1775                1780                1785

Ser Ala Tyr Ser Arg Ala Tyr Glu Glu Thr Phe Thr Leu Thr Phe
    1790                1795                1800

Val Thr Gly Arg Thr Val Gly Ile Gly Ala Tyr Leu Ala Arg Leu
    1805                1810                1815

Gly Ile Arg Cys Ile Gln Arg Ile Asp Gln Pro Ile Ile Leu Thr
    1820                1825                1830

Gly Phe Ser Ala Leu Asn Lys Leu Leu Gly Arg Glu Val Tyr Ser
    1835                1840                1845

Ser His Met Gln Leu Gly Gly Pro Lys Ile Met Ala Thr Asn Gly
    1850                1855                1860

Val Val His Leu Thr Val Pro Asp Asp Leu Glu Gly Val Ser Asn
    1865                1870                1875

Ile Leu Arg Trp Leu Ser Tyr Val Pro Ala Asn Ile Gly Gly Pro
    1880                1885                1890
```

```
Leu Pro Ile Thr Lys Ser Leu Asp Pro Ile Asp Arg Pro Val Ala
1895                1900                1905

Tyr Ile Pro Glu Asn Thr Cys Asp Pro Arg Ala Ala Ile Ser Gly
1910                1915                1920

Ile Asp Asp Ser Gln Gly Lys Trp Leu Gly Gly Met Phe Asp Lys
1925                1930                1935

Asp Ser Phe Val Glu Thr Phe Glu Gly Trp Ala Lys Thr Val Val
1940                1945                1950

Thr Gly Arg Ala Lys Leu Gly Gly Ile Pro Val Gly Val Ile Ala
1955                1960                1965

Val Glu Thr Gln Thr Met Met Gln Leu Val Pro Ala Asp Pro Gly
1970                1975                1980

Gln Pro Asp Ser His Glu Arg Ser Val Pro Arg Ala Gly Gln Val
1985                1990                1995

Trp Phe Pro Asp Ser Ala Thr Lys Thr Ala Gln Ala Met Leu Asp
2000                2005                2010

Phe Asn Arg Glu Gly Leu Pro Leu Phe Ile Leu Ala Asn Trp Arg
2015                2020                2025

Gly Phe Ser Gly Gly Gln Arg Asp Leu Phe Glu Gly Ile Leu Gln
2030                2035                2040

Ala Gly Ser Thr Ile Val Glu Asn Leu Arg Thr Tyr Asn Gln Pro
2045                2050                2055

Ala Phe Val Tyr Ile Pro Lys Ala Ala Glu Leu Arg Gly Gly Ala
2060                2065                2070

Trp Val Val Ile Asp Ser Lys Ile Asn Pro Asp Arg Ile Glu Cys
2075                2080                2085

Tyr Ala Glu Arg Thr Ala Lys Gly Asn Val Leu Glu Pro Gln Gly
2090                2095                2100

Leu Ile Glu Ile Lys Phe Arg Ser Glu Glu Leu Lys Glu Cys Met
2105                2110                2115

Gly Arg Leu Asp Pro Glu Leu Ile Asp Leu Lys Ala Arg Leu Gln
2120                2125                2130

Gly Ala Asn Gly Ser Leu Ser Asp Gly Glu Ser Leu Gln Lys Ser
2135                2140                2145

Ile Glu Ala Arg Lys Lys Gln Leu Leu Pro Leu Tyr Thr Gln Ile
2150                2155                2160

Ala Val Arg Phe Ala Glu Leu His Asp Thr Ser Leu Arg Met Ala
2165                2170                2175

Ala Lys Gly Val Ile Arg Lys Val Val Asp Trp Glu Asp Ser Arg
2180                2185                2190

Ser Phe Phe Tyr Lys Arg Leu Arg Arg Arg Leu Ser Glu Asp Val
2195                2200                2205

Leu Ala Lys Glu Ile Arg Gly Val Ile Gly Glu Lys Phe Pro His
2210                2215                2220

Lys Ser Ala Ile Glu Leu Ile Lys Lys Trp Tyr Leu Ala Ser Glu
2225                2230                2235

Ala Ala Ala Ala Gly Ser Thr Asp Trp Asp Asp Asp Ala Phe
2240                2245                2250

Val Ala Trp Arg Glu Asn Pro Glu Asn Tyr Lys Glu Tyr Ile Lys
2255                2260                2265

Glu Leu Arg Ala Gln Arg Val Ser Arg Leu Leu Ser Asp Val Ala
2270                2275                2280

Gly Ser Ser Ser Asp Leu Gln Ala Leu Pro Gln Gly Leu Ser Met
```

```
                    2285               2290              2295
Leu Leu Asp Lys Met Asp Pro Ser Lys Arg Ala Gln Phe Ile Glu
            2300              2305                 2310

Glu Val Met Lys Val Leu Lys
        2315            2320

<210> SEQ ID NO 25
<211> LENGTH: 6936
<212> TYPE: DNA
<213> ORGANISM: Aegilops tauschii

<400> SEQUENCE: 25
atgggatcca cacatttgcc cattgtcggc cttaatgcct cgacaacacc atcgctatcc      60
actattcgcc cggtaaattc agccggtgct gcattccaac catctgcccc ttctagaacc     120
tccaagaaga aaagtcgtcg tgttcagtca ttaagggatg gaggcgatgg aggcgtgtca     180
gaccctaacc agtctattcg ccaaggtctt gccggcatca ttgacctccc aaaggagggc     240
acatcagctc cggaagtgga tatttcacat gggtccgaag aacccagggg ctcctaccaa     300
atgaatggga tactgaatga agcacataat gggaggcatg cttcgctgtc taaggttgtc     360
gaattttgta tggcattggg cggcaaaaca ccaattcata gtgtattagt tgcgaacaat     420
ggaatggcag cagctaagtt catgcggagt gtccgaacat gggctaatga acatttggg     480 tcagagaagg caattcagtt gatagctatg ctactccag aagacatgag gataaatgca     540
gagcacatta gaattgctga tcaatttgtt gaagtacccg gtggaacaaa caataacaac     600
tatgcaaatg tccaactcat agtggagata gcagtgagaa ccggtgtttc tgctgtttgg     660
cctggttggg gccatgcatc tgagaatcct gaacttccag atgcactaaa tgcaaacgga     720
attgtttttc ttgggccacc atcatcatca atgaacgcac taggtgacaa ggttggttca     780
gctctcattg ctcaagcagc aggggttccg actcttcctt ggagtggatc acaggtggaa     840
attccattag aagtttgttt ggactcgata cctgcggata tgtataggaa gcttgtgtt     900 agtactacgg aggaagcact tgcgagttgt cagatgattg ggtatccagc catgattaaa     960
gcatcatggg gtggtggtgg taaagggatc cgaaaggtta ataacgacga tgatgtcaga    1020
gcactgttta gcaagtgca aggtgaagtt cctggctccc caatatttat catgagactt    1080
gcatctcaga gtcgacatct tgaagttcag ttgctttgtg atcaatatgg caatgtagct    1140
gcgcttcaca gtcgtgactg cagtgtgcaa cggcgacacc aaaagattat tgaggaagga    1200
ccagttactg ttgctcctcg cgagacagtg aaagagctag agcaagcagc aaggaggctt    1260
gctaaggctg tgggttatgt tggtgctgct actgttgaat atctctacag catggagact    1320
ggtgaatact attttctgga acttaatcca cggttgcagg ttgagcatcc agtcaccgag    1380
tggatagctg aagtaaactt gcctgcagct caagttgcag ttggaatggg tatacccctt    1440
tggcaggttc cagagatcag acgtttctat ggaatggaca atggaggagg ctatgacatt    1500
tggaggaaaa cagcagctct tgctaccca tttaactttg atgaagtgga ttctcaatgg    1560
ccaaagggtc attgtgtagc agttaggata accagtgagg atccagatga cggattcaag    1620
cctaccggtg aaaagtaaa ggagatcagt tttaaaagca agccaaatgt ttgggcctat    1680
ttctctgtta agtccggtgg aggcattcat gaatttgctg attctcagtt tggacatgtt    1740
tttgcatatg gagtgtctag agcagcagca ataaccaaca tgtctcttgc gctaaaagag    1800
attcaaattc gtgagaaat tcattcaaat gttgattaca cagttgatct cttgaatgcc    1860
tcagacttca agaaaacag gattcatact ggctggctgg ataacagaat agcaatgcga    1920
```

```
gtccaagctg agagacctcc gtggtatatt tcagtggttg gaggagctct atataaaaca    1980
ataacgagca acacagacac tgtttctgaa tatgttagct atctcgtcaa gggtcagatt    2040
ccaccgaagc atatatccct tgtccattca actgtttctt tgaatataga ggaaagcaaa    2100
tatacaattg aaactataag gagcggacag ggtagctaca gattgcgaat gaatggatca    2160
gttattgaag caaatgtcca acattatgt gatggtggac ttttaatgca gttggatgga     2220
aacagccatg taatttatgc tgaagaagag gccggtggta cacggcttct aattgatgga    2280
aagacatgct tgttacagaa tgatcacgat ccttcaaggt tattagctga cacccctgc     2340 aaacttcttc gtttcttggt tgccgatggt gctcatgttg aagctgatgt accatatgcg    2400
gaagttgagg ttatgaagat gtgcatgccc ctcttgtcac ctgctgctgg tgtcattaat    2460
gttttgttgt ctgagggcca gcctatgcag gctggtgatc ttatagcaag acttgatctt    2520 gatgacccctt ctgctgtgaa gagagctgag ccgtttaacg gatctttccc agaaatgagc   2580
cttcctattg ctgcttctgg ccaagttcac aaaagatgtg ccacaagctt gaatgctgct    2640
cggatggtcc ttgcaggata tgatcacccg atcaacaaag ttgtacaaga tctggtatcc    2700
tgtctagatg ctcctgagct tccttttccta caatgggaag agcttatgtc tgttttagca   2760
actagacttc aaggcttct taagagcgag ttggagggta aatacagtga atataagtta    2820
aatgttggcc atggaaagag caaggatttc ccttccaaga tgctaagaga gataatcgag    2880
gaaaatcttg cacatggttc tgagaaggaa attgctacaa atgagaggct tgttgagcct    2940
cttatgagcc tactgaagtc atatgagggt ggcagagaaa gccatgcaca ctttattgtg    3000
aagtcccttt tcgaggacta tctctcggtt gaggaactat tcagtgatgg cattcagtct    3060
gatgtgattg aacgcctgcg ccaacaacat agtaaagatc tccagaaggt tgtagacatt    3120
gtgttgtctc accagggtgt gagaaacaaa actaagctga tactaacact catggagaaa    3180
ctggtctatc caaaccctgc tgcctacaag gatcagttga ctcgcttttc ctccctcaat    3240
cacaaaagat attataagtt ggcccttaaa gctagcgagc ttcttgaaca aaccaagctt    3300
agtgagctcc gcacaagcat tgcaaggagc cttttcagaac ttgagatgtt tactgaagaa    3360
aggacggcca ttagtgagat catgggagat ttagtgactg ccccactgcc agttgaagat    3420
gcactggttt ctttgtttga ttgtagtgat caaactcttc agcagagggt gatcgagacg    3480
tacatatctc gattataccca gcctcatctt gtcaaggata gtatccagct gaaatatcag    3540
gaatctggtg ttattgcttt atgggaattc gctgaagcgc attcagagaa gagattgggt    3600
gctatggtta ttgtgaagtc gttagaatct gtatcagcag caattggagc tgcactaaag    3660
ggtacatcac gctatgcaag ctctgagggt aacataatgc atattgcttt attgggtgct    3720
gataatcaaa tgcatggaac tgaagacagt ggtgataacg atcaagctca agtcaggata    3780
gacaaacttt ctgcgacact ggaacaaaat actgtcacag ctgatctccg tgctgctggt    3840
gtgaaggtta ttagttgcat tgttcaaagg gatggagcac tcatgcctat cgccatacc     3900 ttcctcttgt cggatgaaaa gctttgttat gaggaagagc cggttctccg gcatgtggag    3960
cctcctcttt ctgctcttct tgagttgggt aagttgaaag tgaaaggata caatgaggtg    4020
aagtatacac cgtcacgtga tcgtcagtgg aacatatata cacttagaaa tacagagaac    4080
cccaaaatgt tgcacagggt gttttttccga actcttgtca ggcaacccgg tgcttccaac    4140
aaattcacat caggcaacat cagtgatgtt gaagtgggag gagctgagga atctctttca    4200
tttacatcga gcagcatatt aagatcgctg atgactgcta tagaagagtt ggagcttcac    4260
```

```
gcgattagga caggtcactc tcatatgttt ttgtgcatat tgaaagagca aaagcttctt    4320
gatcttgttc ccgtttcagg gaacaaagtt gtggatattg ccaagatga agctactgca    4380
tgcttgcttc tgaaagaaat ggctctacag atacatgaac ttgtgggtgc aaggatgcat    4440
catctttctg tatgccaatg ggaggtgaaa cttaagttgg acagcgatgg gcctgccagt    4500
ggtacctgga gagttgtaac aaccaatgtt actagtcaca cctgcactgt ggatatctac    4560
cgtgaggttg aagatacaga atcacagaaa ctagtgtacc actctgctcc atcgtcatct    4620
ggtcctttgc atggcgttgc actgaatact ccatatcagc ctttgagtgt tattgatctg    4680
aaacgttgct ccgctagaaa taacagaact acatactgct atgattttcc gttggcattt    4740
gaaactgcag tgcagaagtc atggtctaac atttctagtg acactaaccg atgttatgtt    4800
aaagcgacgg agctggtgtt tgctcacaag aacgggtcat ggggcactcc tgtaattcct    4860
atggagcgtc ctgctgggct caatgacatt ggtatggtag cttggatctt ggacatgtcc    4920
actcctgaat atcccaatgg caggcagatt gttgtcatcg caaatgatat tacttttaga    4980
gctggatcgt ttggtccaag ggaagatgca ttttttgaaa ctgttaccaa cctagcttgt    5040
gagaggaagc ttcctctcat ctacttggca gcaaactctg gtgctcggat cggcatagca    5100
gatgaagtaa atcttgctt ccgtgttgga tggtctgatg atggcagccc tgaacgtggg    5160
tttcaatata tttatctgac tgaagaagac catgctcgta ttagcgcttc tgttatagcg    5220
cacaagatgc agcttgataa tggtgaaatt aggtgggtta ttgattctgt tgtagggaag    5280
gaggatgggc taggtgtgga aacatacat ggaagtgctg ctattgccag tgcctattct    5340
agggcctatg aggagacatt tacgcttaca tttgtgactg aaggactgt tggaatagga    5400
gcatatcttg ctcgacttgg catacggtgc attcagcgta ctgaccagcc cattatccta    5460
actgggttct ctgccttgaa caagcttctt ggccgggaag tgtacagctc ccacatgcag    5520
ttgggtggcc ccaaaattat ggccacaaac ggtgttgtcc atctgacagt ttcagatgac    5580
cttgaaggtg tatctaatat attgaggtgg ctcagctatg ttcctgccaa cattggtgga    5640
cctcttccta ttacaaaatc tttggaccca cctgacagac ccgttgctta catccctgag    5700
aatacatgtg atcctcgtgc agccatcagt ggcattgatg atagccaagg gaaatggttg    5760
gggggtatgt tcgacaaaga cagttttgtg gagacatttg aaggatgggc gaagtcagta    5820
gttactggca gagcgaaact cggagggatt ccggtgggtg ttatagctgt ggagacacag    5880
actatgatgc agctcatccc tgctgatcca ggtcagcttg attcccatga gcggtctgtt    5940
cctcgtgctg gcaagtctg gtttccagat tcagctacta agacagcgca ggcaatgctg    6000
gacttcaacc gtgaaggatt acctctgttc atccttgcta actggagagg cttctctggt    6060
gggcaaagag atctttttga aggaatcctt caggctgggt caacaattgt tgagaacctt    6120
aggacataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct tgaacctcaa gggttgattg agatcaagtt caggtcagag    6300
gaactccaag agtgcatggg caggcttgac ccagaattga taaatttgaa ggcaaaactc    6360
ctgggagcaa agcatgaaaa tggaagtcta tctgagtcag aatcccttca gaagagcata    6420
gaagcccgga agaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcttttctt ctacaagaga ttacggagga ggatatccga ggatgttctt    6600
gcaaaggaaa ttagaggtgt aagtggcaag cagttttctc accaatcggc aatcgagctg    6660
```

```
atccagaaat ggtacttggc ctctaaggga gctgaaacgg aaacactga atgggatgat      6720 gacgatgctt tgttgcctg gagggaaaac cctgaaaact accaggagta tatcaaagaa      6780
ctcagggctc aaagggtatc tcagttgctc tcagatgttg cagactccag tccagatcta      6840
gaagccttgc cacagggtct ttctatgcta ctagagaaga tggatccctc aaggagagca      6900
cagtttgttg aggaagtcaa gaaggccctt aaatga                               6936
```

<210> SEQ ID NO 26
<211> LENGTH: 2311
<212> TYPE: PRT
<213> ORGANISM: Aegilops tauschii

<400> SEQUENCE: 26

```
Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Met Ala Ala
    130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Ser Gly Ser Gln Val Glu Ile Pro Leu Glu Val Cys Leu Asp
        275                 280                 285

Ser Ile Pro Ala Asp Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320
```

Ala Ser Trp Gly Gly Gly Gly Lys Gly Ile Arg Lys Val Asn Asn Asp
            325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
            355                 360                 365

Val Gln Leu Leu Cys Asp Gln Tyr Gly Asn Val Ala Ala Leu His Ser
            370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
            405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
            435                 440                 445

Asn Pro Arg Leu Gln Val Glu His Pro Val Thr Glu Trp Ile Ala Glu
            450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
            485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
            515                 520                 525

Arg Ile Thr Ser Glu Asp Pro Asp Gly Phe Lys Pro Thr Gly Gly
            530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
            565                 570                 575

Phe Gly His Val Phe Ala Tyr Gly Val Ser Arg Ala Ala Ala Ile Thr
            580                 585                 590

Asn Met Ser Leu Ala Leu Lys Glu Ile Gln Ile Arg Gly Glu Ile His
            595                 600                 605

Ser Asn Val Asp Tyr Thr Val Asp Leu Leu Asn Ala Ser Asp Phe Lys
            610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
            645                 650                 655

Leu Tyr Lys Thr Ile Thr Ser Asn Thr Asp Thr Val Ser Glu Tyr Val
            660                 665                 670

Ser Tyr Leu Val Lys Gly Gln Ile Pro Pro Lys His Ile Ser Leu Val
            675                 680                 685

His Ser Thr Val Ser Leu Asn Ile Glu Glu Ser Lys Tyr Thr Ile Glu
            690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
            725                 730                 735

Gln Leu Asp Gly Asn Ser His Val Ile Tyr Ala Glu Glu Glu Ala Gly

```
                740                 745                 750
Gly Thr Arg Leu Leu Ile Asp Gly Lys Thr Cys Leu Leu Gln Asn Asp
            755                 760                 765
His Asp Pro Ser Arg Leu Leu Ala Glu Thr Pro Cys Lys Leu Leu Arg
            770                 775                 780
Phe Leu Val Ala Asp Gly Ala His Val Glu Ala Asp Val Pro Tyr Ala
785                 790                 795                 800
Glu Val Glu Val Met Lys Met Cys Met Pro Leu Leu Ser Pro Ala Ala
                805                 810                 815
Gly Val Ile Asn Val Leu Leu Ser Glu Gly Gln Pro Met Gln Ala Gly
            820                 825                 830
Asp Leu Ile Ala Arg Leu Asp Leu Asp Pro Ser Ala Val Lys Arg
            835                 840                 845
Ala Glu Pro Phe Asn Gly Ser Phe Pro Glu Met Ser Leu Pro Ile Ala
            850                 855                 860
Ala Ser Gly Gln Val His Lys Arg Cys Ala Thr Ser Leu Asn Ala Ala
865                 870                 875                 880
Arg Met Val Leu Ala Gly Tyr Asp His Pro Ile Asn Lys Val Val Gln
                885                 890                 895
Asp Leu Val Ser Cys Leu Asp Ala Pro Glu Leu Pro Phe Leu Gln Trp
            900                 905                 910
Glu Glu Leu Met Ser Val Leu Ala Thr Arg Leu Pro Arg Leu Leu Lys
            915                 920                 925
Ser Glu Leu Glu Gly Lys Tyr Ser Glu Tyr Lys Leu Asn Val Gly His
            930                 935                 940
Gly Lys Ser Lys Asp Phe Pro Ser Lys Met Leu Arg Glu Ile Ile Glu
945                 950                 955                 960
Glu Asn Leu Ala His Gly Ser Glu Lys Glu Ile Ala Thr Asn Glu Arg
                965                 970                 975
Leu Val Glu Pro Leu Met Ser Leu Leu Lys Ser Tyr Glu Gly Gly Arg
            980                 985                 990
Glu Ser His Ala His Phe Ile Val  Lys Ser Leu Phe Glu  Asp Tyr Leu
            995                 1000                1005
Ser Val  Glu Glu Leu Phe Ser  Asp Gly Ile Gln Ser  Asp Val Ile
    1010                1015                1020
Glu Arg  Leu Arg Gln Gln His  Ser Lys Asp Leu Gln  Lys Val Val
    1025                1030                1035
Asp Ile  Val Leu Ser His Gln  Gly Val Arg Asn Lys  Thr Lys Leu
    1040                1045                1050
Ile Leu  Thr Leu Met Glu Lys  Leu Val Tyr Pro Asn  Pro Ala Ala
    1055                1060                1065
Tyr Lys  Asp Gln Leu Thr Arg  Phe Ser Leu Asn  His Lys Arg
    1070                1075                1080
Tyr Tyr  Lys Leu Ala Leu Lys  Ala Ser Glu Leu Leu  Glu Gln Thr
    1085                1090                1095
Lys Leu  Ser Glu Leu Arg Thr  Ser Ile Ala Arg Ser  Leu Ser Glu
    1100                1105                1110
Leu Glu  Met Phe Thr Glu Glu  Arg Thr Ala Ile Ser  Glu Ile Met
    1115                1120                1125
Gly Asp  Leu Val Thr Ala Pro  Leu Pro Val Glu Asp  Ala Leu Val
    1130                1135                1140
Ser Leu  Phe Asp Cys Ser Asp  Gln Thr Leu Gln Gln  Arg Val Ile
    1145                1150                1155
```

Glu Thr Tyr Ile Ser Arg Leu Tyr Gln Pro His Leu Val Lys Asp
1160                     1165              1170

Ser Ile Gln Leu Lys Tyr Gln Glu Ser Gly Val Ile Ala Leu Trp
1175                     1180              1185

Glu Phe Ala Glu Ala His Ser Glu Lys Arg Leu Gly Ala Met Val
1190                     1195              1200

Ile Val Lys Ser Leu Glu Ser Val Ser Ala Ala Ile Gly Ala Ala
1205                     1210              1215

Leu Lys Gly Thr Ser Arg Tyr Ala Ser Ser Glu Gly Asn Ile Met
1220                     1225              1230

His Ile Ala Leu Leu Gly Ala Asp Asn Gln Met His Gly Thr Glu
1235                     1240              1245

Asp Ser Gly Asp Asn Asp Gln Ala Gln Val Arg Ile Asp Lys Leu
1250                     1255              1260

Ser Ala Thr Leu Glu Gln Asn Thr Val Thr Ala Asp Leu Arg Ala
1265                     1270              1275

Ala Gly Val Lys Val Ile Ser Cys Ile Val Gln Arg Asp Gly Ala
1280                     1285              1290

Leu Met Pro Met Arg His Thr Phe Leu Leu Ser Asp Glu Lys Leu
1295                     1300              1305

Cys Tyr Glu Glu Glu Pro Val Leu Arg His Val Glu Pro Pro Leu
1310                     1315              1320

Ser Ala Leu Leu Glu Leu Gly Lys Leu Lys Val Lys Gly Tyr Asn
1325                     1330              1335

Glu Val Lys Tyr Thr Pro Ser Arg Asp Arg Gln Trp Asn Ile Tyr
1340                     1345              1350

Thr Leu Arg Asn Thr Glu Asn Pro Lys Met Leu His Arg Val Phe
1355                     1360              1365

Phe Arg Thr Leu Val Arg Gln Pro Gly Ala Ser Asn Lys Phe Thr
1370                     1375              1380

Ser Gly Asn Ile Ser Asp Val Glu Val Gly Gly Ala Glu Glu Ser
1385                     1390              1395

Leu Ser Phe Thr Ser Ser Ser Ile Leu Arg Ser Leu Met Thr Ala
1400                     1405              1410

Ile Glu Glu Leu Glu Leu His Ala Ile Arg Thr Gly His Ser His
1415                     1420              1425

Met Phe Leu Cys Ile Leu Lys Glu Gln Lys Leu Leu Asp Leu Val
1430                     1435              1440

Pro Val Ser Gly Asn Lys Val Val Asp Ile Gly Gln Asp Glu Ala
1445                     1450              1455

Thr Ala Cys Leu Leu Leu Lys Glu Met Ala Leu Gln Ile His Glu
1460                     1465              1470

Leu Val Gly Ala Arg Met His His Leu Ser Val Cys Gln Trp Glu
1475                     1480              1485

Val Lys Leu Lys Leu Asp Ser Asp Gly Pro Ala Ser Gly Thr Trp
1490                     1495              1500

Arg Val Val Thr Thr Asn Val Thr Ser His Thr Cys Thr Val Asp
1505                     1510              1515

Ile Tyr Arg Glu Val Glu Asp Thr Glu Ser Gln Lys Leu Val Tyr
1520                     1525              1530

His Ser Ala Pro Ser Ser Ser Gly Pro Leu His Gly Val Ala Leu
1535                     1540              1545

Asn Thr Pro Tyr Gln Pro Leu Ser Val Ile Asp Leu Lys Arg Cys
1550                 1555                1560

Ser Ala Arg Asn Asn Arg Thr Thr Tyr Cys Tyr Asp Phe Pro Leu
1565                 1570                1575

Ala Phe Glu Thr Ala Val Gln Lys Ser Trp Ser Asn Ile Ser Ser
1580                 1585                1590

Asp Thr Asn Arg Cys Tyr Val Lys Ala Thr Glu Leu Val Phe Ala
1595                 1600                1605

His Lys Asn Gly Ser Trp Gly Thr Pro Val Ile Pro Met Glu Arg
1610                 1615                1620

Pro Ala Gly Leu Asn Asp Ile Gly Met Val Ala Trp Ile Leu Asp
1625                 1630                1635

Met Ser Thr Pro Glu Tyr Pro Asn Gly Arg Gln Ile Val Val Ile
1640                 1645                1650

Ala Asn Asp Ile Thr Phe Arg Ala Gly Ser Phe Gly Pro Arg Glu
1655                 1660                1665

Asp Ala Phe Phe Glu Thr Val Thr Asn Leu Ala Cys Glu Arg Lys
1670                 1675                1680

Leu Pro Leu Ile Tyr Leu Ala Ala Asn Ser Gly Ala Arg Ile Gly
1685                 1690                1695

Ile Ala Asp Glu Val Lys Ser Cys Phe Arg Val Gly Trp Ser Asp
1700                 1705                1710

Asp Gly Ser Pro Glu Arg Gly Phe Gln Tyr Ile Tyr Leu Thr Glu
1715                 1720                1725

Glu Asp His Ala Arg Ile Ser Ala Ser Val Ile Ala His Lys Met
1730                 1735                1740

Gln Leu Asp Asn Gly Glu Ile Arg Trp Val Ile Asp Ser Val Val
1745                 1750                1755

Gly Lys Glu Asp Gly Leu Gly Val Glu Asn Ile His Gly Ser Ala
1760                 1765                1770

Ala Ile Ala Ser Ala Tyr Ser Arg Ala Tyr Glu Glu Thr Phe Thr
1775                 1780                1785

Leu Thr Phe Val Thr Gly Arg Thr Val Gly Ile Gly Ala Tyr Leu
1790                 1795                1800

Ala Arg Leu Gly Ile Arg Cys Ile Gln Arg Thr Asp Gln Pro Ile
1805                 1810                1815

Ile Leu Thr Gly Phe Ser Ala Leu Asn Lys Leu Leu Gly Arg Glu
1820                 1825                1830

Val Tyr Ser Ser His Met Gln Leu Gly Gly Pro Lys Ile Met Ala
1835                 1840                1845

Thr Asn Gly Val Val His Leu Thr Val Ser Asp Asp Leu Glu Gly
1850                 1855                1860

Val Ser Asn Ile Leu Arg Trp Leu Ser Tyr Val Pro Ala Asn Ile
1865                 1870                1875

Gly Gly Pro Leu Pro Ile Thr Lys Ser Leu Asp Pro Pro Asp Arg
1880                 1885                1890

Pro Val Ala Tyr Ile Pro Glu Asn Thr Cys Asp Pro Arg Ala Ala
1895                 1900                1905

Ile Ser Gly Ile Asp Asp Ser Gln Gly Lys Trp Leu Gly Gly Met
1910                 1915                1920

Phe Asp Lys Asp Ser Phe Val Glu Thr Phe Glu Gly Trp Ala Lys
1925                 1930                1935

Ser Val Val Thr Gly Arg Ala Lys Leu Gly Gly Ile Pro Val Gly

```
                1940                1945                1950

Val Ile Ala Val Glu Thr Gln Thr Met Met Gln Leu Ile Pro Ala
        1955                1960                1965

Asp Pro Gly Gln Leu Asp Ser His Glu Arg Ser Val Pro Arg Ala
        1970                1975                1980

Gly Gln Val Trp Phe Pro Asp Ser Ala Thr Lys Thr Ala Gln Ala
        1985                1990                1995

Met Leu Asp Phe Asn Arg Glu Gly Leu Pro Leu Phe Ile Leu Ala
        2000                2005                2010

Asn Trp Arg Gly Phe Ser Gly Gly Gln Arg Asp Leu Phe Glu Gly
        2015                2020                2025

Ile Leu Gln Ala Gly Ser Thr Ile Val Glu Asn Leu Arg Thr Tyr
        2030                2035                2040

Asn Gln Pro Ala Phe Val Tyr Ile Pro Lys Ala Ala Glu Leu Arg
        2045                2050                2055

Gly Gly Ala Trp Val Val Ile Asp Ser Lys Ile Asn Pro Asp Arg
        2060                2065                2070

Ile Glu Phe Tyr Ala Glu Arg Thr Ala Lys Gly Asn Val Leu Glu
        2075                2080                2085

Pro Gln Gly Leu Ile Glu Ile Lys Phe Arg Ser Glu Glu Leu Gln
        2090                2095                2100

Glu Cys Met Gly Arg Leu Asp Pro Glu Leu Ile Asn Leu Lys Ala
        2105                2110                2115

Lys Leu Leu Gly Ala Lys His Glu Asn Gly Ser Leu Ser Glu Ser
        2120                2125                2130

Glu Ser Leu Gln Lys Ser Ile Glu Ala Arg Lys Lys Gln Leu Leu
        2135                2140                2145

Pro Leu Tyr Thr Gln Ile Ala Val Arg Phe Ala Glu Leu His Asp
        2150                2155                2160

Thr Ser Leu Arg Met Ala Ala Lys Gly Val Ile Lys Lys Val Val
        2165                2170                2175

Asp Trp Glu Asp Ser Arg Ser Phe Phe Tyr Lys Arg Leu Arg Arg
        2180                2185                2190

Arg Ile Ser Glu Asp Val Leu Ala Lys Glu Ile Arg Gly Val Ser
        2195                2200                2205

Gly Lys Gln Phe Ser His Gln Ser Ala Ile Glu Leu Ile Gln Lys
        2210                2215                2220

Trp Tyr Leu Ala Ser Lys Gly Ala Glu Thr Gly Asn Thr Glu Trp
        2225                2230                2235

Asp Asp Asp Ala Phe Val Ala Trp Arg Glu Asn Pro Glu Asn
        2240                2245                2250

Tyr Gln Glu Tyr Ile Lys Glu Leu Arg Ala Gln Arg Val Ser Gln
        2255                2260                2265

Leu Leu Ser Asp Val Ala Asp Ser Ser Pro Asp Leu Glu Ala Leu
        2270                2275                2280

Pro Gln Gly Leu Ser Met Leu Leu Glu Lys Met Asp Pro Ser Arg
        2285                2290                2295

Arg Ala Gln Phe Val Glu Glu Val Lys Lys Ala Leu Lys
        2300                2305                2310
```

(12) POST-GRANT REVIEW CERTIFICATE (257th)

United States Patent
Mankin et al.

(10) Number: US 11,096,345 J1
(45) Certificate Issued: Jun. 1, 2023

(54) METHOD FOR TREATING POST-EMERGENT RICE

(71) Applicants: S. Luke Mankin; Leon Neuteboom; Ulrich Schoefl; Allan Wenck; John A. McElver; Sherry R. Whitt; Haiping Hong; Dale R. Carlson; Jill M. Stevenson-Paulik

(72) Inventors: S. Luke Mankin; Leon Neuteboom; Ulrich Schoefl; Allan Wenck; John A. McElver; Sherry R. Whitt; Haiping Hong; Dale R. Carlson; Jill M. Stevenson-Paulik

(73) Assignee: BASF SE

Trial Number:

PGR2021-00113 filed Aug. 24, 2021

Post-Grant Review Certificate for:

Patent No.: 11,096,345
Issued: Aug. 24, 2021
Appl. No.: 15/395,832
Filed: Dec. 30, 2016

The results of PGR2021-00113 are reflected in this post-grant review certificate under 35 U.S.C. 328(b).

POST-GRANT REVIEW CERTIFICATE
U.S. Patent 11,096,345 J1
Trial No. PGR2021-00113
Certificate Issued Jun. 1, 2023

AS A RESULT OF THE POST-GRANT REVIEW PROCEEDING, IT HAS BEEN DETERMINED THAT:

Claims 1-15 are cancelled.

\* \* \* \* \*